(12) United States Patent
Nakahira et al.

(10) Patent No.: US 7,601,728 B2
(45) Date of Patent: *Oct. 13, 2009

(54) BICYCLIC PYRROLE DERIVATIVES

(75) Inventors: Hiroyuki Nakahira, Osaka (JP);
Hidenori Kimura, Osaka (JP); Hitoshi Hochigai, Osaka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/127,858

(22) Filed: May 28, 2008

(65) Prior Publication Data

US 2009/0149483 A1 Jun. 11, 2009

Related U.S. Application Data

(63) Continuation of application No. 11/722,037, filed as application No. PCT/JP2005/023449 on Dec. 21, 2005.

(30) Foreign Application Priority Data

Dec. 24, 2004 (JP) ............................. 2004-372772

(51) Int. Cl.
*A61K 31/519* (2006.01)
(52) U.S. Cl. ................................... 514/265.1; 544/280
(58) Field of Classification Search ........................ None
See application file for complete search history.

(56) References Cited

U.S. PATENT DOCUMENTS

| 2002/0198205 A1 | 12/2002 | Himmelsbach et al. |
| 2003/0105077 A1 | 6/2003 | Kanstrup et al. |
| 2003/0199528 A1 | 10/2003 | Kanstrup et al. |
| 2004/0116328 A1 | 6/2004 | Yoshikawa et al. |

FOREIGN PATENT DOCUMENTS

| JP | 2003-300977 A | 10/2003 |
| WO | 03/004496 A1 | 1/2003 |
| WO | 03/024965 A2 | 3/2003 |
| WO | 03/104229 A1 | 12/2003 |
| WO | 2007/071738 A1 | 6/2007 |

OTHER PUBLICATIONS

R.A. Pederson, et al., "Improved Glucode Tolerance in Zucker Fatty Rats by Oral Administration of the Dipeptidyl peptidase IV Inhibitor Isoleucine Thiazolidide", *Diabetes*, vol. 47, 1998, pp. 1253-1258.

Cellular Peptidases in Immune Functions and Diseases 2, Edited by J. Langer and S. Ansorge, Kluwer Acadamic/Plenum Publishers, 2000, pp. 111-122, 336-338 and 522.
L. B. Knudsen and Lone Pridal, "Glucagon-like peptide-1-(9-36) amide is a major metabolite of glucagons-like peptide-1-(7-36) amide after in vivo administration to dogs, and it acts as an antagonist on the pancreatic receptor", European Journal of Pharmacology, vol. 318, 1996, pp. 429-435.
T.J. Kieffer, et al., "Degradation of Glucose-Dependent Insulinotropic Polypeptide and Truncated Glucagon-Like Peptide 1 in Vitro and in Vivo by Dipeptidyl Peptidase IV", *Endocrinology*, vol. 136, No. 8, 1995, pp. 3585-3596.
U.S. Appl. No. 12/144,430 to Hiroyuki Nakahira, et al., filed Jun. 23, 2008.

*Primary Examiner*—Kamal A Saeed
(74) *Attorney, Agent, or Firm*—Sughrue Mion, PLLC

(57) ABSTRACT

Compounds represented by the general formula (I), prodrugs thereof, or pharmaceutically acceptable salts of both are provided as compounds which have high DPP-IV inhibiting activity and are improved in safety, toxicity and so on: (I)

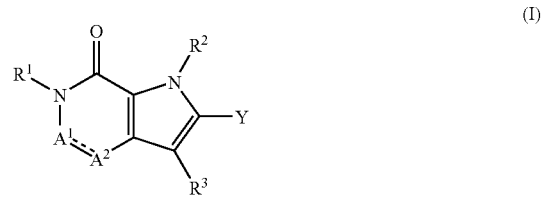

wherein the solid line and dotted line between $A^1$ and $A^2$ represents a double bond ($A^1=A^2$) or the like; $A^1$ is $C(R^4)$ or the like; $A^2$ is nitrogen atom or the like; $R^1$ is hydrogen atom, optionally substituted alkly group, or the like; $R^2$ is hydrogen atom, optionally substituted alkyl group, or the like; $R^3$ is hydrogen atom, halogen atom, or the like; $R^4$ is hydrogen atom, hydroxyl, halogen atom, or the like; and Y is a group represented by the general formula (A) or the like; (A)

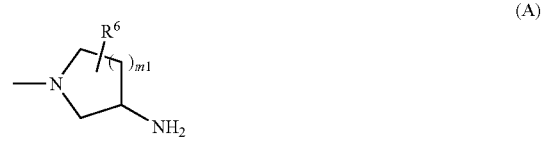

[wherein m1 is 0, 1, 2 or 3; and the group (A) may be freed from $R^6$ or substituted with one or two $R^6$'s which are each independently halogen atom or the like.]

4 Claims, No Drawings

BICYCLIC PYRROLE DERIVATIVES

This application is a continuation of pending U.S. application Ser. No. 11/722,037 filed Jun. 18, 2007, which is a National Stage Entry of PCT/JP2005/023449, filed Dec. 21, 2005, which claims benefit of priority under 35 U.S.C. § 119 based on Japanese Patent Application No. 2004-372772, filed Dec. 24, 2004. The entire disclosures of the prior applications are hereby incorporated by reference.

TECHNICAL FIELD

The present invention relates to bicyclic pyrrole derivatives useful as drugs. More particularly, it relates to novel bicyclic pyrrole derivatives effective as a dipeptidyl peptidase IV (DPP-IV) inhibitor. Furthermore, it relates to a pharmaceutical composition for the treatment of diabetes containing a bicyclic pyrrole derivative effective as a dipeptidyl peptidase IV (DPP-IV) inhibitor, as an active ingredient.

BACKGROUND ART

DPP-IV is a serine protease widely present in the body, is one of dipeptidyl aminopeptidases capable of hydrolyzing and releasing a N-terminal dipeptide and markedly acts on, in particular, peptides containing proline as the second amino acid from the N-terminal. Therefore, DPP-IV is referred to also as prolyl end peptidase. DPP-IV is known to accept, as substrates, various biological peptides concerned in the endocrine system, the neuroendocrine system, immunological functions and the like. It is known that many physiologically active peptides such as the pancreatic polypeptide family represented by pancreatic polypeptides (PP), neuropeptide Y (NPY) and the like; the glucagon/VIP family represented by vasoactive intestinal polypeptides (VIP), glucagon-like peptide-1 (GLP-1), glucose-dependent insulinotropic polypeptides (GIP), growth hormone-releasing factor (GRF) and the like; and the chemocaine family are substrates for DPP-IV and are subject to the influences of DPP-IV, such as activation/inactivation, metabolism acceleration and the like (non-patent document 1).

DPP-IV severs two amino acids (His-Ala) from the N-terminal of GLP-1. It is known that although the severed peptide binds weekly to a GLP-1 receptor, it has no activating effect on the receptor and acts as an antagonist (non-patent document 2). The metabolism of GLP-1 by DPP-IV in blood is known to be very rapid, and the concentration of active GLP-1 in blood is increased by the inhibition of DPP-IV (non-patent document 3). GLP-1 is a peptide secreted from intestinal tract by the ingestion of sugars and is a main accelerating factor for the glucose-responsive secretion of insulin by pancreas. In addition, GLP-1 is known to have accelerating effect on insulin synthesis in pancreatic β cells and accelerating effect on β cell proliferation. Moreover, it is known that GLP-1 receptors appear also in digestive tracts, liver, muscle, adipose tissue and the like, and it is also known that in these tissues, GLP-1 affects working of the digestive tracts, the secretion of acid in stomach, the synthesis and degradation of glycogen, insulin-dependent glucose uptake, and the like. Accordingly, there is expected the development of a DPP-IV inhibitor effective against type 2 diabetes (non-insulin-dependent diabetes) which brings about effects such as the acceleration of insulin secretion dependent on blood sugar level, the improvement of pancreas function, the improvement of a high postprandial blood sugar level, the improvement of glucose tolerance abnormality, the improvement of insulin resistance, and the like, by increasing the concentration of GLP-1 in blood (non-patent document 4).

Various DPP-IV inhibitors have been reported. For example, patent documents 1 and 2 report that derivatives having an imidazole ring are effective as DPP-IV inhibitors.

Patent document 1: International Publication No. WO 02/068420 pamphlet

Patent document 2: International Publication No. WO 03/104229 pamphlet

Non-patent document 1: J. Langner and S. Ansorge, "Cellular Peptidases in Immune Functions and Disease 2", *Advances in Experimental Medicine and Biology*, Vol. 477

Non-patent document 2: L. B. Knudsen et al., *European Journal of Pharmacology*, Vol. 318, p 429-435, 1996

Non-patent document 3: T. J. Kieffer et al., *Endocrinology*, Vol. 136, p 3585-3596, 1995

Non-patent document 4: R. A. Pederson et al., *Diabetes*, Vol. 47, p 1253-1258, 1998

DISCLOSURE OF THE INVENTION

Problem to be Solved by the Invention

An object of the present invention is to provide a novel compound having an excellent DPP-IV inhibiting activity.

Means for Solving the Problem

The present inventors earnestly investigated in order to achieve the above object, and consequently found that the following compound, a prodrug thereof or a pharmaceutically acceptable salt of the compound or prodrug (if necessary, they are hereinafter abbreviated as the present inventive compounds in some cases) has an excellent DPP-IV inhibiting effect, whereby the present invention has been accomplished.

That is, the present invention relates to the following:

[1] A compound represented by the formula (I):

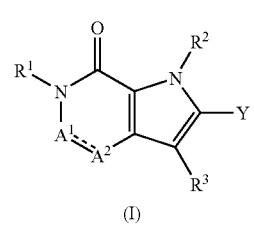

[Formula 1]

(I)

wherein $R^1$ is a hydrogen atom, an optionally substituted alkyl group, an optionally substituted cycloalkyl group, an optionally substituted aryl group, or an optionally substituted heteroaryl group;

the solid line and dotted line between $A^1$ and $A^2$ indicate a double bond ($A^1$=$A^2$) or a single bond ($A^1$—$A^2$);

$A^1$ is a group represented by the formula $C(R^4)$ and $A^2$ is a nitrogen atom, in the case of the solid line and dotted line between $A^1$ and $A^2$ being a double bond ($A^1$=$A^2$);

$A^1$ is a group represented by the formula C=O and $A^2$ is a group represented by the formula $N(R^5)$, in the case of the solid line and dotted line between $A^1$ and $A^2$ being a single bond ($A^1$—$A^2$);

$R^2$ is a hydrogen atom, an optionally substituted alkyl group, an optionally substituted aryl group, an optionally substituted heteroaryl group, an optionally substituted aralkyl group, an optionally substituted heteroarylalkyl group, an optionally substituted alkenyl group or an optionally substituted alkynyl group;

$R^3$ is a hydrogen atom, a halogen atom, a cyano group, a formyl group, a carboxyl group, an optionally substituted alkyl group, an optionally substituted alkenyl group, an optionally substituted alkynyl group, an optionally substituted cycloalkyl group, an optionally substituted aryl group, an optionally substituted heteroaryl group, an optionally substituted aralkyl group, an optionally substituted heteroarylalkyl group, an optionally substituted alkylcarbonyl group, an optionally substituted cycloalkylcarbonyl group, an optionally substituted aroyl group, an optionally substituted heteroarylcarbonyl group, an optionally substituted alkoxycarbonyl group, an optionally substituted aryloxycarbonyl group, an optionally substituted carbamoyl group, a hydroxyl group, an optionally substituted alkoxy group, or the formula: -Rd-C(O)O—Re wherein Rd is a single bond, an alkylene group or an alkenylene group and Re is tetrahydrofuranyl, cinnamyl, 5-methyl-2-oxo-1,3-dioxolen-4-ylmethyl, 5-(tert-butyl)-2-oxo-1,3-dioxolen-4-ylmethyl or the formula: —CH($R^{4a}$)OC(O)$R^{4b}$ wherein $R^{4a}$ is a hydrogen atom, an alkyl group, an alkenyl group, a cycloalkyl group or an alkoxy group and $R^{4b}$ is an optionally substituted alkyl group, an optionally substituted alkenyl group, a cycloalkyl group, a cycloalkyloxy group, an optionally substituted alkoxy group, an optionally substituted alkenyloxy group, a 2-indanyloxy group, a 5-indanyloxy group or an optionally substituted aryloxy group;

$R^4$ is a hydrogen atom, a hydroxyl group, a halogen atom, a cyano group, a formyl group, an optionally substituted alkyl group, an optionally substituted cycloalkyl group, an optionally substituted cycloalkyloxy group, an optionally substituted alkenyl group, an optionally substituted alkynyl group, an optionally substituted amino group, an optionally substituted carbamoyl group, a carboxyl group, an optionally substituted alkoxy group, an optionally substituted aryl group, an optionally substituted aryloxy group, an optionally substituted aralkyl group, an optionally substituted aralkyloxy group, an optionally substituted aroyl group, an optionally substituted arylthio group, an optionally substituted arylsulfinyl group, an optionally substituted arylsulfonyl group, an optionally substituted alkylthio group, an optionally substituted alkylsulfinyl group, an optionally substituted alkylsulfonyl group, an optionally substituted heteroaryl group, an optionally substituted heteroarylalkyl group, an optionally substituted heteroarylcarbonyl group, an optionally substituted heteroaryloxy group, an optionally substituted alkylcarbonyl group, an optionally substituted nitrogen-containing saturated heterocyclic group, an optionally substituted alkoxycarbonyl group, an optionally substituted aryloxycarbonyl group, an optionally substituted aralkyloxycarbonyl group, an optionally substituted cycloalkyloxycarbonyl group, or the formula: -Rd-C(O)O—Re wherein Rd and Re are as defined above;

$R^5$ is a hydrogen atom, an optionally substituted alkyl group, an optionally substituted cycloalkyl group, an optionally substituted aryl group, an optionally substituted vinyl group, an optionally substituted nitrogen-containing saturated heterocyclic group, or an optionally substituted heteroaryl group;

—Y is a group represented by any of the formula (A), formula (B), formula (C) and formula (D) shown below:

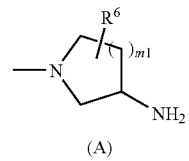

(A)

[Formula 2]

wherein m1 is 0, 1, 2 or 3, and $R^6$ is absent or one or two $R^6$s are present and are independently a halogen atom, a hydroxyl group, an oxo group, an optionally substituted alkoxy group, an optionally substituted alkyl group, an optionally substituted aryl group, an optionally substituted aralkyl group, an optionally substituted amino group, a carboxyl group, an optionally substituted alkoxycarbonyl group or an optionally substituted carbamoyl group, or two $R^6$s, when taken together, represent methylene or ethylene and may bind to two carbon atoms constituting the ring, to form a new ring;

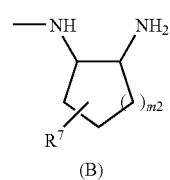

(B)

[Formula 3]

wherein m2 is 0, 1, 2 or 3, and $R^7$ is absent or one or two $R^7$s are present and are independently a halogen atom, a hydroxyl group, an oxo group, an optionally substituted alkoxy group, an optionally substituted alkyl group, an optionally substituted aryl group, an optionally substituted aralkyl group, an optionally substituted amino group, a carboxyl group, an optionally substituted alkoxycarbonyl group or an optionally substituted carbamoyl group, or two $R^7$s, when taken together, represent methylene or ethylene and may bind to two carbon atoms constituting the ring, to form a new ring;

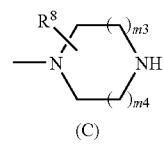

(C)

[Formula 4]

wherein m3 and m4 are independently 0 or 1, and $R^8$ is absent or one or two $R^8$s are present and are independently a halogen atom, a hydroxyl group, an oxo group, an optionally substituted alkoxy group, an optionally substituted alkyl group, an optionally substituted aryl group, an optionally substituted aralkyl group, an optionally substituted amino group, a carboxyl group, an optionally substituted alkoxycarbonyl group or an optionally substituted carbamoyl group, or two $R^8$s, when taken together, represent methylene or ethylene and may bind to two carbon atoms constituting the ring, to form a new ring; and

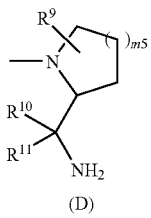

(D)

wherein m5 is 1, 2 or 3, $R^9$ is absent or one or two $R^9$s are present and are independently a halogen atom, a hydroxyl group, an oxo group, an optionally substituted alkoxy group, an optionally substituted alkyl group, an optionally substituted aryl group, an optionally substituted aralkyl group, an optionally substituted amino group, a carboxyl group, an optionally substituted alkoxycarbonyl group or an optionally substituted carbamoyl group, or two $R^9$s, when taken together, represent methylene or ethylene and may bind to two carbon atoms constituting the ring, to form a new ring, and $R^{10}$ and $R^{11}$ are independently a hydrogen atom, methyl, ethyl, propyl or isopropyl, or $R^{10}$ and $R^{11}$, when taken together, represent cyclopropyl, cyclobutyl or cyclopentyl, a prodrug of said compound, or a pharmaceutically acceptable salt of said compound or prodrug.

[2] A compound according to [1], which is represented by the formula (II):

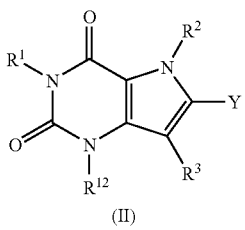

(II)

wherein $R^1$, $R^2$, $R^3$ and Y are as defined in [1] and $R^{12}$ is a hydrogen atom, an optionally substituted alkyl group or an optionally substituted aryl group, a prodrug of the compound or a pharmaceutically acceptable salt of the compound or prodrug.

[3] A compound according to [1], which is represented by the formula (III):

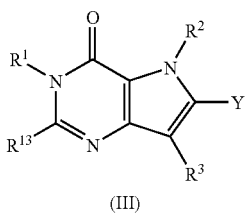

(III)

wherein $R^1$, $R^2$, $R^3$ and Y are as defined in [1] and $R^{13}$ is a hydrogen atom, a hydroxyl group, a cyano group, a carboxyl group, an optionally substituted alkyl group, an optionally substituted cycloalkyl group, an optionally substituted alkoxy group, an optionally substituted cycloalkyloxy group, an optionally substituted aryl group, an optionally substituted aryloxy group, an optionally substituted aralkyl group, an optionally substituted aralkyloxy group, an optionally substituted aroyl group, an optionally substituted heteroaryl group, an optionally substituted heteroarylalkyl group, an optionally substituted heteroarylcarbonyl group, an optionally substituted heteroaryloxy group, an optionally substituted alkylcarbonyl group, an optionally substituted alkoxycarbonyl group, an optionally substituted aryloxycarbonyl group, an optionally substituted aralkyloxycarbonyl group, an optionally substituted cycloalkyloxycarbonyl group, an optionally substituted alkylsulfonyl group, or the formula: -Rd-C(O)O—Re wherein Rd and Re are as defined in [1], a prodrug of the compound or a pharmaceutically acceptable salt of the compound or prodrug.

[4] A compound, a prodrug thereof or a pharmaceutically acceptable salt of the compound or prodrug according to [3], wherein $R^{13}$ is a hydrogen atom, a hydroxyl group, a cyano group, a carboxyl group, a trifluoromethyl group, an optionally substituted aryl group, an optionally substituted aryloxy group, an optionally substituted aroyl group, an optionally substituted alkylcarbonyl group, an optionally substituted alkoxycarbonyl group, an optionally substituted aryloxycarbonyl group, an optionally substituted aralkyloxycarbonyl group, an optionally substituted cycloalkyloxycarbonyl group, an optionally substituted alkylsulfonyl group, or the formula: -Rd-C(O)O—Re wherein Rd and Re are as defined in [1].

[5] A compound, a prodrug thereof or a pharmaceutically acceptable salt of the compound or prodrug according to any one of [1] to [4], wherein $R^2$ is a group represented by any of the following formula (E), formula (F), formula (G), formula (H), formula (I) and formula (J):

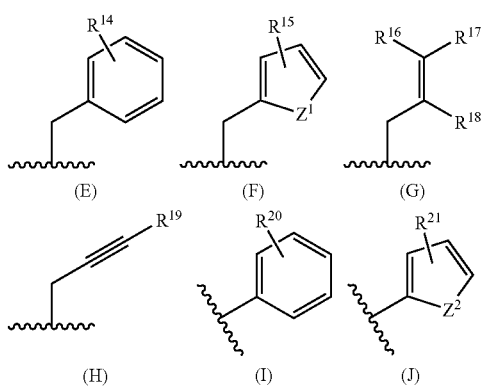

wherein each of $Z^1$ and $Z^2$ is an oxygen atom, the formula S(O)p or the formula $N(R^{22})$;

each of $R^{14}$ and $R^{20}$ is absent or one or two $R^{14}$s and/or one or two $R^{20}$s are present and are independently a halogen atom, a hydroxyl group, a formyl group, a carboxyl group, a cyano group, an alkylthio group, an alkylsulfinyl group, an alkylsulfonyl group, an alkyl group, a haloalkyl group, a cycloalkyl group, an alkoxy group, a haloalkoxy group, an optionally substituted amino group, an optionally substituted carbamoyl group, an alkoxycarbonyl group, an optionally substituted alkylcarbonyl group, a cycloalkylcarbonyl group, an optionally substituted aryl group, an optionally substituted heteroaryl group or an optionally substituted nitrogen-containing heteroaryl group, or two $R^{14}$s or two $R^{20}$s, when taken together, represent a $C_{1-3}$ alkylenedioxy group;

each of $R^{15}$ and $R^{21}$ is absent or one or two $R^{15}$s and/or one or two $R^{21}$s are present and are independently a halogen atom, a cyano group, an alkyl group, a haloalkyl group, a cycloalkyl group, an alkoxy group or a haloalkoxy group;

$R^{16}$ is methyl, ethyl, a chlorine atom or a bromine atom;

$R^{17}$ is a hydrogen atom, methyl, ethyl, a chlorine atom or a bromine atom;

$R^{18}$ is a hydrogen atom, methyl or ethyl;

$R^{19}$ is a hydrogen atom, methyl, ethyl, cyclopropyl or cyclobutyl;

p is 0, 1 or 2; and $R^{22}$ is a hydrogen atom or an alkyl group.

[6] A compound, a prodrug thereof or a pharmaceutically acceptable salt of the compound or prodrug according to any one of [1] to [5], wherein —Y is a group represented by the formula (A) in which m1 is 1 or 2, or —Y is a group represented by the formula (B) in which m2 is 1 or 2, or —Y is a group represented by the formula (C) in which each of m3 and m4 is 1.

[7] A compound, a prodrug thereof or a pharmaceutically acceptable salt of the compound or prodrug according to any one of [1] to [6], wherein $R^2$ is a group represented by any of the formula (E), formula (H) and formula (I).

[8] A compound, a prodrug thereof or a pharmaceutically acceptable salt of the compound or prodrug according to any one of [1] to [7], wherein $R^1$ is a hydrogen atom, an optionally substituted $C_1$-$C_3$ alkyl group or an optionally substituted aryl group, and the substituent(s) of the optionally substituted alkyl group is selected from fluorine atom, optionally substituted aroyl groups, carboxyl group, optionally substituted alkoxycarbonyl groups, optionally substituted aryl groups and optionally substituted aryloxy groups.

[9] A compound, a prodrug thereof or a pharmaceutically acceptable salt of the compound or prodrug according to any one of [1] to [7], wherein $R^1$ is a group represented by the formula: —Ra—Rb-Rc in which Ra is an alkylene group;

Rb is a single bond or a carbonyl group; and

Rc is an optionally substituted alkyl group, an optionally substituted alkoxy group, an optionally substituted aryl group, an optionally substituted aryloxy group or an optionally substituted heteroarylamino group.

[10] A compound, a prodrug thereof or a pharmaceutically acceptable salt of the compound or prodrug according to any one of [1] to [7], wherein $R^1$ is a hydrogen atom, methyl or ethyl.

[11] A compound according to [1], which is represented by the formula (IV):

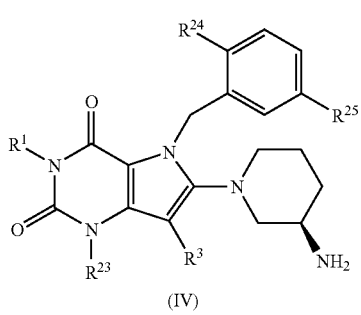

(IV)

wherein $R^1$ and $R^3$ are as defined in [1]; $R^{23}$ is a hydrogen atom or an optionally substituted alkyl group; $R^{24}$ is a halogen atom, a cyano group, a carbamoyl group, a methyl group, a trifluoromethyl group, a difluoromethyl group, a monofluoromethyl group, a methoxy group, a trifluoromethoxy group, difluoromethoxy group or a monofluoromethoxy group; and $R^{25}$ is a hydrogen atom, a fluorine atom or a chlorine atom, a prodrug of the compound or a pharmaceutically acceptable salt of the compound or prodrug.

[12] A compound according to [1], which is represented by the formula (V):

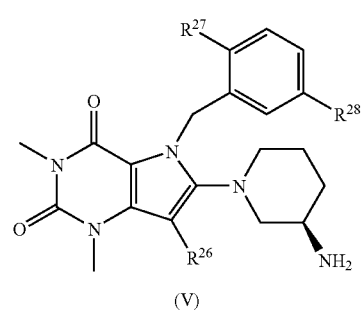

(V)

wherein $R^{26}$ is a hydrogen atom, a cyano group, an optionally substituted alkyl group, an optionally substituted carbamoyl group, a hydroxyl group or an optionally substituted alkoxy group; $R^{27}$ is a chlorine atom, a bromine atom, a cyano group, a carbamoyl group, a methyl group, a trifluoromethyl group, a difluoromethyl group, a monofluoromethyl group, a methoxy group, a trifluoromethoxy group, difluoromethoxy group or a monofluoromethoxy group; and $R^{28}$ is a hydrogen atom or a fluorine atom, a prodrug of the compound or a pharmaceutically acceptable salt of the compound or prodrug.

[13] A compound, a prodrug thereof or a pharmaceutically acceptable salt of the compound or prodrug according to [12], wherein $R^{27}$ is a chlorine atom or a cyano group.

[14] A compound, a prodrug thereof or a pharmaceutically acceptable salt of the compound or prodrug according to either [12] or [13], wherein $R^{26}$ is a hydrogen atom or an optionally substituted carbamoyl group.

[15] A compound represented by the formula (VI):

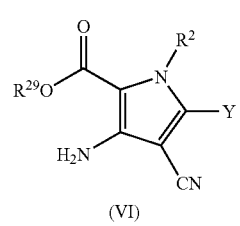

(VI)

wherein $R^2$ and Y are as defined in [1] and $R^{29}$ is a hydrogen atom, an optionally substituted alkyl group, an optionally substituted alkenyl group, an optionally substituted alkynyl group, an optionally substituted cycloalkyl group, an optionally substituted aryl group, an optionally substituted heteroaryl group, an optionally substituted aralkyl group or an optionally substituted heteroarylalkyl group, a prodrug of the compound or a pharmaceutically acceptable salt of the compound or prodrug.

[16] A pharmaceutical composition comprising a compound, a prodrug thereof or a pharmaceutically acceptable salt of the compound or prodrug according to any one of [1] to [15] as an active ingredient.
[17] A dipeptidyl peptidase IV inhibitor comprising a compound, a prodrug thereof or a pharmaceutically acceptable salt of the compound or prodrug according to any one of [1] to [15] as an active ingredient.
[18] A pharmaceutical composition for the treatment of diabetes comprising a compound, a prodrug thereof or a pharmaceutically acceptable salt of the compound or prodrug according to any one of [1] to [15] as an active ingredient.
[19] Use of a compound, a prodrug thereof or a pharmaceutically acceptable salt of the compound or prodrug according to any one of [1] to [15] in the manufacture of a dipeptidyl peptidase IV inhibitor.
[20] Use of a compound, a prodrug thereof or a pharmaceutically acceptable salt of the compound or prodrug according to any one of [1] to [15] in the manufacture of a pharmaceutical composition for the treatment of diabetes.
[21] A method for treating diabetes comprising administering an effective amount of a compound, a prodrug thereof or a pharmaceutically acceptable salt of the compound or prodrug according to any one of [1] to [15] to a patient who needs the treatment.

The compound represented by the formula (I), a prodrug thereof or a pharmaceutically acceptable salt of the compound or prodrug is hereinafter generically named "the present inventive compound" if necessary.

ADVANTAGES OF THE INVENTION

The present inventive compound has an excellent DPP-IV inhibiting activity and is useful as a therapeutic agent for diabetes.

BEST MODE FOR CARRYING OUT THE INVENTION

The present invention is explained below in further detail.

In the present description, the number of substituents of each group defined by the term "optionally substituted" or "substituted" is not particularly limited as long as the substitution is possible, and it is 1 or more. Unless otherwise specified, the explanation of each group applies also to the case where the group is a portion or the substituent of another group.

The "halogen atom" includes, for example, fluorine atom, chlorine atom, bromine atom and iodine atom.

The "alkyl group" includes, for example, linear or branched alkyl groups of 1 to 6 carbon atoms. Specific examples thereof are methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, etc. Preferable examples thereof are linear or branched alkyl groups of 1 to 4 carbon atoms. Specific examples of such groups are methyl, ethyl, propyl, isopropyl, butyl, tert-butyl, etc.

The "alkenyl group" includes, for example, alkenyl groups of 2 to 6 carbon atoms. Specific examples thereof are vinyl, propenyl, methylpropenyl, butenyl, methylbutenyl, etc.

The "alkynyl group" includes, for example, alkynyl groups of 2 to 6 carbon atoms. Specific examples thereof are ethynyl, 1-propynyl, 2-propynyl, 2-butynyl, pentynyl, hexynyl, etc.

The "cycloalkyl group" includes, for example, cycloalkyl groups of 3 to 10 carbon atoms. Specific examples thereof are cyclopropyl, cyclobutyl, cyclopentyl, cyclohexyl, cycloheptyl, adamantyl, norbornyl, etc. Preferable examples thereof are cycloalkyl groups of 3 to 6 carbon atoms. Specific examples of such groups are cyclopropyl, cyclobutyl, cyclopentyl, cyclohexyl, etc.

The "alkylene group" includes, for example, alkylene groups of 1 to 3 carbon atoms. Specific examples thereof are methylene, ethylene, trimethylene, etc.

The "alkenylene group" includes, for example, alkenylene groups of 2 to 4 carbon atoms. Specific examples thereof are vinylene, propenylene, butenylene, etc.

The "aryl group" includes, for example, aryl groups of 6 to 10 carbon atoms. Specific examples thereof are phenyl, 1-naphthyl, 2-naphthyl, etc.

The "aralkyl group" includes, for example, groups formed by bonding of an aryl group to an alkylene group. Specific examples thereof are benzyl, 2-phenylethyl, 1-naphthylmethyl, etc.

The "heteroaryl group" includes, for example, 5- to 10-membered monocyclic or polycyclic groups containing one or more (for example, 1 to 4) heteroatoms selected from nitrogen atom, sulfur atom and oxygen atom. Specific examples thereof are pyrrolyl, thienyl, benzothienyl, benzofuranyl, benzoxazolyl, benzothiazolyl, furyl, oxazolyl, thiazolyl, isoxazolyl, imidazolyl, pyrazolyl, pyridyl, pyrazyl, pyrimidyl, pyridazyl, quinolyl, isoquinolyl, triazolyl, triazinyl, tetrazolyl, indolyl, imidazo[1,2-a]pyridyl, dibenzofuranyl, benzimidazolyl, quinoxalyl, cinnolyl, quinazolyl, indazolyl, naphthyridyl, quinolinolyl, isoquinolinolyl, etc. Preferable examples thereof are 5- or 6-membered groups containing a heteroatom selected from nitrogen atom, sulfur atom and oxygen atom. Specific examples of such groups are pyridyl, thienyl, furyl, etc.

The heteroaryl portion of the "heteroarylalkyl group" includes the groups exemplified above as the heteroaryl group.

The "alkylcarbonyl group" includes, for example, alkylcarbonyl groups of 2 to 4 carbon atoms. Specific examples thereof are acetyl, propionyl, butyryl, etc.

The "cycloalkylcarbonyl group" includes cycloalkylcarbonyl groups of 4 to 11 carbon atoms, and the like. Specific examples thereof are cyclopropylcarbonyl, cyclobutylcarbonyl, cyclopentylcarbonyl, cyclohexylcarbonyl, adamantylcarbonyl, norbornylcarbonyl, etc. Preferable examples thereof are cycloalkylcarbonyl groups of 4 to 7 carbon atoms. Specific examples of such groups are cyclopropylcarbonyl, cyclobutylcarbonyl, cyclopentylcarbonyl, cyclohexylcarbonyl, etc.

The "aroyl group" includes, for example, aroyl groups of 7 to 11 carbon atoms. Specific examples thereof are benzoyl, 1-naphthoyl, 2-naphthoyl, etc.

The heteroaryl portion of the "heteroarylcarbonyl group" includes the groups exemplified above as the heteroaryl group.

The "alkoxycarbonyl group" includes, for example, alkoxycarbonyl groups of 2 to 5 carbon atoms. Specific examples thereof are methoxycarbonyl, ethoxycarbonyl, propoxycarbonyl, 2-propoxycarbonyl, tert-butoxycarbonyl, etc.

The "aryloxycarbonyl group" includes aryloxycarbonyl groups of 7 to 11 carbon atoms, and the like. Specific examples thereof are phenyloxycarbonyl, 2-naphthyloxycarbonyl, 1-naphthyloxycarbonyl, etc.

The "alkoxy group" includes, for example, alkoxy groups of 1 to 4 carbon atoms. Specific examples thereof are methoxy, ethoxy, propoxy, isopropoxy, butoxy, isobutoxy, sec-butoxy, tert-butoxy, etc.

The "cycloalkyloxy group" includes, for example, cycloalkyloxy groups of 3 to 10 carbon atoms. Specific examples thereof are cyclopropyloxy, cyclobutoxy, cyclopentyloxy, cyclohexyloxy, cycloheptyloxy, adamantyloxy, norbornyloxy, etc. Preferable examples thereof are cycloalkyloxy groups of 3 to 6 carbon atoms. Specific examples of such groups are cyclopropyloxy, cyclobutyloxy, cyclopentyloxy, cyclohexyloxy, etc.

The cycloalkyloxy portion of the "cycloalkyloxycarbonyl group" includes the groups exemplified above as the cycloalkyloxy group.

The "aryloxy group" includes, for example, aryloxy groups of 6 to 10 carbon atoms. Specific examples thereof are phenoxy, 1-naphthyloxy, 2-naphthyloxy, etc.

The aralkyl portion of the "aralkyloxy group" includes the groups exemplified above as the aralkyl group. Specific examples thereof are benzyloxy, 2-phenylethyloxy, etc.

The aralkyl portion of the "aralkyloxycarbonyl group" includes the groups exemplified above as the aralkyl group.

The heteroaryl portion of the "heteroaryloxy group" includes the groups exemplified above as the heteroaryl group.

The "alkylthio group" includes, for example, alkylthio groups of 1 to 6 carbon atoms. Specific examples thereof are methylthio, ethylthio, propylthio, isopropylthio, butylthio, sec-butylthio, tert-butylthio, pentylthio, hexylthio, etc. Preferable examples thereof are alkylthio groups of 1 to 4 carbon atoms. Specific examples of such groups are methylthio, ethylthio, propylthio, isopropylthio, butylthio, sec-butylthio, tert-butylthio, etc.

The "alkylsulfinyl group" includes, for example, alkylsulfinyl groups of 1 to 6 carbon atoms. Specific examples thereof are methylsulfinyl, ethylsulfinyl, propylsulfinyl, isopropylsulfinyl, butylsulfinyl, pentylsulfinyl, hexylsulfinyl, etc. Preferable examples thereof are alkylsulfinyl groups of 1 to 4 carbon atoms. Specific examples of such groups are methylsulfinyl, ethylsulfinyl, propylsulfinyl, isopropylsulfinyl, butylsulfinyl, etc.

The "alkylsulfonyl group" includes, for example, alkylsulfonyl groups of 1 to 6 carbon atoms. Specific examples thereof are methylsulfonyl, ethylsulfonyl, propylsulfonyl, isopropylsulfonyl, butylsulfonyl, pentylsulfonyl, hexylsulfonyl, etc. Preferable examples thereof are alkylsulfonyl groups of 1 to 4 carbon atoms. Specific examples of such groups are methylsulfonyl, ethylsulfonyl, propylsulfonyl, isopropylsulfonyl, butylsulfonyl, etc.

The "arylthio group" includes, for example, arylthio groups of 6 to 10 carbon atoms. Specific examples thereof are phenylthio, 1-naphthylthio, 2-naphthylthio, etc.

The "arylsulfinyl group" includes, for example, arylsulfinyl groups of 6 to 10 carbon atoms. Specific examples thereof are phenylsulfinyl, 1-naphthylsulfinyl, 2-naphthylsulfinyl, etc.

The "arylsulfonyl group" includes, for example, arylsulfonyl groups of 6 to 10 carbon atoms. Specific examples thereof are phenylsulfonyl, tosyl, 1-naphthylsulfonyl, 2-naphthylsulfonyl, etc.

The "nitrogen-containing saturated heterocyclic group" includes, for example, 5- or 6-membered saturated heterocyclic groups which have one or two nitrogen atoms and may further have an oxygen atom or a sulfur atom. Specific examples thereof are pyrrolidinyl, imidazolidinyl, piperidinyl, morpholinyl, thiomorpholinyl, dioxothiomorpholinyl, hexamethyleneiminyl, oxazolidinyl, thiazolidinyl, imidazolidinyl, oxoimidazolidinyl, dioxoimidazolidinyl, oxooxazolidinyl, dioxooxazolidinyl, dioxothiazolidinyl, tetrahydrofuranyl, tetrahydropyridinyl, etc.

The substituent(s) of the "optionally substituted alkyl group" includes, for example, (1) halogen atoms, (2) hydroxyl group, (3) cyano group, (4) carboxyl group, (5) optionally substituted cycloalkyl groups, (6) optionally substituted aryl groups, (7) optionally substituted heteroaryl groups, (8) optionally substituted aroyl groups, (9) optionally substituted heteroarylcarbonyl groups, (10) optionally substituted arylaminocarbonyl groups, (11) optionally substituted heteroarylaminocarbonyl groups, (12) optionally substituted aryloxy groups, (13) optionally substituted arylsulfonyl groups, (14) optionally substituted aralkylsulfonyl groups, (15) optionally substituted alkoxy groups, (16) optionally substituted cycloalkyloxy groups, (17) optionally substituted alkoxycarbonyl groups, (18) optionally substituted aryloxycarbonyl groups (19) optionally substituted amino groups (20) optionally substituted carbamoyl groups, (21) alkylsulfonyl groups, (22) optionally substituted alkylcarbonyl groups, (23) cycloalkyloxycarbonyl groups, (24) tetrahydrofuranyloxycarbonyl group, and (25) tetrahydrofuranyl group.

The above items (1) to (25) are explained below.

The substituents of the "optionally substituted cycloalkyl groups" of the above item (5) include, for example, alkyl groups, aralkyl groups, alkoxy groups, alkoxycarbonyl groups and fluorine atom.

The substituents of the "optionally substituted aryl groups" of the above item (6) include those exemplified hereinafter as the substituent(s) of the "optionally substituted aryl group".

The substituents of the "optionally substituted heteroaryl groups" of the above item (7) include, for example, (a) hydroxyl group,
(b) halogen atoms,
(c) alkyl groups,
(d) alkyl groups substituted by a halogen atom(s) or an alkoxy group (for example, fluoromethyl, difluoromethyl, trifluoromethyl, 2,2-difluoroethyl, 2,2,2-trifluoroethyl, perfluoroethyl, 2-fluoro-1-(fluoromethyl)ethyl, 1-(difluoromethyl)-2,2-difluoroethyl, methoxymethoxy, ethoxymethoxy, methoxyethoxy, ethoxyethoxy, methoxypropoxy and ethoxypropoxy),
(e) alkoxy groups,
(f) alkoxy groups substituted by a halogen atom(s) or an alkoxy group (for example, fluoromethoxy, difluoromethoxy, trifluoromethoxy, 2,2-difluoroethoxy, 2,2,2-trifluoroethoxy, perfluoroethoxy, 2-fluoro-1-(fluoromethyl)ethoxy, 1-(difluoromethyl)-2,2-difluoroethoxy, methoxymethoxy, ethoxymethoxy, methoxyethoxy, ethoxyethoxy, methoxypropoxy and ethoxypropoxy),
(g) cyano group,
(h) carboxyl group,
(i) alkoxycarbonyl groups,
(j) carbamoyl groups which may be substituted by an alkyl group(s) (for example, carbamoyl, methylcarbamoyl, dimethylcarbamoyl, ethylcarbamoyl and diethylcarbamoyl),
(k) aryl groups,
and (l) amino group.

The substituents of the "optionally substituted aroyl groups" of the above item (8) include those exemplified as the substituents of the "optionally substituted aryl groups" of the above item (6).

The substituents of the "optionally substituted heteroarylcarbonyl groups" of the above item (9) include those exemplified as the substituents of the "optionally substituted heteroaryl groups" of the above item (7).

The substituents of the "optionally substituted arylaminocarbonyl groups" of the above item (10) include those exemplified as the substituents of the "optionally substituted aryl groups" of the above item (6).

The substituents of the "optionally substituted heteroarylaminocarbonyl groups" of the above item (11) include those exemplified as the substituents of the "optionally substituted heteroaryl groups" of the above item (7).

The substituents of the "optionally substituted aryloxy groups" of the above item (12) and the "optionally substituted arylsulfonyl groups" of the above item (13) include those exemplified as the substituents of the "optionally substituted aryl groups" of the above item (6).

The aralkyl portion of the "optionally substituted aralkylsulfonyl group" of the above item (14) includes the groups exemplified above as the aralkyl group.

The substituents of the "optionally substituted aralkylsulfonyl groups" include those exemplified as the substituents of the "optionally substituted aryl groups" of the above item (6).

The substituents of the "optionally substituted alkoxy groups" of the above item (15) include, for example,
(a) hydroxyl group,
(b) carboxyl group,
(c) alkoxy groups,
(d) alkoxycarbonyl groups,
(e) amino groups which may be substituted by an alkyl group(s) (for example, amino, dimethylamino and diethylamino),
(f) carbamoyl groups substituted by an alkyl group(s),
(g) sulfamoyl groups substituted by an alkyl group(s),
(h) ureido groups substituted by an alkyl group(s),
(i) phenyl groups which may be substituted by a halogen atom or an alkoxy group (for example, phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-ethoxyphenyl, 3-ethoxyphenyl, 4-ethoxyphenyl, 2-isopropoxyphenyl and 3-isopropoxyphenyl),
(j) 5-oxo-2-tetrahydrofuranyl,
(k) 1,3-dihydro-3-oxo-1-isobenzofuranyl,
(l) tetrahydrofuranyl,
(m) nitrogen-containing saturated heterocyclic groups,
(n) alkoxy groups substituted by a halogen atom(s) or an alkoxy group (for example, fluoromethoxy, difluoromethoxy, trifluoromethoxy, 2,2-difluoroethoxy, 2,2,2-trifluoroethoxy, perfluoroethoxy, 2-fluoro-1-(fluoromethyl)ethoxy, 1-(difluoromethyl)-2,2-difluoroethoxy, methoxymethoxy, ethoxymethoxy, methoxyethoxy, ethoxyethoxy, methoxypropoxy and ethoxypropoxy)
(o) cycloalkyl groups,
(p) cycloalkyl groups substituted by a halogen atom or an alkoxy group (for example, 2-fluorocyclopropyl, 2-methoxycyclopropyl, 2-fluorocyclobutyl, 3-fluorocyclobutyl and 3-methoxycyclobutyl), and
(q) halogen atoms.

The substituents of the "optionally substituted cycloalkyloxy groups" of the above item (16) and the "optionally substituted alkoxycarbonyl groups" of the above item (17) include those exemplified as the substituents of the "optionally substituted alkoxy groups" of the above item (15).

The substituents of the "optionally substituted aryloxycarbonyl groups" of the above item (18) include those exemplified as the substituents of the "optionally substituted aryl groups" of the above item (6).

The substituents of the "optionally substituted amino groups" of the above item (19) include, for example,
(a) alkyl groups,
(b) alkylcarbonyl groups,
(c) aroyl groups,
(d) alkylsulfonyl groups,
(e) arylsulfonyl groups,
(f) optionally substituted aryl groups (their substituents include, for example, halogen atoms, alkyl groups and alkoxy groups),
(g) alkoxycarbonylmethyl groups (the carbon atom of the methyl portion may be substituted by one or two alkyl groups, and the two alkyl groups on the carbon atom of the methyl portion may bind to each other to form cyclopropyl, cyclobutyl or cyclopentyl together with the carbon atom of the methyl portion),
and (h) aralkyl groups.

As the optionally substituted amino groups,
(i) imides are also exemplified.

The substituents of the "optionally substituted carbamoyl groups" of the above item (20) include, for example, alkyl groups and cycloalkyl groups. The two substituents of the carbamoyl group may bind to each other to form an aliphatic heterocyclic ring which may contain carbon atoms, a nitrogen atom(s) and/or an oxygen atom(s), such as pyrrolidine (which may be substituted by a hydroxyl group), piperidine, morpholine, thiomorpholine, thiomorpholine oxide, thiomorpholine dioxide, piperazine (the nitrogen atom of this piperazine may be substituted by methyl or ethyl), or the like.

Specific examples of the "optionally substituted carbamoyl groups" are carbamoyl, methylcarbamoyl, dimethylcarbamoyl, ethylcarbamoyl, diethylcarbamoyl, ethylmethylcarbamoyl, methylpropylcarbamoyl, cyclopropylcarbamoyl, cyclopropylmethylcarbamoyl, pyrrolidinocarbonyl, piperidinocarbonyl, morpholinocarbonyl, etc.

The substituents of the "optionally substituted alkylcarbonyl groups" of the above item (22) include, for example,
(a) halogen atoms,
(b) alkoxy groups,
(c) cycloalkyl groups,
(d) alkoxycarbonyl groups,
(e) optionally substituted aryl groups (their substituents include, for example, halogen atoms, alkyl groups, alkoxy groups and alkoxycarbonyl groups),
and (f) hydroxyl group.

The substituent(s) of each of the "optionally substituted alkylthio group", "optionally substituted alkylsulfinyl group" and "optionally substituted alkylsulfonyl group" includes those exemplified as the substituent(s) of the above-mentioned "optionally substituted alkyl group".

The substituent(s) of each of the "optionally substituted alkenyl group" and the "optionally substituted alkynyl group" includes, for example,
(1) hydroxyl group,
(2) halogen atoms,
(3) alkyl groups,
(4) alkyl groups substituted by a halogen atom(s) or an alkoxy group (for example, fluoromethyl, difluoromethyl, trifluoromethyl, 2,2-difluoroethyl, 2,2,2-trifluoroethyl, perfluoroethyl, 2-fluoro-1-(fluoromethyl)ethyl, 1-(difluoromethyl)-2,2-difluoroethyl, methoxymethyl, ethoxymethyl, methoxyethyl, ethoxyethyl, methoxypropyl and ethoxypropyl),
(5) alkoxy groups,
(6) alkoxy groups substituted by a halogen atom(s) or an alkoxy group (for example, fluoromethoxy, difluoromethoxy, trifluoromethoxy, 2,2-difluoroethoxy, 2,2,2-trifluoroethoxy, perfluoroethoxy, 2-fluoro-1-(fluoromethyl)ethoxy, 1-(difluoromethyl)-2,2-difluoroethoxy, methoxymethoxy, ethoxymethoxy, methoxyethoxy, ethoxyethoxy, methoxypropoxy and ethoxypropoxy),
(7) phenyl groups or aroyl groups, which may be substituted by the following (aa), (bb) or (cc):

(aa) an alkoxy group(s) which may be substituted by a halogen atom(s) or an alkoxy group (for example, methoxy, ethoxy, propoxy, isopropoxy, butoxy, isobutoxy, sec-butoxy, tert-butoxy, fluoromethoxy, difluoromethoxy, trifluoromethoxy, 2,2-difluoroethoxy, 2,2,2-trifluoroethoxy, perfluoroethoxy, 2-fluoro-1-(fluoromethyl)ethoxy, 1-(difluoromethyl)-2,2-difluoroethoxy, methoxymethoxy, ethoxymethoxy, methoxyethoxy, ethoxyethoxy, methoxypropoxy and ethoxypropoxy), (bb) an alkyl group(s) which may be substituted by a halogen atom(s) (for example, methyl, ethyl, propyl, isopropyl, butyl, fluoromethyl, difluoromethyl, trifluoromethyl, 2,2-difluoroethyl, 2,2,2-trifluoroethyl, perfluoroethyl, 2-fluoro-1-(fluoromethyl)ethyl and 1-(difluoromethyl)-2,2-difluoroethyl), (cc) a halogen atom(s),
(8) cyano group,
(9) carboxyl group,
(10) alkoxycarbonyl groups,
(11) carbamoyl groups which may be substituted by an alkyl group(s) (for example, carbamoyl, methylcarbamoyl, dimethylcarbamoyl, ethylcarbamoyl and diethylcarbamoyl),
(12) alkylsulfonyl groups,
and (13) phenyloxy group.

The substituent(s) of the "optionally substituted vinyl group" includes, for example, halogen atoms and alkyl groups.

Specific examples of the substituted vinyl groups are 1-propylene, 2-methyl-1-propylene, 2-chloro-1-propylene, etc.

The substituent(s) of the "optionally substituted cycloalkyl group" includes those exemplified as the substituents of (5) the "optionally substituted cycloalkyl groups" as the substituent(s) of the above-mentioned "optionally substituted alkyl group".

The substituent(s) of the "optionally substituted aryl group" includes, for example,
(1) hydroxyl group,
(2) halogen atoms,
(3) alkyl groups,
(4) alkyl groups substituted by a halogen atom(s), an alkoxy group or a cycloalkyl group (for example, fluoromethyl, difluoromethyl, trifluoromethyl, 2,2-difluoroethyl, 2,2,2-trifluoroethyl, perfluoroethyl, 2-fluoro-1-(fluoromethyl)ethyl, 1-(difluoromethyl)-2,2-difluoroethyl, methoxymethyl, ethoxymethyl, methoxyethyl, ethoxyethyl, methoxypropyl and ethoxypropyl),
(5) phenyl groups which may be substituted by the following (aa), (bb) or (cc):
(aa) an alkoxy group(s) which may be substituted by a halogen atom(s) or an alkoxy group (for example, methoxy, ethoxy, propoxy, isopropoxy, butoxy, isobutoxy, sec-butoxy, tert-butoxy, fluoromethoxy, difluoromethoxy, trifluoromethoxy, 2,2-difluoroethoxy, 2,2,2-trifluoroethoxy, perfluoroethoxy, 2-fluoro-1-(fluoromethyl)ethoxy, 1-(difluoromethyl)-2,2-difluoroethoxy, methoxymethoxy, ethoxymethoxy, methoxyethoxy, ethoxyethoxy, methoxypropoxy and ethoxypropoxy),
(bb) an alkyl group(s) which may be substituted by a halogen atom(s) (for example, methyl, ethyl, propyl, isopropyl, butyl, fluoromethyl, difluoromethyl, trifluoromethyl, 2,2-difluoroethyl, 2,2,2-trifluoroethyl, perfluoroethyl, 2-fluoro-1-(fluoromethyl)ethyl and 1-(difluoromethyl)-2,2-difluoroethyl),
(cc) a halogen atom(s),
(6) cyano group,
(7) carboxyl group,
(8) alkoxycarbonyl groups which may be substituted by a halogen atom(s) (for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, fluoromethoxycarbonyl, difluoromethoxycarbonyl, 2,2-difluoroethoxycarbonyl, 2,2,2-trifluoroethoxycarbonyl, methoxycarbonyl and ethoxycarbonyl),
(9) carbamoyl groups which may be substituted by an alkyl group(s) (for example, carbamoyl, methylcarbamoyl, dimethylcarbamoyl, ethylcarbamoyl and diethylcarbamoyl),
(10) alkylsulfonyl groups,
(11) $C_{1-3}$ alkylenedioxy groups,
(12) formyl group,
(13) optionally substituted phenyloxy groups (their substituents include, for example, halogen atoms, alkyl groups and alkoxy groups),
(14) nitrogen-containing saturated heterocyclic groups (for example, pyrrolidinyl, piperidinyl, morpholinyl and piperazinyl (the nitrogen atom of the piperazine may be substituted, for example, by methyl, ethyl or propyl)),
(15) cycloalkyloxy groups which may be substituted by a hydroxyl group, an oxo group, a carboxyl group, a carboxymethyl group, an alkoxycarbonyl group, an alkoxycarbonylalkyl group (e.g. methoxycarbonylmethyl, ethoxycarbonylmethyl or isopropoxycarbonylmethyl), an alkyl group, a fluoroalkyl group (e.g. fluoromethyl, difluoromethyl, trifluoromethyl, 2,2-difluoroethyl, 2,2,2-trifluoroethyl or perfluoroethyl), an alkoxyalkyl group (e.g. methoxymethyl, ethoxymethyl or isopropoxymethyl), a cycloalkyloxyalkyl group (e.g. cyclopropyloxymethyl, cyclopropyloxyethyl or cyclobutyloxy), an alkoxy group, a cycloalkyloxy group or a halogen atom(s) (for example, 3-carboxycyclobutyloxy, 3-methoxycarbonylcyclobutyloxy, 3-ethoxycarbonylbutyloxy, 2-methylcyclopropyloxy, 2-fluorocyclopropyloxy, 3-methoxycyclobutyloxy, 3-fluorocyclobutyloxy, 3,3-difluorocyclobutyloxy and 3-(2-fluoroethyl)cyclobutyloxy),
(16) alkoxy groups which may be substituted by a hydroxyl group, an oxo group, a carboxyl group, an alkoxycarbonyl group, a cycloalkyl group, an alkoxy group, a cycloalkyloxy group, an optionally substituted oxygen-containing heterocyclic group (e.g. a 5- or 6-membered saturated heterocyclic group having an oxygen atom(s), specific examples of which are tetrahydrofuranyl, tetrahydropyranyl, etc.; the substituent(s) includes, for example, halogen atoms, oxo group and alkoxy groups), or a halogen atom(s) (for example, methoxy, ethoxy, propoxy, isopropoxy, butoxy, isobutoxy, sec-butoxy, tert-butoxy, 2-hydroxyethoxy, carboxymethoxy, methoxycarbonylmethoxy, ethoxycarbonylmethoxy, tert-butoxycarbonylmethoxy, cyclopropylmethoxy, cyclobutylmethoxy, methoxymethoxy, ethoxymethoxy, methoxyethoxy, ethoxyethoxy, isopropoxymethoxy, cyclopropyloxymethoxy, cyclobutoxymethoxy, fluoromethoxy, difluoromethoxy, trifluoromethoxy, 2,2-difluoroethoxy, 2,2,2-trifluoroethoxy, perfluoroethoxy, 2-fluoro-1-(fluoromethyl)ethoxy and 1-(difluoromethyl)-2,2-difluoroethoxy),
(17) difluoromethylenedioxy,
(18) alkenyl groups which may be substituted by a halogen atom (for example, vinyl, propenyl, methylpropenyl, butenyl and methylbutenyl),
(19) amino groups which may be substituted by an alkyl group(s) (for example, amino, methylamino, ethylamino, propylamino, dimethylamino, methylethylamino and diethylamino),

(20) optionally substituted alkylcarbonyl groups (their substituents include, for example, halogen atoms, alkoxy groups and cycloalkyl groups),
(21) alkylcarbonyloxy groups (for example, methylcarbonyloxy, ethylcarbonyloxy and isopropylcarbonyloxy),
(22) cycloalkyl groups which may be substituted by a fluorine atom (for example, cyclopropyl, cyclobutyl, cyclopentyl, 2-fluorocyclopropyl, 2-fluorocyclobutyl, 3-fluorocyclobutylcyclobutyl, adamantyl and norbornyl),
(23) cycloalkylcarbonyl groups which may be substituted by a fluorine atom (for example, cyclopropylcarbonyl, 2-fluorocyclopropylcarbonyl, cyclobutylcarbonyl and cyclopentylcarbonyl),
(24) alkylthio groups,
(25) alkylsulfinyl groups,
(26) optionally substituted heteroaryl groups (their substituents include, for example, halogen atoms, alkyl groups, alkoxy groups, haloalkyl groups and haloalkoxy groups),
(27) groups represented by the following formulas (T1) to (T16):

[Formula 12]

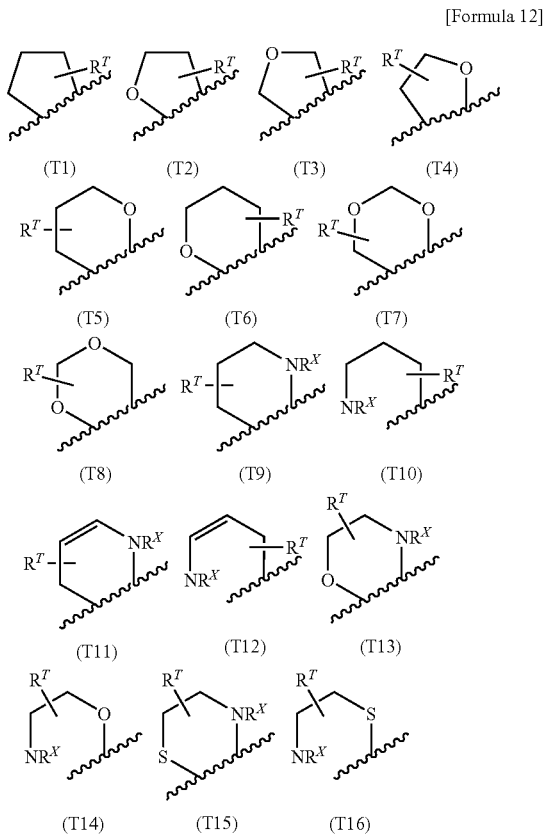

wherein $R^T$ is absent or one or more $R^T$s are present and are independently a halogen atom, a hydroxyl group, an oxo group, a carboxyl group, an optionally substituted alkyl group (its substituent(s) includes, for example, halogen atoms and alkoxy groups), an optionally substituted alkoxycarbonyl group (its substituent(s) includes, for example, halogen atoms and alkoxy groups), an optionally substituted alkoxy group (its substituent(s) includes, for example, halogen atoms and alkoxy groups), an optionally substituted carbamoyl group (its substituent(s) includes, for example, alkyl groups), or a saturated heterocyclic group oxycarbonyl group (the saturated heterocyclic group includes, for example, 5- or 6-membered saturated heterocyclic groups having an oxygen atom(s), a nitrogen atom(s) and/or a sulfur atom(s), each in a number of 1 or 2, specific examples of which are tetrahydrofuranyl, tetrahydropyranyl, dihydrofuranyl, tetrahydrothiopyranyl, tetrahydrodioxothiopyranyl, pyrrolidinyl, piperidinyl, piperazinyl, imidazolidinyl, oxazolidinyl and thiazolidinyl), or two $R^T$s, when taken together, may represent methylene, ethylene, trimethylene, tetramethylenel or butenylene and may bind to one or more carbon atoms constituting the ring, to form a new ring; and $R^X$ is a hydrogen atom or an alkyl group,
(28) aroyl groups, and
(29) groups represented by the formula: -Rd-CO(O)—Re wherein Rd and Re are as defined above.

The substituent(s) of each of the "optionally substituted heteroaryl group", "optionally substituted aralkyl group", "optionally substituted heteroarylalkyl group", "optionally substituted aroyl group", "optionally substituted heteroarylcarbonyl group", "optionally substituted aryloxycarbonyl group", "optionally substituted aryloxy group", "optionally substituted aralkyloxy group", "optionally substituted aralkyloxycarbonyl group", "optionally substituted heteroaryloxy group", "optionally substituted arylthio group", "optionally substituted arylsulfinyl group" and "optionally substituted arylsulfonyl group" includes those exemplified as the substituent(s) of the above-mentioned "optionally substituted aryl group".

The substituent(s) of the "optionally substituted alkylcarbonyl group" includes those exemplified as the substituents of (22) the "optionally substituted alkylcarbonyl groups" as the substituent(s) of the above-mentioned "optionally substituted alkyl group".

The substituent(s) of the "optionally substituted cycloalkylcarbonyl group" includes, for example, halogen atoms and alkoxy groups.

The substituent(s) of each of the "optionally substituted alkoxy group" and the "optionally substituted alkoxycarbonyl group" includes those exemplified as the substituents of (15) the "optionally substituted alkoxy groups" as the substituent(s) of the above-mentioned "optionally substituted alkyl group".

The substituent(s) of each of the "optionally substituted cycloalkyloxy group" and the "optionally substituted cycloalkyloxycarbonyl group" includes those exemplified as the substituents of (16) the "optionally substituted cycloalkyloxy groups" as the substituent(s) of the above-mentioned "optionally substituted alkyl group".

The substituent(s) of the "optionally substituted amino group" includes those exemplified as the substituents of (19) the "optionally substituted amino groups" as the substituent(s) of the above-mentioned "optionally substituted alkyl group".

The substituent(s) of the "optionally substituted carbamoyl group" includes, for example,
(1) optionally substituted alkyl groups (their substituents include, for example, hydroxyl group, halogen atoms, alkoxy groups optionally substituted by a halogen atom(s), cycloalkoxy groups optionally substituted by a halogen atom(s), and tetrahydrofuranyl),
(2) cycloalkyl groups which may be substituted by a halogen atom(s),
(3) aryl groups which may be substituted by the following (aa), (bb), (cc) or (dd):
    (aa) a halogen atom(s)
    (bb) an alkoxy group(s) which may be substituted by a halogen atom(s) (for example, methoxy, ethoxy, propoxy, isopropoxy, butoxy, isobutoxy, sec-butoxy, tert-butoxy, fluoromethoxy, difluoromethoxy, trifluoromethoxy, 2,2-difluoroethoxy, 2,2,2-trifluoroethoxy, perfluoroethoxy, 2-fluoro-1-(fluoromethyl)ethoxy and 1-(difluoromethyl)-2,2-difluoroethoxy), (cc) an alkyl group(s) which may be substituted by a halogen atom(s) (for example, methyl, ethyl, propyl, isopropyl, butyl, methyl, ethyl, propyl, isopropyl, butyl, fluoromethyl, difluoromethyl, trifluoromethyl, 2,2-difluoroethyl, 2,2,2-trifluoroethyl, perfluoroethyl, 2-fluoro-1-(fluoromethyl)ethyl and 1-(difluoromethyl)-2,2-difluoroethyl), (dd) a $C_{1-3}$ alkylenedioxy group(s),
(4) alkylsulfonyl groups,
(5) cycloalkylsulfonyl groups,
(6) optionally substituted arylsulfonyl groups (their substituents include, for example, halogen atoms, alkyl groups, haloalkyl groups, alkoxy groups and haloalkoxy groups),
(7) alkylcarbonyl groups,
(8) alkoxycarbonyl groups,
(9) optionally substituted aroyl groups (their substituents include, for example, halogen atoms, alkyl groups, haloalkyl groups, alkoxy groups, haloalkoxy groups, alkoxycarbonyl groups and $C_{1-3}$ alkylenedioxy groups),
(10) cycloalkylalkyl groups,
(11) isoxazolyl group,
and (12) optionally substituted adamantyl groups (their substituents include, for example, hydroxyl group).

Specific examples of the "optionally substituted carbamoyl group" are carbamoyl, methylcarbamoyl, dimethylcarbamoyl, ethylcarbamoyl, diethylcarbamoyl, ethylmethylcarbamoyl, phenylcarbamoyl, phenylmethylcarbamoyl, cyclopropylcarbamoyl, cyclobutylcarbamoyl, cyclopropylmethylcarbamoyl, cyclohexylmethylcarbamoyl, 2,3-dihydroxypropylcarbamoyl, tetrahydrofuranylalkylcarbamoyl, methoxyethylcarbamoyl, trifluoroethylcarbamoyl, adamantylcarbamoyl, hydroxyadamantylcarbamoyl, etc.

The two substituents of the carbamoyl group may bind to each other to form a 4- to 6-membered aliphatic heterocyclic ring which may contain carbon, nitrogen, oxygen or sulfur, such as pyrrolidine, piperidine, morpholine, thiomorpholine, thiomorpholine oxide, thiomorpholine dioxide, piperazine (the nitrogen atom of this piperazine may be substituted by methyl, ethyl or propyl), or the like, and the carbamoyl group may be further substituted by a hydroxyl group. Specific examples of such a substituted carbamoyl group are pyrrolidinocarbamoyl, piperidinocarbamoyl, morpholinocarbamoyl, 4-hydroxypiperidinocarbamoyl, etc.

The substituent(s) of the "optionally substituted nitrogen-containing saturated heterocyclic group" includes, for example,
(1) halogen atoms,
(2) alkyl groups,
(3) alkyl groups substituted by a halogen atom(s) or an alkoxy group (for example, fluoromethyl, difluoromethyl, trifluoromethyl, 2-fluoroethyl, 2,2-difluoroethyl, perfluoroethyl and methoxyethyl),
(4) alkoxy groups,
(5) alkoxy groups substituted by a halogen atom(s) or an alkoxy group (for example, fluoromethoxy, difluoromethoxy, trifluoromethoxy, methoxymethoxy, ethoxymethoxy, methoxyethoxy, ethoxyethoxy, methoxypropoxy and ethoxypropoxy),
(6) cyano group,
and (7) oxo group.

When two $R^6$s, $R^7$s, $R^8$s or $R^9$s are present, they may be present on one and the same carbon atom or may be present on different carbon atoms, respectively.

The phrase "two $R^6$s, $R^7$s, $R^8$s or $R^9$s, when taken together, represent methylene or ethylene and bind to one or more carbon atoms constituting the ring, to form a new ring" means that they form a spiro ring or a bicyclo ring through one and the same carbon atom or different carbon atoms, respectively.

The phrase "two $R^7$s, when taken together, represent methylene, ethylene, trimethylene, tetramethylene or butenylene and bind to one or two carbon atoms constituting the ring, to form a new ring" means that they form a spiro ring or a bicyclo ring through one and the same carbon atom or different carbon atoms, respectively.

The "haloalkoxy group" includes, for example, alkoxy groups of 1 to 4 carbon atoms substituted by a halogen atom(s). Specific examples thereof are fluoromethoxy, difluoromethoxy, trifluoromethoxy, etc.

The "haloalkyl group" includes, for example, alkyl groups of 1 to 4 carbon atoms substituted by a halogen atom(s). Specific examples thereof are fluoromethyl, difluoromethyl, trifluoromethyl, 2-fluoroethyl, perfluoroethyl, etc.

The "$C_{1-3}$ alkylenedioxy group" includes, for example, methylenedioxy, ethylenedioxy and trimethylenedioxy.

The "substituted alkyl group" for $R^{4b}$ includes, for example, alkyl groups of 1 to 3 carbon atoms substituted by a cycloalkyl group of 3 to 7 carbon atoms (e.g. cyclopentyl, cyclohexyl or cycloheptyl) or an optionally substituted aryl group (e.g. phenyl group). Specific examples thereof are benzyl, p-chlorobenzyl, p-methoxybenzyl, p-fluorobenzyl, cyclopentylmethyl, cyclohexymethyl, etc.

The "substituted alkenyl group" for $R^{4b}$ includes, for example, alkenyl groups of 2 or 3 carbon atoms substituted by a cycloalkyl group of 5 to 7 carbon atoms (e.g. cyclopentyl, cyclohexyl or cycloheptyl) or an aryl group (e.g. phenyl group). Examples thereof are vinyl, propenyl, allyl, isopropenyl, etc., which are substituted by phenyl, cyclopropyl, cyclobutyl, cyclopentyl, cyclohexyl or the like.

The "alkenyloxy group" for $R^{4b}$ includes, for example, linear or branched alkenyloxy groups of 2 to 8 carbon atoms. Specific examples thereof are allyloxy, isobutenyloxy, etc.

The "substituted alkoxy group" for $R^{4b}$ includes, for example, alkoxy groups of 1 to 3 carbon atoms substituted by a cycloalkyl group of 3 to 7 carbon atoms (e.g. cyclopropyl, cyclopentyl, cyclohexyl or cycloheptyl) or an optionally substituted aryl group (e.g. phenyl group). Specific examples thereof are benzyloxy, phenethyloxy, cyclopropylmethyloxy, cyclopropylethyloxy, cyclopentylmethyloxy, etc.

The "substituted alkenyloxy group" for $R^{4b}$ includes, for example, alkenyloxy groups of 2 or 3 carbon atoms substituted by a cycloalkyl group of 3 to 7 carbon atoms (e.g. cyclopropyl, cyclopentyl, cyclohexyl or cycloheptyl) or an optionally substituted aryl group (e.g. phenyl group). Examples thereof are vinyloxy, propenyloxy, allyloxy, isopropenyloxy, etc., which are substituted by phenyl, cyclopropyl, cyclobutyl, cyclopentyl, cyclohexyl or the like.

Specific examples of the "optionally substituted aryloxy group" for $R^{4b}$ are phenoxy, p-nitrophenoxy, p-methoxyphenoxy, p-fluorophenoxy, naphthoxy, etc.

Specific examples of each of the "substituted alkoxycarbonyl group" and the group represented by the formula: -Rd-CO(O)—Re wherein Rd and Re are as defined above, are pivaloyloxymethoxycarbonyl, 1-(pivaloyloxy)ethoxycarbonyl, 1-(cyclohexyloxycarbonyloxy)ethoxycarbonyl, 5-methyl-2-oxo-1,3-dioxolen-4-ylmethoxycarbonyl, 5-(tert-butyl)-2-oxo-1,3-dioxolen-4-ylmethoxycarbonyl, acetoxymethyloxycarbonyl, propyloxymethoxycarbonyl, n-butoxymethoxycarbonyl, isobutoxymethoxycarbonyl, 1-(ethoxycarbonyloxy)ethoxycarbonyl, 1-(tert-butoxycarbonyloxy)ethoxycarbonyl, 1-(acetyloxy)ethoxycarbonyl, 1-(isobutoxy)ethoxycarbonyl, cyclohexylcarbonyloxymethoxycarbonyl, 1-(cyclohexylcarbonyloxy)ethoxycarbonyl, cyclopentylcarbonyloxymethoxycarbonyl, 1-(cyclopentylcarbonyloxy)ethoxycarbonyl, etc.

The substituent(s) of each of the "optionally substituted alkyl group" and the "optionally substituted alkoxy group" for Rc includes, for example, halogen atoms, alkoxy groups and cycloalkyl groups.

The substituent(s) of the "optionally substituted heteroarylamino group" for Rc includes those exemplified as the substituents of (7) the "optionally substituted heteroaryl groups" as the substituent(s) of the above-mentioned "optionally substituted alkyl group".

As the "alkylene group" for Rd, there are exemplified the above-exemplified ones, preferably methylene.

As the "alkenylene group" for Rd, there are exemplified the above-exemplified ones, preferably vinylene.

As the "prodrug", there are exemplified those which can easily be hydrolyzed in a living body to regenerate the compound (I) of the present invention. Specific examples thereof are compounds obtained by converting the amino group of the compound represented by the formula (I) to —NHQ$^X$. Here, the following are exemplified as Q$^X$:

[Formula 13]

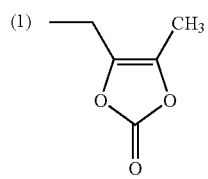

(2) —COR$^{33}$
(3) —COO—CR$^{34}$(R$^{35}$)—OCOR$^{36}$
(4) —COOR$^{37}$ wherein R$^{33}$ is a hydrogen atom, an alkyl group or an optionally substituted aryl group; R$^{34}$ and R$^{35}$ are independently a hydrogen atom or an alkyl group; R$^{36}$ is a hydrogen atom, an alkyl group, an aryl group or a benzyl group; and R$^{37}$ is an alkyl group or a benzyl group.

Preferable examples of Q$^X$ are the group of (1) and the groups of (3). Preferable examples of the groups of (3) are groups in which R$^{34}$ is a hydrogen atom, R$^{35}$ is a hydrogen atom, methyl or ethyl and R$^{36}$ is methyl or ethyl. These compounds may be produced according to conventional processes (for example, J. Med. Chem. 35, 4727 (1992) and WO 01/40180). In addition, the prodrug may be one which is converted to the original compound under physiological conditions, such as those described in "Development of Medicines Vol. 7, Molecular Design", pp. 163-198, Hirokawa Shoten, 1990.

As the "pharmaceutically acceptable salt", there are exemplified inorganic acid salts such as hydrochloride, hydrobromide, sulfate, phosphate, nitrate, etc., and organic acid salts such as acetic acid salt, propionic acid salt, oxalic acid salt, succinic acid salt, lactic acid salt, malic acid salt, tartaric acid salt, citric acid salt, maleic acid salt, fumaric acid salt, methanesulfonic acid salt, benzenesulfonic acid salt, p-toluenesulfonic acid salt, ascorbic acid salt, etc.

In addition, the present invention includes compounds represented by the formula (I), prodrugs thereof and pharmaceutically acceptable salts of the compounds or prodrugs. The present invention also includes their hydrates or solvates (e.g. ethanol solvates). Furthermore, the present invention includes all tautomers, all existing stereoisomers and all crystal forms of the compound (I) of the present invention.

Preferable examples of the compound of the present invention are the following compounds. In the compounds listed in the following tables, the following abbreviations are used in some cases for the simplification of description.

2-Py: 2-pyridyl group, 3-Py: 3-pyridyl group, 4-Py: 4-pyridyl group, Ph: phenyl group, Et: ethyl group, Me: methyl group, n-Pr: n-propyl group, i-Pr: isopropyl group, n-Bu: n-butyl group, t-Bu: tert-butyl group, Bn: benzyl group, Ac: acetyl group, cycpro: cyclopropyl group, cycbu: cyclobutyl group, cychex: cyclohexyl group, etoet: ethoxyethyl group, meoet: methoxyethyl group, f2etoet: 2,2-difluoroethoxyethyl group, f2meoet: difluoromethoxyethyl group, cycprooet: cyclopropyloxyethyl group, isoproet: isopropoxyethyl group, ms: methanesulfonyl group, etomet: ethoxymethyl group, meomet: methoxymethyl group, f2meomet: difluoromethoxymethyl group, and f2etomet: 2,2-difluoroethoxymethyl group.

The following abbreviations for partial structures are used in some cases.

[Formula 14]

Q1:

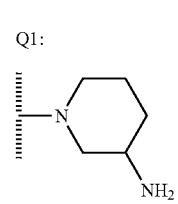

Q2:

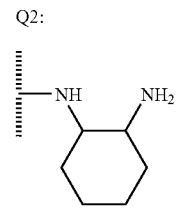

Q3:

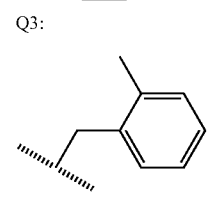

Q4:

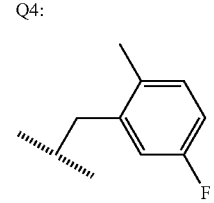

Q5:

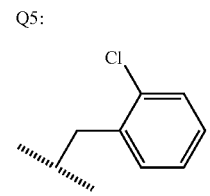

-continued
Q6:
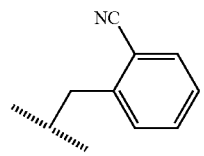
Q7:
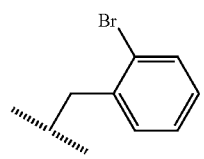
Q8:
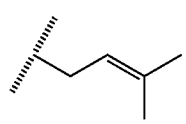
Q9:
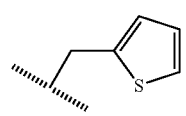
Q10:
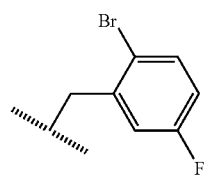
Q11:
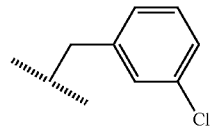
Q12:
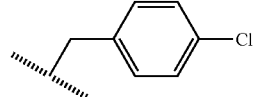
Q13:
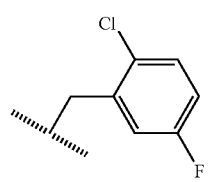
Q14:
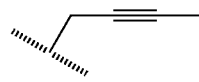
-continued
Q15:
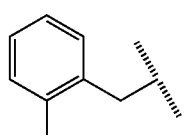
Q16:
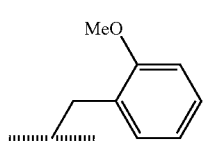
Q17:
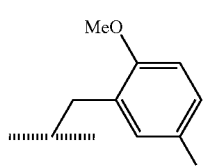
Q18:
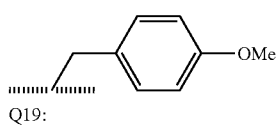
Q19:
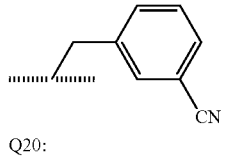
Q20:
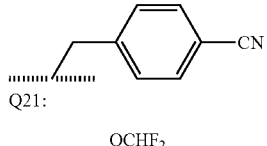
Q21:
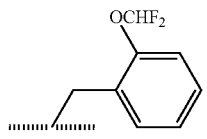
Q22:
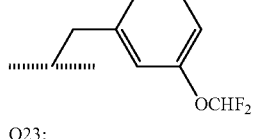
Q23:
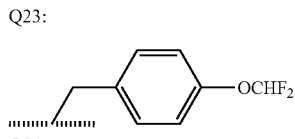
Q24:
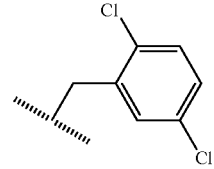

Q25: 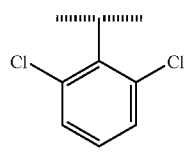
Q26: 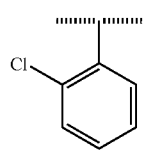
Q27: 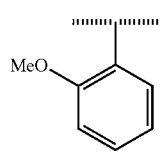
Q28: 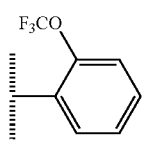
Q29: 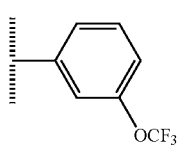
Q30: 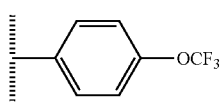
Q31: 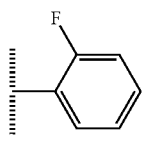
Q32: 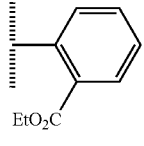
Q33: 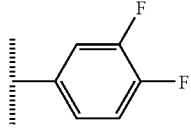
Q34: 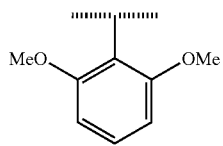
Q35: 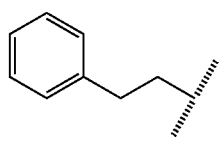
Q36: 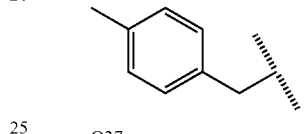
Q37: 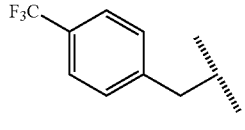
Q38: 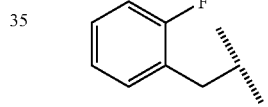
Q39: 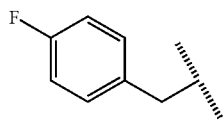
Q40: 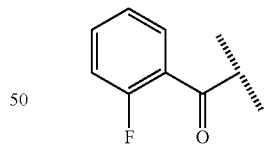
Q41: 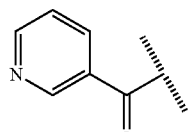
Q42: 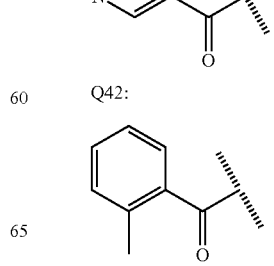

-continued
Q43:
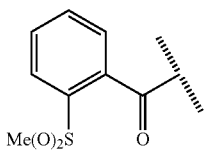
Q44:
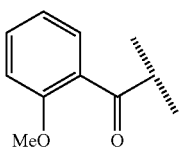
Q45:
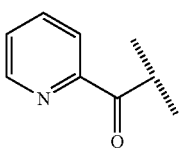
Q46:
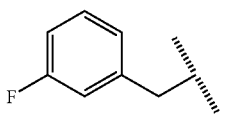
Q47:
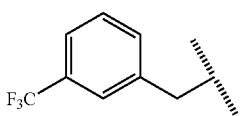
Q48:
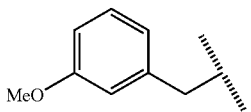
Q49:
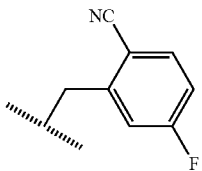
Q50:
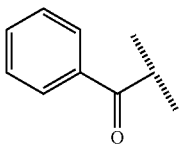
Q51:
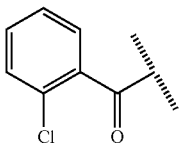
-continued
Q52:
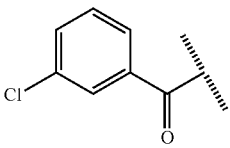
Q53:
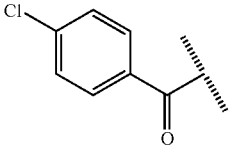
Q54:
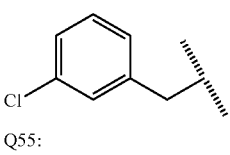
Q55:
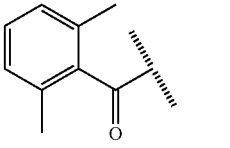
Q56:
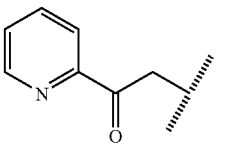
Q57:
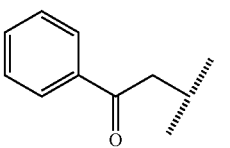
Q58:
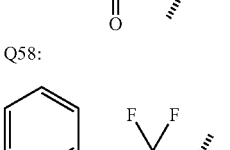
Q59:
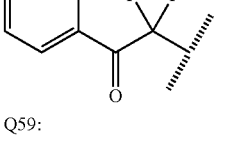
Q60:
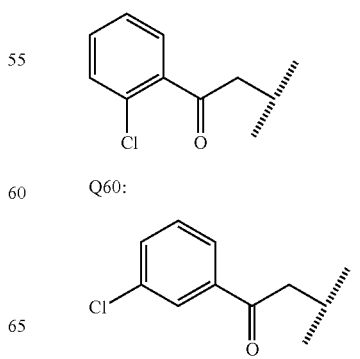
[Formula 15]

-continued

Q61:, Q62:, Q63:, Q64:, Q65:, Q66:, Q67:, Q68:, Q69:, Q70:, Q71:, Q72:, Q73:, Q74:, Q75:, Q76:, Q77:

-continued
Q78:
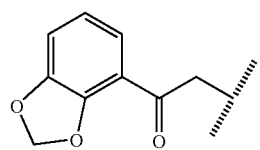
Q79:
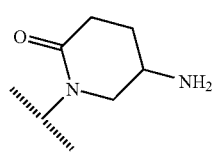
Q80:
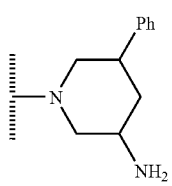
Q81:
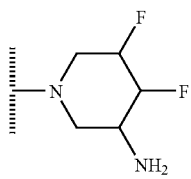
Q82:
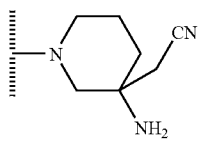
Q83:
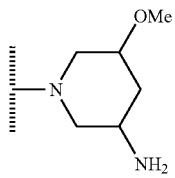
Q84:
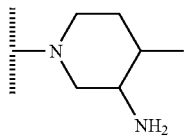
Q85:
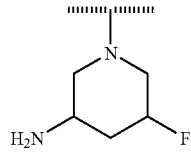
-continued
Q86:
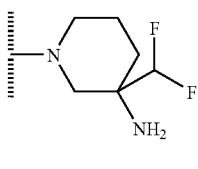
Q87:
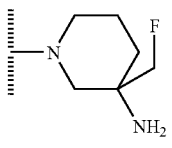
Q88:
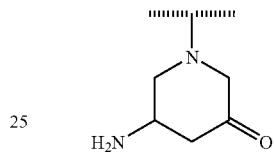
Q89:
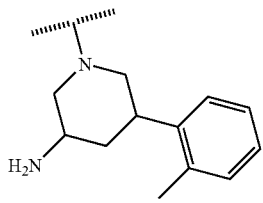
Q90:
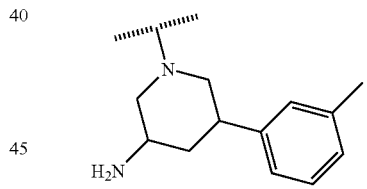
Q91:
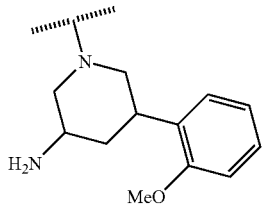
Q92:
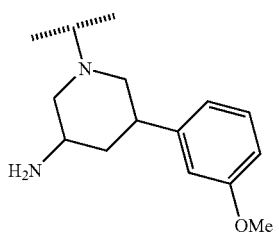

-continued
Q93:
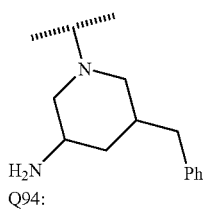
Q94:
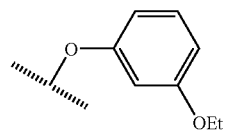
Q95:
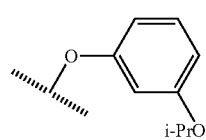
Q96:
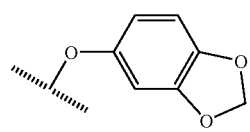
Q97:
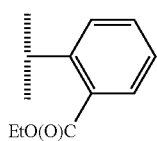
Q98:
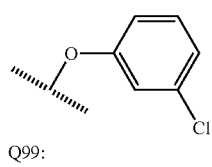
Q99:
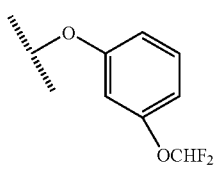
Q100:
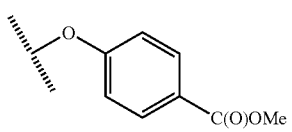
Q101:
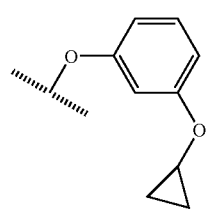
-continued
Q102:
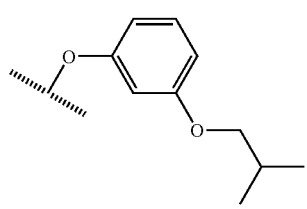
Q103:
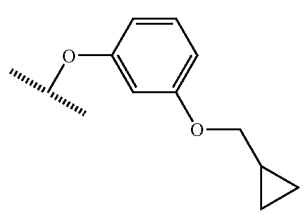
Q104:
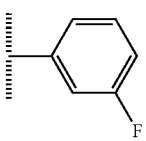
Q105:
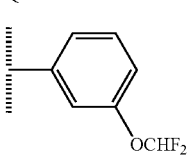
Q106:
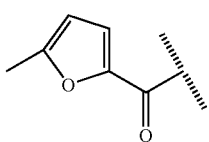
Q107:
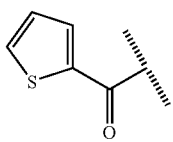
Q108:
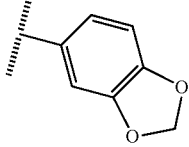
Q109:
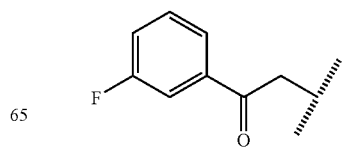

-continued
Q110:
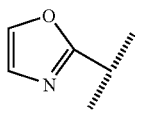
Q111:
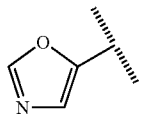
Q112:
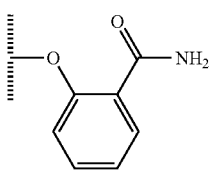
Q113:
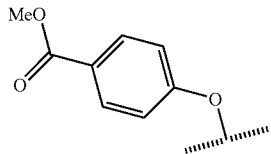
Q114:
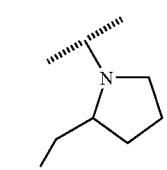
Q115:
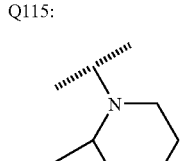
Q116:
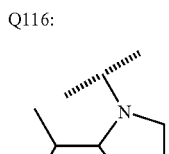
Q117:
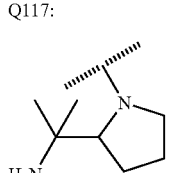
Q118:
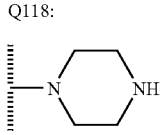
-continued
Q119:
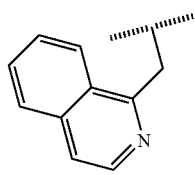
Q120:
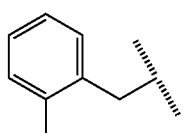
Q121:
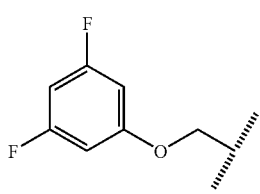
[Formula 16]
Q122:
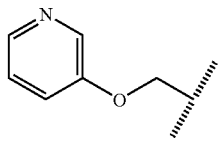
Q123:
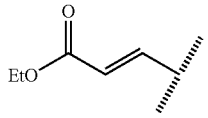
Q124:
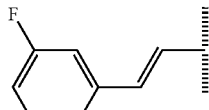
Q125:
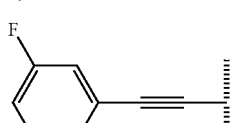
Q126:
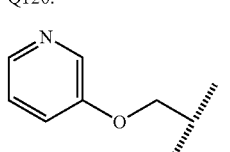
Q127:
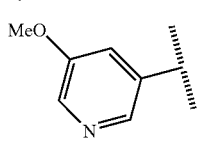

-continued
Q128:
MeOC(O)
Q129:
EtOC(O)
Q130:
i-PrOC(O)
Q131:
t-BuOC(O)
Q132:
H₂NC(O)
Q133:
Me₂NC(O)
Q134:
Et₂NC(O)
Q135:
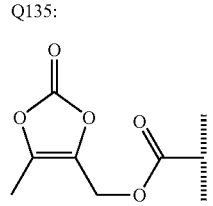
Q136:
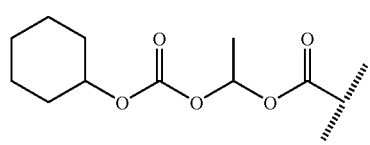
Q137:
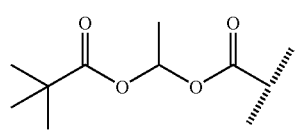
Q138:
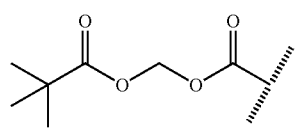
Q139:
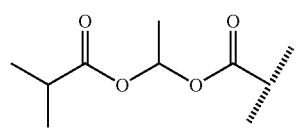
Q140:
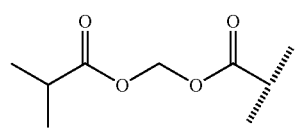
Q141:
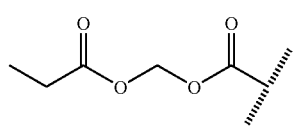
-continued
Q142:
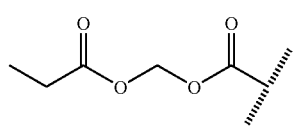
Q143:
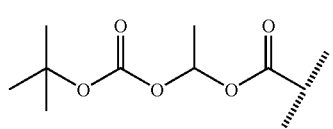
Q144:
CH₂C(O)OH
Q145:
CH₂C(O)OEt
Q146:
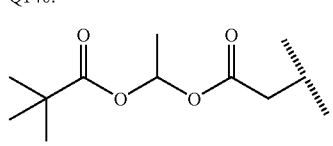
Q147:
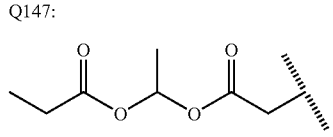
Q148:
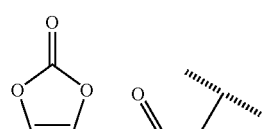
Q149:
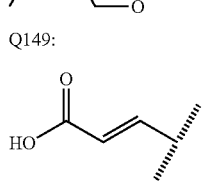
Q150:
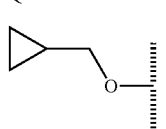
Q151:
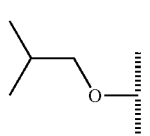
Q152:
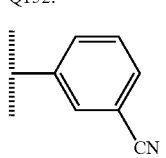

-continued
Q153:
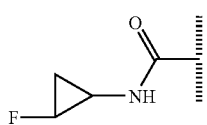
Q154:
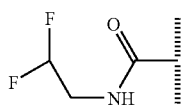
Q155:
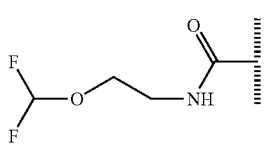
Q156:
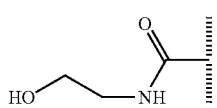
Q157:
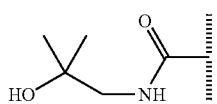
Q158:
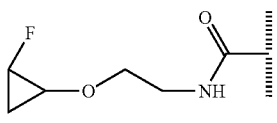
Q159:
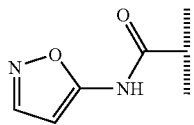
Q160:
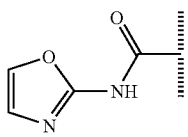
Q161:
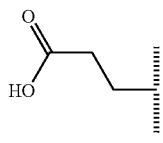
[Formula 17]
| No. | Y | $R^2$ |
|---|---|---|
| 1 | Q1 | Q13 |
| 2 | Q2 | Q13 |
| 3 | Q79 | Q13 |
| 4 | Q80 | Q13 |
| 5 | Q81 | Q13 |
| 6 | Q82 | Q13 |
| 7 | Q83 | Q13 |
| 8 | Q84 | Q13 |
| 9 | Q85 | Q13 |
| 10 | Q86 | Q13 |
| 11 | Q87 | Q13 |
| 12 | Q88 | Q13 |
| 13 | Q89 | Q13 |
| 14 | Q90 | Q13 |
| 15 | Q91 | Q13 |
| 16 | Q92 | Q13 |
| 17 | Q93 | Q13 |
| 18 | Q1 | Q3 |
| 19 | Q1 | Q4 |
| 20 | Q1 | Q5 |
| 21 | Q1 | Q6 |
| 22 | Q1 | Q7 |
| 23 | Q1 | Q8 |
| 24 | Q1 | Q9 |
| 25 | Q1 | Q10 |
| 26 | Q1 | Q11 |
| 27 | Q1 | Q12 |
| 28 | Q1 | Q13 |
| 29 | Q1 | Q14 |
| 30 | Q1 | Q15 |
| 31 | Q1 | Q16 |
| 32 | Q1 | Q17 |
| 33 | Q1 | Q18 |
| 34 | Q1 | Q19 |
| 35 | Q1 | Q20 |
| 36 | Q1 | Q21 |
| 37 | Q1 | Q22 |
| 38 | Q1 | Q23 |
| 39 | Q1 | Q24 |
| 40 | Q2 | Q3 |
| 41 | Q2 | Q4 |
| 42 | Q2 | Q5 |
| 43 | Q2 | Q6 |
| 44 | Q2 | Q7 |
| 45 | Q2 | Q10 |
| 46 | Q1 | Q26 |
| 47 | Q1 | Q27 |
| 48 | Q114 | Q13 |
| 49 | Q115 | Q13 |
| 50 | Q116 | Q13 |
| 51 | Q117 | Q13 |
| 52 | Q118 | Q13 |

-continued

[Formula 17]

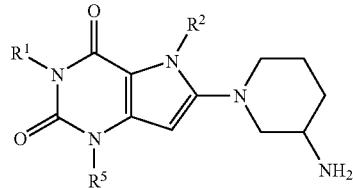

| No. | R¹ | R² | R⁵ |
|---|---|---|---|
| 53 | Q35 | Q4 | Me |
| 54 | Q36 | Q5 | Me |
| 55 | Q37 | Q13 | Me |
| 56 | Q38 | Q4 | Me |
| 57 | Q39 | Q5 | Me |
| 58 | H | Q13 | Me |
| 59 | Q47 | Q4 | Me |
| 60 | Q48 | Q5 | Me |
| 61 | Q54 | Q13 | Me |
| 62 | Q56 | Q4 | Me |
| 63 | Q57 | Q5 | Me |
| 64 | Q58 | Q13 | Me |
| 65 | Q59 | Q4 | Me |
| 66 | Q60 | Q5 | Me |
| 67 | Q61 | Q13 | Me |
| 68 | Q62 | Q4 | Me |
| 69 | Q63 | Q5 | Me |
| 70 | Q64 | Q13 | Me |
| 71 | Q65 | Q4 | Me |
| 72 | Q66 | Q5 | Me |
| 73 | Q67 | Q13 | Me |
| 74 | Q68 | Q4 | Me |
| 75 | Q69 | Q5 | Me |
| 76 | Q70 | Q13 | Me |
| 77 | Q71 | Q4 | Me |
| 78 | Q72 | Q5 | Me |
| 79 | Q73 | Q4 | Me |
| 80 | Q74 | Q5 | Me |
| 81 | Q75 | Q13 | Me |
| 82 | Q76 | Q4 | Me |
| 83 | Q77 | Q5 | Me |
| 84 | Q78 | Q13 | Me |
| 85 | Q119 | Q4 | Me |
| 86 | Q120 | Q5 | Me |
| 87 | Q121 | Q13 | Me |
| 88 | Q122 | Q4 | Me |
| 89 | Q77 | Q5 | Me |
| 90 | Q78 | Q13 | Me |
| 91 | Me | Q4 | etoet |
| 92 | Me | Q5 | meoet |
| 93 | Me | Q13 | f2etoet |
| 94 | Me | Q4 | f2meoet |
| 95 | Me | Q5 | cycproet |
| 96 | Me | Q13 | isoproet |
| 97 | Me | Q4 | etomet |
| 98 | Me | Q5 | meomet |
| 99 | Me | Q13 | f2meomet |
| 100 | Me | Q13 | Q144 |
| 101 | Me | Q13 | Q145 |
| 102 | Me | Q13 | Q146 |
| 103 | Me | Q13 | Q147 |
| 104 | Me | Q13 | Q148 |

[Formula 18]

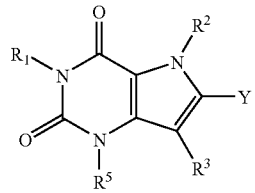

| No. | R¹ | R² | R³ | R⁵ | Y |
|---|---|---|---|---|---|
| 105 | Me | Q13 | Ac | Me | Q1 |
| 106 | Me | Q13 | Me | Me | Q1 |
| 107 | Me | Q13 | Et | Me | Q1 |
| 108 | Me | Q5 | etomet | Me | Q1 |
| 109 | Me | Q5 | meomet | Me | Q1 |
| 110 | Me | Q5 | f2meomet | Me | Q1 |
| 111 | Me | Q13 | Q149 | Me | Q1 |
| 112 | Me | Q13 | Q123 | Me | Q1 |
| 113 | Me | Q13 | $CO_2H$ | Me | Q1 |
| 114 | Me | Q13 | Q135 | Me | Q1 |
| 115 | Me | Q13 | Q136 | Me | Q1 |
| 116 | Me | Q13 | Q137 | Me | Q1 |
| 117 | Me | Q13 | Q138 | Me | Q1 |
| 118 | Me | Q13 | Q139 | Me | Q1 |
| 119 | Me | Q13 | Q140 | Me | Q1 |
| 120 | Me | Q13 | Q141 | Me | Q1 |
| 121 | Me | Q13 | Q142 | Me | Q1 |
| 122 | Me | Q13 | Q143 | Me | Q1 |
| 123 | Me | Q13 | Q124 | Me | Q1 |
| 124 | Me | Q5 | Q125 | Me | Q1 |
| 125 | Me | Q13 | Q126 | Me | Q1 |
| 126 | Me | Q4 | Q127 | Me | Q1 |
| 127 | Me | Q13 | etomet | Me | Q2 |
| 128 | Me | Q13 | meomet | Me | Q118 |
| 129 | Me | Q4 | Q103 | Me | Q1 |
| 130 | Me | Q13 | Q49 | Me | Q1 |
| 131 | Me | Q4 | Q49 | Me | Q1 |
| 132 | Me | Q5 | Q50 | Me | Q1 |
| 133 | Me | Q13 | Q51 | Me | Q1 |
| 134 | H | Q13 | Q52 | Me | Q1 |
| 135 | Me | Q5 | Q53 | Me | Q1 |
| 136 | Me | Q13 | Q54 | Me | Q1 |
| 137 | Me | Q4 | Q56 | Me | Q1 |
| 138 | Me | Q5 | Q128 | Me | Q1 |
| 139 | Me | Q13 | Q129 | Me | Q1 |
| 140 | Me | Q4 | Q130 | Me | Q1 |
| 141 | Me | Q5 | Q131 | Me | Q1 |
| 142 | Me | Q13 | Q132 | Me | Q1 |
| 143 | Q66 | Q13 | etomet | Me | Q1 |
| 144 | Q67 | Q5 | meomet | Me | Q1 |
| 145 | Q68 | Q13 | etomet | Me | Q1 |
| 146 | Q69 | Q13 | etomet | Me | Q1 |
| 147 | Me | Q5 | Ac | Me | Q2 |
| 148 | Me | Q13 | Me | Me | Q2 |
| 149 | Q65 | Q5 | Et | Me | Q2 |
| 150 | Me | Q5 | CN | Me | Q2 |
| 151 | Me | Q13 | meomet | Me | Q2 |
| 152 | Me | Q5 | f2meomet | Me | Q2 |
| 153 | Me | Q5 | isoproet | Me | Q2 |
| 154 | Me | Q13 | cycproet | Me | Q2 |
| 155 | H | Q5 | Q50 | Me | Q2 |
| 156 | Me | Q5 | Q27 | Me | Q2 |

[Formula 19]

| No. | T²¹ | R² | Y |
|---|---|---|---|
| 157 | 3-OCHF₂ | Q13 | Q1 |
| 158 | 3-OEt | Q13 | Q1 |
| 159 | 3-O(i-Pr) | Q13 | Q1 |
| 160 | 3-Q150 | Q5 | Q1 |
| 161 | 3-Q151 | Q5 | Q1 |
| 162 | 3-OMe/5-OMe | Q5 | Q1 |
| 163 | 4-OCHF₂ | Q13 | Q1 |
| 164 | 2-OCHF₂ | Q13 | Q1 |
| 165 | 2-Q132 | Q13 | Q1 |
| 166 | 3-OCHF₂ | Q5 | Q2 |
| 167 | 3-OEt | Q5 | Q2 |
| 168 | 3-O(i-Pr) | Q5 | Q2 |
| 169 | 3-Q150 | Q13 | Q2 |
| 170 | 3-Q151 | Q5 | Q2 |
| 171 | 3-OMe/5-OMe | Q13 | Q2 |
| 172 | CO₂H | Q5 | Q2 |
| 173 | 2-Q132 | Q14 | Q118 |
| 174 | 2-OMe | Q13 | Q118 |
| 175 | 3-OCHF₂ | Q13 | Q114 |
| 176 | 3-OEt | Q5 | Q115 |
| 177 | 3-O(i-Pr) | Q13 | Q83 |
| 178 | 3-Q150 | Q4 | Q84 |
| 179 | 3-Q151 | Q13 | Q85 |
| 180 | 4-Q135 | Q13 | Q1 |
| 181 | 4-OCHF₂ | Q4 | Q87 |
| 182 | H | Q13 | Q1 |

| No. | R² | R⁴ |
|---|---|---|
| 183 | Q4 | CN |
| 184 | Q5 | CF₃ |
| 185 | Q13 | Ph |
| 186 | Q13 | Ac |
| 187 | Q13 | CO₂H |
| 188 | Q13 | Q135 |
| 189 | Q13 | Q136 |
| 190 | Q13 | Q137 |
| 191 | Q13 | Q138 |
| 192 | Q13 | Q139 |
| 193 | Q13 | Q140 |
| 194 | Q13 | Q141 |
| 195 | Q13 | Q142 |
| 196 | Q13 | Q143 |
| 197 | Q13 | Q129 |
| 198 | Q13 | Q130 |
| 199 | Q5 | Q132 |
| 200 | Q13 | i-Pr |
| 201 | Q5 | EtO |
| 202 | Q5 | Q50 |
| 203 | Q13 | Q46 |
| 204 | Q5 | Q152 |
| 205 | Q5 | Q111 |
| 206 | Q13 | Q110 |
| 207 | Q5 | NMe₂ |
| 208 | Q5 | Q34 |

[Formula 20]

| No. | T²¹ | R³ |
|---|---|---|
| 209 | 3-OCHF₂ | Ac |
| 210 | 3-OEt | Me |
| 211 | 3-O(i-Pr) | Et |
| 212 | 3-Q150 | CN |
| 213 | 3-Q151 | Q50 |
| 214 | 3-OMe/5-OMe | Q52 |
| 215 | 4-OCHF₂ | Q54 |
| 216 | 2-OCHF₂ | Q128 |
| 217 | 2-Q132 | Q129 |
| 218 | 3-OCHF₂ | Q130 |
| 219 | 3-OEt | Q131 |
| 220 | 3-O(i-Pr) | Q132 |
| 221 | 3-Q150 | etomet |
| 222 | 3-Q151 | meomet |
| 223 | 3-OMe/5-OMe | etomet |
| 224 | 4-OCHF₂ | etomet |
| 225 | 2-Q132 | f2meomet |
| 226 | 2-OMe | isoproet |
| 227 | 3-OCHF₂ | cycproet |
| 228 | 3-OEt | Q149 |
| 229 | 3-O(i-Pr) | Q123 |
| 230 | 3-OEt | CO₂H |
| 231 | 3-OEt | Q135 |
| 232 | 3-OEt | Q136 |
| 233 | 3-OEt | Q137 |
| 234 | 3-OEt | Q138 |
| 235 | 3-OEt | Q139 |
| 236 | 3-OEt | Q140 |
| 237 | 3-OEt | Q141 |
| 238 | 3-OEt | Q142 |
| 239 | 3-OEt | Q143 |

[Formula 21]

| No. | T²² |
|---|---|
| 240 | 3-CO₂H |
| 241 | 3-Q135 |
| 242 | 3-Q136 |
| 243 | 3-Q137 |

-continued
[Formula 21]
| No. | |
|---|---|
| 244 | 3-Q138 |
| 245 | 3-Q139 |
| 246 | 3-Q140 |
| 247 | 3-Q141 |
| 248 | 3-Q142 |
| 249 | 3-Q143 |
| 250 | 4-CO$_2$H |
| 251 | 4-Q135 |
| 252 | 4-Q136 |
| 253 | 4-Q137 |
| 254 | 4-Q138 |
| 255 | 4-Q139 |
| 256 | 4-Q140 |
| 257 | 4-Q141 |
| 258 | 4-Q142 |
| 259 | 4-Q143 |
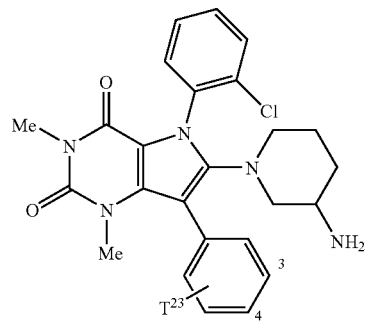
| No. | T$^{23}$ |
|---|---|
| 260 | 3-CO$_2$H |
| 261 | 3-Q135 |
| 262 | 3-Q136 |
| 263 | 3-Q137 |
| 264 | 3-Q138 |
| 265 | 3-Q139 |
| 266 | 3-Q140 |
| 267 | 3-Q141 |
| 268 | 3-Q142 |
| 269 | 3-Q143 |
| 270 | 4-CO$_2$H |
| 271 | 4-Q135 |
| 272 | 4-Q136 |
| 273 | 4-Q137 |
| 274 | 4-Q138 |
| 275 | 4-Q139 |
| 276 | 4-Q140 |
| 277 | 4-Q141 |
-continued
[Formula 21]
| No. | |
|---|---|
| 278 | 4-Q142 |
| 279 | 4-Q143 |
[Formula 22]
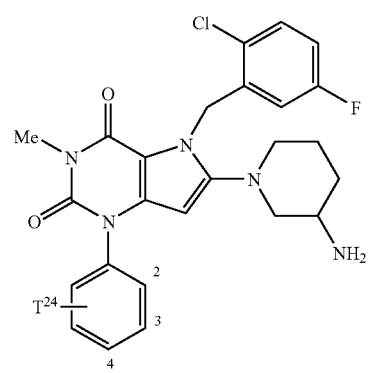
| No. | T$^{24}$ |
|---|---|
| 280 | 2-CO$_2$H |
| 281 | 2-Q135 |
| 282 | 2-Q136 |
| 283 | 2-Q137 |
| 284 | 2-Q138 |
| 285 | 2-Q139 |
| 286 | 2-Q140 |
| 287 | 2-Q141 |
| 288 | 2-Q142 |
| 289 | 2-Q143 |
| 290 | 3-CO$_2$H |
| 291 | 3-Q135 |
| 292 | 3-Q136 |
| 293 | 3-Q137 |
| 294 | 3-Q138 |
| 295 | 3-Q139 |
| 296 | 3-Q140 |
| 297 | 3-Q141 |
| 298 | 3-Q142 |
| 299 | 3-Q143 |
| 300 | 4-CO$_2$H |
| 301 | 4-Q135 |
| 302 | 4-Q136 |
| 303 | 4-Q137 |
| 304 | 4-Q138 |
| 305 | 4-Q139 |
| 306 | 4-Q140 |
| 307 | 4-Q141 |
| 308 | 4-Q142 |
| 309 | 4-Q143 |

[Formula 23]
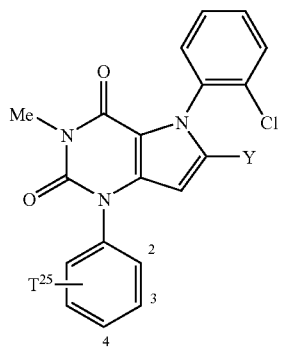
| No. | T$^{25}$ | Y |
|---|---|---|
| 310 | 2-CO$_2$H | Q1 |
| 311 | 2-Q135 | Q1 |
| 312 | 3-CO$_2$H | Q1 |
| 313 | 3-Q135 | Q1 |
| 314 | 4-CO$_2$H | Q1 |
| 315 | 4-Q135 | Q1 |
| 316 | 2-CN | Q1 |
| 317 | 3-CN | Q1 |
| 318 | 4-CN | Q1 |
| 319 | 2-CO$_2$H | Q118 |
| 320 | 2-Q135 | Q118 |
| 321 | 3-CO$_2$H | Q118 |
| 322 | 3-Q135 | Q118 |
| 323 | 4-CO$_2$H | Q118 |
| 324 | 4-Q135 | Q118 |
| 325 | 2-CN | Q118 |
| 326 | 3-CN | Q118 |
| 327 | 4-CN | Q118 |
[Formula 24]
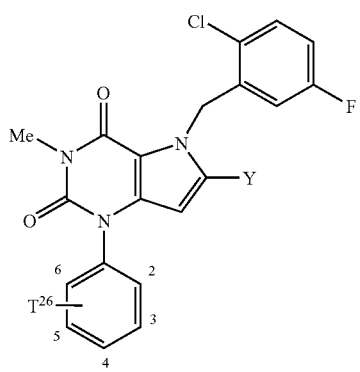
| No. | T$^{26}$ | Y |
|---|---|---|
| 328 | 3-CN/5-CO$_2$H | Q1 |
| 329 | 3-CN/5-Q135 | Q1 |
| 330 | 2-CN/5-CO$_2$H | Q1 |
| 331 | 2-CN/5-Q135 | Q1 |
| 332 | 4-CN/5-CO$_2$H | Q1 |
| 333 | 4-CN/5-Q135 | Q1 |
| 334 | 2-CN | Q1 |
| 335 | 3-CN | Q1 |
| 336 | 4-CN | Q1 |
| 337 | 2-CO$_2$H | Q118 |
| 338 | 2-Q135 | Q118 |
| 339 | 3-CO$_2$H | Q118 |
-continued
[Formula 24]
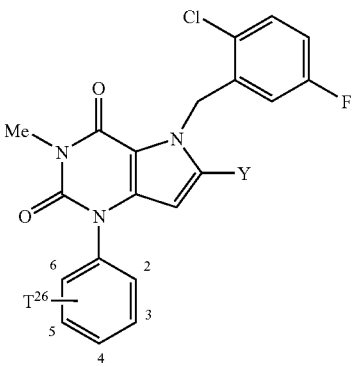
| No. | T$^{26}$ | Y |
|---|---|---|
| 340 | 3-Q135 | Q118 |
| 341 | 4-CO$_2$H | Q118 |
| 342 | 4-Q135 | Q118 |
| 343 | 2-CN | Q118 |
| 344 | 3-CN | Q118 |
| 345 | 4-CN | Q118 |
[Formula 25]
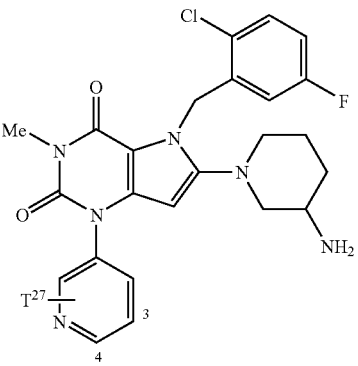
| No. | T$^{27}$ |
|---|---|
| 346 | 4-CN |
| 347 | 3-CN |
| 348 | 4-CO$_2$H |
| 349 | 4-Q135 |
| 350 | 3-CO$_2$H |
| 351 | 3-Q135 |

[Formula 26]

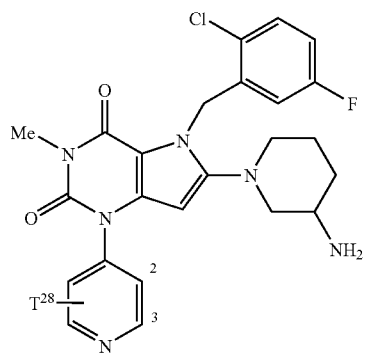

| No. | T²⁸ |
|---|---|
| 352 | 2-CN |
| 353 | 3-CN |
| 354 | 2-CO₂H |
| 355 | 2-Q135 |
| 356 | 3-CO₂H |
| 357 | 3-Q135 |

[Formula 27]

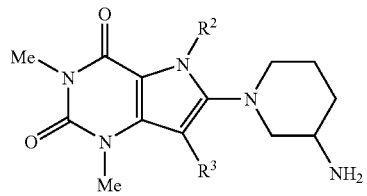

| No. | R² | R³ |
|---|---|---|
| 358 | Q6 | Q153 |
| 359 | Q6 | Q154 |
| 360 | Q6 | Q155 |
| 361 | Q13 | Q156 |
| 362 | Q13 | Q157 |
| 363 | Q6 | Q158 |
| 364 | Q6 | Q159 |
| 365 | Q6 | Q160 |
| 366 | Q13 | Q161 |

When the portion corresponding to Y described in the item [1] is an unsubstituted or substituted 3-aminopyrrolidin-1-yl group, an unsubstituted or substituted 3-aminopiperidin-1-yl group or an unsubstituted or substituted (3-amino)hexahydroazepin-1-yl group in the above compounds having compound numbers 1 to 366, bicyclic pyrrole derivatives are more preferable in which the amino group at the 3-position is in an absolute configuration represented by the following formula (F₁):

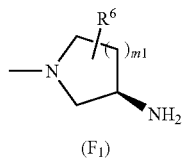

(F₁)

wherein m1 and R⁶ are as defined in the item [1].

When the portion corresponding to Y described in the item [1] is an unsubstituted or substituted (2-aminocycloalkyl) amino group in the above compounds having compound numbers 1 to 366, compounds are more preferable in which the amino groups at the 1-position and 2-position are in an absolute configuration represented by the following formula (F₂) or (F₃)

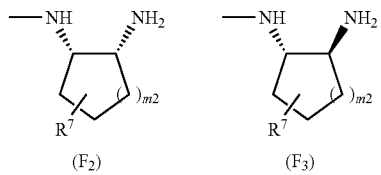

wherein m2 and R⁷ are as defined in the item [1].

In addition, compounds are still more preferable in which the amino groups at the 1-position and 2-position are in an absolute configuration represented by the following formula (F₄):

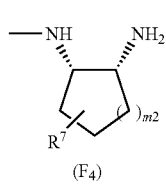

(F₄)

wherein m2 and R⁷ are as defined in the item [1].

In the following description, a bond shown by a wedge-shaped solid line or broken line as in the formula (J₁) and formula (J₂) indicates an absolute configuration relating to an amino group, and a bond shown by a thick line as in the formula (J₃) indicates a relative configuration relating to an amino group (for example, the formula (J₃) represents a (±)-cis form)

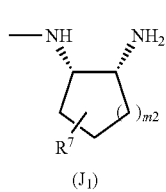 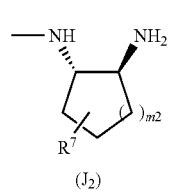

(J₁)                  (J₂)

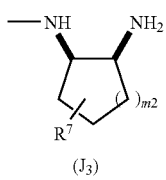

(J₃)

wherein m2 and $R^7$ are as defined in the item [1].

Of the above compounds having compound numbers 1 to 366 as the compound of the formula (I) described in the item [1], compounds containing in the formula "an alkoxycarbonyl group", "an optionally substituted alkoxycarbonyl group", "an optionally substituted cycloalkoxycarbonyl group", "an optionally substituted aryloxycarbonyl group", "an optionally substituted aralkyloxycarbonyl group" or the formula: -Rd-C(O)O—Re wherein Rd and Re are as defined above, are such that such a substituent is converted to "a carboxyl group" in some cases under physiological conditions in a living body by oxidation, reduction, hydrolysis or the like by an enzyme, or hydrolysis by acid in the stomach, or the like.

A process for producing the compound represented by the formula (I) of the present invention is explained below with reference to examples, which should not be construed as limiting the scope of the invention. In the present description, the following abbreviations are used in some cases for the simplification of description.

Boc: tert-butoxycarbonyl group
Cbz: benzyloxycarbonyl group
TMS: trimethylsilyl group
TBS: tert-butyldimethylsilyl group
SEM: 2-[(trimethylsilyl)ethoxy]methyl group
Ac: acetyl group
Me: methyl group
Et: ethyl group
Pr: propyl group
i-Pr: isopropyl group
Bu: butyl group
i-Bu: isobutyl group
t-Bu: tert-butyl group
Ph: phenyl group
Bn: benzyl group
Ms: methanesulfonyl group
TFA: trifluoroacetic acid
Alloc: allyloxycarbonyl group The compound represented by the formula (I) may be synthesized from a well-known compound by a combination of well-known synthesis processes. It may be synthesized, for example, by any of the following processes.

Production Process 1

A compound represented by the formula (1-17) or a salt thereof is produced, for example, by the following process:

[Formula 32]

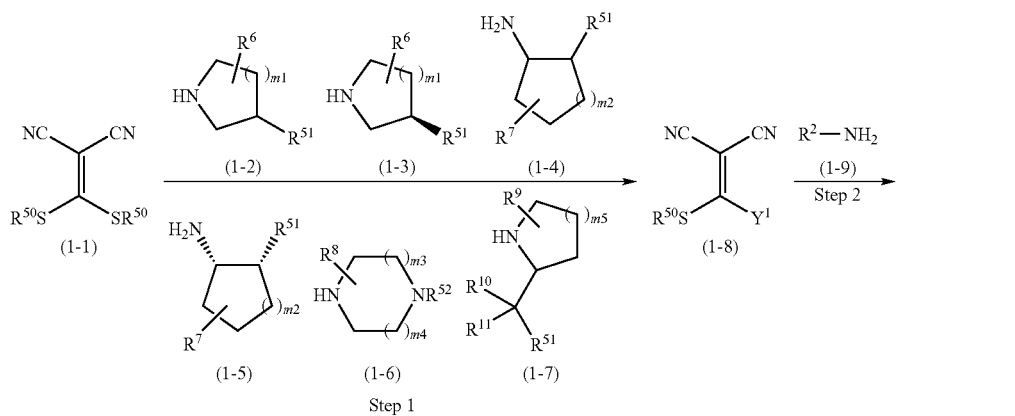

Step 1

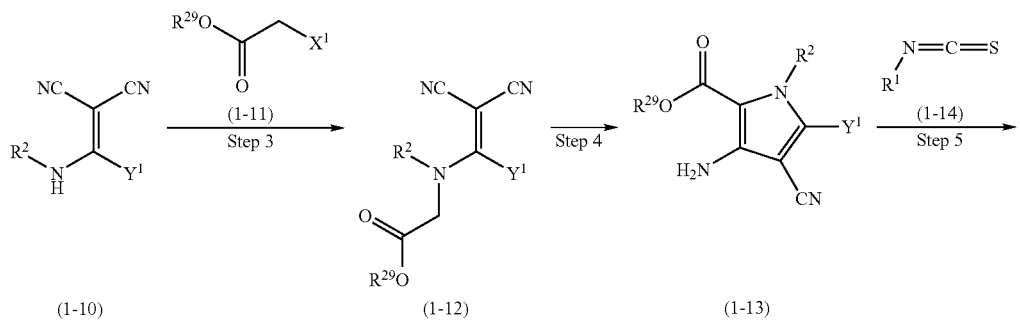

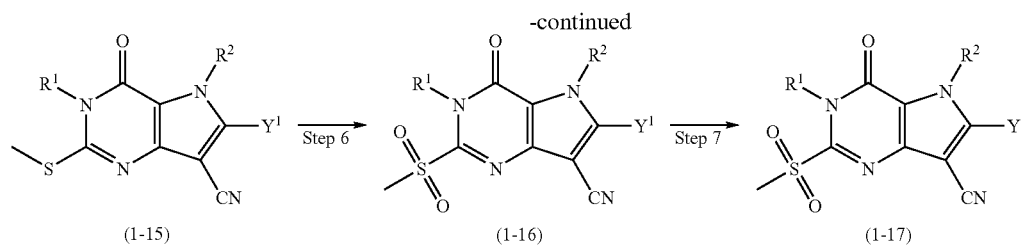

(1-15)  (1-16)  (1-17)

wherein $R^1$, $R^2$, $R^6$, $R^7$, $R^8$, $R^9$, $R^{10}$, $R^{11}$, $R^{29}$, $m^1$, $m^2$, $m^3$, $m^4$ and $m^5$ are as defined above; $X^1$ is a leaving group (for example, an iodine atom, a bromine atom, a chlorine atom, methanesulfonyloxy, trifluoromethanesulfonyloxy or p-toluenesulfonyloxy); $R^{51}$ is Alloc, N=C(Ph)$_2$, NHBoc, NHCbz or the following formula (G1):

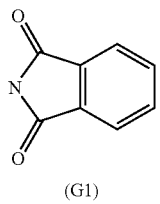

[Formula 33]

(G1)

$R^{52}$ is Alloc, Boc or Cbz; and $Y^1$ is the protected state of the primary or secondary amino group in Y described in the item [1].

1) Step 1

A compound (1-8) may be produced by reacting a compound (1-1) with a compound selected from a compound (1-2), a compound (1-3), a compound (1-4), a compound (1-5), a compound (1-6) and a compound (1-7) in an inert solvent in the presence or absence of a base. The base includes, for example, organic bases (e.g. 1-hydroxybenzotriazole, N-methylmorpholine, triethylamine, diisopropylethylamine, tributylamine, 1,8-diazabicyclo[5,4,0]undec-7-ene, 1,5-diazabicyclo[4,3,0]nona-5-ene, 1,4-diazabicyclo[5,4,0]undec-7-ene, pyridine, dimethylaminopyridine and picoline), and inorganic bases (e.g. sodium ethoxide, sodium methoxide, potassium tert-butoxide and sodium hydride). The amount of the base used is usually chosen in the range of 1 to 5 equivalents per equivalent of the compound (1-1). The amount of the compound (1-2), compound (1-3), compound (1-4), compound (1-5), compound (1-6) or compound (1-7) used is usually chosen in the range of 1 to 2 equivalents per equivalent of the compound (1-1). The inert solvent includes, for example, alcohol solvents (e.g. methanol, ethanol and 2-propanol), ether solvents (tetrahydrofuran and 1,4-dioxane), and mixed solvents thereof. The reaction temperature may be chosen in the range of about 50° C. to about 120° C.

The compound (1-2) may be produced by the process described in the production process 19 described hereinafter, the compound (1-3) by the process described in the production process 20 described hereinafter, and the compound (1-5) by the process described in the production process 21 described hereinafter. As the compound (1-6), a commercial reagent may be used, or the compound (1-6) may be produced by the process described in literature (for example, Synthesis 391 (1994), Org. Lett. 5, 1591 (2003), Synthesis 1065 (1992), Synlett 755 (2002), J. Org. Chem. 56, 3063 (1991), J. Org. Chem. 60, 4177 (1995) and J. Org. Chem. 57, 6653 (1992)). The compound (1-7) may be produced by the same process as that described in literature (for example, J. Org. Chem. 61, 6700 (1996)) or the like.

2) Step 2

A compound (1-10) is produced by reacting the compound (1-8) with a compound (1-9) in an inert solvent. The amount of the compound (1-9) used is usually chosen in the range of 1 equivalent to excess equivalents per equivalent of the compound (1-8). The inert solvent includes, for example, organic bases (e.g. 1-hydroxybenzotriazole, N-methylmorpholine, triethylamine, diisopropylethylamine, tributylamine, 1,8-diazabicyclo[5,4,0]undec-7-ene, 1,5-diazabicyclo[4,3,0]nona-5-ene, 1,4-diazabicyclo[5,4,0]undec-7-ene, pyridine, dimethylaminopyridine and picoline), alcohol solvents (e.g. methanol, ethanol and 2-propanol), acetic acid, and mixed solvent thereof. The reaction temperature is chosen in the range of about 50° C. to about 150° C. and the reaction is usually carried out with refluxing.

3) Step 3

A compound (1-12) may be produced by reacting the compound (1-10) with a compound (1-11) in an inert solvent in the presence or absence of a base (see, for example, J. Heterocycl. Chem. 37, 1033 (2000), J. Chem. Soc., Perkin Trans. 1, 13, 1833 (1999) and J. Med. Chem. 38, 3838 (1995)). The amount of the compound (1-11) used is usually chosen in the range of 1 to 5 equivalents per equivalent of the compound (1-10). The base includes, for example, alkali carbonates (e.g. potassium carbonate, sodium carbonate, potassium hydrogencarbonate and sodium hydrogencarbonate), alkali hydrides (e.g. sodium hydride and potassium hydride), and alkali hydroxides (e.g. potassium hydroxide and sodium hydroxide). A suitable example thereof is potassium carbonate. The amount of the base used is usually chosen in the range of 1 to 3 equivalents per equivalent of the compound (1-10). The inert solvent includes, for example, aprotic solvents (e.g. N,N-dimethylformamide and dimethyl sulfoxide), ether solvents (e.g. diethyl ether, tetrahydrofuran and 1,4-dioxane), ketones (e.g. acetone), and mixed solvents thereof. Suitable examples thereof are N,N-dimethylformamide and dimethyl sulfoxide. The reaction temperature may be chosen in the range of about 10° C. to about 180° C.

4) Step 4

A compound (1-13) may be produced by reacting the compound (1-12) with a base in an inert solvent (see, for example, WO02/068420). The base includes alkali hydrides (e.g. sodium hydride and potassium hydride) and the like. A suitable example thereof is sodium hydride. The amount of the base used is usually chosen in the range of 1 to 3 equivalents per equivalent of the compound (1-12). The inert solvent includes N,N-dimethylformamide, ether solvents (e.g. diethyl ether, tetrahydrofuran and 1,4-dioxane), and mixed solvents thereof. A suitable example thereof is tetrahydrofuran. The reaction temperature may be chosen in the range of about 10° C. to about 100° C.

5) Step 5

A compound (1-15) may be produced from the compound (1-13) by carrying out the following reactions (1) to (3).

(1) The compound (1-13) is reacted with a compound (1-14) in pyridine in the presence of a base. The reaction temperature may be chosen in the range of about 50° C. to about 160° C. The amount of the compound (1-14) used is usually chosen in the range of 1 to 5 equivalents.

(2) A base is added to the reaction mixture obtained in the above item (1) and the reaction is carried out. The base includes cesium carbonate, potassium carbonate, sodium carbonate, etc. The amount of the base used is usually chosen in the range of 1 to 5 equivalents. The reaction temperature is chosen in the range of about 50° C. to about 160° C.

The reaction temperature may be chosen in the range of about −10° C. to about 70° C. Production process (B): A compound (1-16) may be produced by reacting the compound (1-15) with Oxon (a registered trade name; Aldrich) in an inert solvent. The inert solvent includes alcohol solvents (e.g. ethanol, methanol and 2-propanol), etc. The amount of Oxon (a registered trade name; Aldrich) used is usually chosen in the range of 1 to 20 equivalents per equivalent of the compound (1-15). The reaction temperature may be chosen in the range of about −10° C. to about 70° C.

7) Step 7

The compound (1-17) may be produced from the compound (1-16) by the same process as in the step 2 described in production process 2.

Production Process 2

Each of compounds of the formula (2-2) and the formula (2-5) as the compound of the formula (I), or a salt thereof is produced, for example, by the following process:

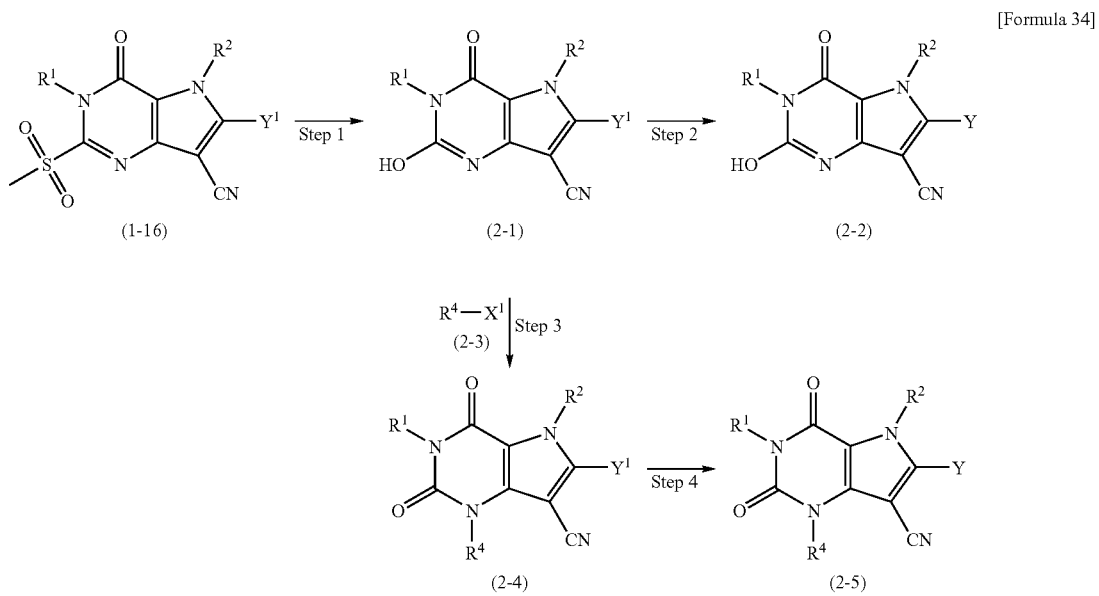

[Formula 34]

(3) Methyl iodide is added to the reaction mixture obtained in the above item (2) and the reaction is carried out. The amount of methyl iodide used is usually chosen in the range of 1 to 5 equivalents. The reaction temperature is chosen in the range of about 10° C. to about 40° C.

6) Step 6

In this step 6, the following production process (A) or production process (B) may be adopted. Production process (A): A compound (1-16) may be produced by reacting the compound (1-15) with a mixture of sodium tungstate and an aqueous hydrogen peroxide solution in an inert solvent. The inert solvent includes alcohol solvents (e.g. ethanol, methanol and 2-propanol), organic acids (e.g. acetic acid and propionic acid), etc. A mixed solvent of the alcohol solvent and the organic acid is usually used as the inert solvent. The amount of sodium tungstate used is usually chosen in the range of 1 to 5 equivalents per equivalent of the compound (1-15). The amount of the aqueous hydrogen peroxide solution (usually a 30% aqueous solution) used is usually chosen in the range of 10 to 100 equivalents per equivalent of the compound (1-15).

wherein $R^1$, $R^2$, $R^4$, $X^1$, $Y^1$ and Y are as defined above.

1) Step 1

A compound (2-1) may be produced by reacting a compound (1-16) with a base in an inert solvent. The base includes, for example, inorganic bases such as sodium hydroxide, potassium hydroxide, sodium hydrogencarbonate, potassium carbonate, etc. A suitable example thereof is sodium hydroxidec. The amount of the base used is usually chosen in the range of 1 equivalent to large-excess equivalents per equivalent of the compound (1-16). The inert solvent includes, for example, water, alcohol solvents (e.g. methanol, ethanol and 2-propanol), tetrahydrofuran, and mixed solvents thereof. The reaction temperature is chosen in the range of about 50° C. to about 100° C.

In this step, a compound in which a protective group for the primary amino group or secondary amino group in Y has been removed is produced in some cases. The compound (2-1) in which the primary amino group or secondary amino group in Y has been protected again with a protective group (e.g. Boc or Cbz) may be produced by the same production process as described in literature (for example, Protective Groups in Organic Synthesis 2nd Edition (John Wiley & Sons, Inc.)).

2) Step 2

The compound (2-2) may be produced from the compound (2-1) by the same process as that described in literature (for example, Protective Groups in Organic Synthesis 2nd Edition (John Wiley & Sons, Inc.)) or the like.

3) Step 3

A compound (2-4) may be produced by reacting the compound (2-1) with a compound (2-3) in an inert solvent in the presence of a base. The amount of the compound (2-3) used is usually chosen in the range of 1 to 5 equivalents per equivalent of the compound (2-1). The base includes, for example, alkali carbonates (e.g. potassium carbonate, sodium carbonate, potassium hydrogencarbonate and sodium hydrogencarbonate), alkali hydrides (e.g. sodium hydride and potassium hydride), and alkali hydroxides (e.g. potassium hydroxide and sodium hydroxide). A suitable example thereof is potassium carbonate. The amount of the base used is usually chosen in the range of 1 to 5 equivalents per equivalent of the compound (2-1). The inert solvent includes, for example, aprotic solvents (e.g. N,N-dimethylformamide and dimethyl sulfoxide), ether solvents (e.g. diethyl ether, tetrahydrofuran and 1,4-dioxane), ketones (e.g. acetone), and mixed solvents thereof. A suitable example thereof is N,N-dimethylformamide. The reaction temperature may be chosen in the range of about 0° C. to about 180° C.

4) Step 4

The compound (2-5) may be produced from the compound (2-4) by the same process as in the above step 2.

Production Process 3

A compound of the formula (3-3) as the compound of the formula (I), or a salt thereof is produced, for example, by the following process:

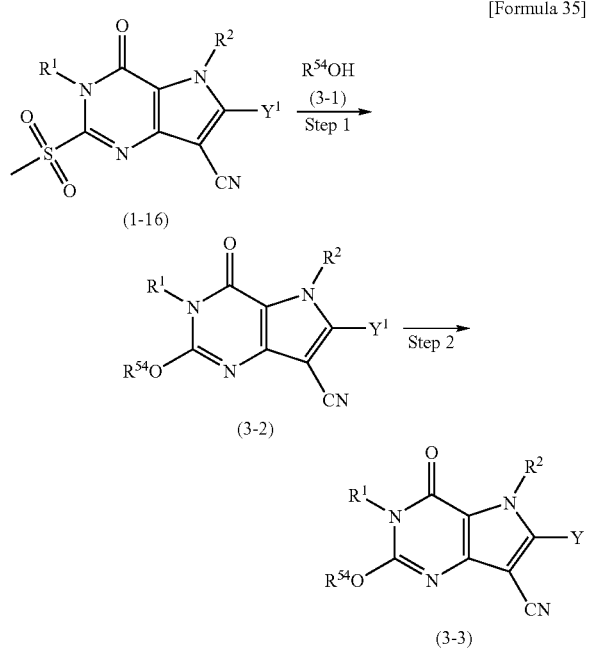

[Formula 35]

wherein $R^1$, $R^2$, $Y^1$ and Y are as defined above, and $R^{54}O$ is "an optionally substituted alkoxy group", "an optionally substituted aryloxy group", "an optionally substituted aralkyloxy group", "an optionally substituted heteroaryloxy group" or "an optionally substituted cycloalkyloxy group".

1) Step 1

A compound (3-2) may be produced by reacting a compound (1-16) with a compound (3-1) in an inert solvent in the presence of a base. The base includes potassium tert-butoxide, sodium tert-butoxide, cesium carbonate, potassium carbonate, sodium carbonate, sodium phenoxide, potassium phenoxide, sodium hydride, etc. A suitable example thereof is sodium hydride. The amount of the base used is usually chosen in the range of 1 to 5 equivalents per equivalent of the compound (3-1). The inert solvent includes tetrahydrofuran, 1,4-dioxane, N,N-dimethylformamide, mixed solvents thereof, etc. The reaction temperature may be chosen in the range of about −10° C. to about 50° C.

2) Step 2

The compound (3-3) may be produced from the compound (3-2) by the same process as in the step 2 described in production process 2.

Production Process 4

A compound of the formula (4-3) as the compound of the formula (I), or a salt thereof is produced, for example, by the following process:

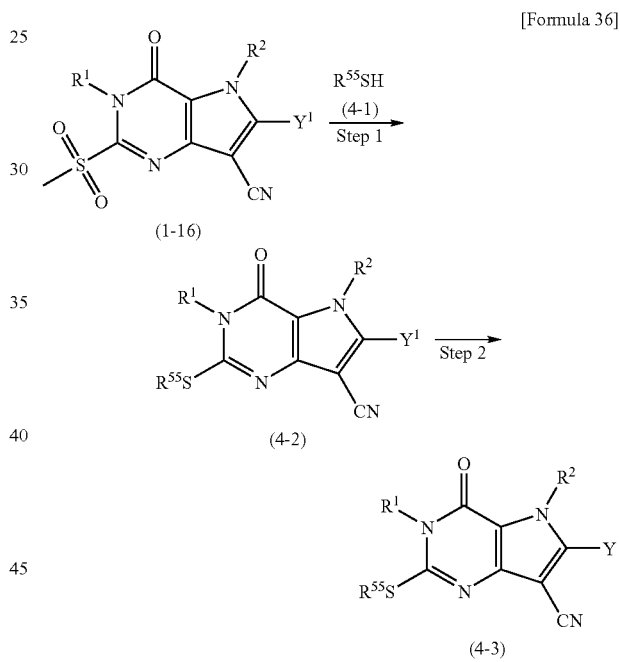

[Formula 36]

wherein $R^1$, $R^2$, $Y^1$ and Y are as defined above, and $R^{55}S$ is "an optionally substituted alkylthio group" or "an optionally substituted arylthio group".

1) Step 1

A compound (4-2) may be produced from a compound (1-16) by the same process as in the step 1 described in production process 3.

2) Step 2

The compound (4-3) may be produced from the compound (4-2) by the same process as in the step 2 described in production process 2.

Production Process 5

Each of compounds of the formula (5-2) and the formula (5-4) as the compound of the formula (I), or a salt thereof is produced, for example, by the following process:

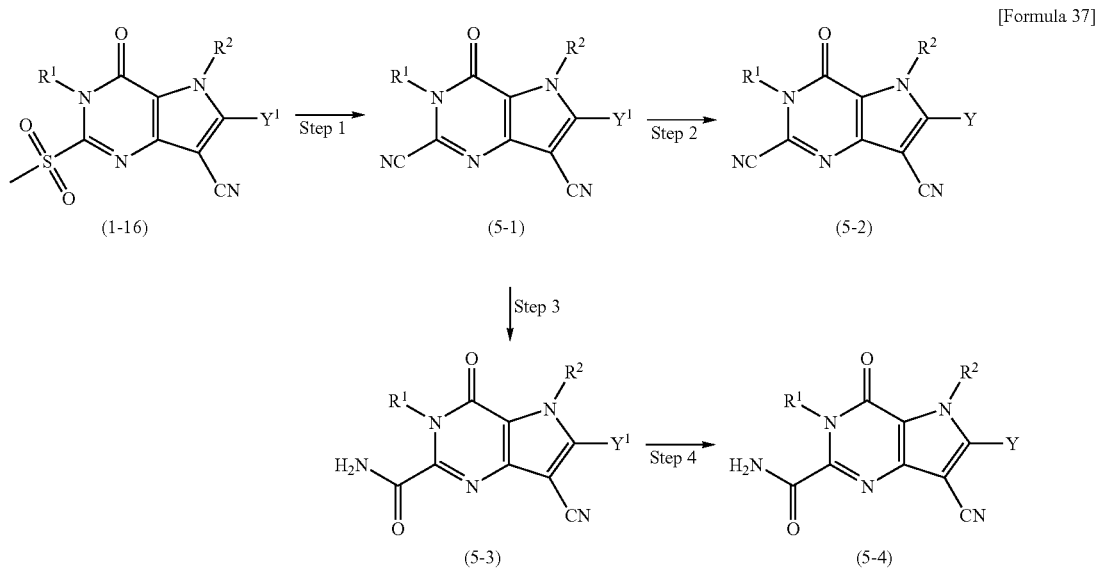

wherein $R^1$, $R^2$, $Y^1$ and Y are as defined above.

1) Step 1

A compound (5-1) may be produced by reacting a compound (1-16) with sodium cyanide or potassium cyanide in an inert solvent. The amount of sodium cyanide or potassium cyanide used is usually chosen in the range of 0.8 to 5 equivalents per equivalent of the compound (1-16). The inert solvent includes tetrahydrofuran, 1,4-dioxane, N,N-dimethylformamide, mixed solvents thereof, etc. The reaction temperature may be chosen in the range of about 10° C. to about 100° C.

2) Step 2

The compound (5-2) may be produced from the compound (5-1) by the same process as in the step 2 described in production process 2.

3) Step 3

A compound (5-3) may be produced by reacting the compound (5-1) with an aqueous hydrogen peroxide solution in an inert solvent in the presence of a base. The base includes, for example, inorganic bases such as sodium hydrogencarbonate, potassium hydrogencarbonate, sodium carbonate, potassium carbonate, etc. The amount of the base used is usually chosen in the range of 0.5 to 10 equivalents per equivalent of the compound (5-1). The amount of the aqueous hydrogen peroxide solution used is usually chosen in the range of 1 to 20 equivalents per equivalent of the compound (5-1). The inert solvent includes dimethyl sulfoxide, acetone, etc. A suitable example thereof is dimethyl sulfoxide. The reaction temperature may be chosen in the range of about 10° C. to about 100° C.

4) Step 4

The compound (5-4) may be produced from the compound (5-3) by the same process as in the step 2 described in production process 2.

Production Process 6

A compound of the formula (6-3) as the compound of the formula (I), or a salt thereof is produced, for example, by the following process:

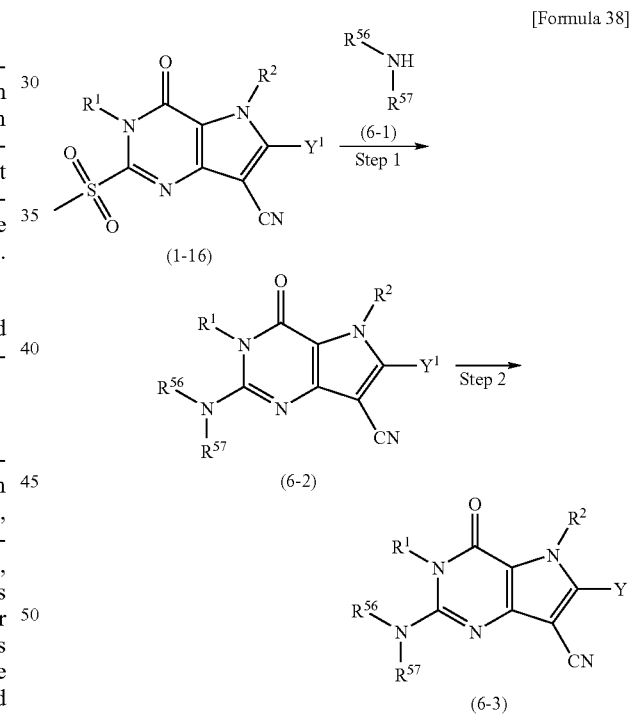

wherein $R^1$, $R^2$, $Y^1$ and Y are as defined above, and $R^{56}R^{57}N$ is "an optionally substituted nitrogen-containing saturated heterocyclic group" or "an optionally substituted amino group".

1) Step 1

A compound (6-2) may be produced by reacting a compound (1-16) with a compound (6-1) in the presence or absence of an inert solvent. The amount of the compound (6-1) used is usually chosen in the range of 1 to 100 equivalents per equivalent of the compound (1-16). When the compound (6-1) is liquid, it may be used also as a solvent. The inert solvent includes alcohol solvents (e.g. ethanol, methanol and 2-propanol), etc. The reaction temperature may be chosen in the range of about 50° C. to about 150° C.

2) Step 2

The compound (6-3) may be produced from the compound (6-2) by the same process as in the step 2 described in production process 2.

Production Process 7

A compound of the formula (7-3) as the compound of the formula (I), or a salt thereof is produced, for example, by the following process:

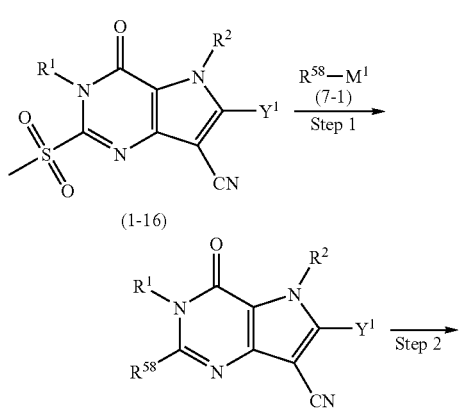

wherein $R^1$, $R^2$, $Y^1$ and Y are as defined above; $R^{58}$ is "an optionally substituted alkyl group", "an optionally substituted cycloalkyl group", "an optionally substituted alkenyl group", "an optionally substituted aryl group", "an optionally substituted heteroaryl group", "an optionally substituted heteroarylalkyl group" or "an optionally substituted aralkyl group"; and $M^1$ is lithium, magnesium chloride or magnesium bromide.

1) Step 1

A compound (7-2) may be produced by reacting a compound (1-16) with a compound (7-1) in an inert solvent. The amount of the compound (7-1) used is usually chosen in the range of 1 to 10 equivalents per equivalent of the compound (1-16). The inert solvent includes tetrahydrofuran, 1,4-dioxane, N,N-dimethylformamide, mixed solvents thereof, etc. The reaction temperature may be chosen in the range of about −10° C. to about 50° C.

2) Step 2

The compound (7-3) may be produced from the compound (7-2) by the same process as in the step 2 described in production process 2.

Production Process 8

A compound of the formula (8-3) as the compound of the formula (I), or a salt thereof is produced, for example, by the following process:

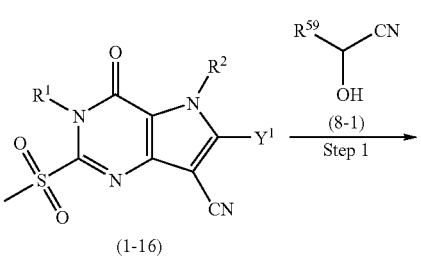

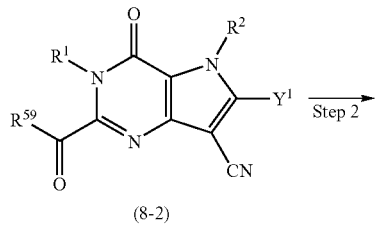

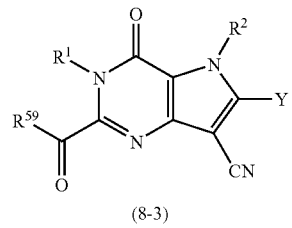

wherein $R^1$, $R^2$, $Y^1$ and Y are as defined above, and $R^{59}C(O)$ is "an optionally substituted aroyl group", "an optionally substituted heteroarylcarbonyl group" or "an optionally substituted alkylcarbonyl group".

1) Step 1

A compound (8-2) may be produced by reacting a compound (1-16) with a compound (8-1) in an inert solvent in the presence of a base. The amount of the compound (8-1) used is usually chosen in the range of 1 to 10 equivalents per equivalent of the compound (1-16). The base includes sodium hydride, etc. The inert solvent includes tetrahydrofuran, 1,4-dioxane, N,N-dimethylformamide, mixed solvents thereof, etc. The reaction temperature may be chosen in the range of about 50° C. to about 150° C.

2) Step 2

The compound (8-3) may be produced from the compound (8-2) by the same process as in the step 2 described in production process 2.

Production Process 9

A compound of the formula (9-4) as the compound of the formula (I), or a salt thereof is produced, for example, by the following process:

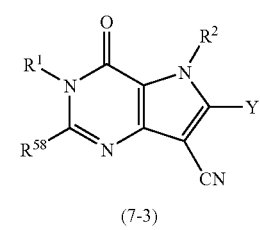

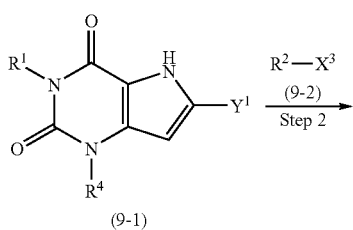

(9-1)

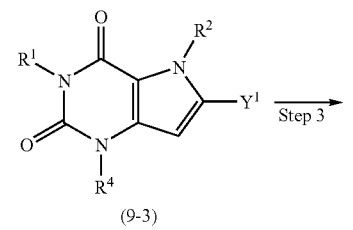

(9-3)

(9-4)

wherein $R^1$, $R^2$, $R^4$, $Y^1$ and Y are as defined above, and $X^3$ is a leaving group (e.g. an iodine atom, a bromine atom, a chlorine atom, methanesulfonyloxy, trifluoromethanesulfonyloxy or p-toluenesulfonyloxy).

1) Step 1

When $R^2$ in the item [4] is a group of any of the formula (E), formula (F), formula (G) and formula (H), a compound (9-1) may be produced from a compound (2-4) by the following process 1.

Process 1

A compound (9-1) may be produced by reacting a compound (2-4) with an acid in an inert solvent. The acid includes inorganic acids such as hydrochloric acid, hydrobromic acid, sulfuric acid, phosphoric acid, nitric acid, etc. A suitable example thereof is sulfuric acid. The amount of the acid used is usually chosen in the range of 1 equivalent to large-excess equivalents per equivalent of the compound (2-4). The inert solvent includes water and the like. The reaction temperature is chosen in the range of about 50° C. to about 200° C.

In this step, a compound in which a protective group for the primary amino group or secondary amino group in Y has been removed is produced in some cases. The compound (9-1) in which the primary amino group or secondary amino group in Y has been protected again with a protective group (e.g. Boc or Cbz) may be produced by the same production process as described in literature (for example, Protective Groups in Organic Synthesis 2nd Edition (John Wiley & Sons, Inc.)).

When $R^2$ in the item [4] is a group of either the formula (I) or the formula (J), a compound (9-1) may be produced from a compound (2-4) by the following process 2 [(1)~(2)].

Process 2

(1) $R^2$ of the compound (2-4) is removed by the same method as that described in literature (for example, Protective Groups in Organic Synthesis 2nd Edition (John Wiley & Sons, Inc.), Tetrahedron 27, 5523 (1971) and Aus. J. Chem. 22, 1321 (1969)) or the like.

(2) The same reaction as in the process 1 in the step 1 described in production process 9 is carried out.

2) Step 2

A compound (9-3) may be produced from the compound (9-1) by the same process as that described in literature (for example, R. C. Larock Comprehensive Organic transformation VCH publisher Inc., 1989, Bioorg. Med. Chem. Lett. 11, 1993 (2001) Organic Letters 4, 4033 (2002) Organic Letters 5, 4987 (2003), Synlett 128 (2004), and J. Am. Chem. Soc. 124, 116847 (2002)) or the like.

When $R^2$ in the item [4] is a group of any of the formula (E), formula (F), formula (G) and formula (H), a compound (9-3) may be produced from the compound (9-1) by the same process as in the step 3 described in production process 1.

3) Step 3

The compound (9-4) may be produced from the compound (9-3) by the same process as in the step 2 described in production process 2.

Production Process 10

Each of compounds of the formula (10-6), formula (10-8) and formula (10-10) as the compound of the formula (I), or a salt thereof is produced, for example, by the following process:

[Formula 42]

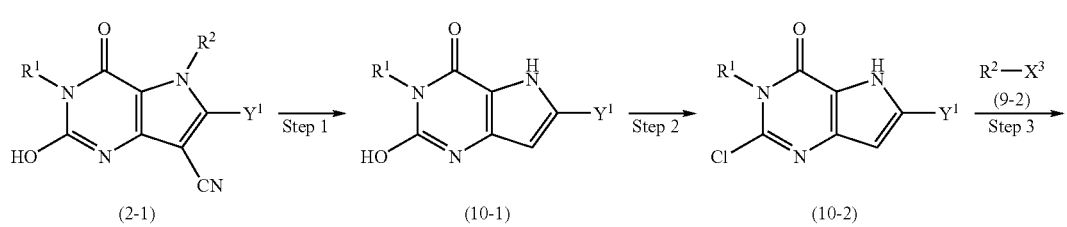

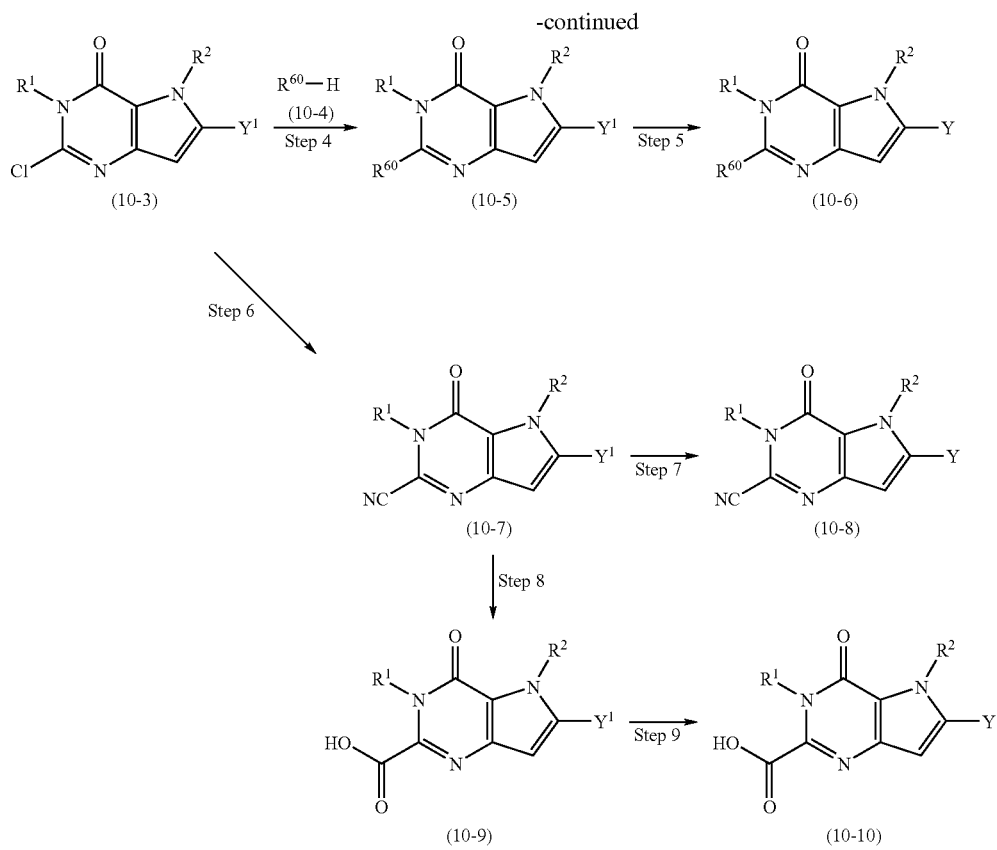

wherein $R^1$, $R^2$, $X^3$, $Y^1$ and Y are as defined above, and $R^{60}$ is the above-mentioned $R^{54}O$, $R^{55}S$ or $R^{56}R^{57}N$.

1) Step 1

A compound (10-1) may be produced from a compound (2-1) by the same process as in the step 1 described in production process 9.

2) Step 2

A compound (10-2) may be produced from the compound (10-1) by the same production process as described in literature (for example, WO03/104229 and Chem. Pharm. Bull. 50, 1163 (2002)).

3) Step 3

A compound (10-3) may be produced from the compound (10-2) by the same process as in the step 2 described in production process 9.

4) Step 4

A compound (10-5) may be produced from the compound (10-3) by the same process as in the step 1 described in production process 3, the step 1 described in production process 4 or the step 1 described in production process 6.

5) Step 5

The compound (10-6) may be produced from the compound (10-5) by the same process as in the step 2 described in production process 2.

6) Step 6

A compound (10-7) may be produced from the compound (10-3) by the same process as in the step 1 described in production process 5.

7) Step 7

The compound (10-8) may be produced from the compound (10-7) by the same process as in the step 2 described in production process 2.

8) Step 8

A compound (10-9) may be produced from the compound (10-7) by the same production process as described in literature (for example, R. C. Larock Comprehensive Organic transformation VCH publisher Inc., 1989, WO03/104229 and WO03/104229).

In this step, a compound in which a protective group for the primary amino group or secondary amino group in Y has been removed is produced in some cases. The compound (10-9) in which the primary amino group or secondary amino group in Y has been protected again with a protective group (e.g. Boc or Cbz) may be produced by the same production process as described in literature (for example, Protective Groups in Organic Synthesis 2nd Edition (John Wiley & Sons, Inc.)).

9) Step 9

The compound (10-10) may be produced from the compound (10-9) by the same process as in the step 2 described in production process 2.

Production Process 11

A compound of the formula (11-4) as the compound of the formula (I), or a salt thereof is produced, for example, by the following process:

[Formula 43]

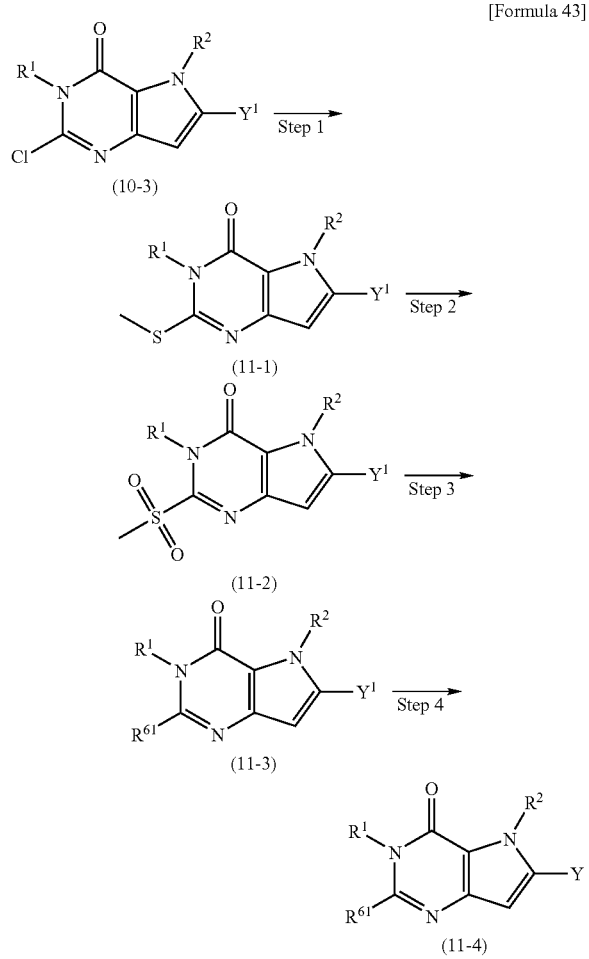

wherein $R^1$, $R^2$, $Y^1$ and Y are as defined above, and $R^{61}$ is "an optionally substituted alkoxy group", "an optionally substituted aryloxy group", "an optionally substituted aralkyloxy group", "an optionally substituted heteroaryloxy group", "an optionally substituted cycloalkyloxy group", "an optionally substituted alkylthio group", "an optionally substituted arylthio group", cyano, "an optionally substituted nitrogen-containing saturated heterocyclic group", "an optionally substituted amino group", "an optionally substituted alkyl group", "an optionally substituted cycloalkyl group", "an optionally substituted alkenyl group", "an optionally substituted aryl group", "an optionally substituted heteroaryl group", "an optionally substituted heteroarylalkyl group", "an optionally substituted aralkyl group", "an optionally substituted aroyl group", "an optionally substituted heteroarylcarbonyl group" or "an optionally substituted alkylcarbonyl group".

1) Step 1

A compound (11-1) may be produced by reacting a compound (10-3) with sodium methanethiol in an inert solvent in the presence or absence of a base. The base includes, for example, inorganic bases such as sodium hydride, sodium hydrogencarbonate, potassium hydrogencarbonate, sodium carbonate, potassium carbonate, etc.; and organic bases such as 1-hydroxybenzotriazole, N-methylmorpholine, triethylamine, diisopropylethylamine, tributylamine, 1,8-diazabicyclo[5,4,0]undec-7-ene, 1,5-diazabicyclo[4,3,0]nona-5-ene, 1,4-diazabicyclo[5,4,0]undec-7-ene, pyridine, dimethylaminopyridine, picoline, etc. The amount of the base used is usually chosen in the range of 1 equivalent to large-excess equivalents per equivalent of the compound (10-3). The amount of sodium methanethiol used is usually chosen in the range of 1 equivalent to large-excess equivalents per equivalent of the compound (10-3). The inert solvent includes, for example, aprotic solvents (e.g. N,N-dimethylformamide and dimethyl sulfoxide), ether solvents (e.g. diethyl ether, tetrahydrofuran and 1,4-dioxane), ketones (e.g. acetone), and mixed solvents thereof. The reaction temperature may be chosen in the range of about 10° C. to about 120° C.

2) Step 2

A compound (11-2) may be produced from the compound (11-1) by the same process as in the step 6 described in production process 1.

3) Step 3

A compound (11-3) may be produced from the compound (11-2) by the same process as in the step 1 described in production process 3, the step 1 described in production process 4, the step 1 described in production process 5, the step 1 described in production process 6, the step 1 described in production process 7 or the step 1 described in production process 8.

4) Step 4

The compound (11-4) may be produced from the compound (11-3) by the same process as in the step 2 described in production process 2.

Production Process 12

Each of compounds of the formula (12-3) and the formula (12-5) as the compound of the formula (I), or a salt thereof is produced, for example, by the following process:

[Formula 44]

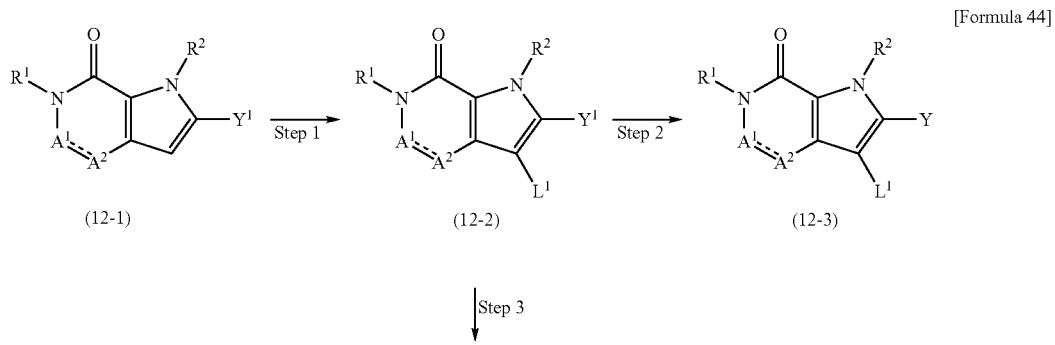

Step 3

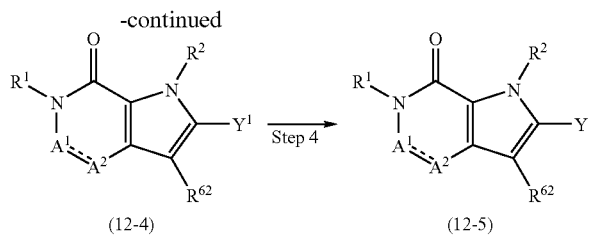

wherein $A^1$, $A^2$, $R^1$, $R^2$, $Y^1$ and Y are as defined above; a compound of the formula (12-1) includes the compound (9-3) described in production process 9 and the compound (11-3) described in production process 11; L1 is a fluorine atom, a chlorine atom, a bromine atom or an iodine atom; and $R^{62}$ is "an optionally substituted alkyl group", "an optionally substituted alkenyl group", "an optionally substituted alkynyl group", "an optionally substituted cycloalkyl group", "an optionally substituted aryl group", "an optionally substituted heteroaryl group", "an optionally substituted aralkyl group" or "an optionally substituted heteroarylalkyl group".

1) Step 1

A compound (12-2) may be produced from a compound (12-1) by the same production process as described in literature (for example, Synth. Commun. 33, 2671 (2003), Tetrahedron Letters 42, 863 (2001), Synthesis 926 (1995), Tetrahedron Letters 37, 1095 (1996), J. Org. Chem. 64, 5366 (1999) Indian J. Chem., Sect B 35, 141 (1996) and J. Heterocycl. Chem. 24, 1313 (1987)).

2) Step 2

The compound (12-3) may be produced from the compound (12-2) by the same process as in the step 2 described in production process 2.

3) Step 3

A compound (12-4) may be produced from the compound (12-2) by the same production process as described in literature (for example, Chem. Rev. 95, 2457 (1995), Chem. Rev. 103, 1979 (2003), Chem. Rev. 100, 3009 (2000) Organic Process Research & Development 5, 254 (2001), J. Med. Chem. 45, 999 (2002), Synthesis 563 (1997), J. Org. Chem. 65, 9001 (2000), J. Org. Chem. 64, 4196 (1999), J. Org. Chem. 67, 3904 (2002), Adv. Synth. Catal. 345, 620 (2003) and J. Med. Chem. 43, 675 (2000)).

4) Step 4

The compound (12-5) may be produced from the compound (12-4) by the same process as in the step 2 described in production process 2.

Production Process 13

A compound of the formula (13-4) as the compound of the formula (I), or a salt thereof is produced, for example, by the following process:

[Formula 45]

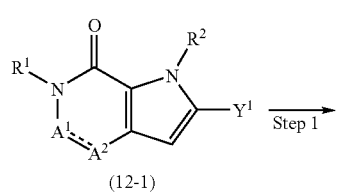

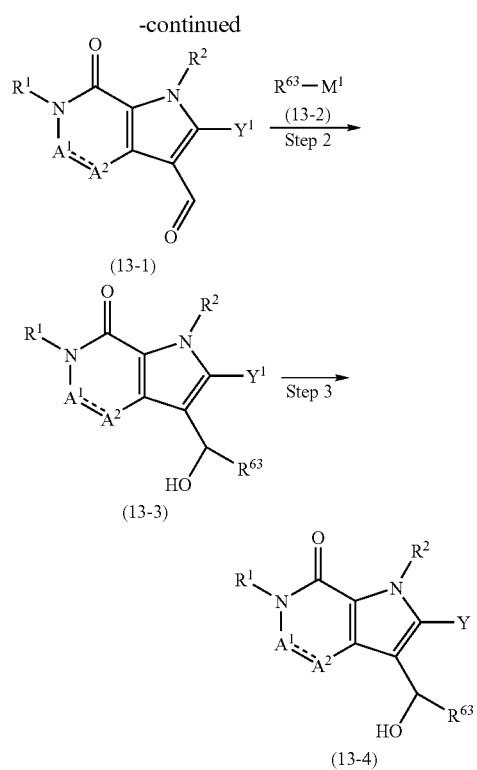

wherein $A^1$, $A^2$, $R^1$, $R^2$, $M^1$, $Y^1$ and Y are as defined above; a compound of the formula (12-1) is as described above; and $R^{63}$ is "an optionally substituted alkyl group", "an optionally substituted cycloalkyl group", "an optionally substituted aryl group" or "an optionally substituted heteroaryl group".

1) Step 1

A compound (13-1) may be produced from a compound (12-1) by the same production process as described in literature (for example, J. Heterocycl. Chem. 30, 957 (1993), Chem. Pharm. Bull. 42, 237 (1994), Aust. J. Chem. 47, 1009 (1994) and J. Heterocycl. Chem. 12, 517 (1975)).

2) Step 2

A compound (13-3) may be produced from the compound (13-1) by the same production process as described in literature (for example, R. C. Larock Comprehensive Organic transformation VCH publisher Inc., 1989).

As a compound (13-2), a commercial one may be used, or the compound (13-2) may be produced by the process described, for example, in Japanese Chemical Association, Jikken Kagaku Koza (Experimental Chemistry) Vol. 25, Maruzen Co., Ltd.

3) Step 3

The compound (13-4) may be produced from the compound (13-3) by the same process as in the step 2 described in production process 2.

Production Process 14

A compound of the formula (14-2) as the compound of the formula (I), or a salt thereof is produced, for example, by the following process:

[Formula 46]

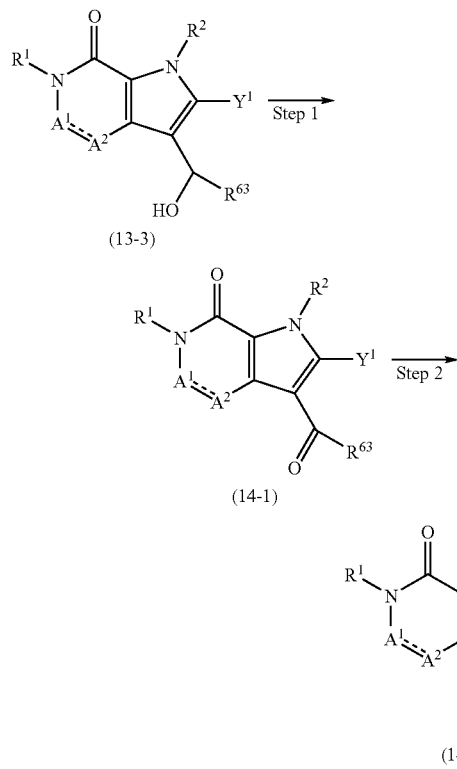

wherein $A^1$, $A^2$, $R^1$, $R^2$, $R^{63}$, $Y^1$ and Y are as defined above.

1) Step 1

A compound (14-1) may be produced from a compound (13-3) by the same production process as described in literature (for example, R. C. Larock Comprehensive Organic transformation VCH publisher Inc., 1989).

2) Step 2

The compound (14-2) may be produced from the compound (14-1) by the same process as in the step 2 described in production process 2.

Production Process 15

A compound of the formula (15-4) as the compound of the formula (I), or a salt thereof is produced, for example, by the following process:

[Formula 47]

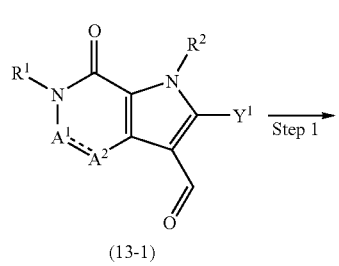

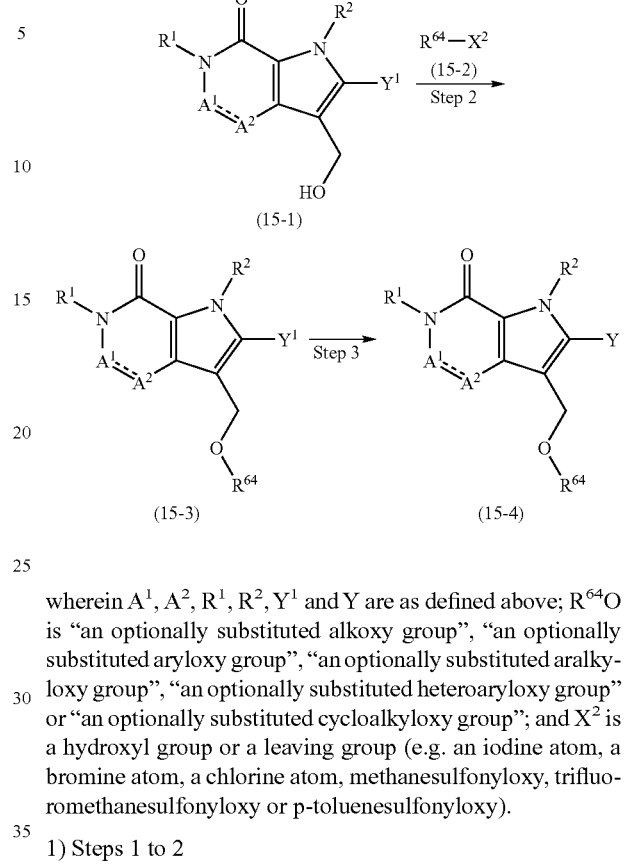

wherein $A^1$, $A^2$, $R^1$, $R^2$, $Y^1$ and Y are as defined above; $R^{64}O$ is "an optionally substituted alkoxy group", "an optionally substituted aryloxy group", "an optionally substituted aralkyloxy group", "an optionally substituted heteroaryloxy group" or "an optionally substituted cycloalkyloxy group"; and $X^2$ is a hydroxyl group or a leaving group (e.g. an iodine atom, a bromine atom, a chlorine atom, methanesulfonyloxy, trifluoromethanesulfonyloxy or p-toluenesulfonyloxy).

1) Steps 1 to 2

A compound (15-3) may be produced from a compound (13-1) by the same production process as described in literature (for example, R. C. Larock Comprehensive Organic transformation VCH publisher Inc., (1989) Organic Reactions (N.Y.) 42, 335-656 (1992), Tetrahedron Lett. 44, 4873 (2003) and J. Am. Chem. Soc. 125, 4978 (2003)).

2) Step 3

The compound (15-4) may be produced from the compound (15-3) by the same process as in the step 2 described in production process 2.

Production Process 16

A compound of the formula (16-2) as the compound of the formula (I), or a salt thereof is produced, for example, by the following process:

[Formula 48]

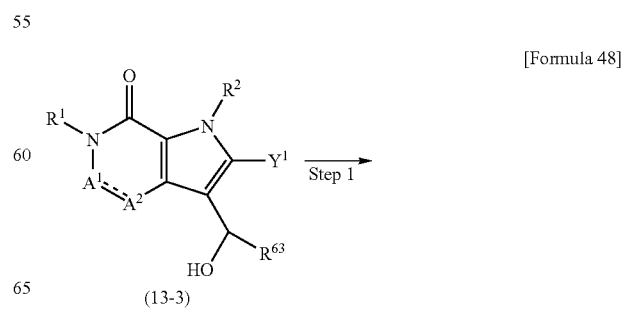

-continued

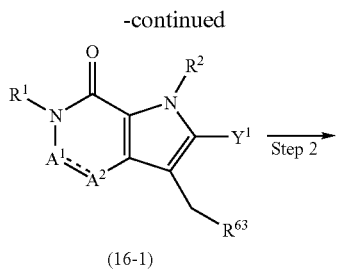

(16-1)

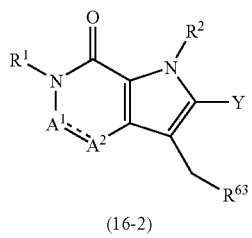

(16-2)

wherein $A^1$, $A^2$, $R^1$, $R^2$, $R^{63}$, $Y^1$ and Y are as defined above.

1) Step 1

A compound (16-1) may be produced from a compound (13-3) by the same production process as described in literature (for example, R. C. Larock Comprehensive Organic transformation VCH publisher Inc., (1989), J. Org. Chem. 65, 6179 (2000), J. Org. Chem. 58, 6913 (1993), Bull. Chem. Soc. Jpn. 67, 1107 (1994) and J. Org. Chem. 60, 2430 (1995).

2) Step 2

The compound (16-2) may be produced from the compound (16-1) by the same process as in the step 2 described in production process 2.

Production Process 17

A compound of the formula (17-2) as the compound of the formula (I), or a salt thereof is produced, for example, by the following process:

[Formula 49]

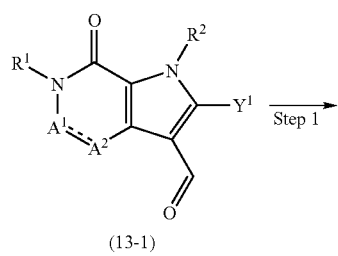

(13-1)

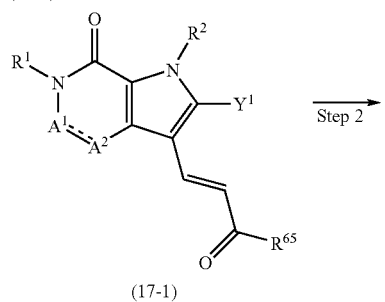

(17-1)

-continued

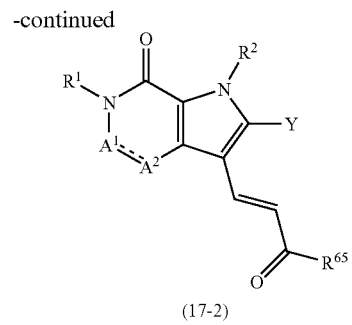

(17-2)

wherein $A^1$, $A^2$, $R^1$, $R^2$, $Y^1$ and Y are as defined above, and $R^{65}C(O)$ is a carboxyl group, "an optionally substituted carbamoyl group", "an optionally substituted alkoxycarbonyl group", "an optionally substituted aryloxycarbonyl group", "an optionally substituted aralkyloxycarbonyl group", "an optionally substituted cycloalkyloxycarbonyl group", "an optionally substituted alkylcarbonyl group", "an optionally substituted heteroarylcarbonyl group", "an optionally substituted aroyl group" or "an optionally substituted cycloalkylcarbonyl group".

1) Step 1

A compound (17-1) may be produced from a compound (13-1) by the same production process as described in literature (for example, R. C. Larock Comprehensive Organic transformation VCH publisher Inc., (1989) and A. Hassner et al. Organic Synthesis Based On Name Reactions And Unnamed Reactions, Elsevier Science Ltd., (1994)).

In the case of a compound (17-1) in which $R^{65}C(O)$ is "an optionally substituted alkoxycarbonyl group", "an optionally substituted aryloxycarbonyl group", "an optionally substituted aralkyloxycarbonyl group" or "an optionally substituted cycloalkyloxycarbonyl group", this compound may be converted to another compound (17-1) in which $R^{65}C(O)$ is a carboxyl group by the same process as that described in literature (for example, Protective Groups in Organic Synthesis 2nd Edition (John Wiley & Sons, Inc.)) or the like.

2) Step 2

The compound (17-2) may be produced from the compound (17-1) by the same process as in the step 2 described in production process 2.

Production Process 18

A compound of the formula (18-4) as the compound of the formula (I), or a salt thereof is produced, for example, by the following process:

[Formula 50]

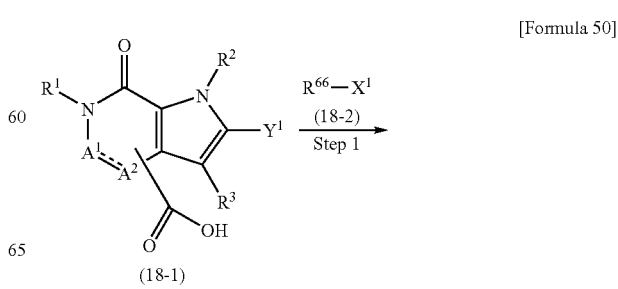

(18-1)

-continued

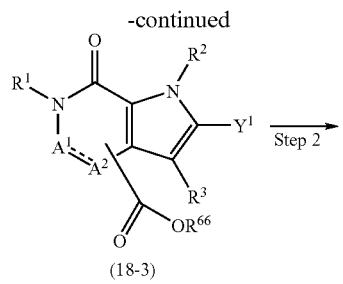
(18-3)

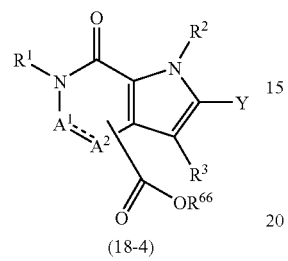
(18-4)

wherein $A^1, A^2, R^1, R^2, R^3, X^1, Y^1$ and Y are as defined above; $CO_2H$ shown in a compound (18-1) indicates that $R^3$ or $R^4$ shown in the formula (I) is a carboxyl group or that a carboxyl group is present in the partial structure of $R^3$, $R^4$ or $R^5$; and $CO_2R^{66}$ shown in a compound (18-3) and the compound (18-4) indicates a state in which the $CO_2H$ of the compound (18-1) has been converted to $CO_2R^{66}$, and specifically, $CO_2R^{66}$ indicates, for example, the formula: C(O)O—Re wherein Re is as defined above.

1) Step 1

A compound (18-3) may be produced by reacting a compound (18-1) with a compound (18-2) in an inert solvent in the presence of a base. The amount of the compound (18-2) used is usually chosen in the range of 1 to 3 equivalents per equivalent of the compound (18-1). The base includes, for example, alkali carbonates (e.g. potassium carbonate, sodium carbonate, potassium hydrogencarbonate and sodium hydrogencarbonate), alkali hydroxides (e.g. potassium hydroxide and sodium hydroxide), alkali hydrides (e.g. sodium hydride and potassium hydride), and alkoxyalkalis (e.g. potassium tert-butoxide). Suitable examples thereof are potassium carbonate and sodium hydride. The amount of the base used is usually chosen in the range of 1 to 5 equivalents per equivalent of the compound (18-1). The inert solvent includes, for example, aprotic solvents (e.g. N,N-dimethylformamide and dimethyl sulfoxide), ether solvents (e.g. diethyl ether, tetrahydrofuran and 1,4-dioxane), ketones (e.g. acetone), and mixed solvents thereof. A suitable example thereof is N,N-dimethylformamide. The reaction temperature may be chosen in the range of about 10° C. to about 100° C.

As the compound (18-2), a commercial reagent may be used, or the compound (18-2) may be produced by the same production process as described in literature (for example, WO03/027098, WO00/06581, and R. C. Larock Comprehensive Organic transformation VCH publisher Inc., 1989).

2) Step 2

The compound (18-4) may be produced from the compound (18-3) by the same process as in the step 2 described in production process 2.

Production Process 19

The compound (1-2) described in production process 1 may be produced, for example, by the following process:

[Formula 51]

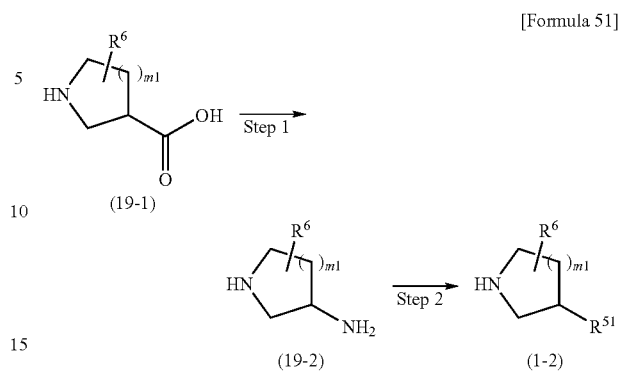

wherein m1, $R^6$ and $R^{51}$ are as defined above.

1) Step 1

A compound (19-2) may be produced from a compound (19-1) by the same production process as described in literature (for example, J. Org. Chem. 58, 879 (1993)).

2) Step 2

The compound (1-2) may be produced from the compound (19-2) by the same process as that described in literature (for example, Protective Groups in Organic Synthesis 2nd Edition (John Wiley & Sons, Inc.)) or the like.

Production Process 20

The compound (1-3) described in production process 1 may be produced, for example, by the following process:

[Formula 52]

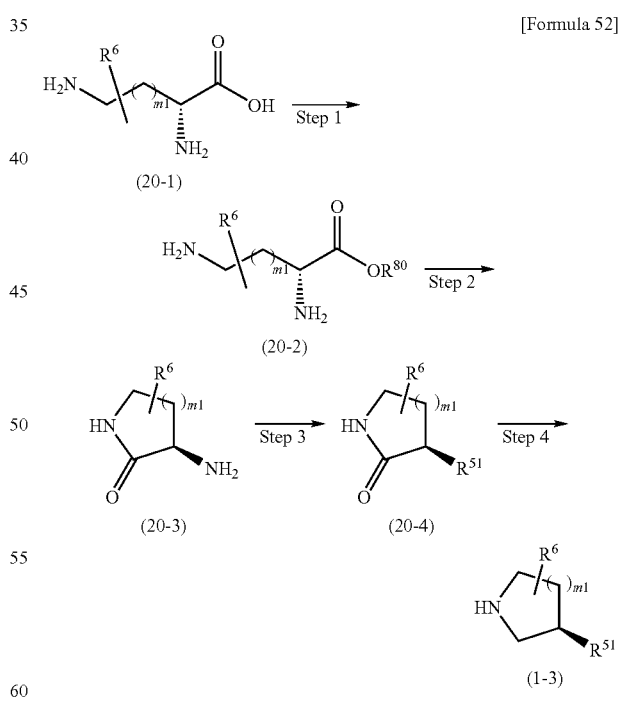

wherein m1, $R^6$ and $R^{51}$ are as defined above, and $R^{80}$ is an alkyl group.

1) Step 1

A compound (20-2) may be produced by reacting a compound (20-1) with thionyl chloride in an alcohol solvent. The alcohol solvent includes methanol, ethanol, etc. The amount of thionyl chloride used is usually chosen in the range of 2 to 10 equivalents per equivalent of the compound (20-1). The reaction temperature may be chosen in the range of about −90° C. to about 30° C.

2) Step 2

A compound (20-3) may be produced by reacting the compound (20-2) with a base in water solvent. The base includes sodium hydrogencarbonate, potassium hydrogencarbonate, sodium carbonate, potassium carbonate, etc. The reaction temperature may be chosen in the range of about 30° C. to about 100° C.

3) Step 3

A compound (20-4) may be produced from the compound (20-3) by the same process as that described in literature (for example, Protective Groups in Organic Synthesis 2nd Edition (John Wiley & Sons, Inc.)) or the like.

4) Step 4

The compound (1-3) may be produced by reacting the compound (20-4) with a reducing agent in an inert solvent. The reducing agent includes aluminum lithium hydride, borane complexes (e.g. borane-dimethyl sulfide complexes and borane-tetrahydrofuran complexes) and the like. The inert solvent includes tetrahydrofuran, 1,4-dioxane, mixed solvents thereof and the like. The reaction temperature is chosen in the range of about −20° C. to about 60° C.

Examples of the synthesis of compounds (1-2a) to (1-2j) as specific examples of the compound (1-2) are given below. The compounds (1-2a) to (1-2j) include pharmaceutically acceptable salts thereof.

[Formula 53]

| Compound | Production process |
|---|---|
| 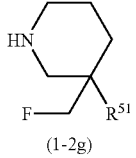<br>(1-2a): $X^4$ = CH$_3$<br>(1-2b): $X^4$ = CH$_2$CH$_3$<br>(1-2c): $X^4$ = CH$_2$CH$_2$OH<br>(1-2d): $X^4$ = CH$_2$CH$_2$F<br>(1-2e): $X^4$ = H | WO 02/48138<br>J. Chem. Soc., Perkin Trans. 1, 2233 (1999)<br>Protective Groups in Organic Synthesis<br>2nd Edition (John Wiley & Sons, Inc.) |
| 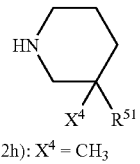<br>(1-2f) | J. Org. Chem. 44, 2732 (1979)<br>J. Chem. Soc., Perkin Trans. 1, 2233 (1999)<br>Protective Groups in Organic Synthesis<br>2nd Edition (John Wiley & Sons, Inc.) |

[Formula 54]

| Compound | Production process |
|---|---|
| 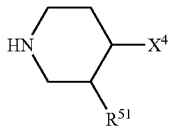<br>(1-2g) | Synthesized from compound (1-2f) as a starting material according to, for example, the process described in J. Org. Chem. 44, 3872 (1979)<br>J. Chem. Soc., Perkin Trans. 1, 2233 (1999)<br>Protective Groups in Organic Synthesis<br>2nd Edition (John Wiley & Sons, Inc.) |
| 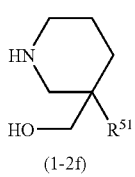<br>(1-2h): $X^4$ = CH$_3$<br>(1-2i): $X^4$ = CH$_2$CH$_3$<br>(1-2j): $X^4$ = CH$_2$CH$_2$CH$_3$ | Arch. Pharm. 322, 499 (1989)<br>J. Chem. Soc., Perkin Trans. 1, 2233 (1999)<br>Protective Groups in Organic Synthesis<br>2nd Edition (John Wiley & Sons, Inc.) | wherein $R^{51}$ is as defined above.

As hydrochloride of the compound (1-2e) a commercial one may also be used. It is also possible to synthesize the compound (1-2) from a substituted DL-ornithine by a well-known process. A specific example of the process is that described in literature (for example, R. C. Ralock, "Comprehensive Organic transformation", VCH publisher Inc., 1989).

Examples of the synthesis of compounds (1-3a) to (1-3i) as specific examples of the compound (1-3) are given below. The compounds (1-3a) to (1-3i) include pharmaceutically acceptable salts thereof.

[Formula 55]

| Compound | Production process |
|---|---|
| 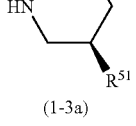<br>(1-3a) | WO 01/27082<br>J. Chem. Soc., Perkin Trans. 1, 2233 (1999)<br>Protective Groups in Organic Synthesis<br>2nd Edition (John Wiley & Sons, Inc.) |
| 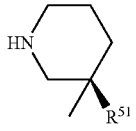<br>(1-3b) | Int. J. Peptide Protein Res. 40, 119 (1992)<br>WO 01/27082<br>J. Chem. Soc., Perkin Trans. 1, 2233 (1999)<br>Protective Groups in Organic Synthesis<br>2nd Edition (John Wiley & Sons, Inc.) |
| 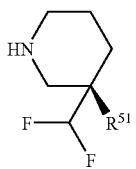<br>(1-3c) | U.S. Pat. No. 4,413,141<br>WO 01/27082<br>J. Chem. Soc., Perkin Trans. 1, 2233 (1999)<br>Protective Groups in Organic Synthesis<br>2nd Edition (John Wiley & Sons, Inc.) |

-continued

[Formula 55]

| Compound | Production process |
|---|---|
|  (1-3d) | Tetrahedron: Asymmetry 8, 327 (1997)<br>WO 01/27082<br>J. Chem. Soc., Perkin Trans. 1, 2233 (1999)<br>Protective Groups in Organic Synthesis<br>2nd Edition (John Wiley & Sons, Inc.) |
| 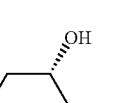 (1-3e) | Tetrahedron: Asymmetry 11, 567 (2000)<br>J. Chem. Soc., Perkin Trans. 1, 2233 (1999)<br>Protective Groups in Organic Synthesis<br>2nd Edition (John Wiley & Sons, Inc.) | wherein $R^{51}$ is as defined above.

[Formula 56]

| Compound | Production process |
|---|---|
| 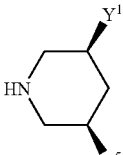 (1-3f) | Chem. Eur. J. 6, 2830 (2000)<br>WO 00/26332<br>J. Chem. Soc., Perkin Trans. 1, 2233 (1999)<br>Protective Groups in Organic Synthesis<br>2nd Edition (John Wiley & Sons, Inc.) |
| 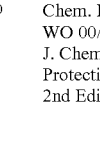 (1-3g) | JP-T-2002-525325<br>J. Chem. Soc., Perkin Trans. 1, 2233 (1999)<br>Protective Groups in Organic Synthesis<br>2nd Edition (John Wiley & Sons, Inc.) |
| 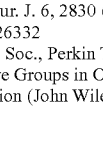 (1-3h) | Bull. Chem. Soc. Jpn. 53, 2605 (1980)<br>J. Chem. Soc., Perkin Trans. 1, 2233 (1999)<br>Protective Groups in Organic Synthesis<br>2nd Edition (John Wiley & Sons, Inc.) |
| 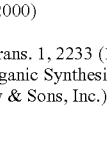 (1-3i) | Synthesized from compound (1-3h) as a starting material according to, for example, the process described in J. Am. Chem. Soc. 80, 2584 (1958)<br>J. Chem. Soc. PT1 499 (1972) J. Chem. Soc., Perkin Trans. 1, 2233 (1999)<br>Protective Groups in Organic Synthesis<br>2nd Edition (John Wiley & Sons, Inc.) | wherein $R^{51}$ is as defined above, and $Y^{10}$ is $NH_2$, Alloc, NHBoc or NHCbz.

Examples of the synthesis of compounds (1-3j) to (1-3v) as specific examples of the compound (1-3) are given below. The compounds (1-3j) to (1-3v) include pharmaceutically acceptable salts thereof.

[Formula 57]

| Compound | Production process |
|---|---|
|  (1-3j) | Synthesized from compound (1-3f in which $Y^{10}$ is $NH_2$) as a starting material according to, for example, the process described in<br>J. Chem. Soc. Chem. Commun. 611 (1981)<br>J. Chem. Soc., Perkin Trans. 1, 2233 (1999)<br>Protective Groups in Organic Synthesis<br>2nd Edition (John Wiley & Sons, Inc.) |
| 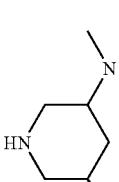 (1-3k) | Synthesized from compound (1-3f in which $Y^{10}$ is $NH_2$) as a starting material according to, for example, the process described in<br>J. Chem. Soc. Chem. Commun. 611 (1981)<br>J. Chem. Soc., Perkin Trans. 1, 2233 (1999)<br>Protective Groups in Organic Synthesis<br>2nd Edition (John Wiley & Sons, Inc.) |
| 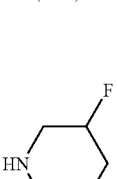 (1-3l) | Synthesized from compound (1-3h) as a starting material according to, for example, the process described in<br>J. Org. Chem. 44, 3872 (1979),<br>J. Chem. Soc., Perkin Trans. 1, 2233 (1999)<br>Protective Groups in Organic Synthesis<br>2nd Edition (John Wiley & Sons, Inc.) |
| 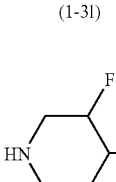 (1-3m) | Synthesized from compound (1-3e) as a starting material according to, for example, the process described in<br>J. Org. Chem. 44, 3872 (1979)<br>J. Chem. Soc., Perkin Trans. 1, 2233 (1999)<br>Protective Groups in Organic Synthesis<br>2nd Edition (John Wiley & Sons, Inc.) |
| 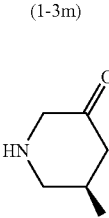 (1-3n) | Synthesized from compound (1-3h) as a starting material according to, for example, the process described in<br>Bull Chem. Soc. Jpn. 64, 2857 (1991)<br>J. Chem. Soc., Perkin Trans. 1, 2233 (1999)<br>Protective Groups in Organic Synthesis<br>2nd Edition (John Wiley & Sons, Inc.) | wherein $R^{51}$ is as defined above.

[Formula 58]

| Compound | Production process |
|---|---|
| 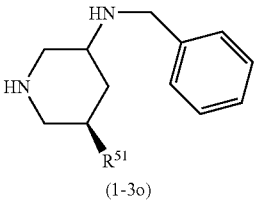<br>(1-3o) | Synthesized from compound (1-3f in which $Y^{10}$ is $NH_2$) as a starting material according to, for example, the process described in Tetrahedron Lett. 40, 5609 (1999)<br>J. Chem. Soc., Perkin Trans. 1, 2233 (1999)<br>Protective Groups in Organic Synthesis 2nd Edition (John Wiley & Sons, Inc.) |
| 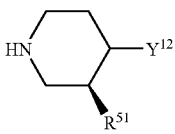<br>(1-3p): $Y^{12}$ = (R)—$C_6H_5$<br>(1-3q): $Y^{12}$ = (S)—$C_6H_5$ | J. Med. Chem. 35, 833 (1992),<br>R. C. Larock, "Comprehensive Organic transformation",<br>VCH publisher Inc., 1989,<br>J. Chem. Soc., Perkin Trans. 1, 2233 (1999)<br>Protective Groups in Organic Synthesis 2nd Edition (John Wiley & Sons, Inc.) |
| 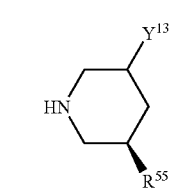<br>(1-3r): $Y^{13}$ = $NHS(O)_2CH_3$<br>(1-3s): $Y^{13}$ = $NHC(O)CH_3$<br>(1-3t): $Y^{13}$ = $NHC(O)C_6H_5$<br>(1-3u): $Y^{13}$ = $N(CH_3)C(O)CH_3$ | Synthesized from compound (1-3f in which $Y^{10}$ is $NH_2$) as a starting material according to, for example, the process described in R. C. Larock "Comprehensive Organic transformation",<br>VCH publisher Inc., 1989,<br>J. Chem. Soc., Perkin Trans. 1, 2233 (1999)<br>Protective Groups in Organic Synthesis 2nd Edition (John Wiley & Sons, Inc.) |
| 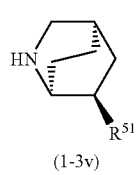<br>(1-3v) | WO 02/068420<br>J. Chem. Soc., Perkin Trans. 1, 2233 (1999)<br>Protective Groups in Organic Synthesis 2nd Edition (John Wiley & Sons, Inc.) | wherein $R^{51}$ is as defined above.

Examples of the synthesis of compounds (1-3w) to (1-3dd) as specific examples of the compound (1-3) are given below. The compounds (1-3w) to (1-3dd) include pharmaceutically acceptable salts thereof.

[Formula 59]

| Compound | Production process |
|---|---|
| 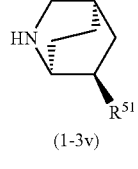<br>(1-3w): $Y^{14}$ = 2-$CH_3$—$C_6H_5$<br>(1-3x): $Y^{14}$ = 3-$CH_3$—$C_6H_5$<br>(1-3y): $Y^{14}$ = 4-$CH_3$—$C_6H_5$<br>(1-3z): $Y^{14}$ = 2-$CH_3O$—$C_6H_5$<br>(1-3aa): $Y^{14}$ = 3-$CH_3O$—$C_6H_5$<br>(1-3bb): $Y^{14}$ = 4-$CH_3O$—$C_6H_5$<br>(1-3cc): $Y^{14}$ = $C_6H_5$<br>(1-3dd): $Y^{14}$ = $CH_2C_6H_5$ | Synthesized from compound (1-3f in which $Y^{10}$ is $NH_2$) as a starting material according to, for example, the process described in R. C. Larock, "Comprehensive Organic transformation",<br>VCH publisher Inc., 1989<br>J. Org., Chem. 66, 3593 (2001),<br>J. Prakt. Chem. 342, 421 (2000),<br>Tetrahedron Lett. 36, 5611 (1994),<br>J. Org., Chem. 53, 5143 (1988),<br>Bioorg. Med. Chem. Lett. 11, 1281 (2001),<br>J. Chem. Soc., Perkin Trans. 1, 2233 (1999)<br>Protective Groups in Organic Synthesis 2nd Edition (John Wiley & Sons, Inc.) | wherein $R^{51}$ is as defined above.

The compound (1-3) may be synthesized from a substituted D-ornithine by a well-known process. A specific example of the process is that described in literature (for example, R. C. Larock Comprehensive Organic transformation VCH publisher Inc., 1989).

Production Process 21

The compound (1-5) described in production process 1 may be produced, for example, by the following process:

[Formula 60]

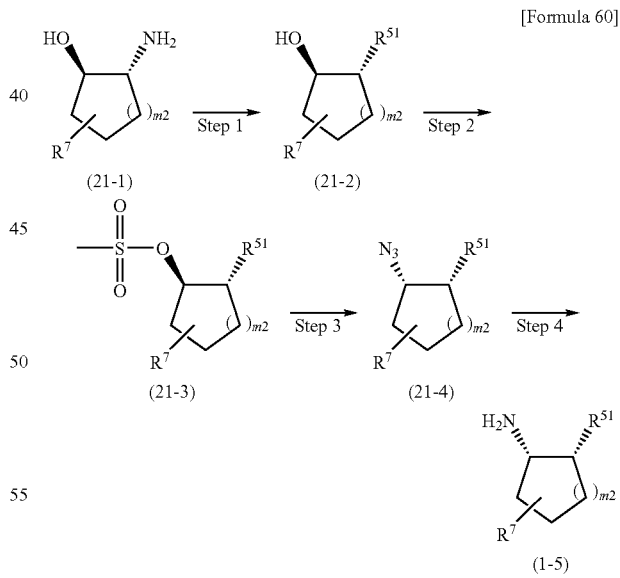

wherein m2, $R^7$ and $R^{51}$ are as defined above.

1) Step 1

A compound (21-2) may be produced from a compound (21-1) by the same process as that described in literature (for example, Protective Groups in Organic Synthesis 2nd Edition (John Wiley & Sons, Inc.)) or the like.

2) Steps 2 to 4

The compound (1-5) may be produced from the compound (21-2) by the same process as described in literature (for example, R. C. Larock Comprehensive Organic transformation VCH publisher Inc., 1989).

Examples of the synthesis of compounds (1-5a) to (1-5aa) as specific examples of the compound (1-5) are given below. The compounds (1-5a) to (1-5aa) include pharmaceutically acceptable salts thereof.

The compounds (1-5a) to (1-5aa) may be produced according to the processes described in literature (for example, WO01/74774 and R. C. Larock Comprehensive Organic transformation VCH publisher Inc., 1989).

[Formula 61]

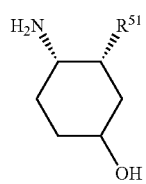 (1-5a)

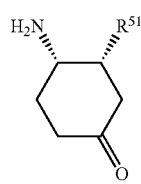 (1-5b)

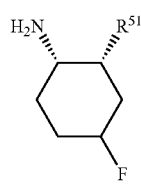 (1-5c)

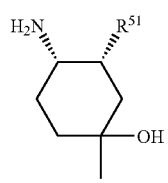 (1-5d)

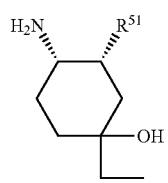 (1-5e)

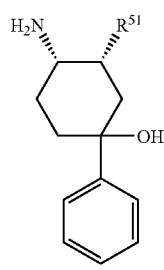 (1-5f)

-continued

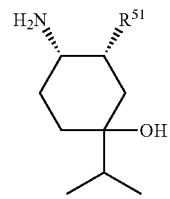 (1-5g)

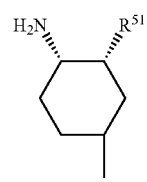 (1-5h)

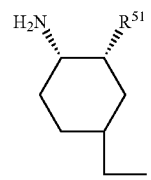 (1-5i)

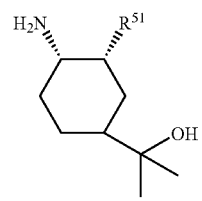 (1-5j)

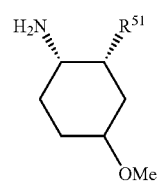 (1-5k)

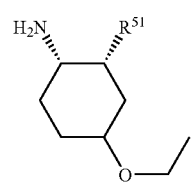 (1-5l)

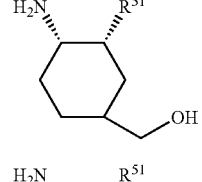 (1-5m)

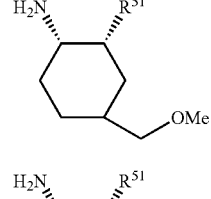 (1-5n)

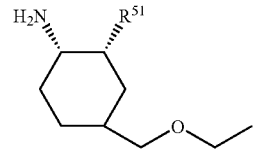 (1-5o)

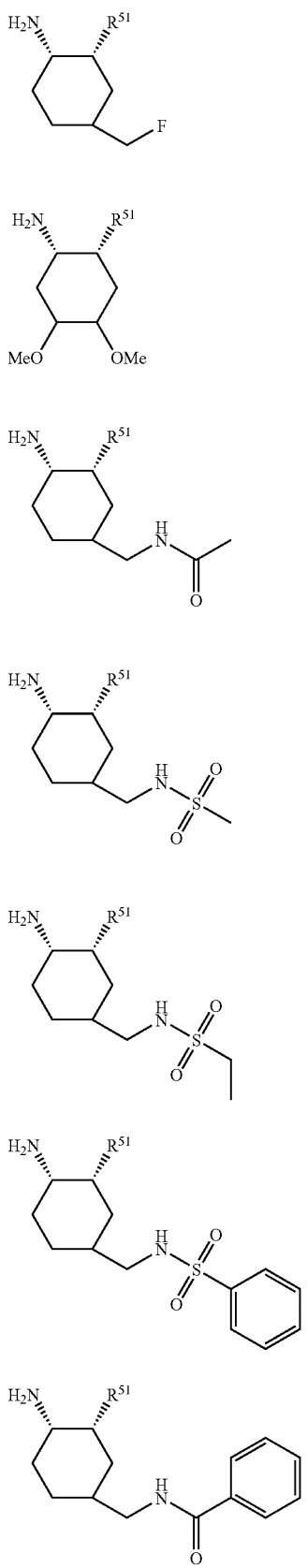
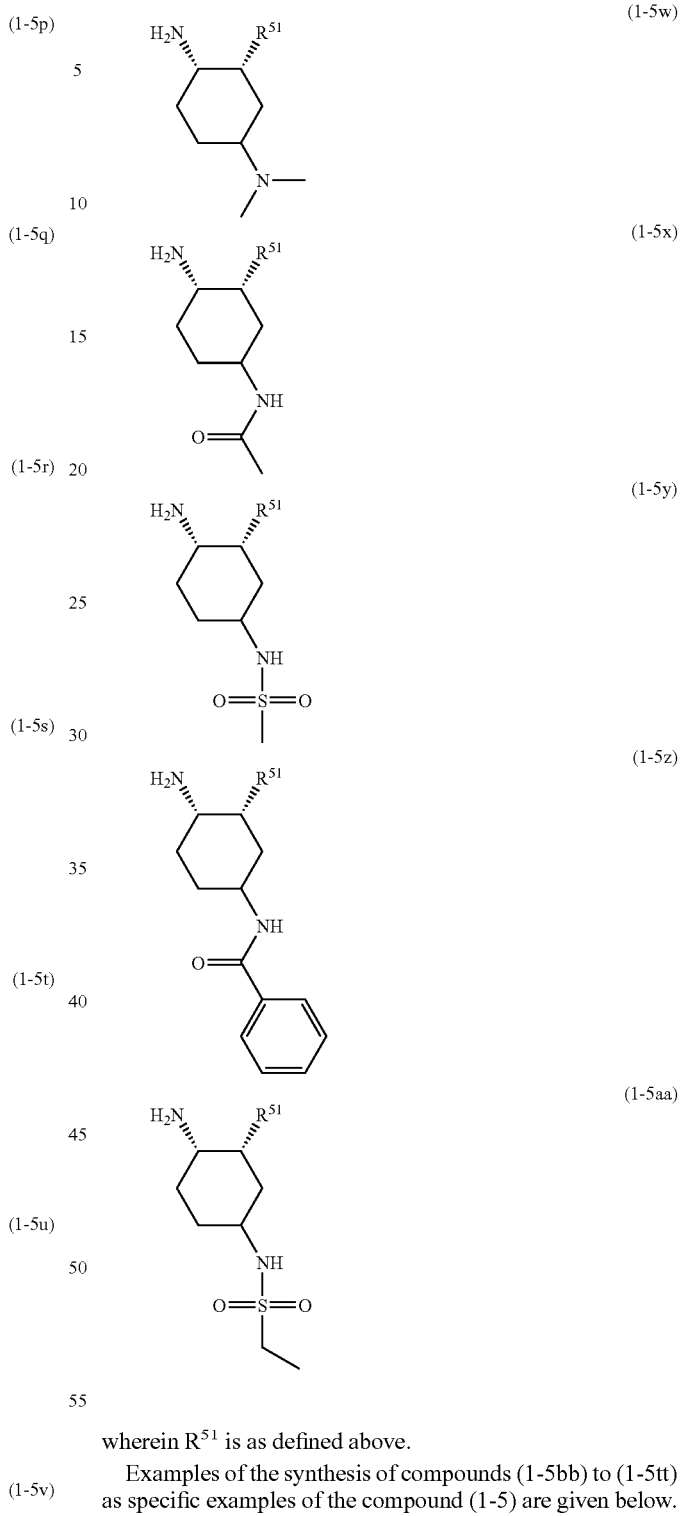

wherein $R^{51}$ is as defined above.

Examples of the synthesis of compounds (1-5bb) to (1-5tt) as specific examples of the compound (1-5) are given below. The compounds (1-5bb) to (1-5tt) include pharmaceutically acceptable salts thereof.

The compounds (1-5bb) to (1-5tt) may be produced according to the processes described in literature (for example, WO01/74774, R. C. Larock Comprehensive Organic transformation VCH publisher Inc., 1989, and Protective Groups in Organic Synthesis 2nd Edition (John Wiley & Sons, Inc.)).

[Formula 62]
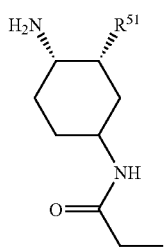 (1-5bb)
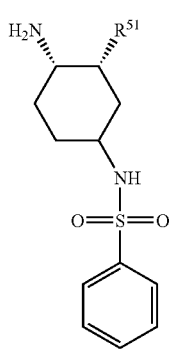 (1-5cc)
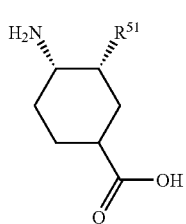 (1-5dd)
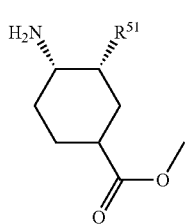 (1-5ee)
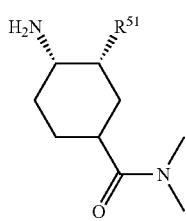 (1-5ff)
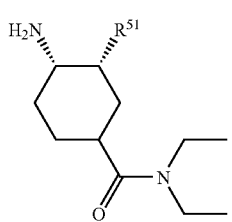 (1-5gg)
-continued
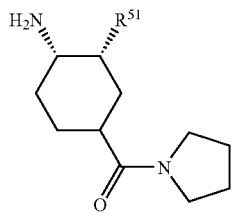 (1-5hh)
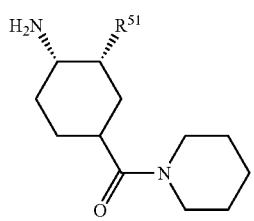 (1-5ii)
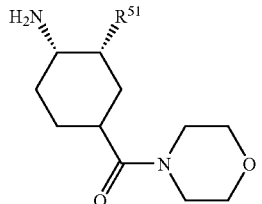 (1-5jj)
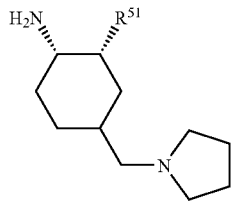 (1-5kk)
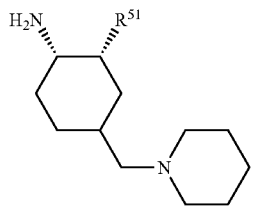 (1-5ll)
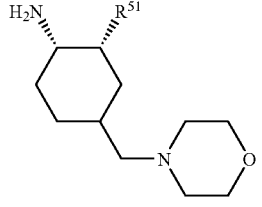 (1-5mm)
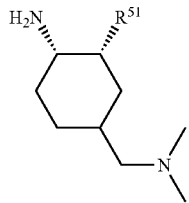 (1-5nn)

-continued
(1-5oo) 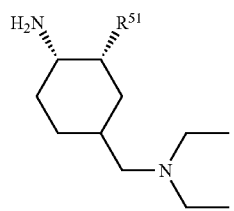
(1-5pp) 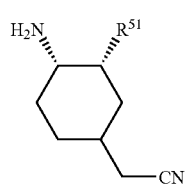
(1-5qq) 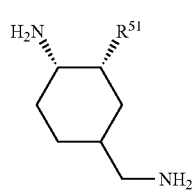
(1-5rr) 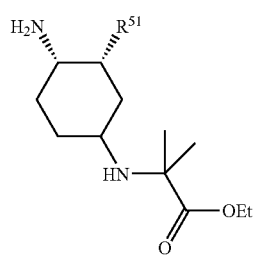
(1-5ss) 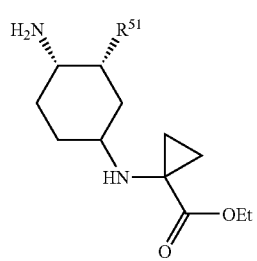
(1-5tt) 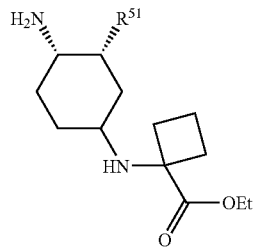
wherein $R^{51}$ is as defined above.
Production Process 22
A compound (22-10) as a specific example of the compound (1-6) described in production process 1 may be produced, for example, by the following process:
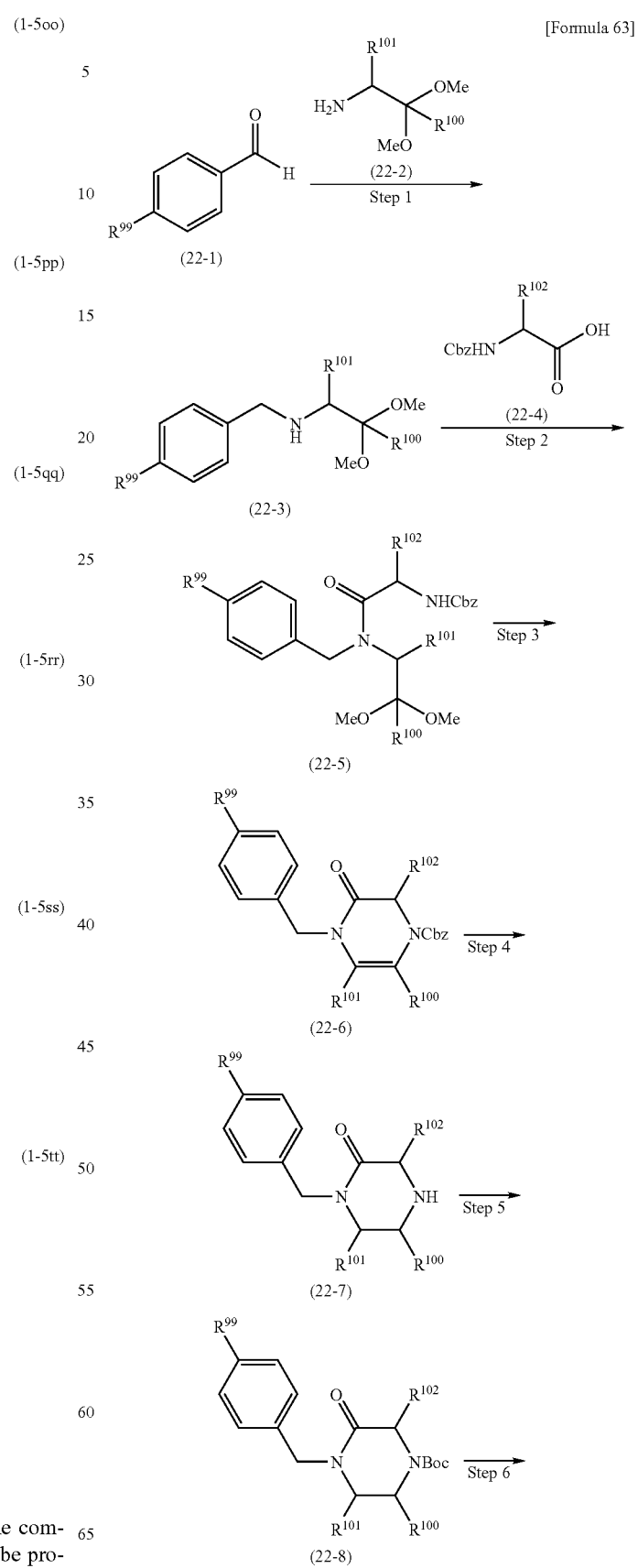

-continued

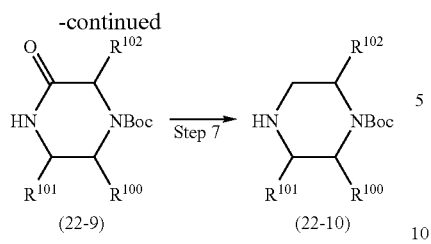

wherein $R^{100}$, $R^{101}$ and $R^{102}$ are independently a hydrogen atom, "an optionally substituted alkyl group", "an optionally substituted aryl group" or "an optionally substituted aralkyl group", and R99 is a hydrogen atom or methoxy.

1) Step 1

A compound (22-3) may be produced by carrying out reductive amination of a compound (22-1) with a compound (22-2) by the same method as described in literature (for example, R. C. Larock Comprehensive Organic transformation VCH publisher Inc., 1989).

2) Steps 2 to 4

A compound (22-7) may be produced from the compound (22-3) by the same production process as described in literature (e.g. WO01/07436).

3) Step 5

A compound (22-8) may be produced from the compound (22-7) by the same production process as described in literature (for example, Protective Groups in Organic Synthesis 2nd Edition (John Wiley & Sons, Inc.)).

4) Step 6

A compound (22-9) may be produced from the compound (22-8) by the same production process as described in literature (for example, J. Chem. Soc. Perkin Trans. I 3281 (2001), Heterocycles 38, 17 (1994), Tetrahedron Lett. 34, 6673 (1993), J. Org. Chem. 60, 4602 (1995) and J. Med. Chem. 38, 2866 (1995)).

5) Step 7

The compound (22-10) may be produced from the compound (22-9) by the same process as that described in literature (for example, R. C. Larock Comprehensive Organic transformation VCH publisher Inc., 1989) or the like.

Examples of the synthesis of compounds (22-10a) to (22-101) as specific examples of the compound (22-10) are given below. The compounds (22-10a) to (22-101) include pharmaceutically acceptable salts thereof.

[Formula 64]

(22-10a)

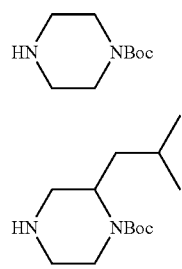

(22-10b)

-continued (22-10c)

(22-10d)

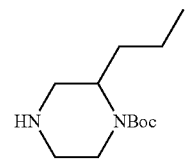

(22-10e)

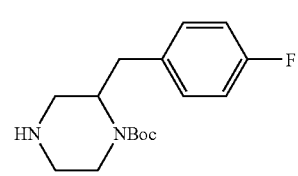

(22-10f)

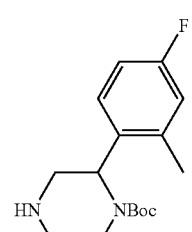

(22-10g)

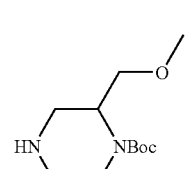

(22-10h)

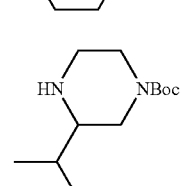

(22-10i)

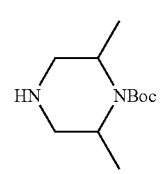

(22-10j)

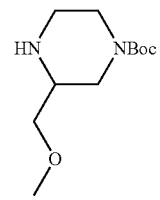

(22-10k)

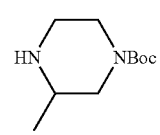

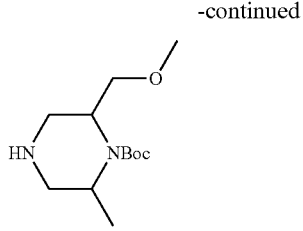
(22-101)

Production Process 23

Each of compounds of the formula (23-2), formula (23-3), formula (23-5), formula (23-6), formula (23-7), formula (23-8) and formula (12-1) is produced, for example, by the following process:

equivalents per equivalent of the compound (23-2), and 2,5-dimethoxytetrahydrofuran may be used also as a solvent. The inert solvent includes, for example, aprotic solvents (e.g. N,N-dimethylformamide and dimethyl sulfoxide), ether solvents (e.g. diethyl ether, tetrahydrofuran and 1,4-dioxane), ketones (e.g. acetone), aprotic solvents (e.g. acetonitrile, N,N-dimethylformamide and dimethyl sulfoxide), and mixed solvents thereof. Suitable examples thereof are N,N-dimethylformamide and dimethyl sulfoxide. The reaction temperature may be chosen in the range of about 10° C. to about 80° C.

3) Step 3

The compound (23-5) may be produced by reacting the compound (23-3) with a compound (23-4) in an inert solvent. The amount of the compound (23-4) used is usually chosen in

[Formula 65]

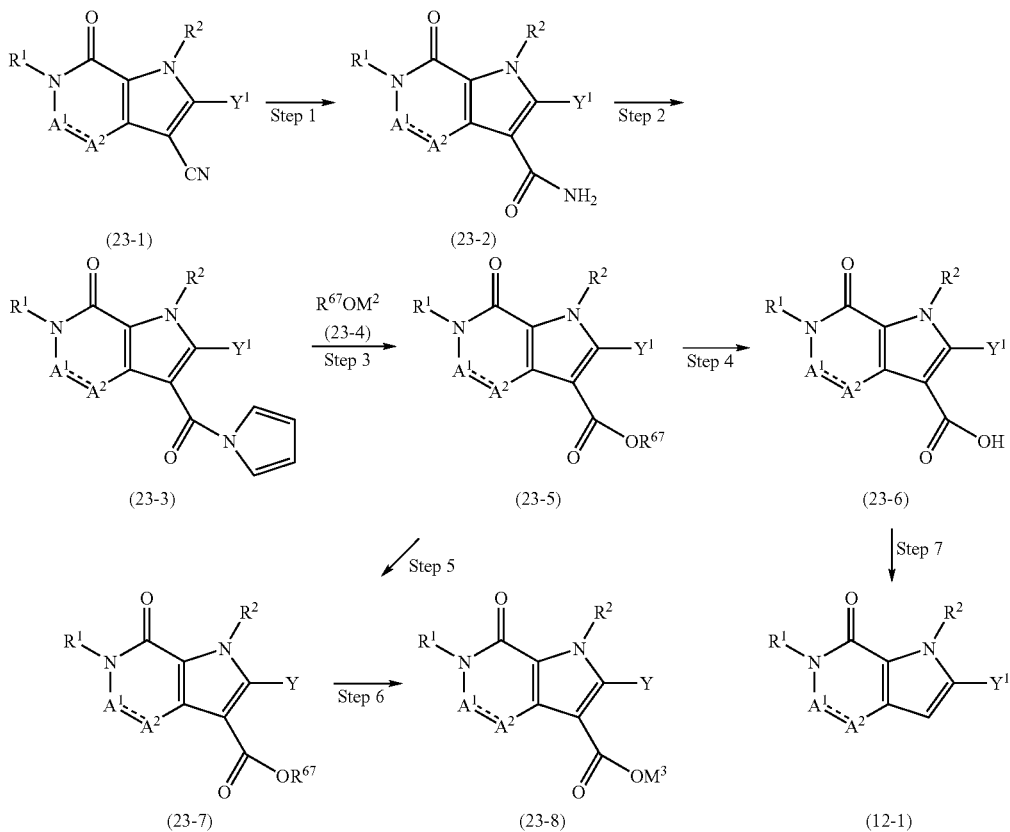

wherein $A^1$, $A^2$, $R^1$, $R^2$ and $Y^1$ are as defined above; $R^{67}O$ is "an optionally substituted alkoxy group"; and each of $M^2$ and $M^3$ is lithium, sodium or potassium.

1) Step 1

The compound (23-2) may be produced from a compound (23-1) by the same production process as described in literature (for example, Can. J. Chem. 78, 697 (2000)).

2) Step 2

The compound (23-3) may be produced by reacting the compound (23-2) with 2,5-dimethoxytetrahydrofuran in the presence of thionyl chloride and in the presence or absence of an inert solvent. The amount of thionyl chloride used is usually chosen in the range of 0.1 to 3 equivalents per equivalent of the compound (23-2). The amount of 2,5-dimethoxytetrahydrofuran used is usually chosen in the range of 10 to 100 the range of 1 to 5 equivalents per equivalent of the compound (23-3). The inert solvent includes alcohol solvents (e.g. methanol, ethanol and 2-propanol) and the like. The reaction temperature may be chosen in the range of about 30° C. to about 100° C.

4) Step 4

The compound (23-6) may be produced by reacting the compound (23-5) with a base in an inert solvent. As the base, alkali hydroxides (e.g. potassium hydroxide and sodium hydroxide) are exemplified, and an aqueous solution of the base may be used. The amount of the base used is usually chosen in the range of 1 to 30 equivalents per equivalent of the compound (23-5). The inert solvent includes alcohol solvents (e.g. methanol, ethanol and 2-propanol), water, mixed solvents thereof, and the like. The reaction temperature may be chosen in the range of about 30° C. to about 130° C.

5) Step 5

The compound (23-7) may be produced from the compound (23-5) by the same process as in the step 2 described in production process 2.

6) Step 6

The compound (23-8) may be produced from the compound (23-7) by the same process as in the above step 4.

7) Step 7

The compound (12-1) may be produced by reacting the compound (23-6) in an inert solvent in the presence or absence of an organic acid. The organic acid includes, for example, acetic acid, propionic acid, oxalic acid, succinic acid, lactic acid, malic acid, tartaric acid, citric acid, maleic acid, fumaric acid, methanesulfonic acid, p-toluenesulfonic acid and ascorbic acid. The inert solvent includes, for example, alcohol solvents (e.g. methanol, ethanol and 2-propanol), ether solvents (e.g. tetrahydrofuran and 1,4-dioxane), ketones (e.g. acetone), aprotic solvents (e.g. acetonitrile, N,N-dimethylformamide and dimethyl sulfoxide), and mixed solvents thereof. The reaction temperature may be chosen in the range of about 0° C. to about 100° C.

Production Process 24

Each of compounds of the formula (24-3), formula (24-6) and formula (24-8) as the compound of the formula (I), or a salt thereof and a compound of the formula (13-1) are produced, for example, by the following processes:

[Formula 66]

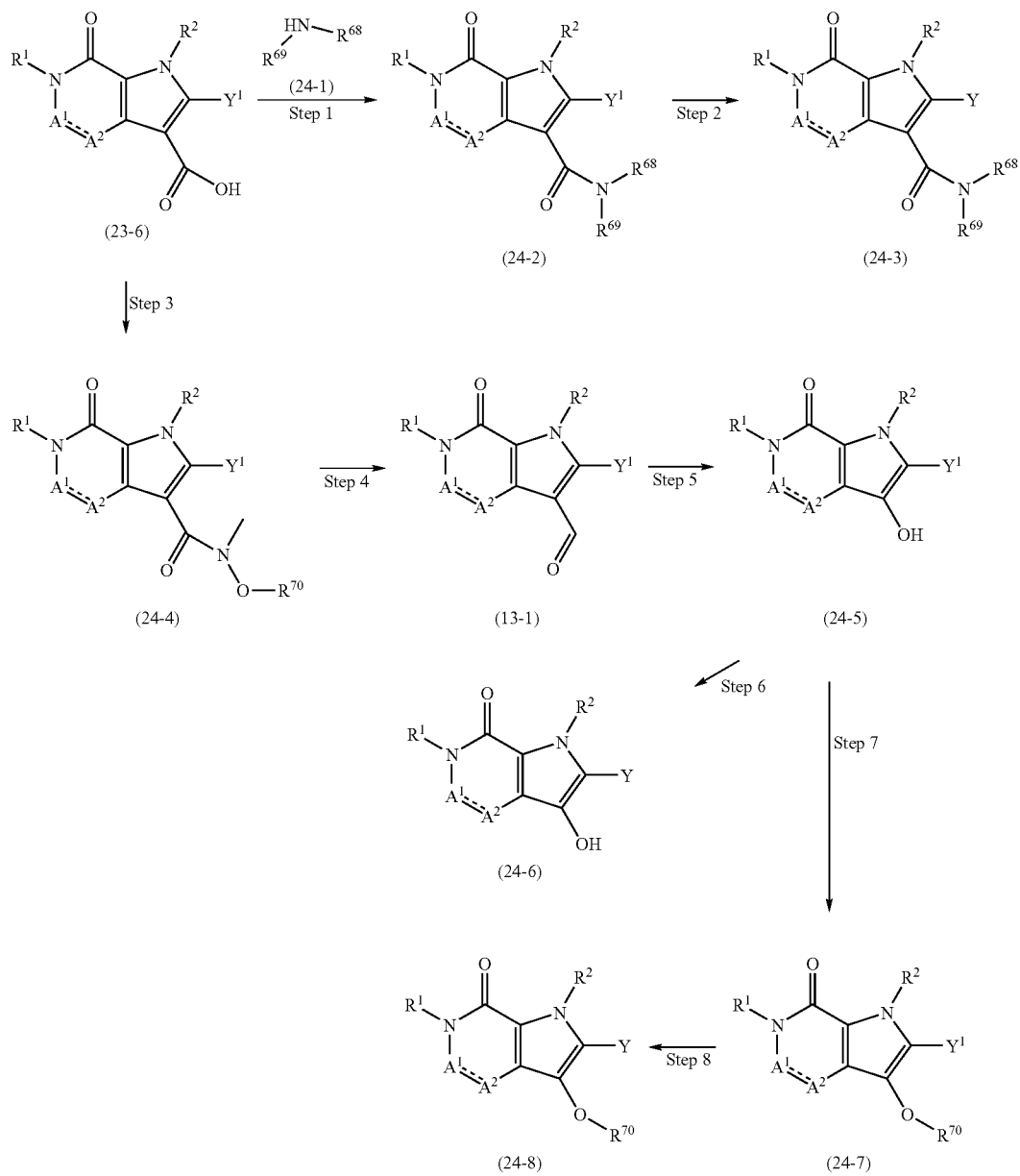

wherein $A^1$, $A^2$, $R^1$, $R^2$, $Y^1$ and Y are as defined above; $C(O)NR^{68}R^{69}$ is "an optionally substituted carbamoyl group"; and $R^{70}$ is "an optionally substituted alkyl group", "an optionally substituted alkenyl group", "an optionally substituted alkynyl group", "an optionally substituted cycloalkyl group", "an optionally substituted aryl group", "an optionally substituted heteroaryl group", "an optionally substituted aralkyl group" or "an optionally substituted heteroarylalkyl group".

1) Step 1

A compound (24-2) may be produced from a compound (23-6) by the same production process as described in literature (for example, R. C. Larock Comprehensive Organic transformation VCH publisher Inc., 972-976 (1989)).

2) Step 2, Step 6 and Step 8

By the same process as in the step 2 described in production process 2, the compound (24-3) may be produced from the compound (24-2), the compound (24-6) from a compound (24-5), and the compound (24-8) from a compound (24-7).

3) Step 3

A compound (24-4) may be produced from a compound (23-6) by the same production process as described in literature (for example, Bioorg. Med. Chem. Lett. 11, 2951 (2001), Tetrahedron Letters 42, 8955 (2001) Organic Letters 2, 4091 (2000), Synlett 5, 715 (2002), Bioorg. Med. Chem. Lett. 11, 287 (2001), Tetrahedron Letters 45, 7107 (2004) and Tetrahedron Letters 42, 3763 (2001)).

4) Step 4

The compound (13-1) may be produced from the compound (24-4) by the same production process as described in literature (for example, Tetrahedron Letters 45, 7107 (2004)).

5) Step 5

The compound (24-5) may be produced from the compound (13-1) by the same production process as described in literature (for example Indian J. Chem. 33B, 1103 (1994)).

6) Step 6 and Step 8

The compound (24-6) may be produced from the compound (24-5) by the same process as in the step 2 described in production process 2.

7) Step 7

The compound (24-7) may be produced from the compound (24-5) by the same process as that described in literature (for example, R. C. Larock Comprehensive Organic transformation VCH publisher Inc., 1989) or the like.

Production Process 25

A compound of the formula (25-1) as the compound of the formula (I), or a salt thereof is produced, for example, by the following process:

[Formula 67]

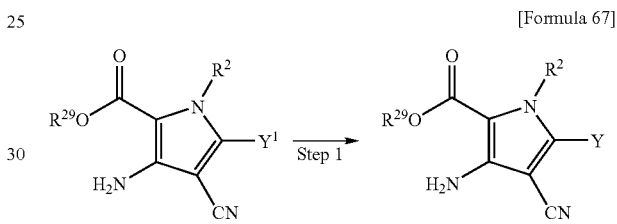

wherein $R^2$, $R^{29}$, Y and $Y^1$ are as defined above.

1) Step 1

The compound (25-1) may be produced from a compound (1-13) by the same process as in the step 2 described in production process 2.

Production Process 26

Each of compounds of the formula (26-2), formula (26-4), formula (26-6) and formula (26-8) as the compound of the formula (I), or a salt thereof is produced, for example, by the following process:

[Formula 68]

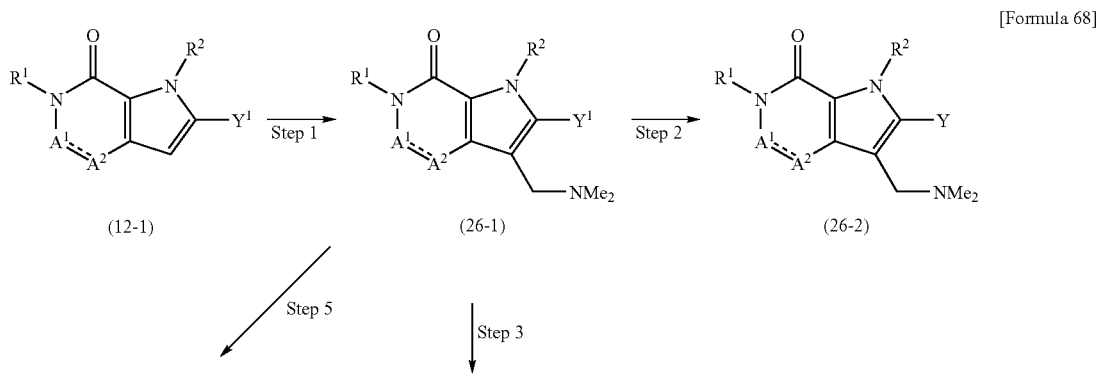

-continued

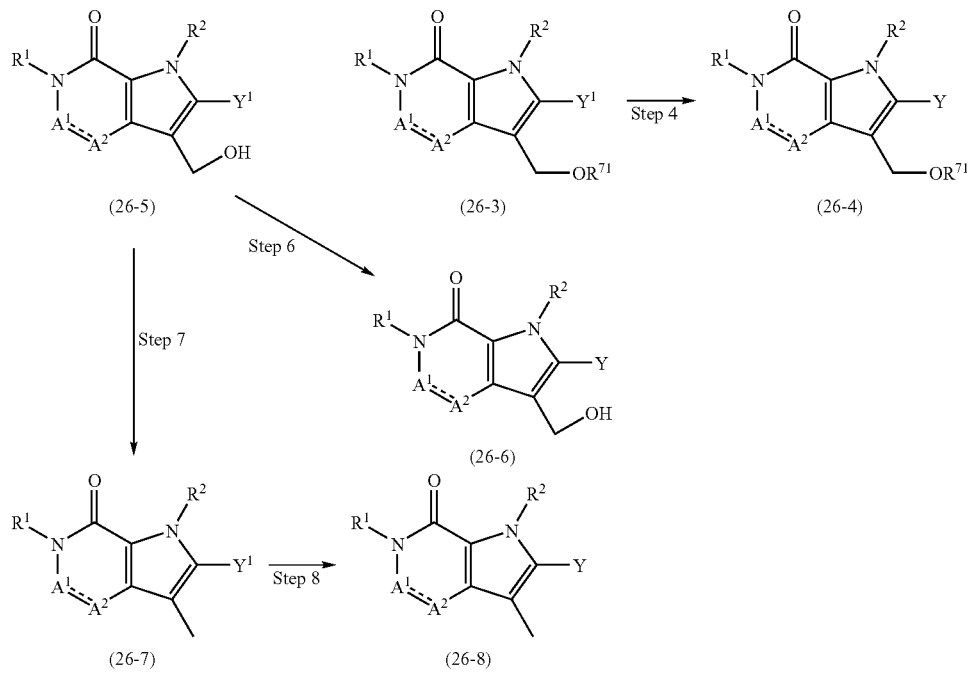

wherein $A^1$, $A^2$, $R^1$, $R^2$, $Y^1$ and Y are as defined above, and $R^{71}$ is an alkyl group.

1) Step 1 and Step 3

A compound (26-3) may be produced from a compound (12-1) by the same production process as described in literature (for example, J. Am. Chem. Soc. 74, 3916 (1952)).

2) Step 2

The compound (26-2) may be produced from a compound (26-1) by the same process as in the step 2 described in production process 2.

3) Step 4

The compound (26-4) may be produced from the compound (26-3) by the same process as in the step 2 described in production process 2.

4) Step 5 and Step 7

A compound (26-7) may be produced from a compound (26-1) by the same production process as described in literature (for example, J. Org. Chem. 22, 355 (1957)).

6) Step 6

The compound (26-6) may be produced from a compound (26-5) by the same process as in the step 2 described in production process 2.

7) Step 8

The compound (26-8) may be produced from the compound (26-7) by the same process as in the step 2 described in production process 2.

Production Process 27

A compound of the formula (27-2) as the compound of the formula (23-1) described in production process 23 is produced, for example, by the following process:

[Formula 69]

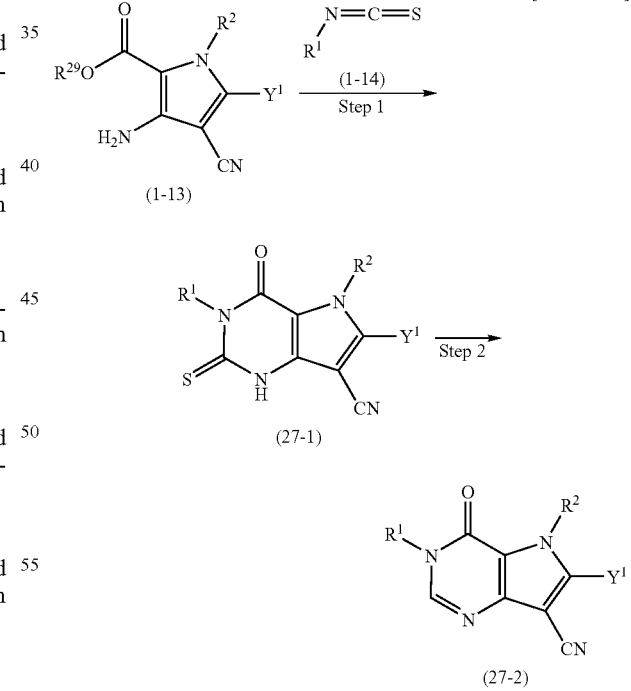

wherein $R^1$, $R^2$, $R^{29}$ and $Y^1$ are as defined above.

1) Step 1

A compound (27-1) may be produced from a compound (1-13) by the same production process as described in literature (for example, Tetrahedron 50, 3259 (1994)).

2) Step 2

The compound (27-2) may be produced from the compound (27-1) by the same production process as described in literature (for example, Tetrahedron 50, 3259 (1994)).

Unless otherwise specified, the starting materials, reagents and the like used above may be commercial compounds or may be produced from well-known compounds by well-known processes.

In each of the production processes described above, when the starting compound in each reaction has a reactive group such as hydroxyl group, amino group or carboxyl group, the reactive group in a site other than a site where the reaction is desired is previously protected with a suitable protective group if necessary, and the protective group is removed after carrying out each reaction or after carrying out several reactions, whereby a desired compound may be obtained. As the protective group for protecting the hydroxyl group, amino group, carboxyl group or the like, conventional protective groups used in the field of organic synthetic chemistry may be used. The introduction and removal of such a protective group may be carried out according to a conventional method (for example, the method described in T. W. Greene, P. G. M. Wuts, Protective Groups in Organic Synthesis, 2nd Edition John Wiley & Sons, Inc. (1991)).

For example, the protective group for the hydroxyl group includes tert-butyldimethylsilyl group, methoxymethyl group, tetrahydropyranyl group and the like. The protective group for the amino group includes tert-butoxycarbonyl group, benzyloxycarbonyl group and the like. Such a protective group for the hydroxyl group may be removed by reaction in a solvent such as aqueous methanol, aqueous ethanol or aqueous tetrahydrofuran in the presence of an acid such as hydrochloric acid, sulfuric acid or acetic acid. In the case of tert-butyldimethylsilyl group, it is also possible to carry out the removal in a solvent such as tetrahydrofuran in the presence of, for example, tetrabutylammonium fluoride. When the protective group for the amino group is tert-butoxycarbonyl group, it may be removed, for example, by reaction in a solvent such as aqueous tetrahydrofuran, methylene chloride, chloroform or aqueous methanol in the presence of an acid such as hydrochloric acid or trifluoroacetic acid. In the case of benzyloxycarbonyl group, the removal may be carried out, for example, by reaction in a solvent such as acetic acid in the presence of an acid such as hydrobromic acid.

As a form in which the carboxyl group is protected, tert-butyl esters, orthoesters and acid amides are exemplified. The protective group used for this protection is removed as follows. In the case of the tert-butyl esters, the removal is carried out, for example, by reaction in an aqueous solvent in the presence of hydrochloric acid. In the case of the orthoesters, the removal is carried out, for example, by treatment with an acid and then an alkali such as sodium hydroxide in a solvent such as aqueous methanol, aqueous tetrahydrofuran or aqueous 1,2-dimethoxyethane. In the case of the acid amides, the removal may be carried out, for example, by reaction in a solvent such as water, aqueous methanol or aqueous tetrahydrofuran in the presence of an acid such as hydrochloric acid or sulfuric acid.

The compound of the formula (I) includes those having a center for optical activity. Such a compound having a center for optical activity may be obtained as a racemic modification, or it may be obtained as an optically active substance when an optically active starting material is used. If necessary, the racemic modification obtained may be physically or chemically resolved into optical antipodes by a well-known method. Preferably, diastereomers are formed from the racemic modification by a reaction using a reagent for optical resolution. The diastereomers different in form may be resolved by a well-known method such as fractional crystallization.

The compound or prodrug thereof of the present invention may be converted to a salt, for example, by mixing with a pharmaceutically acceptable acid in a solvent such as water, methanol, ethanol or acetone. The pharmaceutically acceptable acid includes, for example, inorganic acids such as hydrochloric acid, hydrobromic acid, sulfuric acid, phosphoric acid, nitric acid, etc.; and organic acids such as acetic acid, propionic acid, oxalic acid, succinic acid, lactic acid, malic acid, tartaric acid, citric acid, maleic acid, fumaric acid, methanesulfonic acid, p-toluenesulfonic acid, ascorbic acid, etc.

The present inventive compounds are expected to be usable for the treatment of various diseases because of their inhibitory effect on DPP-IV. The compounds described in the present description are useful for the suppression of postprandial hyperglycemia in prediabetes, the treatment of non-insulin-dependent diabetes, the treatment of autoimmune diseases such as arthritis and articular rheumatism, the treatment of intestinal mucosa diseases, growth acceleration, the inhibition of transplantation rejection, the treatment of obesity, the treatment of eating disorder, the treatment of HIV infection, the suppression of cancer metastasis, the treatment of prostatomegaly, the treatment of periodontitis, and the treatment of osteoporosis.

When used for the treatment, the present inventive compounds may be administered as a pharmaceutical composition orally or parenterally (for example, by intravenous, subcutaneous or intramuscular injection, locally, intrarectally, percutaneously, or through nose). Compositions for the oral administration include, for example, tablets, capsules, pills, granules, powders, solutions and suspensions. Compositions for the parenteral administration include, for example, aqueous or oily preparations for injection, ointments, creams, lotions, aerosols, suppositories and patches. These pharmaceutical compositions are prepared by conventional techniques and may contain non-toxic and inactive carriers or excipients conventionally used in the field of formulation.

Although the dose is varied depending on the individual compounds, the disease, age, body weight and sex of a patient, symptom, administration route and the like, the bicyclic pyrrole derivative of the present invention, the prodrug thereof or the pharmaceutically acceptable salt of the derivative or prodrug is administered to an adult (body weight: 50 kg) usually in a dose of 0.1 to 1000 mg/day, preferably 1 to 300 mg/day in one portion or two or three portions a day. It is also possible to administer the derivative, prodrug or salt at intervals of several days to several weeks.

The present inventive compounds may be used in combination with drugs such as remedies for diabetes, remedies for diabetic complications, hypolipidemic drugs, hypotensors, antiobesity drugs, diuretics, etc. (these drugs are hereinafter abbreviated as concomitant drugs) in order to enhance the effects of the compounds. The timing of administration of the present inventive compound and the concomitant drug(s) is not limited. They may be administered to an object of administration either at the same time or at different times. It is also possible to prepare a mixture of the present inventive compound and the concomitant drug(s). The dose of the concomitant drug(s) may be properly chosen on the basis of a dose clinically employed. The proportions of the present inventive compound and the concomitant drug(s) may be properly chosen depending on an object of administration, an administration route, a disease to be treated, symptoms, a combination of the compound and the concomitant drug(s), and the like. For example, when the object of administration is a human being, the concomitant drug(s) is used in an amount of 0.01 to 100 parts by weight per part by weight of the present inventive compound.

The remedies for diabetes include insulin products (e.g. animal insulin products extracted from bovine or porcine pancreas; and human insulin products synthesized by a genetic engineering technique by the use of *Escherichia coli* or yeast), insulin resistance improving agents (e.g. pioglitazone or its hydrochloride, troglitazone, rosiglitazone or its maleate, GI-262570, JTT-501, MCC-555, YM-440, KRP-297 and CS-011), α-glucosidase inhibitors (e.g. voglibose, acarbose, miglitol and emiglitate), biguanide preparations (e.g. metformin), insulin secretion accelerators (e.g. sulfonylurea preparations such as tolbutamide, glibenclamide, gliclazide, chlorpropamide, tolazamide, acetohexamide, glyclopyramide, glimepiride, etc.; repaglinide, senaglinide, nateglinide and mitiglinide), GLP-1, GLP-1 analogs (e.g. exenatide, liraglutide, SUN-E7001, AVE010, BIM-51077 and CJC1131), protein tyrosine phosphatase inhibitors (e.g. vanadates), and β3 agonists (e.g. GW-427353B and N-5984).

The remedies for diabetic complications includes aldose reductase inhibitors (e.g. tolrestat, epalresat, zenarestat, zopolrestat, minarestat, fidarestat, SK-860 and CT-112), neurotrophic factors (e.g. NGF, NT-3 and BDNF), PKC inhibitors (e.g. LY-333531), AGE inhibitors (e.g. ALT946, pimagedine, pyratoxathine and N-phenacylthiazolium bromide (ALT766)), active-oxygen removers (e.g. thioctic acid), and cerebrovasodilators (e.g. tiapride and mexiletine). The hypolipidemic drugs include HMG-CoA reductase inhibitors (e.g. pravastatin, simvastatin, lovastatin, atorvastatin, fluvastatin, itavastatin, and their sodium salts), squalene synthetase inhibitors, ACAT inhibitors, and the like. The hypotensors include angiotensin-converting-enzyme inhibitors (e.g. captopril, enalapril, aracepril, delapril, lisinopril, imidapril, benazepril, cilazapril, temocapril and trandolapril), angiotensin II antagonists (e.g. ormesartan, medoxomill, candesartan, cilexetil, losartan, eprosartan, valsartan, telmisartan, irbesartan and tasosartan), calcium antagonists (e.g. nicardipine hydrochloride, manidipine hydrochloride, nisoldipine, nitrendipine, nilvadipine and amlodipine), and the like.

The antiobesity drugs include, for example, central antiobesity drugs (e.g. phentermine, sibutramine, amfepramone, dexamfetamine, mazindol and SR-141716A), pancreas lipase inhibitors (e.g. orlistat), peptidergic anorexiants (e.g. leptin and CNTF (ciliary nerve trophic factor)) and cholecystokinin agonists (e.g. lintitript and FPL-15849). The diuretics include, for example, xanthine derivatives (e.g. sodium salicylate theobromine and calcium salicylate theobromine), thiazide preparations (e.g. ethiazide, cyclopenthiazide, trichlormethiazide, hydrochlorothiazide, hydroflumethiazide, bentylhydrochlorothiazide, penflutizide, polythiazide and methyclothiazide), anti-aldosterone preparations (e.g. spironolactone and triamterene), carbonate dehydratase inhibitors (e.g. acetazolamide), chlorobenzenesulfoneamide preparations (e.g. chlorthalidone, mefruside and indapamide), azosemide, isosorbide, ethacrynic acid, piretanide, bumetanide and furosemide.

The concomitant drugs are preferably GLP-1, the GLP-1 analogs, the α-glucosidase inhibitors, the biguanide preparations, the insulin secretion accelerators, the insulin resistance improving agents, and the like. The above-exemplified concomitant drugs may be used in combination of two or more thereof in proper proportions.

When the present inventive compound is used in combination with the concomitant drug(s), the amount of the drug(s) used may be reduced so as to be within a safe range in view of the side effects of the drug(s). In particular, the dose of the biguanide preparations may be reduced as compared with a conventional dose. Therefore, side effects causable by these drugs are safely preventable. In addition, the doses of the remedies for diabetic complications, the hypolipidemic drugs, the hypotensors and the like may be reduced. As a result, side effects causable by these drugs are effectively preventable.

EXAMPLES

The present invention is more concretely illustrated below with reference examples, working examples and test examples, which should not be construed as limiting the scope of the invention. The nomenclature of compounds shown in the reference examples and working examples mentioned below is not always based on IUPAC. Abbreviations are used in these examples for the simplification of description in some cases and they have the same meanings as defined above.

Example 1

Example 1

6-[(3R)-3-Aminopiperidin-1-yl]-5-(2-chlorobenzyl)-2-(3-ethoxyphenoxy)-3-methyl-4-oxo-4,5-dihydro-3H-pyrrolo[3,2-d]pyrimidine-7-carbonitrile hydrochloride

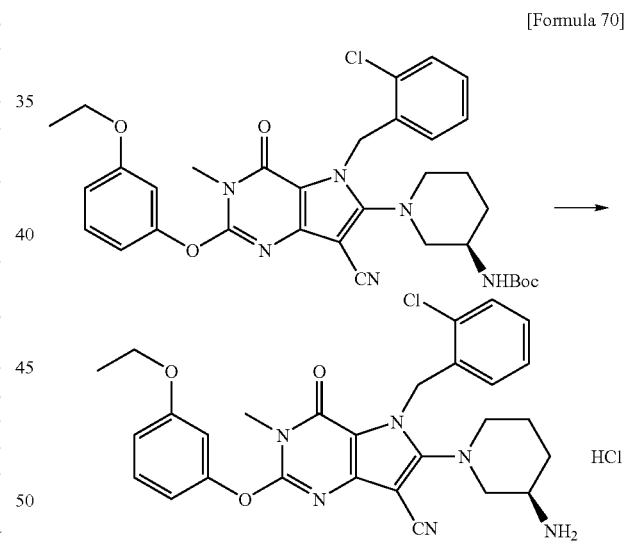

[Formula 70]

A 4N hydrochloric acid/1,4-dioxane solution (5 ml) was added to a solution of tert-butyl {(3R)-1-[5-(2-chlorobenzyl)-7-cyano-2-(3-ethoxyphenoxy)-3-methyl-4-oxo-4,5-dihydro-3H-pyrrolo[3,2-d]pyrimidin-6-yl]piperidine-3-yl}carbamate (185 mg) in 1,4-dioxane (3 ml), and the resulting mixture was stirred at 25° C. for 2 hours and then concentrated under reduced pressure to obtain the title compound (170 mg).

$^1$H NMR (400 MHz, CD$_3$OD) δ 7.48-7.41 (m, 1H), 7.36-7.16 (m, 3H), 6.91-6.78 (m, 3H), 6.57-6.49 (m, 1H), 5.69 (s, 2H), 4.06 (q, J=7.0 Hz, 2H), 3.73-3.60 (m, 2H), 3.50 (s, 3H), 3.49-3.42 (m, 1H), 3.10-2.92 (m, 2H), 2.10-1.98 (m, 1H), 1.80-1.70 (m, 1H), 1.65-1.45 (m, 2H), 1.40 (t, J=7.0 Hz, 3H).

MS (ESI+) 533 (M$^+$+1, 100%).

Example 2

6-[(3R)-3-Aminopiperidin-1-yl]-5-(2-chlorobenzyl)-1,3-dimethyl-2,4-dioxo-2,3,4,5-tetrahydro-1H-pyrrolo[3,2-d]pyrimidine-7-carbonitrile hydrochloride

[Formula 71]

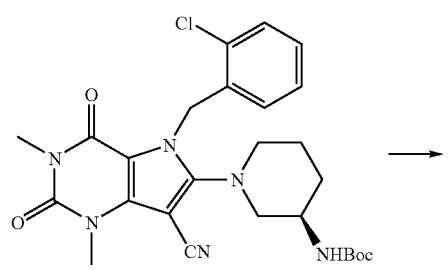

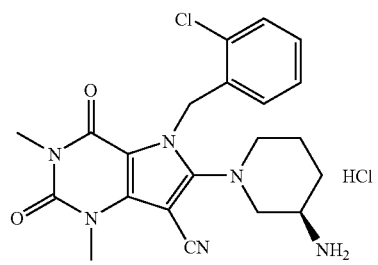

The title compound was synthesized from a corresponding compound by the same process as in Example 1.

$^1$H NMR (400 MHz, CD$_3$OD) δ 7.47-7.44 (m, 1H), 7.30-7.16 (m, 2H), 6.65-6.58 (m, 1H), 5.72-5.62 (m, 2H), 3.73 (s, 3H), 3.70-3.61 (m, 1H), 3.51-3.41 (m, 1H), 3.27 (s, 3H), 3.23-3.10 (m, 1H), 3.05-2.97 (m, 2H), 2.13-2.03 (m, 1H), 1.82-1.72 (m, 1H), 1.63-1.41 (m, 2H).

MS (ESI+) 427 (M$^+$+1, 88%).

Example 3

6-[(3R)-3-Aminopiperidin-1-yl]-5-(2-chlorobenzyl)-2-hydroxy-3-methyl-4-oxo-4,5-dihydro-3H-pyrrolo[3,2-d]pyrimidine-7-carbonitrile hydrochloride

[Formula 72]

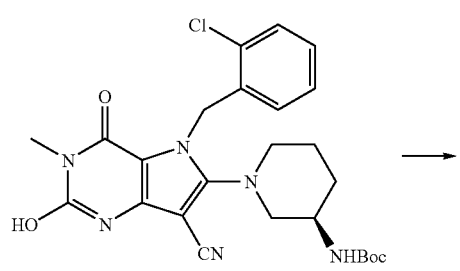

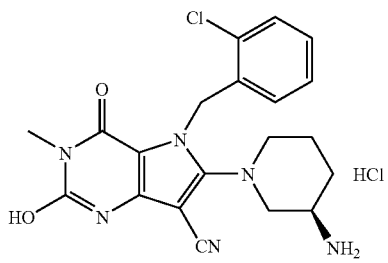

The title compound was synthesized from a corresponding compound by the same process as in Example 1.

$^1$H NMR (400 MHz, CD$_3$OD) δ 7.47-7.44 (m, 1H), 7.32-7.20 (m, 2H), 6.65-6.60 (m, 1H), 5.67-5.57 (m, 2H), 3.52-3.45 (m, 1H), 3.27-3.15 (m, 2H), 3.26 (s, 3H), 3.09-2.94 (m, 2H), 2.12-2.04 (m, 1H), 1.83-1.75 (m, 1H), 1.66-1.43 (m, 2H).

MS (ESI+) 413 (M$^+$+1, 93%).

Example 4

6-[(3R)-3-Aminopiperidin-1-yl]-5-(2-chlorobenzyl)-3-methyl-2-(methylsulfonyl)-4-oxo-4,5-dihydro-3H-pyrrolo[3,2-d]pyrimidine-7-carbonitrile hydrochloride

[Formula 73]

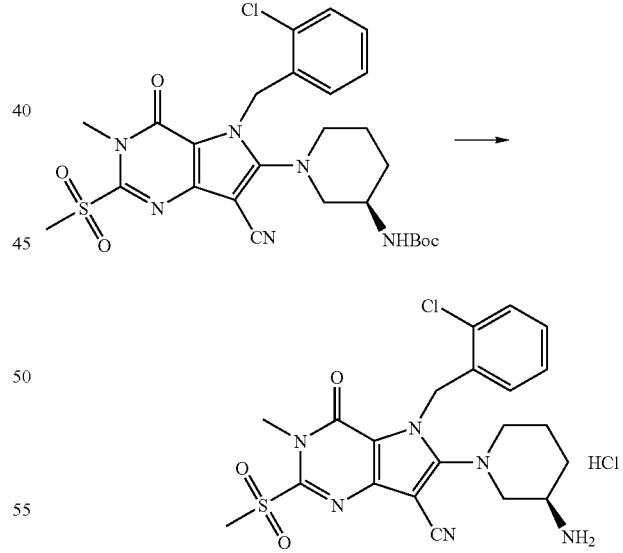

The title compound was synthesized from a corresponding compound by the same process as in Example 1.

$^1$H NMR (400 MHz, CD$_3$OD) δ 7.49-7.44 (m, 1H), 7.31-7.17 (m, 2H), 6.63-6.57 (m, 1H), 5.78-5.63 (m, 2H), 3.81 (s, 3H), 3.79-3.68 (m, 1H), 3.58 (s, 3H), 3.37-3.17 (m, 2H), 3.15-3.05 (m, 1H), 3.03-2.92 (m, 1H), 2.15-2.03 (m, 1H), 1.84-1.76 (m, 1H), 1.67-1.43 (m, 2H).

MS (ESI+) 475 (M$^+$+1, 100%).

Example 5

6-(3-Aminopiperidin-1-yl)-5-(2-chlorobenzyl)-1,3-dimethyl-1H-pyrrolo[3,2-d]pyrimidine-2,4(3H,5H)-dione hydrochloride

[Formula 74]

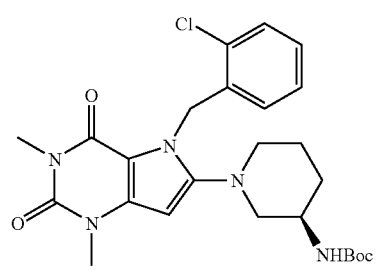

The title compound was synthesized from a corresponding compound by the same process as in Example 1.

¹H NMR (400 MHz, CD$_3$OD) δ 7.43-7.40 (m, 1H), 7.25-7.11 (m, 2H), 6.47-6.42 (m, 1H), 6.04 (s, 1H), 5.66-5.53 (m, 2H), 3.48 (s, 3H), 3.38-3.28 (m, 2H), 3.25 (s, 3H), 2.95-2.85 (m, 2H), 2.81-2.71 (m, 1H), 2.07-1.98 (m, 1H), 1.84-1.73 (m, 1H), 1.67-1.49 (m, 2H).

MS (ESI+) 402 (M$^+$+1, 100%).

Example 6

6-(3-Aminopiperidin-1-yl)-5-(2-chloro-5-fluorobenzyl)-1,3-dimethyl-1H-pyrrolo[3,2-d]pyrimidine-2,4(3H,5H)-dione hydrochloride

[Formula 75]

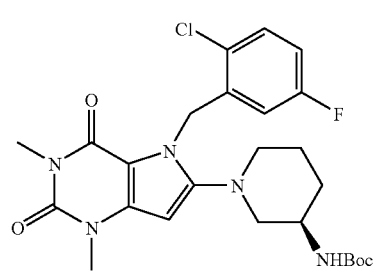

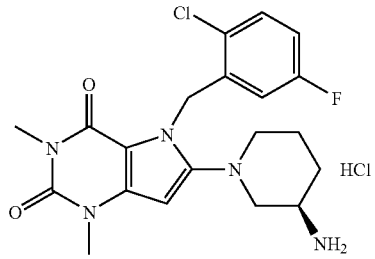

The title compound was synthesized from a corresponding compound by the same process as in Example 1.

¹H NMR (400 MHz, CD$_3$OD) δ 7.47-7.43 (m, 1H), 7.04-6.98 (m, 1H), 6.17-6.14 (m, 1H), 6.05 (s, 1H), 5.56 (s, 2H), 3.49 (s, 3H), 3.40-3.21 (m, 2H), 3.27 (s, 3H), 2.97-2.70 (m, 3H), 2.08-1.98 (m, 1H), 1.86-1.73 (m, 1H), 1.68-1.46 (m, 2H).

MS (ESI+) 420 (M$^+$+1, 100%).

Example 7

2-{[6-(3-Aminopiperidin-1-yl)-5-(2-chlorobenzyl)-7-cyano-3-methyl-4-oxo-4,5-dihydro-3H-pyrrolo[3,2-d]pyrimidin-2-yl]oxy}benzamide hydrochloride

[Formula 76]

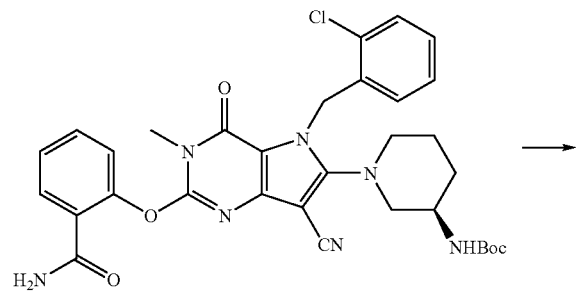

The title compound was synthesized from a corresponding compound by the same process as in Example 1.

¹H NMR (400 MHz, CD$_3$OD) δ 8.04-7.97 (m, 1H), 7.50-7.41 (m, 2H), 7.32-7.17 (m, 2H), 7.00-6.91 (m, 2H), 6.67-6.59 (m, 1H), 5.71 (s, 2H), 3.57 (s, 3H), 3.72-3.20 (m, 3H), 3.15-2.97 (m, 2H), 2.15-2.03 (m, 1H), 1.87-1.75 (m, 1H), 1.70-1.42 (m, 2H).

MS (ESI+) 532 (M$^+$+1, 100%).

Each of the compounds of Examples 8 to 70 was synthesized according to the processes described in a corresponding reference example and Example 1.

[Formula 77]

| Example No. | R² |
|---|---|
| Example 8 | 2-cyanobenzyl |
| Example 9 | 2,3,5-trifluorobenzyl |
| Example 10 | 2-methyl-5-fluorobenzyl |
| Example 11 | 2-methylbenzyl |
| Example 12 | 2-cyano-5-methoxybenzyl |
| Example 13 | 2-cyano-5-fluorobenzyl |
| Example 14 | 2-butynyl |

-continued

[Formula 77]

| Example No. | R² |
|---|---|
| Example 15 | 2-carbamoylbenzyl |

Example 8

$^1$H NMR (300 MHz, DMSO-d$_6$) δ 8.18 (brs, 3H), 7.86 (d, J=6.6 Hz, 1H), 7.57 (m, 1H), 7.43 (t, J=7.6 Hz, 1H), 6.62 (d, J=7.9 Hz, 1H), 6.12 (s, 1H), 5.64 (d, J=16.2 Hz, 1H), 5.56 (d, J=16.2 Hz, 1H), 3.39 (s, 3H), 3.36-3.23 (m, 2H), 3.11 (s, 3H), 2.92-2.75 (m, 3H), 1.91-1.80 (m, 2H), 1.55-1.51 (m, 2H).
MS (ESI+) 393 (M$^+$+1, 100%).

Example 9

$^1$H NMR (400 MHz, CD$_3$OD) δ 7.10-7.03 (m, 1H), 6.28-6.25 (m, 1H), 6.02 (s, 1H), 5.58 (s, 2H), 3.47 (s, 3H), 3.41-2.79 (m, 5H), 3.27 (s, 3H), 2.10-1.52 (m, 4H).
MS (ESI+) 422 (M$^+$+1, 100%).

Example 10

$^1$H NMR (300 MHz, DMSO-d$_6$) δ 8.14 (brs, 3H), 7.23-7.18 (m, 1H), 6.95-6.90 (m, 1H), 6.05 (s, 1H), 5.98-5.94 (m, 1H), 5.40 (d, J=16.5 Hz, 1H), 5.32 (d, J=16.5 Hz, 1H), 3.38 (s, 3H), 3.35-3.23 (m, 2H), 3.11 (s, 3H), 2.86-2.81 (m, 2H), 2.68-2.64 (m, 1H), 2.32 (s, 3H), 1.88-1.74 (m, 2H), 1.49-1.44 (m, 2H).
MS (ESI+) 400 (M$^+$+1, 100%).

Example 11

$^1$H NMR (300 MHz, CD$_3$OD) δ 7.09-6.88 (m, 3H), 6.19 (d, J=7.5 Hz, 1H), 5.93 (s, 1H), 5.43 (d, J=16.3 Hz, 1H), 5.36 (d, J=16.3 Hz, 1H), 3.38 (s, 3H), 3.27-3.21 (m, 2H), 3.14 (s, 3H), 2.89-2.73 (m, 3H), 2.31 (s, 3H), 1.94-1.91 (m, 1H), 1.70-1.49 (m, 3H).
MS (ESI+) 382 (M$^+$+1, 100%).

Example 12

$^1$H NMR (300 MHz, CDCl$_3$) δ 7.64-7.59 (m, 1H), 6.83-6.79 (m, 1H), 6.32 (d, J=2.4 Hz, 1H), 5.67 (s, 1H), 5.66 (s, 1H), 5.60 (s, 1H), 3.74 (s, 3H), 3.47 (s, 3H), 3.36 (s, 3H), 3.03-2.93 (m, 2H), 2.86-2.82 (m, 1H), 2.69-2.61 (m, 1H), 2.52-2.46 (m, 1H), 1.88-1.61 (m, 4H).
MS (ESI+) 423 (M$^+$+1, 100%).

Example 13

$^1$H NMR (300 MHz, CDCl$_3$) δ 8.50 (brs, 3H), 7.71-7.65 (m, 1H), 7.07-7.00 (m, 1H), 6.57-6.53 (m, 1H), 5.84 (d, J=16.7 Hz, 1H), 5.73 (s, 1H), 5.64 (d, J=16.7 Hz, 1H), 3.59-3.57 (m, 1H), 3.45 (s, 3H), 3.39-3.37 (m, 1H), 3.33 (s, 3H), 3.16-3.09 (m, 1H), 2.70-2.68 (m, 2H), 2.08-2.06 (m, 1H), 1.80-1.78 (m, 2H), 1.60-1.58 (m, 1H).

MS (ESI+) 411 (M$^+$+1, 100%).

Example 14

$^1$H NMR (300 MHz, DMSO-d$_6$) δ 8.28 (brs, 3H), 5.91 (s, 1H), 5.08-4.89 (m, 2H), 3.35 (s, 3H), 3.35-3.28 (m, 2H), 3.21 (s, 3H), 2.99-2.89 (m, 3H), 1.95-1.91 (m, 2H), 1.76 (s, 3H), 1.67-1.63 (m, 2H).

MS (ESI+) 330 (M$^+$+1, 100%).

Example 15

$^1$H NMR (300 MHz, DMSO-d$_6$) δ 8.07 (brs, 3H), 7.53-7.49 (m, 1H), 7.32-7.24 (m, 2H), 6.41-6.38 (m, 1H), 6.05 (s, 1H), 5.63 (s, 2H), 3.37 (s, 3H), 3.30-3.19 (m, 2H), 3.14 (s, 3H), 2.82-2.78 (m, 2H), 2.62-2.60 (m, 1H), 1.91-1.87 (m, 1H), 1.71-1.69 (m, 1H), 1.47-1.45 (m, 2H).

MS (ESI+) 411 (M$^+$+1, 100%).

[Formula 78]

| Example No. | R$^1$ | R$^2$ |
|---|---|---|
| Example 16 | 4-methoxybenzyl | 2-chloro-5-fluorobenzyl |
| Example 17 | CH$_3$ | 2-methoxyphenyl |
| Example 18 | isoquinolin-3-ylmethyl | 2-chloro-5-fluorobenzyl |

-continued

[Formula 78]

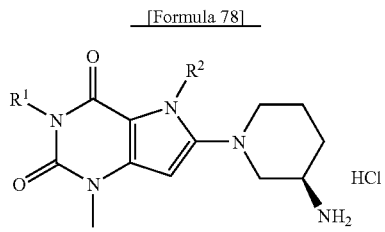

| Example No. | R$^1$ | R$^2$ |
|---|---|---|
| Example 19 | PhC(O)CH$_2$ | 2-chloro-5-fluorobenzyl |
| Example 20 | H | 2-chloro-5-fluorobenzyl |

Example 16

$^1$H NMR (400 MHz, CD$_3$OD) δ 7.47-7.43 (m, 1H), 7.22-7.19 (m, 2H), 7.04-7.01 (m, 1H), 6.79-6.75 (m, 2H), 6.18-6.15 (m, 1H), 6.03 (s, 1H), 5.56 (s, 2H), 5.01 (s, 2H), 3.73 (s, 3H), 3.47 (s, 3H), 3.40-2.73 (m, 5H), 2.12-1.52 (m, 4H).

MS (ESI+) 526 (M$^+$+1, 100%).

Example 17

$^1$H NMR (400 MHz, CD$_3$OD) δ 7.49-7.43 (m, 1H), 7.32-7.27 (m, 1H), 7.18-7.15 (m, 1H), 7.08-7.03 (m, 1H), 5.91 (s, 1H), 3.50 (s, 3H), 3.40-3.30 (m, 1H), 3.12 (s, 3H), 3.11-3.00 (m, 2H), 2.80-2.66 (m, 2H), 2.01-1.92 (m, 1H), 1.68-1.59 (m, 1H), 1.50-1.30 (m, 2H).

MS (ESI+) 384 (M$^+$+1, 100%).

Example 18

$^1$H NMR (400 MHz, CD$_3$OD) δ 8.58-8.56 (m, 1H), 8.36-8.33 (m, 1H), 8.25-8.17 (m, 2H), 8.12-8.07 (m, 1H), 7.90-7.84 (m, 1H), 7.46-7.42 (m, 1H), 7.05-6.99 (m, 1H), 6.27-6.23 (m, 1H), 6.13 (s, 1H), 5.93 (s, 2H), 5.56 (s, 2H), 3.50 (s, 3H), 3.40-3.30 (m, 2H), 3.01-2.92 (m, 2H), 2.89-2.77 (m, 1H), 2.10-2.03 (m, 1H), 1.92-1.81 (m, 1H), 1.75-1.53 (m, 2H).

MS (ESI+) 547 (M$^+$+1, 100%).

Example 19

$^1$H NMR (400 MHz, CD$_3$OD) δ 8.04-8.01 (m, 2H), 7.67-7.63 (m, 1H), 7.54-7.50 (m, 2H), 7.44-7.40 (m, 1H), 7.03-6.98 (m, 1H), 6.24-6.20 (m, 1H), 6.11 (s, 1H), 5.56 (s, 2H), 5.39 (s, 2H), 3.51 (s, 3H), 3.40-3.30 (m, 2H), 3.00-2.91 (m, 2H), 2.85-2.79 (m, 1H), 2.10-2.02 (m, 1H), 1.90-1.80 (m, 1H), 1.72-1.53 (m, 2H).

MS (ESI+) 524 (M$^+$+1, 100%).

Example 20

$^1$H NMR (400 MHz, CD$_3$OD) δ 7.48-7.44 (m, 1H), 7.06-7.01 (m, 1H), 6.22-6.19 (m, 1H), 6.07 (s, 1H), 5.55 (s, 2H), 3.45 (s, 3H), 3.40-3.28 (m, 2H), 3.00-2.92 (m, 2H), 2.85-2.77 (m, 1H), 2.11-2.01 (m, 1H), 1.90-1.81 (m, 1H), 1.82-1.53 (m, 2H).

MS (ESI+) 406 (M$^+$+1, 100%).

[Formula 79]

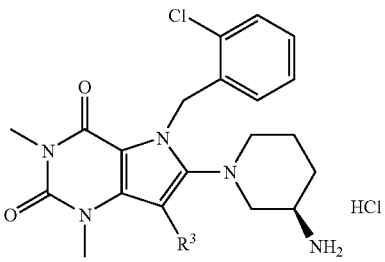

| Example No. | R$^3$ |
|---|---|
| Example 21 | C(O)NH$_2$ |
| Example 22 | 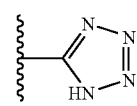 |
| Example 23 | C(O)OCH$_3$ |
| Example 24 | C(O)OCH$_2$CH$_3$ |
| Example 25 | C(O)N(CH$_3$)$_2$ |
| Example 26 | 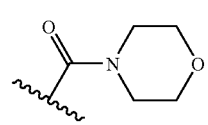 |
| Example 27 | 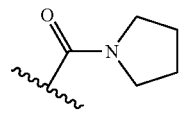 |
| Example 28 | 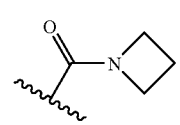 |
| Example 29 | 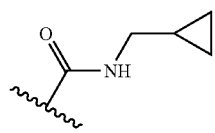 |
| Example 30 | 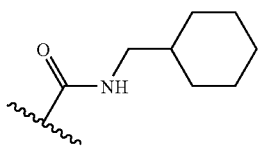 |
| Example 31 | 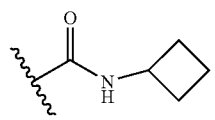 |

-continued

[Formula 79]

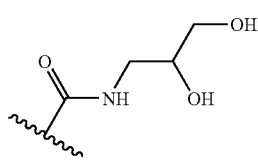

| Example No. | R$^3$ |
|---|---|
| Example 32 | 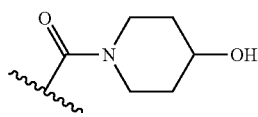 |
| Example 33 | 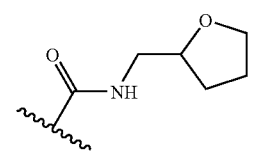 |
| Example 34 | 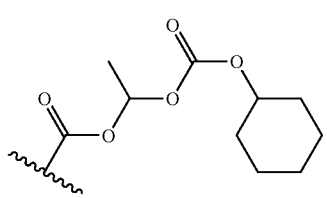 |
| Example 35 |  |

Example 21

$^1$H NMR (400 MHz, CD$_3$OD) δ 7.47-7.43 (m, 1H), 7.30-7.17 (m, 2H), 6.49-6.44 (m, 1H), 5.69 (s, 2H), 3.57 (s, 3H), 3.30 (s, 3H), 3.18-2.90 (m, 5H), 2.08-1.99 (m, 1H), 1.77-1.68 (m, 1H), 1.55-1.35 (m, 2H).

MS (ESI+) 445 (M$^+$+1, 59%).

Example 22

$^1$H NMR (400 MHz, CD$_3$OD) δ 7.49-7.42 (m, 1H), 7.30-7.21 (m, 2H), 6.58-6.54 (m, 1H), 5.76 (s, 2H), 3.29 (s, 3H), 3.10-2.75 (m, 3H), 3.05 (s, 3H), 2.53-2.32 (m, 2H), 1.98-1.85 (m, 1H), 1.62-1.49 (m, 1H), 1.40-1.16 (m, 2H).

MS (ESI+) 470 (M$^+$+1, 100%).

Example 23

¹H NMR (400 MHz, CD₃OD) δ 7.47-7.43 (m, 1H), 7.29-7.21 (m, 2H), 6.47-6.43 (m, 1H), 5.75 (s, 2H), 3.94 (s, 3H), 3.54 (s, 3H), 3.32 (s, 3H), 3.10-2.81 (m, 4H), 2.72-2.62 (m, 1H), 1.96-1.89 (m, 1H), 1.61-1.54 (m, 1H), 1.40-1.25 (m, 2H).

MS (ESI+) 460 (M⁺+1, 100%).

Example 24

¹H NMR (400 MHz, CD₃OD) δ 7.47-7.44 (m, 1H), 7.29-7.17 (m, 2H), 6.47-6.43 (m, 1H), 5.79-5.69 (m, 2H), 4.43-4.34 (m, 2H), 3.56 (s, 3H), 3.35 (s, 3H), 3.17-2.72 (m, 5H), 2.07-1.97 (m, 1H), 1.72-1.63 (m, 1H), 1.48-1.30 (m, 2H), 1.43-1.38 (m, 3H).

MS (ESI+) 474 (M⁺+1, 100%).

Example 25

¹H NMR (400 MHz, CD₃OD) δ 7.47-7.44 (m, 1H), 7.30-7.20 (m, 2H), 6.56-6.52 (m, 1H), 5.72-5.68 (m, 2H), 3.42 (s, 3H), 3.27 (s, 3H), 3.27-3.20 (m, 1H), 3.16-3.11 (m, 6H), 2.95-2.85 (m, 3H), 2.08-1.99 (m, 1H), 1.76-1.68 (m, 1H), 1.50-1.30 (m, 3H).

MS (ESI+) 473 (M⁺+1, 100%).

Example 26

¹H NMR (400 MHz, CD₃OD) δ 7.46-7.43 (m, 1H), 7.30-7.20 (m, 2H), 6.55-6.50 (m, 1H), 5.79-5.60 (m, 2H), 3.91-3.62 (m, 8H), 3.40 (s, 3H), 3.27 (s, 3H), 3.27-3.10 (m, 1H), 2.97-2.75 (m, 3H), 2.05-1.95 (m, 1H), 1.78-1.63 (m, 1H), 1.54-1.25 (m, 3H).

MS (ESI+) 515 (M⁺+1, 100%).

Example 27

¹H NMR (400 MHz, CD₃OD) δ 7.46-7.43 (m, 1H), 7.29-7.20 (m, 2H), 6.53-6.48 (m, 1H), 5.69 (s, 2H), 3.71-3.59 (m, 4H), 3.50-2.78 (m, 5H), 3.44 (s, 3H), 3.34-3.26 (m, 3H), 2.09-1.93 (m, 5H), 1.78-1.68 (m, 1H), 1.65-1.38 (m, 2H).

MS (ESI+) 499 (M⁺+1, 100%).

Example 28

¹H NMR (400 MHz, CD₃OD) δ 7.39-7.34 (m, 1H), 7.22-7.11 (m, 2H), 6.50-6.43 (m, 1H), 5.67-5.52 (m, 2H), 4.48-3.80 (m, 4H), 3.55-3.47 (m, 3H), 3.35 (s, 3H), 3.30-3.10 (m, 2H), 2.85-2.11 (m, 5H), 1.69-1.41 (m, 4H).

MS (ESI+) 485 (M⁺+1, 100%).

Example 29

¹H NMR (400 MHz, CDCl₃) δ 7.39-7.36 (m, 1H), 7.21-7.10 (m, 2H), 6.46-6.42 (m, 1H), 5.69 (d, J=17 Hz, 1H), 5.61 (d, J=17 Hz, 1H), 3.58 (s, 3H), 3.35 (s, 3H), 3.32-3.27 (m, 2H), 3.08-3.03 (m, 1H), 2.91-2.83 (m, 2H), 2.78-2.60 (m, 2H), 1.85-1.16 (m, 4H), 1.10-1.02 (m, 1H), 0.61-0.56 (m, 2H), 0.31-0.27 (m, 2H).

MS (ESI+) 499 (M⁺+1, 100%).

Example 30

¹H NMR (400 MHz, CDCl₃) δ 8.46 (brs, 3H), 7.37-7.33 (m, 1H), 7.25-7.10 (m, 2H), 6.60 (brs, 1H), 6.52-6.42 (m, 1H), 5.72-5.50 (m, 2H), 3.56-3.42 (m, 1H), 3.49 (s, 3H), 3.40-3.13 (m, 4H), 3.32 (s, 3H), 2.88-2.72 (m, 2H), 2.12-1.98 (m, 1H), 1.96-0.99 (m, 15H).

MS (ESI+) 541 (M⁺+1, 100%).

Example 31

¹H NMR (400 MHz, CDCl₃) δ 8.70-8.33 (brs, 3H), 7.38-7.34 (m, 1H), 7.22-7.10 (m, 2H), 6.91-6.77 (brs, 1H), 6.43-6.36 (m, 1H), 5.74 (d, J=16 Hz, 1H), 5.50 (d, J=16 Hz, 1H), 4.51 (m, 1H), 3.49 (s, 3H), 3.32 (s, 3H), 3.28-3.18 (m, 2H), 2.83-2.74 (m, 2H), 2.53-2.30 (m, 2H), 2.09-1.90 (m, 3H), 1.81-1.60 (m, 6H).

MS (ESI+) 499 (M⁺+1, 100%).

Example 32

MS (ESI+) 519 (M⁺+1, 100%).

Example 33

¹H NMR (400 MHz, CDCl₃) δ 8.43 (brs, 3H), 7.39-7.33 (m, 1H), 7.23-7.13 (m, 2H), 6.60-6.53 (m, 1H), 5.74-5.52 (m, 2H), 4.47-2.53 (m, 11H), 3.50-3.31 (m, 6H), 2.20-1.22 (m, 8H).

MS (ESI+) 529 (M⁺+1, 100%).

Example 34

¹H NMR (400 MHz, CDCl₃) δ 7.40-7.35 (m, 1H), 7.21-7.13 (m, 2H), 6.50-6.45 (m, 1H), 5.78-5.52 (m, 2H), 4.27-4.15 (m, 1H), 3.98-3.14 (m, 7H), 3.53-3.49 (m, 3H), 3.35-3.33 (m, 3H), 2.94-2.82 (m, 1H), 2.75-2.65 (m, 1H), 2.13-1.38 (m, 8H).

MS (ESI+) 529 (M⁺+1, 100%).

Example 35

¹H NMR (400 MHz, CD₃OD) δ 7.51-7.45 (m, 1H), 7.31-7.18 (m, 2H), 7.03 (q, J=5.4 Hz, 1H), 6.53-6.45 (m, 1H), 5.81-5.65 (m, 2H), 4.69-4.56 (m, 1H), 3.57 (s, 3H), 3.32 (s, 3H), 3.21-2.67 (m, 5H), 2.13-1.82 (m, 3H), 1.80-1.69 (m, 1H), 1.67 (d, J=5.4 Hz, 3H), 1.66-1.22 (m, 10H).

MS (ESI+) 616 (M⁺+1, 45%).

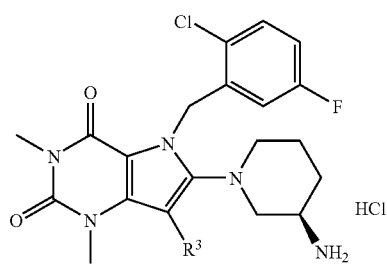

[Formula 80]

| Example No. | R³ |
|---|---|
| Example 36 | C(O)N(CH₃)₂ |
| Example 37 | C(O)NHCH₃ |

-continued

[Formula 80]

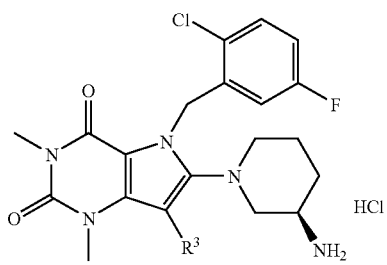

| Example No. | R³ |
|---|---|
| Example 38 | 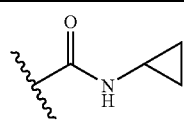 |
| Example 39 | 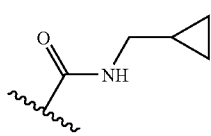 |
| Example 40 | 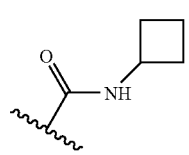 |
| Example 41 | 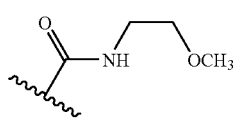 |
| Example 42 | 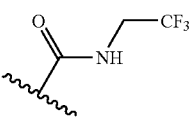 |
| Example 43 | 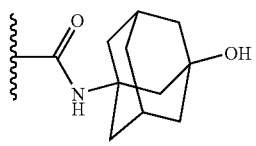 |
| Example 44 | 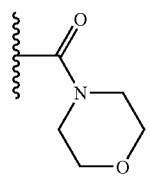 |

Example 36

¹H NMR (400 MHz, CDCl₃) δ 7.37-7.31 (m, 1H), 7.00-6.90 (m, 1H), 6.32-6.25 (m, 1H), 5.63-5.50 (m, 2H), 3.53-3.28 (m, 3H), 3.45-3.33 (m, 6H), 3.28-3.03 (m, 6H), 2.82-2.65 (m, 2H), 2.21-2.10 (m, 1H), 1.81-1.40 (m, 3H).

MS (ESI+) 491 (M⁺+1, 100%).

Example 37

¹H NMR (400 MHz, CDCl₃) δ 8.50 (brs, 3H), 7.37-7.31 (m, 1H), 6.95-6.85 (m, 2H), 6.25-6.18 (m, 1H), 5.62 (d, J=17 Hz, 1H), 5.46 (d, J=17 Hz, 1H), 3.58-3.40 (m, 1H), 3.47 (s, 3H), 3.38-3.20 (m, 2H), 3.32 (s, 3H), 3.01 (s, 3H), 2.82-2.72 (m, 2H), 2.20-1.41 (m, 4H).

MS (ESI+) 477 (M⁺+1, 100%).

Example 38

¹H NMR (400 MHz, CDCl₃) δ 8.59 (brs, 3H), 7.38-7.31 (m, 1H), 7.02 (brs, 1H), 6.93-6.87 (m, 1H), 6.25-6.13 (m, 1H), 5.63 (d, J=17 Hz, 1H), 5.44 (d, J=17 Hz, 1H), 3.61-3.53 (m, 1H), 3.45 (s, 3H), 3.31 (s, 3H), 3.38-3.20 (m, 2H), 3.03-2.95 (m, 1H), 2.83-2.73 (m, 2H), 2.23-1.62 (m, 4H), 0.93-0.83 (m, 2H), 0.74-0.58 (m, 2H).

MS (ESI+) 503 (M⁺+1, 100%).

Example 39

¹H NMR (400 MHz, CDCl₃) δ 8.52 (brs, 3H), 7.41-7.35 (m, 1H), 7.00-6.89 (m, 1H), 6.78 (brs, 1H), 6.30-6.16 (m, 1H), 5.78-5.62 (m, 1H), 5.49-5.38 (m, 1H), 3.59-3.21 (m, 5H), 3.52 (s, 3H), 3.33 (s, 3H), 2.88-2.71 (m, 2H), 2.21-1.45 (m, 4H), 1.16-1.04 (m, 1H), 0.65-0.49 (m, 2H), 0.38-0.25 (m, 2H).

MS (ESI+) 517 (M⁺+1, 100%).

Example 40

¹H NMR (400 MHz, CDCl₃) δ 8.60 (brs, 3H), 7.41-7.30 (m, 1H), 6.96-6.83 (m, 1H), 6.77 (brs, 1H), 6.28-6.10 (m, 1H), 5.75-5.33 (m, 2H), 4.59-4.42 (m, 1H), 3.49 (s, 3H), 3.40-3.19 (m, 2H), 3.33 (s, 3H), 2.84-2.66 (m, 2H), 2.54-2.33 (m, 2H), 2.22-1.91 (m, 3H), 1.87-1.50 (m, 6H).

MS (ESI+) 517 (M⁺+1, 100%).

Example 41

¹H NMR (400 MHz, CDCl₃) δ 8.50 (brs, 3H), 7.37-7.33 (m, 1H), 6.93-6.89 (m, 2H), 6.30-6.23 (m, 1H), 5.64 (d, J=17 Hz, 1H), 5.45 (d, J=17 Hz, 1H), 3.79-3.58 (m, 4H), 3.55-3.22 (m, 3H), 3.51 (s, 3H), 3.36 (s, 3H), 3.34 (s, 3H), 2.89-2.69 (m, 2H), 2.18-1.43 (m, 4H).

MS (ESI+) 521 (M⁺+1, 100%).

Example 42

¹H NMR (400 MHz, CDCl₃) δ 8.57 (brs, 3H), 7.51 (brs, 1H), 7.41-7.29 (m, 1H), 6.95-6.83 (m, 1H), 6.21-6.11 (m, 1H), 5.67 (d, J=17 Hz, 1H), 5.44 (d, J=17 Hz, 1H), 4.31-3.97 (m, 2H), 3.51-3.12 (m, 3H), 3.45 (s, 3H), 3.29 (s, 3H), 2.82-2.69 (m, 2H), 2.11-1.35 (m, 4H).

MS (ESI+) 545 (M⁺+1, 100%).

Example 43

¹H NMR (400 MHz, CD₃OD) δ 7.49-7.44 (m, 1H), 7.08-7.00 (m, 1H), 6.29-6.24 (m, 1H), 5.64 (d, J=17 Hz, 1H), 5.58 (d, J=17 Hz, 1H), 3.57 (s, 3H), 3.30 (s, 3H), 2.30-1.25 (m, 23H).

MS (ESI+) 613 (M⁺+1, 100%).

Example 44

$^1$H NMR (400 MHz, CDCl$_3$) δ 7.38-7.33 (m, 1H), 6.97-6.89 (m, 1H), 6.33-6.24 (m, 1H), 5.72-5.49 (m, 2H), 4.00-3.62 (m, 8H), 3.50-3.34 (m, 6H), 3.45-2.62 (m, 5H), 2.19-1.49 (m, 4H).

MS (ESI+) 533 (M$^+$+1, 100%).

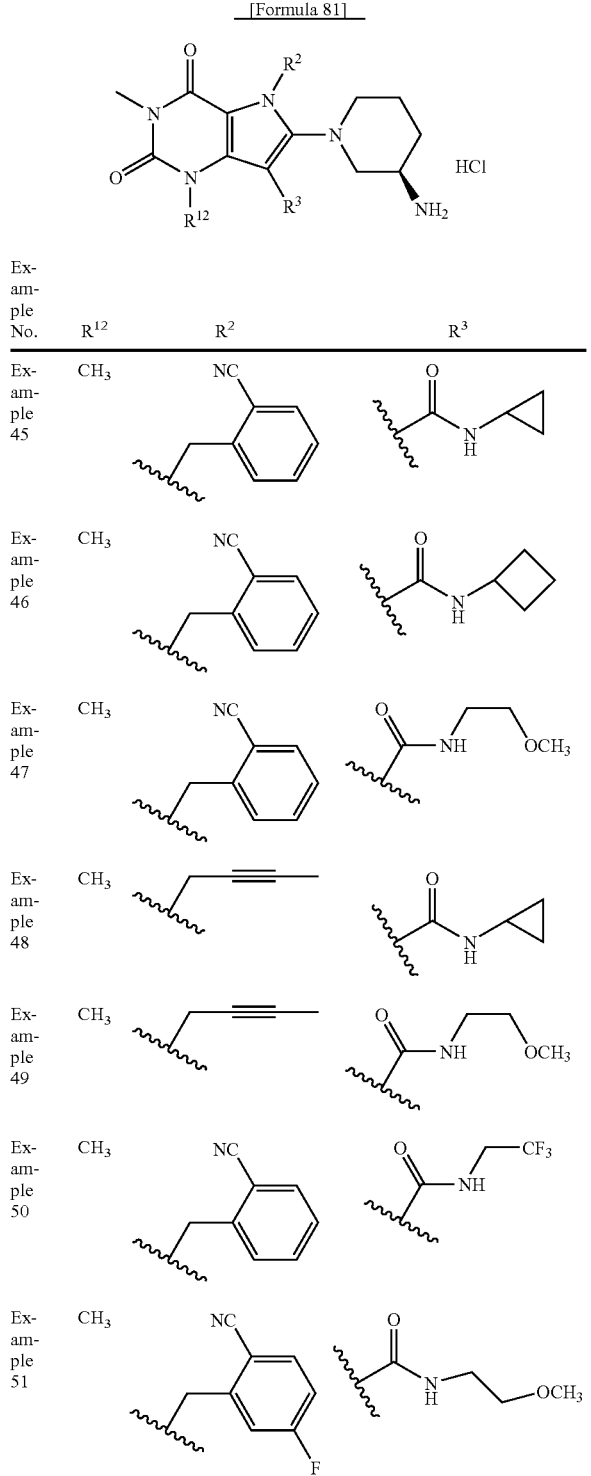

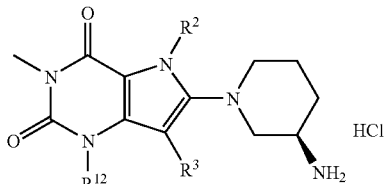

Example 45

$^1$H NMR (300 MHz, DMSO-d$_6$) δ 8.79 (d, J=4.0 Hz, 1H), 8.04 (brs, 3H), 7.88 (d, J=7.5 Hz, 1H), 7.60 (t, J=7.7 Hz, 1H), 7.46 (t, J=7.5 Hz, 1H), 6.62 (d, J=7.5 Hz, 1H), 5.69 (d, J=16.3 Hz, 1H), 5.59 (d, J=16.3 Hz, 1H), 3.36 (s, 3H), 3.24-3.19 (m, 1H), 3.15 (s, 3H), 2.94-2.73 (m, 4H), 1.92-1.90 (m, 1H), 1.70-1.67 (m, 1H), 1.46-1.23 (m, 3H), 0.74-0.68 (m, 2H), 0.58-0.53 (m, 2H).

MS (ESI+) 476 (M$^+$+1, 100%).

Example 46

$^1$H NMR (300 MHz, DMSO-d$_6$) δ 8.96 (d, J=7.5 Hz, 1H), 7.99 (brs, 3H), 7.90-7.87 (m, 1H), 7.61 (m, 1H), 7.45 (t, J=7.4 Hz, 1H), 6.62 (d, J=7.7 Hz, 1H), 5.70 (d, J=16.5 Hz, 1H), 5.59 (d, J=16.5 Hz, 1H), 4.39-4.31 (m, 1H), 3.37 (s, 3H), 3.26-3.19 (m, 1H), 3.15 (s, 3H), 2.92-2.83 (m, 3H), 2.26-2.23 (m, 2H), 2.03-1.87 (m, 3H), 1.74-1.62 (m, 3H), 1.42-1.23 (m, 3H).

MS (ESI+) 490 (M$^+$+1, 100%).

Example 47

$^1$H NMR (400 MHz, CD$_3$OD) δ 7.76-7.73 (m, 1H), 7.57-7.52 (m, 1H), 7.44-7.38 (m, 1H), 6.76-6.72 (m, 1H), 5.81 (d, J=17 Hz, 1H), 5.73 (d, J=17 Hz, 1H), 3.60-3.53 (m, 4H), 3.53 (s, 3H), 3.38 (s, 3H), 3.28 (s, 3H), 3.14-3.11 (m, 1H), 2.92-2.85 (m, 2H), 2.76-2.68 (m, 2H), 1.99-1.84 (m, 1H), 1.78-1.59 (m, 1H), 1.51-1.13 (m, 2H).

MS (ESI+) 494 (M$^+$+1, 100%).

Example 48

$^1$H NMR (400 MHz, CD$_3$OD) δ 5.16-5.01 (m, 2H), 3.47-3.41 (m, 2H), 3.44 (s, 3H), 3.34 (s, 3H), 3.29-3.22 (m, 1H), 3.12-3.03 (m, 2H), 2.94-2.87 (m, 1H), 2.17-1.77 (m, 3H), 1.77-1.73 (m, 3H), 1.64-1.50 (m, 1H), 0.87-0.79 (m, 2H), 0.64-0.58 (m, 2H).

MS (ESI+) 413 (M$^+$+1, 100%).

Example 49

$^1$H NMR (400 MHz, CD$_3$OD) δ 5.15-5.02 (m, 2H), 3.60-3.52 (m, 4H), 3.48-3.06 (m, 5H), 3.47 (s, 3H), 3.37 (s, 3H), 3.34 (s, 3H), 2.14-2.05 (m, 1H), 1.96-1.78 (m, 3H), 1.76-1.73 (m, 3H), 1.66-1.55 (m, 1H).
MS (ESI+) 431 (M$^+$+1, 100%).

Example 50

$^1$H NMR (400 MHz, CD$_3$OD) δ 7.80-7.75 (m, 1H), 7.60-7.53 (m, 1H), 7.47-7.41 (m, 1H), 6.83-6.78 (m, 1H), 5.87 (d, J=17 Hz, 1H), 5.73 (d, J=17 Hz, 1H), 4.21-4.07 (m, 2H), 3.47 (s, 3H), 3.30 (s, 3H), 3.25-2.76 (m, 5H), 2.11-1.98 (m, 1H), 1.78-1.35 (m, 3H).
MS (ESI+) 518 (M$^+$+1, 100%).

Example 51

$^1$H NMR (400 MHz, CD$_3$OD) δ 7.90-7.86 (m, 1H), 7.26-7.19 (m, 1H), 6.59-6.55 (m, 1H), 5.84 (d, J=17 Hz, 1H), 5.73 (d, J=17 Hz, 1H), 3.65-3.55 (m, 4H), 3.53 (s, 3H), 3.41 (s, 3H), 3.37 (s, 3H), 3.14-2.76 (m, 5H), 2.11-2.01 (m, 1H), 1.81-1.71 (m, 1H), 1.61-1.38 (m, 2H).
MS (ESI+) 512 (M$^+$+1, 100%).

Example 52

$^1$H NMR (400 MHz, CD$_3$OD) δ 7.92-7.85 (m, 1H), 7.27-7.20 (m, 1H), 6.60-6.53 (m, 1H), 5.87 (d, J=17 Hz, 1H), 5.74 (d, J=17 Hz, 1H), 4.23-4.10 (m, 2H), 3.49 (s, 3H), 3.40-2.82 (m, 5H), 3.30 (s, 3H), 2.12-2.02 (m, 1H), 1.71-1.37 (m, 3H).
MS (ESI+) 536 (M$^+$+1, 100%).

[Formula 82]

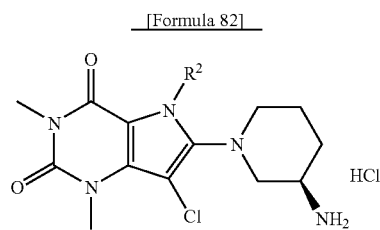

| Example No. | R$^2$ |
|---|---|
| Example 53 | 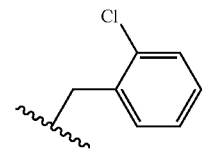 |
| Example 54 | 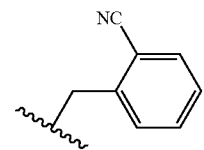 |

Example 53

$^1$H NMR (300 MHz, DMSO-d$_6$) δ 8.15 (bs, 3H), 7.51-7.48 (m, 1H), 7.32-7.21 (m, 2H), 6.43 (d, J=6.8 Hz, 1H), 5.63 (d, J=16.6 Hz, 1H), 5.55 (d, J=16.6 Hz, 1H), 3.66 (s, 3H), 3.36-3.16 (m, 2H), 3.16 (s, 3H), 2.96-2.72 (m, 3H), 1.92-1.90 (m, 1H), 1.62-1.60 (m, 1H), 1.25-1.22 (m, 2H).
MS (ESI+) 436 (M$^+$+1, 100%).

Example 54

$^1$H NMR (300 MHz, DMSO-d$_6$) δ 8.18 (bs, 3H), 7.87 (d, J=6.8 Hz, 1H), 7.60 (t, J=7.5 Hz, 1H), 7.44 (d, J=7.5 Hz, 1H), 6.78-6.76 (m, 1H), 5.74 (d, J=16.4 Hz, 1H), 5.63 (d, J=16.4 Hz, 1H), 3.64 (s, 3H), 3.22-3.18 (m, 2H), 3.15 (s, 3H), 3.01-2.95 (m, 2H), 2.68-2.66 (m, 1H), 1.96-1.92 (m, 1H), 1.63-1.61 (m, 1H), 1.41-1.32 (m, 2H).
MS (ESI+) 427 (M$^+$+1, 100%).

[Formula 83]

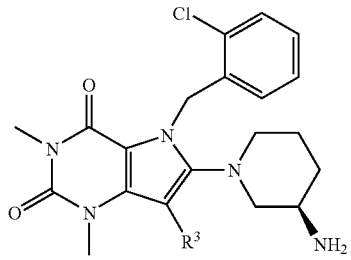

| Example No. | R$^3$ | Salt |
|---|---|---|
| Example 55 | —CH$_2$—N(CH$_3$)$_2$ | 2 HCl |
| Example 56 | CH$_2$OCH$_3$ | HCl |
| Example 57 | Br | CF$_3$CO$_2$H |
| Example 58 | F | CF$_3$CO$_2$H |
| Example 59 | CH$_3$ | HCl |
| Example 60 | CHO | CF$_3$CO$_2$H |
| Example 61 | CH$_3$C(O) | CF$_3$CO$_2$H |
| Example 62 | —⟨C$_6$H$_4$⟩—OMe | CF$_3$CO$_2$H |

Example 55

$^1$H NMR (300 MHz, DMSO-d$_6$) δ 10.01-9.87 (m, 1H), 8.35-8.17 (m, 3H), 7.51 (d, J=7.7 Hz, 1H), 7.32-7.18 (m, 2H), 6.34-6.21 (m, 1H), 5.65-5.56 (m, 2H), 4.42-4.26 (m, 2H), 3.67 (s, 3H), 3.55-3.36 (m, 2H), 3.15 (s, 3H), 2.91-2.60 (m, 3H), 2.79 (s, 6H), 2.01-1.49 (m, 4H).
MS (ESI+) 458 (M$^+$+1, 56%).

Example 56

$^1$H NMR (300 MHz, DMSO-d$_6$) δ 8.12 (brs, 3H), 7.49 (d, J=7.5 Hz, 1H), 7.31-7.22 (m, 2H), 6.31-6.28 (m, 1H), 5.63-5.53 (m, 2H), 4.55-4.51 (m, 2H), 3.70 (s, 3H), 3.65 (s, 3H), 3.50-3.47 (m, 1H), 3.17 (s, 3H), 3.08-3.05 (m, 1H), 2.79-2.75 (m, 3H), 1.94-1.91 (m, 1H), 1.56-1.35 (m, 3H).
MS (ESI+) 446 (M$^+$+1, 10%).

Example 57

$^1$H NMR (300 MHz, CDCl$_3$) δ 9.25 (brs, 3H), 7.44-7.36 (m, 1H), 7.18-7.04 (m, 2H), 6.44-6.39 (m, 1H), 5.68 (s, 2H), 3.83 (s, 3H), 3.46-3.60 (m, 2H), 3.37 (s, 3H), 3.22-3.04 (m, 3H), 2.70-2.64 (m, 1H), 2.12-1.94 (m, 1H), 1.68-1.42 (m, 3H).
MS (ESI+) 482 (M$^+$+1, 48%).

Example 58

$^1$H NMR (300 MHz, CDCl$_3$) δ 7.40-7.37 (m, 1H), 7.20-7.16 (m, 2H), 6.51-6.48 (m, 1H), 5.79 (d, J=16.5 Hz, 1H), 5.57 (d, J=16.5 Hz, 1H), 3.62 (s, 3H), 3.46-3.44 (m, 1H), 3.37 (s, 3H), 3.34-3.32 (m, 1H), 3.14-3.09 (m, 1H), 2.87-2.85 (m, 2H), 1.86-1.62 (m, 4H).

MS (ESI+) 420 (M$^+$+1, 61%).

Example 59

$^1$H NMR (300 MHz, DMSO-d$_6$) δ 8.07 (brs, 3H), 7.50-7.47 (m, 1H), 7.29-7.19 (m, 2H), 6.30-6.28 (m, 1H), 5.58 (d, J=16.1 Hz, 1H), 5.49 (d, J=16.1 Hz, 1H), 3.61 (s, 3H), 3.16 (s, 3H), 3.07-3.04 (m, 2H), 2.91-2.65 (m, 3H), 2.31 (s, 3H), 1.93-1.90 (m, 1H), 1.57-1.54 (m, 1H), 1.25-1.15 (m, 2H).

MS (ESI+) 416 (M$^+$+1, 100%).

Example 60

$^1$H NMR (300 MHz, CDCl$_3$) δ 10.12 (s, 1H), 7.51 (brs, 3H), 7.38-7.35 (m, 1H), 7.24-7.11 (m, 2H), 6.44 (d, J=6.2 Hz, 1H), 5.73-5.69 (m, 2H), 3.79 (s, 3H), 3.49-3.44 (m, 1H), 3.39 (s, 3H), 3.23-3.20 (m, 1H), 3.03-2.78 (m, 3H), 1.90-1.55 (m, 4H).

MS (ESI+) 430 (M$^+$+1, 85%).

Example 61

$^1$H NMR (300 MHz, CDCl$_3$) δ 7.91 (brs, 3H), 7.39-7.36 (m, 1H), 7.21-7.13 (m, 2H), 6.38 (d, J=7.5 Hz, 1H), 5.70 (s, 2H), 3.44 (s, 3H), 3.37 (s, 3H), 3.31-3.27 (m, 1H), 3.20-3.17 (m, 2H), 3.06-2.94 (m, 2H), 2.53 (s, 3H), 2.15-1.85 (m, 2H), 1.65-1.54 (m, 2H).

MS (ESI+) 444 (M$^+$+1, 100%).

Example 62

$^1$H NMR (300 MHz, CDCl$_3$) δ 7.38-7.36 (m, 1H), 7.26-7.19 (m, 4H), 6.96-6.89 (m, 2H), 6.52-6.49 (m, 1H), 6.66-5.52 (m, 2H), 3.84 (s, 3H), 3.39 (s, 3H), 3.19-3.15 (m, 1H), 3.09 (s, 3H), 3.04-2.46 (m, 4H), 1.80-1.40 (m, 4H).

MS (ESI+) 508 (M$^+$+1, 100%).

[Formula 84]

| Example No. | R$^2$ | R$^3$ |
|---|---|---|
| Example 63 | 2-Cl-phenyl-CH$_2$- | CN |
| Example 64 | 2-Cl-5-F-phenyl-CH$_2$- | H |
| Example 65 | 2-Cl-5-F-phenyl-CH$_2$- | C(O)N(CH$_3$)$_2$ |
| Example 66 | 2-Cl-5-F-phenyl-CH$_2$- | C(O)-morpholinyl |

Example 63

$^1$H NMR (300 MHz, DMSO-d$_6$) δ 8.33 (s, 1H), 8.31 (brs, 3H), 7.50 (d, J=6.6 Hz, 1H), 7.33-7.21 (m, 2H), 6.49 (d, J=6.6 Hz, 1H), 5.64 (d, J=17.0 Hz, 1H), 5.56 (d, J=17.0 Hz, 1H), 3.56-3.54 (m, 1H), 3.42 (s, 3H), 3.26-3.19 (m, 1H), 3.08-2.87 (m, 3H), 1.96-1.93 (m, 1H), 1.75-1.72 (m, 1H), 1.52-1.43 (m, 2H).

MS (ESI+) 397 (M$^+$+1, 100%).

Example 64

$^1$H NMR (300 MHz, DMSO-d$_6$) δ 8.40 (s, 1H), 8.21 (brs, 3H), 7.58-7.53 (m, 1H), 7.20-7.13 (m, 1H), 6.19 (s, 1H), 6.05-6.01 (m, 1H), 5.60 (d, J=16.8 Hz, 1H), 5.52 (d, J=16.8 Hz, 1H), 3.42 (s, 3H), 3.31-3.16 (m, 2H), 2.91-2.84 (m, 2H), 2.73-2.67 (m, 1H), 1.92-1.79 (m, 2H), 1.55-1.47 (m, 2H).

MS (ESI+) 390 (M$^+$+1, 100%).

Example 65

$^1$H NMR (300 MHz, DMSO-d$_6$) δ 8.28 (brs, 4H), 7.57-7.52 (m, 1H), 7.19-7.12 (m, 1H), 6.14-6.09 (m, 1H), 5.60 (d, J=17.0 Hz, 1H), 5.53 (d, J=17.0 Hz, 1H), 3.42 (s, 3H), 3.23-3.21 (m, 1H), 3.01 (s, 3H), 3.00 (s, 3H), 2.96-2.94 (m, 2H), 2.79-2.76 (m, 2H), 1.90-1.88 (m, 1H), 1.70-1.67 (m, 1H), 1.35-1.30 (m, 2H).

MS (ESI+) 461 (M$^+$+1, 100%).

Example 66

$^1$H NMR (300 MHz, DMSO-$d_6$) δ 8.23 (s, 1H), 8.19 (brs, 3H), 7.58-7.53 (m, 1H), 7.20-7.13 (m, 1H), 6.19-6.15 (m, 1H), 5.56 (s, 2H), 3.69-3.55 (m, 6H), 3.48-3.41 (m, 2H), 3.41 (s, 3H), 3.22-3.17 (m, 1H), 3.00-2.96 (m, 2H), 2.81-2.79 (m, 2H), 1.90-1.88 (m, 1H), 1.69-1.67 (m, 1H), 1.35-1.33 (m, 2H).

MS (ESI+) 503 (M$^+$+1, 100%).

[Formula 85]

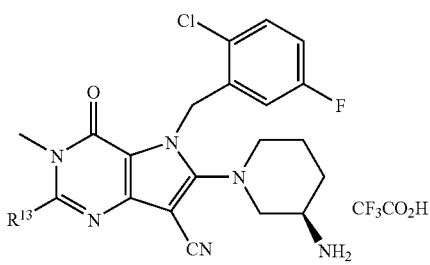

| Example No. | R$^{13}$ |
|---|---|
| Example 67 | SO$_2$Me |
| Example 68 | C(O)NH$_2$ |
| Example 69 | CN |

Example 67

$^1$H NMR (300 MHz, DMSO-$d_6$) δ 8.02 (brs, 3H), 7.61-7.56 (m, 1H), 7.24-7.18 (m, 1H), 6.65-6.61 (m, 1H), 5.55 (s, 2H), 3.69 (s, 3H), 3.64 (s, 3H), 3.53-3.50 (m, 1H), 3.27-3.17 (m, 2H), 3.08-3.03 (m, 1H), 2.96-2.93 (m, 1H), 1.97-1.95 (m, 1H), 1.78-1.75 (m, 1H), 1.49-1.45 (m, 2H).

MS (ESI+) 493 (M$^+$+1, 100%).

Example 68

$^1$H NMR (300 MHz, DMSO-$d_6$) δ 8.34 (s, 1H), 8.21 (s, 1H), 7.99 (brs, 3H), 7.61-7.56 (m, 1H), 7.25-7.17 (m, 1H), 6.48-6.44 (m, 1H), 5.54 (s, 2H), 3.54-3.51 (m, 1H), 3.42 (s, 3H), 3.27-3.21 (m, 2H), 3.11-3.07 (m, 1H), 2.97-2.94 (m, 1H), 1.97-1.95 (m, 1H), 1.79-1.77 (m, 1H), 1.51-1.47 (m, 2H).

MS (ESI+) 458 (M$^+$+1, 100%).

Example 69

$^1$H NMR (300 MHz, DMSO-$d_6$) δ 8.03 (brs, 3H), 7.61-7.55 (m, 1H), 7.24-7.17 (m, 1H), 6.54-6.50 (m, 1H), 5.54 (s, 2H), 3.59 (s, 3H), 3.55-3.53 (m, 1H), 3.29-3.22 (m, 2H), 3.12-3.08 (m, 1H), 2.95-2.93 (m, 1H), 1.96-1.94 (m, 1H), 1.79-1.77 (m, 1H), 1.49-1.47 (m, 2H).

MS (ESI+) 440 (M$^+$+1, 100%).

Example 70

6-[(3S)-3-Aminopiperidin-1-yl]-5-(2-chloro-5-fluorobenzyl)-1,3-dimethyl-2,4-dioxo-2,3,4,5-tetrahydro-1H-pyrrolo[3,2-d]pyrimidine-7-carbonitrile hydrochloride

[Formula 86]

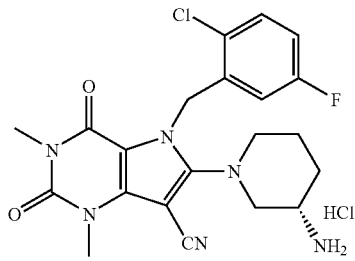

MS (ESI+) 445 (M$^+$+1, 100%).

Example 71

Sodium 6-[(3R)-3-aminopiperidin-1-yl]-5-(2-chlorobenzyl)-1,3-dimethyl-2,4-dioxo-2,3,4,5-tetrahydro-1H-pyrrolo[3,2-d]pyrimidine-7-carboxylate

[Formula 87]

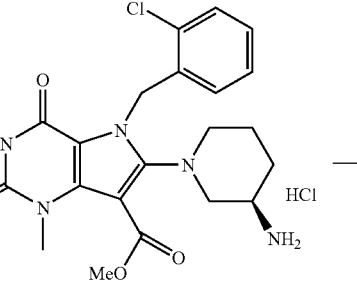

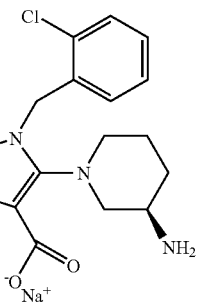

A 1N aqueous sodium hydroxide solution (1 ml), ethanol (1 ml) and tetrahydrofuran (1 ml) were added to methyl 6-[(3R)-3-aminopiperidin-1-yl]-5-(2-chlorobenzyl)-1,3-dimethyl-2,4-dioxo-2,3,4,5-tetrahydro-1H-pyrrolo[3,2-d]pyrimidine-7-carboxylate hydrochloride (53 mg), and the resulting mixture was stirred at 80° C. for 3 hours. After the reaction solution was cooled to 25° C., water was added thereto, followed by washing with ethyl acetate, and the aqueous layer was extracted with chloroform. The organic layer was dried over anhydrous sodium sulfate and filtered and the filtrate was concentrated under reduced pressure to obtain the title compound (41 mg) as a white solid.

$^1$H NMR (400 MHz, CDCl$_3$) δppm 7.41-7.38 (m, 1H), 7.22-7.13 (m, 2H), 6.42-6.38 (m, 1H), 5.67 (d, J=17 Hz, 1H), 5.58 (d, J=17 Hz, 1H), 3.65 (s, 3H), 3.27 (s, 3H), 3.20-3.13 (m, 1H), 3.05-2.95 (m, 1H), 2.93-2.85 (m, 1H), 2.83-2.75 (m, 1H), 2.64-2.54 (m, 1H), 1.83-1.73 (m, 1H), 1.64-1.52 (m, 1H), 1.40-1.25 (m, 2H).

MS (ESI+) 445 (M$^+$+1, 100%).

The compound of Example 72 was synthesized from a corresponding compound according to the process described in Example 1.

Example 72

Ethyl 3-amino-5-[(3R)-3-aminopiperidin-1-yl]-1-(2-chlorobenzyl)-4-cyano-1H-pyrrole-2-carboxylate hydrochloride

[Formula 88]

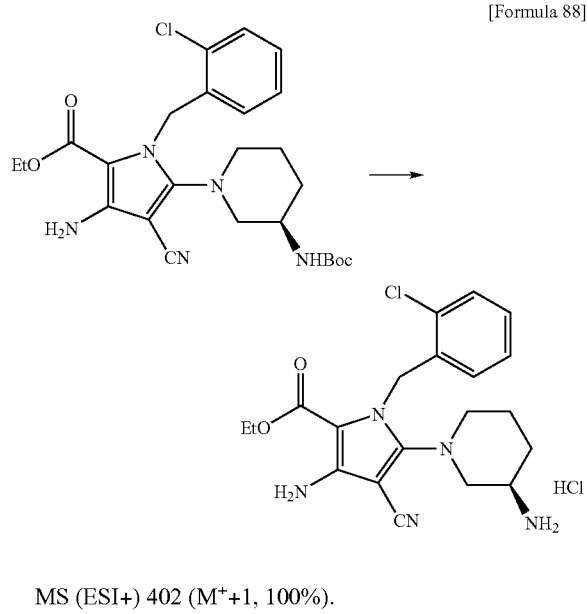

MS (ESI+) 402 (M$^+$+1, 100%).

Example 73

6-[(3R)-3-Aminopiperidin-1-yl]-5-(2-chlorobenzyl)-7-hydroxy-1,3-dimethyl-1H-pyrrolo[3,2-d]pyrimidine-2,4(3H, 5H)dione trifluoroacetate

[Formula 89]

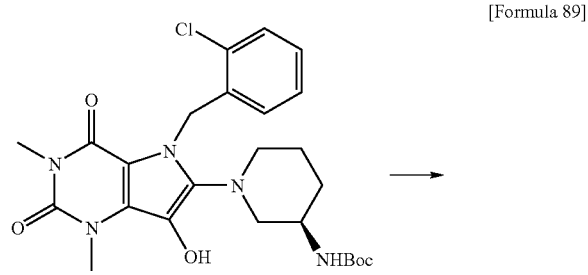

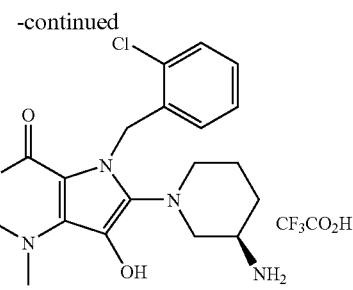

Trifluoroacetic acid (1.5 ml) was added to a solution of tert-butyl {(3R)-1-[5-(2-chlorobenzyl)-7-hydroxy-1,3-dimethyl-2,4-dioxo-2,3,4,5-tetrahydro-1H-pyrrolo[3,2-d]pyrimidin-6-yl]piperidin-3-yl}carbamate (54 g) in chloroform (1 ml), and the resulting mixture was stirred at room temperature for 2 hours. The reaction solution was concentrated under reduced pressure to obtain the title compound (45 mg).

$^1$H NMR (300 MHz, DMSO-d$_6$) δppm 8.27 (s, 1H), 7.90 (brs, 3H), 7.49-7.45 (m, 1H), 7.28-7.18 (m, 2H), 6.29-6.26 (m, 1H), 5.48 (s, 2H), 3.60 (s, 3H), 3.18-3.08 (m, 2H), 3.14 (s, 3H), 2.98-2.72 (m, 3H), 1.87-1.85 (m, 1H), 1.66-1.64 (m, 1H), 1.33-1.31 (m, 2H).

MS (ESI+) 418 (M$^+$+1, 100%).

Example 74

Methyl 6-[(3R)-3-aminopiperidin-1-yl]-5-(2-chloro-5-fluorobenzyl)-7-cyano-4-oxo-4,5-dihydro-3H-pyrrolo[3,2-d]pyrimidine-2-carboxylate

[Formula 90]

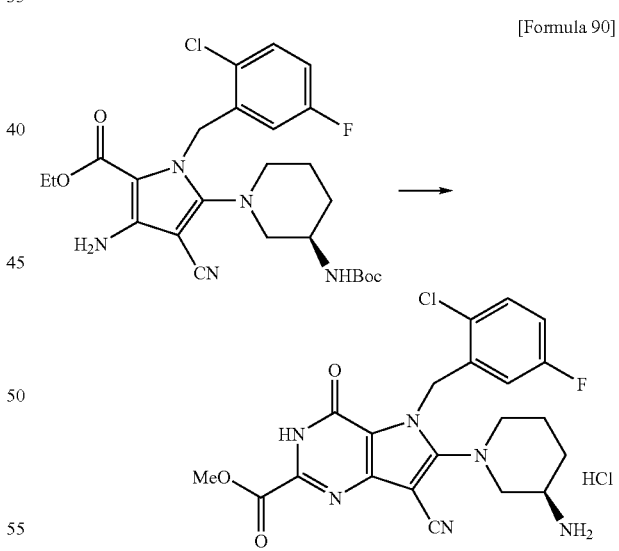

Methyl cyanoformate (170 μl) was added to a solution of ethyl 3-amino-5-{(3R)-3-[(tertbutoxycarbonyl)amino]piperidin-1-yl}-1-(2-chloro-5-fluorobenzyl)-4-cyano-1H-pyrrole-2-carboxylate (104 mg) in hydrochloric acid-methanol reagent 10 (4 ml), and the resulting mixture was stirred with heating at 90° C. in a sealed tube for 15 hours. The reaction solution was concentrated under reduced pressure and chloroform was added to the residue. The solid precipitated was removed by filtration and the filtrate was concentrated under reduced pressure. To the resulting residue was added diethyl ether, and the solid precipitated was collected by filtration to obtain a crude product of the title compound (107 mg).

MS (ESI+) 459 (M⁺+1, 13%).

Each of the compounds of Examples 75 and 76 was synthesized from a corresponding compound according to the process described in Example 1.

Example 75

6-[(3R)-3-Aminopiperidin-1-yl]-5-(2-chlorobenzyl)-7-methoxy-1,3-dimethyl-1H-pyrrolo[3,2-d]pyrimidine-2,4(3H,5H)-dione trifluoroacetate

[Formula 91]

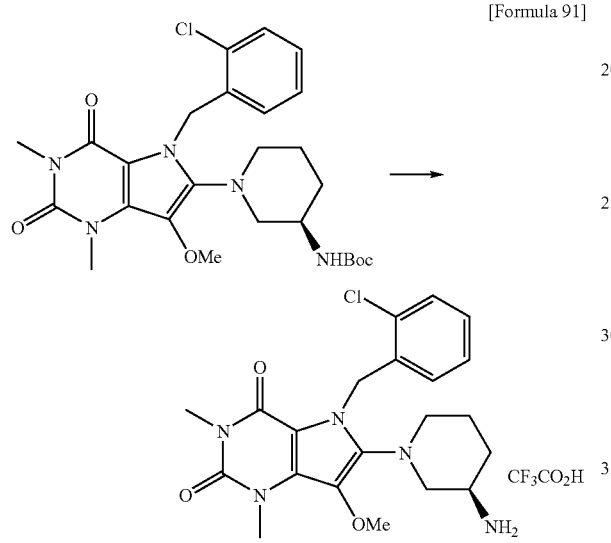

$^1$H NMR (300 MHz, CDCl$_3$) δppm 7.40-7.37 (m, 1H), 7.22-7.12 (m, 2H), 6.39-6.36 (m, 1H), 5.84 (d, J=17.4 Hz, 1H), 5.49 (d, J=17.4 Hz, 1H), 3.77 (s, 3H), 3.70 (s, 3H), 3.42-3.33 (m, 2H), 3.37 (s, 3H), 3.13-3.10 (m, 1H), 2.96-2.88 (m, 2H), 1.87-1.64 (m, 4H).

MS (ESI+) 432 (M⁺+1, 100%).

Example 76

6-[(3R)-3-Aminopiperidin-1-yl]-5-(2-chloro-5-fluorobenzyl)-2,3-dimethyl-4-oxo-4,5-dihydro-3H-pyrrolo[3,2-d]pyrimidine-7-carbonitrile

[Formula 92]

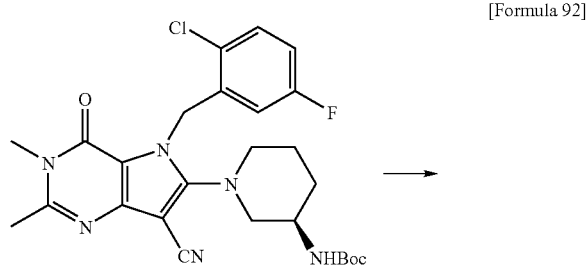

-continued

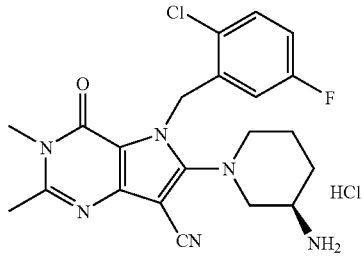

$^1$H NMR (300 MHz, DMSO-d$_6$) δ 8.27 (brs, 3H), 7.57-7.53 (m, 1H), 7.21-7.14 (m, 1H), 6.39-6.34 (m, 1H), 5.54 (d, J=17.4 Hz, 1H), 5.48 (d, J=17.4 Hz, 1H), 3.47-3.44 (m, 1H), 3.40 (s, 3H), 3.25-3.15 (m, 2H), 3.05-3.01 (m, 1H), 2.94-2.87 (m, 1H), 2.53 (s, 3H), 1.94-1.92 (m, 1H), 1.79-1.77 (m, 1H), 1.52-1.48 (m, 2H).

MS (ESI+) 429 (M⁺+1, 100%).

Reference Example 1 tert-Butyl {(3R)-1-[2,2-dicyano-1-(methylthio)vinyl]piperidin-3-yl}carbamate

[Formula 93]

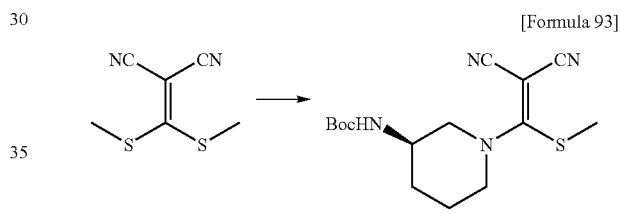

A solution of [bis(methylthio)methylene]-propanedinitrile (10 g) and (R)-tert-3-butyl piperidin-3-ylcarbamate (11.8 g) in ethanol (350 ml) was stirred at 80° C. for 3 hours, and the reaction solution was cooled to 25° C. and then concentrated under reduced pressure to obtain the title compound (19 g) as a light-yellow amorphous substance.

$^1$H NMR (400 MHz, CDCl$_3$) δppm 4.60-4.48 (m, 1H), 4.18-4.03 (m, 1H), 3.94-3.80 (m, 1H), 3.77-3.61 (m, 1H), 3.59-3.35 (m, 2H), 2.61 (s, 3H), 2.12-2.00 (m, 1H), 1.98-1.86 (m, 1H), 1.82-1.68 (m, 1H), 1.68-1.50 (m, 1H), 1.46 (s, 9H).

MS (ESI+) 323 (M⁺+1, 40%).

Reference Example 2

Ethyl 3-amino-5-{(3R)-3-[(tertbutoxycarbonyl)amino]piperidin-1-yl}-1-(2-chlorobenzy)-4-cyano-1H-pyrrole-2-carboxylate

[Formula 94]

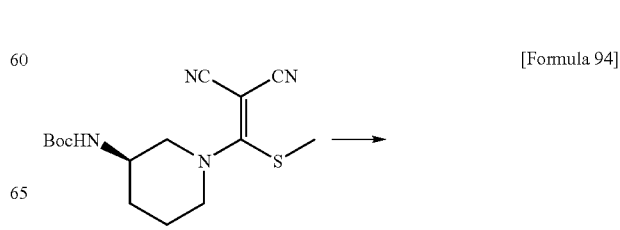

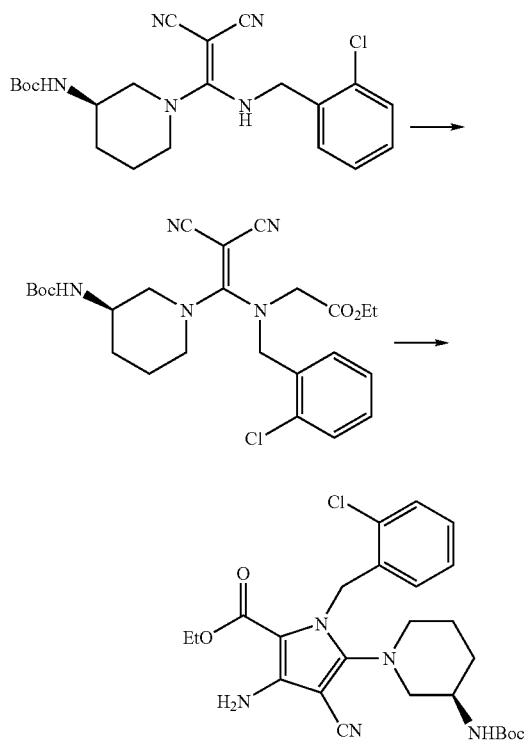

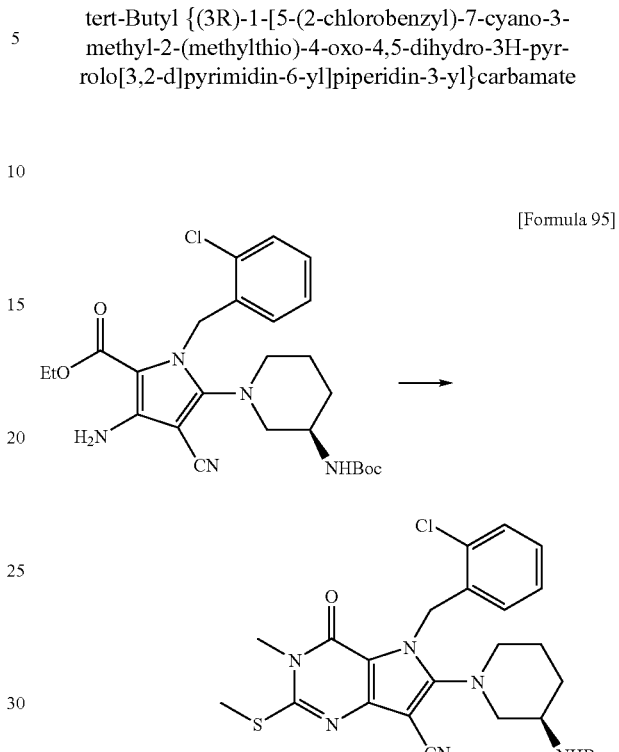

Reference Example 3 tert-Butyl {(3R)-1-[5-(2-chlorobenzyl)-7-cyano-3-methyl-2-(methylthio)-4-oxo-4,5-dihydro-3H-pyrrolo[3,2-d]pyrimidin-6-yl]piperidin-3-yl}carbamate

[Formula 95]

2-Chlorobenzylamine (1.7 ml) was added to a solution of tert-butyl {(3R)-1-[2,2-dicyano-1-(methylthio)vinyl]piperidin-3-yl}carbamate (15 g) in isopropanol (28 ml), and the resulting mixture was heated under reflux. After 5 hours, 2-chlorobenzylamine (2.8 ml) was added thereto, followed by heating under reflux for another 10 hours. The reaction solution was cooled to 25° C. and then concentrated under reduced pressure, and the resulting residue was roughly purified by a silica gel column chromatography (hexane/ethyl acetate=5/1 to 1/1). The reaction mixture (9.82 g) thus obtained was dissolved in acetone (90 ml), followed by adding thereto potassium carbonate (6.2 g) and ethyl bromoacetate (1.5 ml), and the resulting mixture was stirred at 60° C. for 3 hours. The reaction solution was cooled to 25° C. and water was added thereto, followed by extraction with ethyl acetate. The organic layer was washed with a saturated aqueous sodium chloride solution, dried over sodium sulfate and then filtered and the filtrate was concentrated under reduced pressure. The resulting residue (7.53 g) was dissolved in tetrahydrofuran (150 ml) and the resulting solution was cooled to 0° C. Then, sodium hydride (60%, 780 mg) was added thereto and the resulting mixture was stirred for 1 hour while being slowly warmed to 25° C. A saturated aqueous ammonium chloride solution was added to the reaction solution, followed by extraction with ethyl acetate. The organic layer was washed with a saturated aqueous sodium chloride solution and concentrated under reduced pressure, and the resulting residue was purified by a silica gel column chromatography (hexane/ethyl acetate=2/1 to 1/1) to obtain the title compound (2.7 g) as a white amorphous substance.

MS (ESI+) 502 (M$^+$+1, 100%).

Under a nitrogen atmosphere, methyl isothiocyanate (71 μl) and potassium carbonate (143 mg) were added to a solution (2.5 ml) of ethyl 3-amino-5-{(3R)-3-[(tert-butoxycarbonyl)amino]piperidin-1-yl}-1-(2-chlorobenzyl)-4-cyano-1H-pyrrole-2-carboxylate (260 mg) in pyridine, and the resulting mixture was stirred with heating at 130° C. for 3 hours. After the reaction solution was cooled to 25° C. and then concentrated under reduced pressure, toluene (5 ml) was added thereto and the resulting mixture was concentrated under reduced pressure. This procedure was repeated three times. To the resulting residue was added acetone (2.5 ml), and the resulting mixture was cooled to 0° C. Methyl iodide (65 μl) was added dropwise thereto and the resulting mixture was warmed to 25° C. and stirred for 4 hours. A saturated aqueous ammonium chloride solution was added to the reaction solution, followed by extraction with ethyl acetate. The organic layer was dried over anhydrous sodium sulfate and filtered and the filtrate was concentrated under reduced pressure. The resulting residue was purified by a silica gel column chromatography (hexane/ethyl acetate=5/1 to 1/1) to obtain the title compound (250 mg).

$^1$H NMR (400 MHz, CDCl$_3$) δ 7.41-7.36 (m, 1H), 7.23-7.08 (m, 2H), 6.49-6.40 (m, 1H), 5.71 (d, J=17.0 Hz, 1H), 5.61 (d, J=17.0 Hz, 1H), 3.80-3.69 (m, 1H), 3.52 (s, 3H), 3.50-3.42 (m, 1H), 3.04-2.91 (m, 3H), 2.68 (s, 3H), 1.88-1.76 (m, 1H), 1.74-1.50 (m, 3H), 1.42 (s, 9H).

MS (ESI+) 543 (M$^+$+1, 100%).

Reference Example 4 tert-Butyl {(3R)-1-[5-(2-chlorobenzyl)-7-cyano-3-methyl-2-(methylsulfonyl)-4-oxo-4,5-dihydro-3H-pyrrolo[3,2-d]pyrimidin-6-yl]piperidin-3-yl}carbamate

[Formula 96]

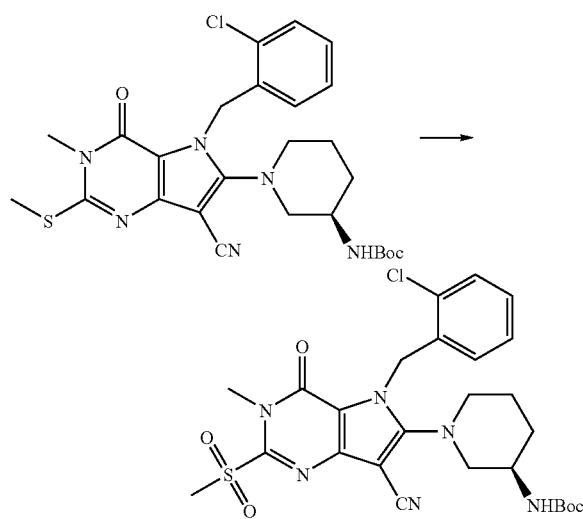

Sodium tungstate dihydrate (139 mg) was added to a solution of tert-butyl {(3R)-1-[5-(2-chlorobenzyl)-7-cyano-3-methyl-2-(methylthio)-4-oxo-4,5-dihydro-3H-pyrrolo[3,2-d]pyrimidin-6-yl]piperidin-3-yl}carbamate (230 mg) in a mixture of methanol (2 ml), acetic acid (0.7 ml) and water (0.25 ml), and the resulting mixture was heated to 50° C. A 30% aqueous hydrogen peroxide solution (0.29 ml) was added dropwise thereto, followed by stirring at 60° C. for 4 hours. After the reaction mixture was allowed to cool, the precipitate formed was collected by filtration, washed with water and then dried under reduced pressure to obtain the title compound (230 mg) as a white solid.

MS (ESI+) 575 (M$^+$+1, 46%).

Reference Example 5 tert-Butyl {(3R)-1-[5-(2-chlorobenzyl)-7-cyano-2-hydroxy-3-methyl-4-oxo-4,5-dihydro-3H-pyrrolo[3,2-d]pyrimidin-6-yl]piperidin-3-yl}carbamate

[Formula 97]

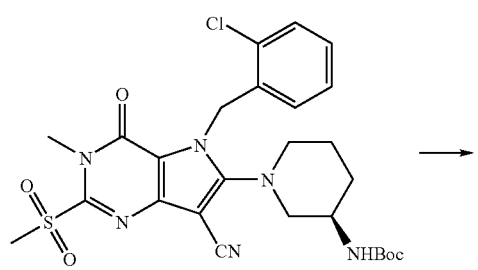

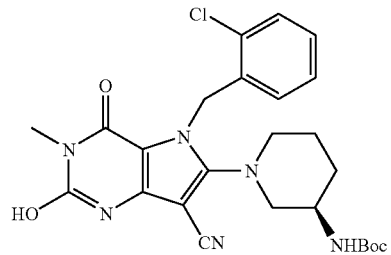

To a solution of tert-butyl {(3R)-1-[5-(2-chlorobenzyl)-7-cyano-3-methyl-2-(methylsulfonyl)-4-oxo-4,5-dihydro-3H-pyrrolo[3,2-d]pyrimidin-6-yl]piperidin-3-yl}carbamate (100 mg) in ethanol (1 ml) was added 1N sodium hydroxide (1 ml), and the resulting mixture was stirred at 80° C. for 5 hours. After the reaction solution was allowed to cool, a saturated aqueous ammonium chloride solution was added thereto, followed by extraction with ethyl acetate. The organic layer was washed with a saturated aqueous sodium chloride solution, dried over sodium sulfate and then filtered and the filtrate was concentrated under reduced pressure. The resulting residue was purified by a silica gel column chromatography (hexane/ethyl acetate=1/1) to obtain the title compound (81 mg) as a white solid.

MS (ESI+) 513 (M$^+$+1, 40%).

Reference Example 6 tert-Butyl {(3R)-1-[5-(2-chlorobenzyl)-7-cyano-1,3-dimethyl-2,4-dioxo-2,3,4,5-tetrahydro-1H-pyrrolo[3,2-d]pyrimidin-6-yl]piperidin-3-yl}carbamate

[Formula 98]

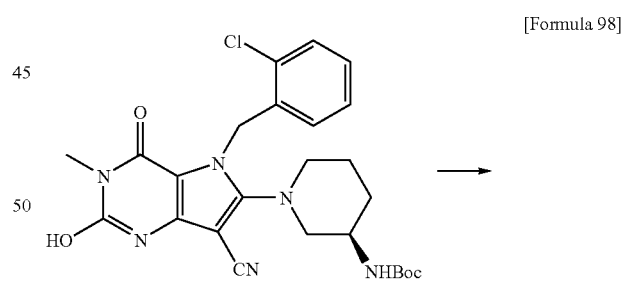

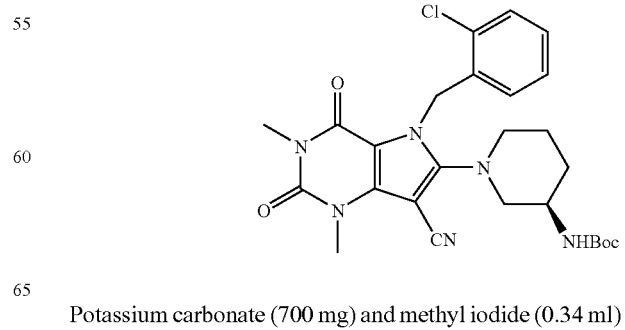

Potassium carbonate (700 mg) and methyl iodide (0.34 ml) were added to a solution of tert-butyl {(3R)-1-[5-(2-chlorobenzyl)-7-cyano-2-hydroxy-3-methyl-4-oxo-4,5-dihydro-3H-pyrrolo[3,2-d]pyrimidin-6-yl]piperidin-3-yl}carbamate (1.3 g) in N,N-dimethylformamide, and the resulting mixture was stirred at 25° C. for 4 hours. After the reaction, water was added to the reaction solution, followed by extraction with ethyl acetate. The organic layer was washed with water and a saturated aqueous sodium chloride solution, dried over sodium sulfate and then filtered and the filtrate was concentrated under reduced pressure. The resulting residue was purified by a silica gel column chromatography (hexane/ethyl acetate=1/1) to obtain the title compound (1.1 g) as a white solid.

$^1$H NMR (400 MHz, CDCl$_3$) δ 7.42-7.38 (m, 1H), 7.25-7.13 (m, 2H), 6.56-6.48 (m, 1H), 5.69 (d, J=16.5 Hz, 1H), 5.59 (d, J=16.5 Hz, 1H), 3.76 (s, 3H), 3.75-3.65 (m, 1H), 3.50-3.41 (m, 1H), 3.35 (s, 3H), 3.01-2.84 (m, 3H), 1.89-1.78 (m, 1H), 1.69-1.45 (m, 3H), 1.42 (s, 9H).

MS (ESI+) 527 (M$^+$+1, 100%).

Reference Example 7

N-(1-{(3R)-3-[(tert-Butoxycarbonyl)amino]-piperidin-1-yl}-2,2-dicyanovinyl)glycine ethyl ester

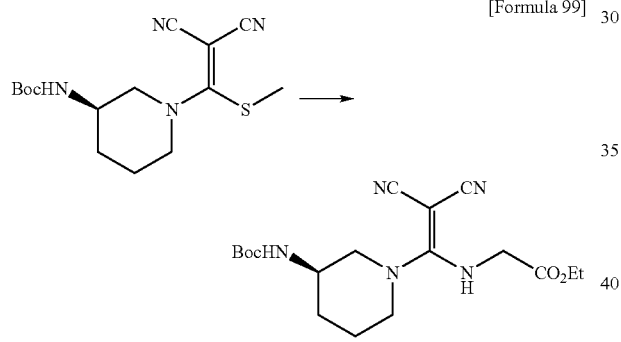

[Formula 99]

Glycine methyl ester hydrochloride (3.3 g) and triethylamine (3.7 ml) were added to a solution of tert-butyl {(3R)-1-[2,2-dicyano-1-(methylthio)vinyl]-piperidin-3-yl}carbamate (1.3 g) in ethanol (30 ml), and the resulting mixture was heated under reflux. After 4 hours, triethylamine (1.5 ml) was added thereto, followed by heating under reflux for another 7 hours. After the reaction solution was cooled to 25° C., a saturated aqueous sodium hydrogencarbonate solution was added thereto, followed by extraction with chloroform. The organic layer was washed with a saturated aqueous sodium chloride solution, dried over sodium sulfate and then filtered and the filtrate was concentrated under reduced pressure. The resulting residue was purified by a silica gel column chromatography (hexane/ethyl acetate=3/1 to 1/1) to obtain the title compound (360 mg) as a white amorphous substance.

$^1$H NMR (400 MHz, CDCl$_3$) δ 5.76 (brs, 1H), 4.58 (brd, 1H), 4.27 (q, J=7.1 Hz, 2H), 4.15 (dd, J=1.0, 5.2 Hz, 2H), 3.84-3.79 (m, 1H), 3.69-3.58 (m, 2H), 3.40-3.30 (m, 1H), 3.28-3.18 (m, 1H), 2.05-1.95 (m, 1H), 1.89-1.79 (m, 1H), 1.74-1.63 (m, 1H), 1.60-1.49 (m, 1H), 1.45 (s, 9H) 1.32 (t, J=7.1 Hz, 3H).

MS (ESI+) 378 (M$^+$+1, 10%).

Reference Example 8

N-(1-{(3R)-3-[(tert-Butoxycarbonyl)amino]-piperidin-1-yl}-2,2-dicyanovinyl)-N-(2-chlorobenzyl)glycine ethyl ester

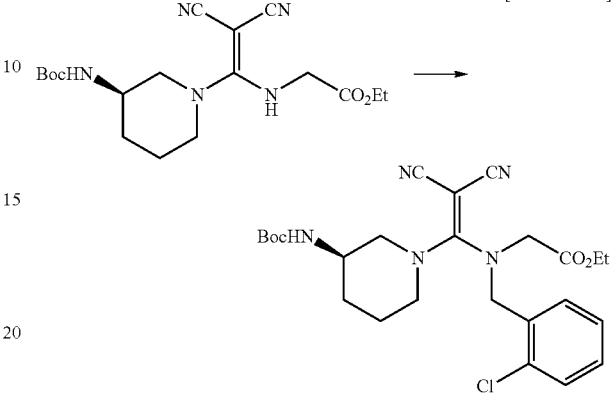

[Formula 100]

A solution of N-(1-{(3R)-3-[(tertbutoxycarbonyl)amino]piperidin-1-yl}-2,2-dicyanovinyl)glycine ethyl ester (300 mg), 2-chlorobenzyl bromide (0.15 ml) and potassium carbonate (330 mg) in acetone (4 ml) was stirred at 25° C. for 24 hours. Water was added to the reaction solution, followed by extraction with ethyl acetate. The organic layer was washed with an aqueous sodium chloride solution, dried over sodium sulfate and then filtered and the filtrate was concentrated under reduced pressure. The resulting residue was purified by a silica gel column chromatography (hexane/ethyl acetate=5/1 to 1/1) to obtain the title compound (340 mg) as a white amorphous substance.

MS (ESI+) 502 (M$^+$+1, 25%).

Reference Example 9

Ethyl 3-amino-5-{(3R)-3-[(tertbutoxycarbonyl)amino]piperidin-1-yl}-1-(2-chlorobenzyl)-4-cyano-1H-pyrrole-2-carboxylate

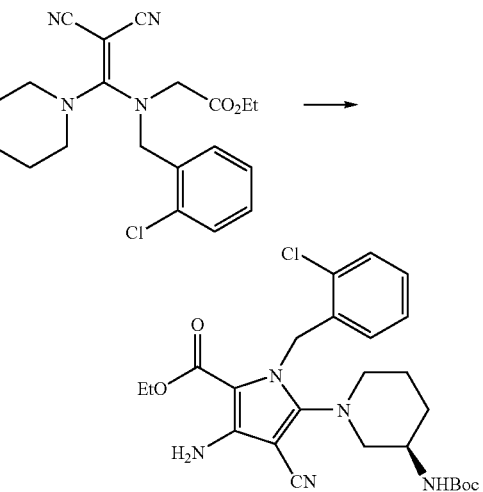

[Formula 101]

A solution of N-(1-{(3R)-3-[(tertbutoxycarbonyl)amino]piperidin-1-yl}-2,2-dicyanovinyl)-N-(2-chlorobenzyl)glycine ethyl ester (320 mg) in tetrahydrofuran (5 ml) was cooled to 0° C., followed by adding thereto sodium hydride (33 mg), and the resulting mixture was stirred for 1 hour while being warmed to 25° C. Water was added to the reaction solution, followed by extraction with ethyl acetate. The organic layer was washed with a saturated aqueous sodium chloride solution, dried over sodium sulfate and then filtered and the filtrate was concentrated under reduced pressure. The resulting residue was purified by a silica gel column chromatography (hexane/ethyl acetate=3/1 to 1/1) to obtain the title compound (300 mg).

$^1$H NMR (400 MHz, CDCl$_3$) δ 7.40-7.35 (m, 1H), 7.21-7.09 (m, 2H), 6.57-6.49 (m, 1H), 5.47-5.30 (m, 2H), 4.07 (q, J=7.0 Hz, 2H), 3.76-3.64 (m, 1H), 3.40-3.30 (m, 1H), 3.00-2.82 (m, 3H), 1.87-1.74 (m, 1H), 1.72-1.46 (m, 3H), 1.41 (s, 9H), 1.07 (t, J=7.0 Hz, 3H).

MS (ESI+) 502 (M$^+$+1, 29%).

Reference Example 10 tert-Butyl [(3R)-1-(1,3-dimethyl-2,4-dioxo-2,3,4,5-tetrahydro-1H-pyrrolo[3,2-d]pyrimidin-6-yl)piperidin-3-yl]carbamate

[Formula 102]

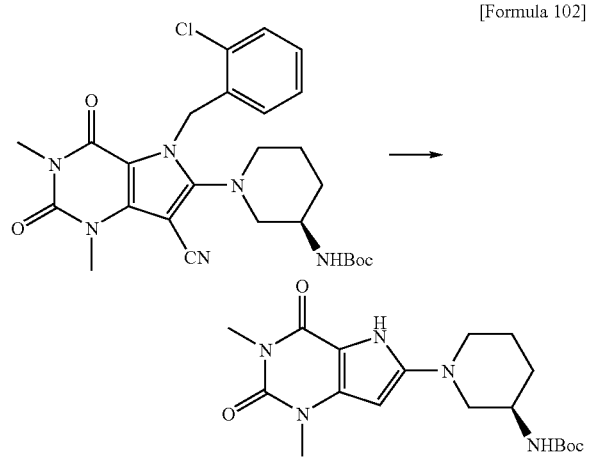

Under ice-cooling, water (2 ml) and concentrated sulfuric acid (4 ml) were added to tert-butyl {(3R)-1-[5-(2-chlorobenzyl)-7-cyano-1,3-dimethyl-2,4-dioxo-2,3,4,5-tetrahydro-1H-pyrrolo[3,2-d]pyrimidin-6-yl]piperidin-3-yl}carbamate (300 mg), and the resulting mixture was stirred at 140° C. After 3 hours, the reaction solution was cooled to 0° C. and adjusted to pH 8 or higher by dropwise addition of a 5N aqueous potassium carbonate solution. The reaction solution was extracted with chloroform and the organic layer was washed with a saturated aqueous sodium chloride solution, dried over sodium sulfate and then filtered, and the filtrate was concentrated under reduced pressure. To the resulting residue were added di-tert-butyl dicarbonate (372 mg), 1,4-dioxane (5 ml) and a saturated aqueous sodium hydrogencarbonate solution (5 ml), and the resulting mixture was stirred at room temperature for 8 hours. Water was added to the reaction solution, followed by extraction with chloroform. The organic layer was washed with a saturated aqueous sodium chloride solution, dried over sodium sulfate and then filtered and the filtrate was concentrated under reduced pressure. To the resulting residue was added diethyl ether, followed by filtration, and the precipitate was washed with hexane to obtain the title compound (200 mg) as a light-yellow solid.

$^1$H NMR (400 MHz, DMSO-d$_6$) δppm 11.07 (s, 1H), 6.90 (d, J=8.0 Hz, 1H), 5.44 (s, 1H), 3.71-3.53 (m, 2H), 3.47-3.35 (m, 1H), 3.31 (s, 3H), 3.19 (s, 3H), 2.76-2.65 (m, 1H), 2.62-2.53 (m, 1H), 1.85-1.65 (m, 2H), 1.57-1.28 (m, 2H), 1.44 (s, 9H).

MS (ESI+) 378 (M$^+$+1, 100%).

Reference Example 11 tert-Butyl {(3R)-1-[5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate

[Formula 103]

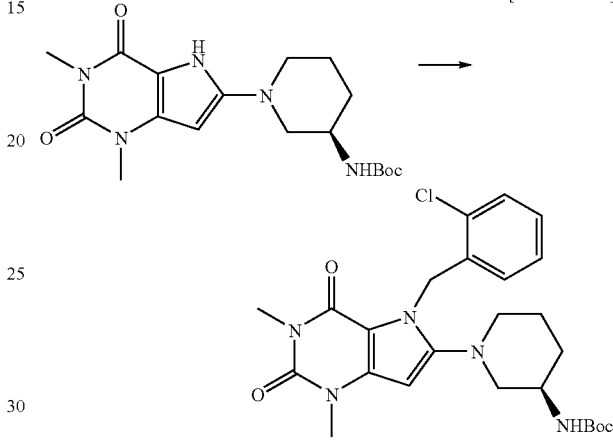

A solution of tert-butyl [(3R)-1-(1,3-dimethyl-2,4-dioxo-2,3,4,5-tetrahydro-1H-pyrrolo[3,2-d]pyrimidin-6-yl)piperidin-3-yl]carbamate (60 mg), 2-chlorobenzyl bromide (32 μl) and potassium carbonate (44 mg) in N,N-dimethylformamide (2 ml) was stirred at room temperature for 2 hours. Water was added to the reaction solution, followed by extraction with ethyl acetate. The organic layer was washed with water and a saturated aqueous sodium chloride solution, dried over sodium sulfate and then filtered, and the filtrate was concentrated under reduced pressure and purified by a preparative thin-layer chromatography (hexane/ethyl acetate=1/2) to obtain the title compound (10 mg) as a white amorphous substance.

$^1$H NMR (400 MHz, CDCl$_3$) δ 7.39-7.36 (m, 1H), 7.18-7.07 (m, 2H), 6.51-6.42 (m, 1H), 5.67 (d, J=16.8 Hz, 1H), 5.59 (s, 1H), 5.56 (d, J=16.8 Hz, 1H), 3.85-3.74 (m, 1H), 3.48 (s, 3H), 3.36 (s, 3H), 3.12-3.03 (m, 1H), 2.82-2.62 (m, 3H), 1.80-1.47 (m, 4H), 1.43 (s, 9H).

MS (ESI+) 502 (M$^+$+1, 100%).

Reference Example 12 tert-Butyl {1-[5-(2-chloro-5-fluorobenzyl)-1,3-dimethyl-2,4-dioxo-2,3,4,5-tetrahydro-1H-pyrrolo[3,2-d]pyrimidin-6-yl]piperidin-3-yl}carbamate

[Formula 104]

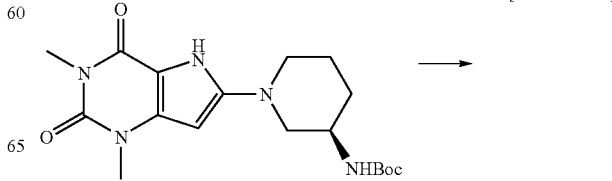

-continued

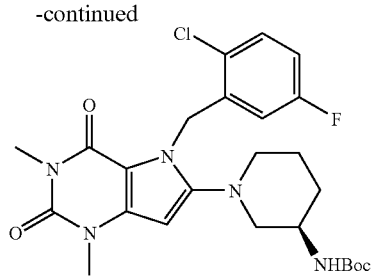

The title compound was synthesized from a corresponding compound by the same process as in Reference Example 13.

$^1$H NMR (400 MHz, CDCl$_3$) δ 7.38-7.30 (m, 1H), 6.92-6.83 (m, 1H), 6.22-6.13 (m, 1H), 5.62 (d, J=17.0 Hz, 1H), 5.61 (s, 1H), 5.52 (d, J=17.0 Hz, 1H), 3.85-3.72 (m, 1H), 3.48 (s, 3H), 3.35 (s, 3H), 3.14-3.03 (m, 1H), 2.83-2.64 (m, 3H), 1.79-1.45 (m, 4H), 1.42 (s, 9H).

MS (ESI+) 520 (M$^+$+1, 100%).

Reference Example 13 tert-Butyl {(3R)-1-[5-(2-chlorobenzyl)-7-cyano-2-(3-ethoxyphenoxy)-3-methyl-4-oxo-4,5-dihydro-3H-pyrrolo[3,2-d]pyrimidin-6-yl]piperidine-3-yl}carbamate

[Formula 105]

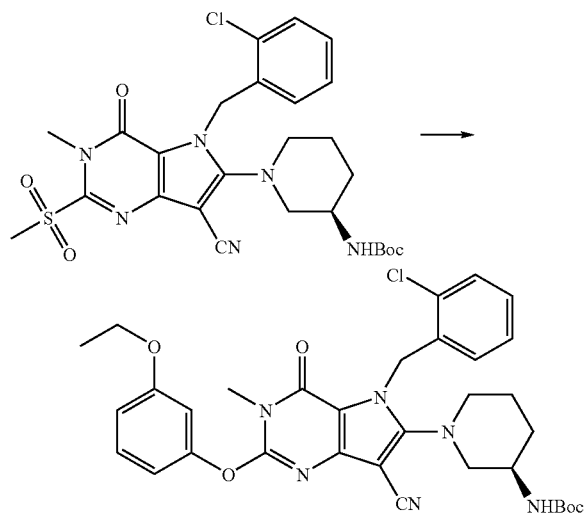

A solution of tert-butyl {(3R)-1-[5-(2-chlorobenzyl)-7-cyano-3-methyl-2-(methylsulfonyl)-4-oxo-4,5-dihydro-3H-pyrrolo[3,2-d]pyrimidin-6-yl]piperidine-3-yl}carbamate (110 mg), 3-ethoxyphenol (31 µl) and potassium carbonate (39 mg) in N,N-dimethylformamide (2 ml) was stirred at 50° C. for 1 hour. After the reaction solution was allowed to cool, a saturated aqueous ammonium chloride solution was added thereto, followed by extraction with ethyl acetate. The organic layer was washed with water and a saturated aqueous sodium chloride solution, dried over sodium sulfate and then filtered and the filtrate was concentrated under reduced pressure. The resulting residue was purified by a silica gel column chromatography (hexane/ethyl acetate=3/1 to 1/1) to obtain the title compound (86 mg) as a white solid.

MS (ESI+) 633 (M$^+$+1, 100%).

Reference Example 14 tert-Butyl {(3R)-1-[2-[2-(aminocarbonyl)phenoxy]-5-(2-chlorobenzyl)-7-cyano-3-methyl-4-oxo-4,5-dihydro-3H-pyrrolo[3,2-d]pyrimidin-6-yl]piperidine-3-yl}carbamate

[Formula 106]

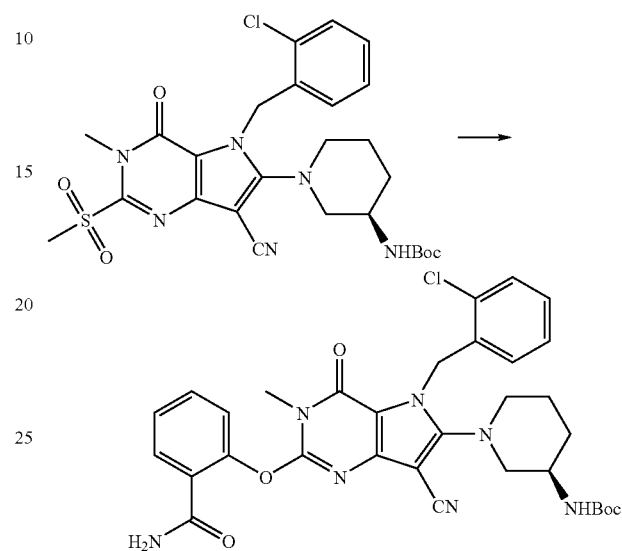

The title compound was synthesized from a corresponding compound by the same process as in Reference Example 1.

MS (ESI+) 632 (M$^+$+1, 100%).

Reference Example 15 tert-Butyl {(3R)-1-[7-(aminocarbonyl)-5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate

[Formula 107]

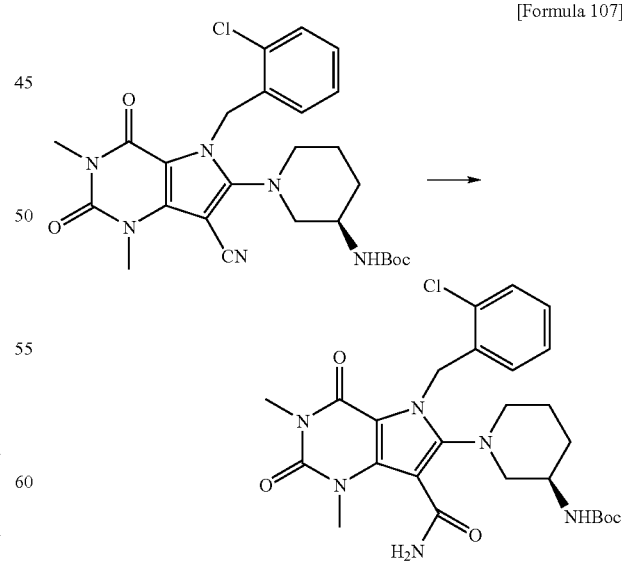

To a mixed solution of dimethyl sulfoxide (250 ml) and water (25 ml) were added tert-butyl {(3R)-1-[5-(2-chlorobenzyl)-7-cyano-1,3-dimethyl-2,4-dioxo-2,3,4,5-tetrahydro-1H-pyrrolo[3,2-d]pyrimidin-6-yl]piperidin-3-yl}carbamate (17.9 g) and potassium carbonate (4.7 g). In a water bath, an aqueous hydrogen peroxide solution (a 30-35% aqueous solution, 17 ml) was added dropwise and the resulting mixture was stirred at 25° C. for 15 hours. Water was added to the reaction solution, followed by extraction with ethyl acetate. The organic layer was washed three times with water and then once with a saturated aqueous sodium chloride solution, dried over anhydrous sodium sulfate and then filtered and the filtrate was concentrated under reduced pressure to obtain the title compound (15.6 g) as a light-yellow amorphous substance.

MS (ESI+) 545 (M$^+$+1, 100%).

Reference Example 16 tert-Butyl {(3R)-1-[5-(2-chlorobenzyl)-1,3-dimethyl-2,4-dioxo-7-(1H-tetrazol-5-yl)-2,3,4,5-tetrahydro-1H-pyrrolo[3,2-d]pyrimidin-6-yl]piperidin-3-yl}carbamate

[Formula 108]

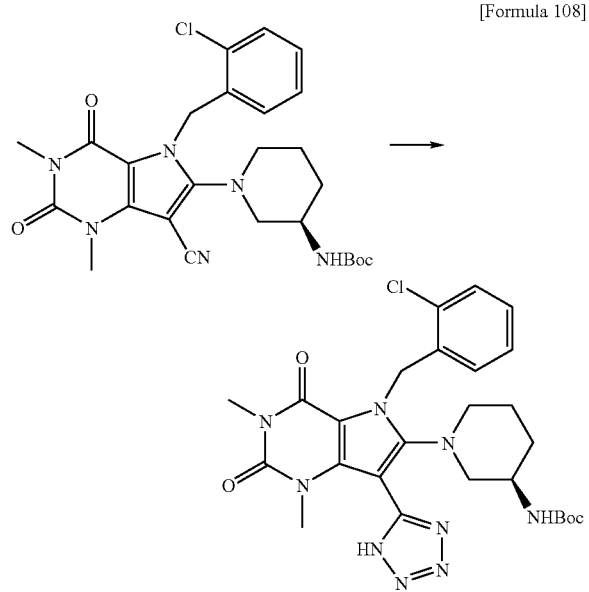

Sodium azide (154 mg) and ammonium chloride (125 mg) were added to a solution of tert-butyl {(3R)-1-[5-(2-chlorobenzyl)-7-cyano-1,3-dimethyl-2,4-dioxo-2,3,4,5-tetrahydro-1H-pyrrolo[3,2-d]pyrimidin-6-yl]piperidin-3-yl}carbamate (250 mg) in N,N-dimethylformamide (4 ml), and the resulting mixture was stirred at 150° C. for 8 hours. Sodium azide (154 mg) and ammonium chloride (125 mg) were further added thereto and stirred for another 6 hours. After the reaction solution was cooled to 25° C., a 10% aqueous potassium hydrogensulfate solution was added thereto, followed by extraction with ethyl acetate. The organic layer was washed with water, dried over anhydrous sodium sulfate and then filtered and the filtrate was concentrated under reduced pressure. The resulting residue was purified by HPLC to obtain the title compound (23 mg) as a white solid.

MS (ESI+) 570 (M$^+$+1, 100%).

Reference Example 17 tert-Butyl {(3R)-1-[5-(2-chlorobenzyl)-1,3-dimethyl-2,4-dioxo-7-(1H-pyrrolo-1-ylcarbonyl)-2,3,4,5-tetrahydro-1H-pyrrolo[3,2-d]pyrimidin-6-yl]piperidin-3-yl}carbamate

[Formula 109]

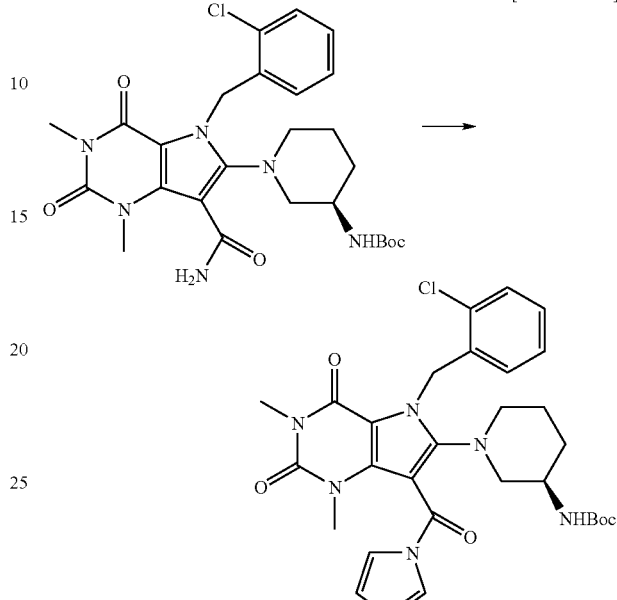

After tert-butyl {(3R)-1-[7-(aminocarbonyl)-5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate (12.6 g) and 2,5-dimethoxytetrahydrofuran (150 ml) were stirred at 25° C., thionyl chloride (1.7 ml) was added dropwise thereto and the resulting mixture was stirred at 40° C. for 6 hours. After the reaction solution was cooled to 25° C., a saturated aqueous sodium hydrogencarbonate solution was added thereto, followed by extraction with ethyl acetate. The organic layer was washed with a saturated aqueous sodium chloride solution, dried over anhydrous sodium sulfate and then filtered and the filtrate was concentrated under reduced pressure. The resulting residue was purified by a silica gel column chromatography (hexane/ethyl acetate=2/1) to obtain the title compound (15.9 g) as a yellow amorphous substance.

MS (ESI+) 595 (M$^+$+1, 100%).

Reference Example 18

Methyl 6-{(3R)-3-[(tert-butoxycarbonyl)amino]piperidin-1-yl}-5-(2-chlorobenzyl)-1,3-dimethyl-2,4-dioxo-2,3,4,5-tetrahydro-1H-pyrrolo[3,2-d]pyrimidine-7-carboxylate

[Formula 110]

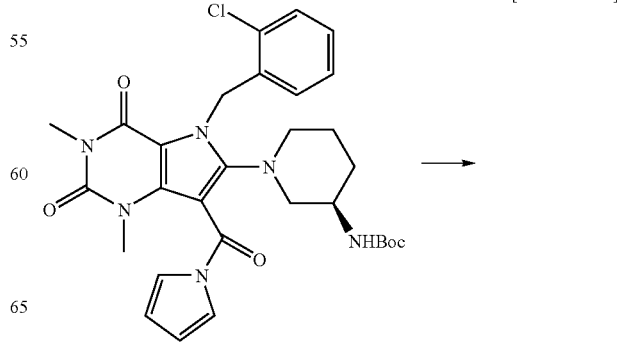

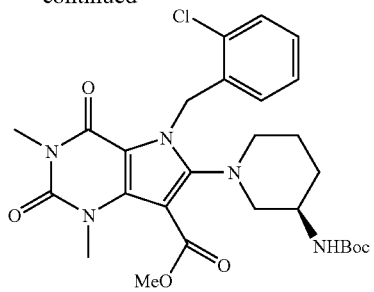

Sodium methoxide (a 28% methanol solution, 0.2 ml) was added to a solution of tert-butyl {(3R)-1-[5-(2-chlorobenzyl)-1,3-dimethyl-2,4-dioxo-7-(1H-pyrrolo-1-ylcarbonyl)-2,3,4,5-tetrahydro-1H-pyrrolo[3,2-d]pyrimidin-6-yl]piperidin-3-yl}carbamate (410 mg) in methanol (5 ml), and the resulting mixture was stirred at 60° C. for 2 hours. After the reaction solution was cooled to 25° C., a saturated aqueous ammonium chloride solution was added thereto, followed by extraction with ethyl acetate. The organic layer was washed with a saturated aqueous sodium chloride solution, dried over anhydrous sodium sulfate and then filtered and the filtrate was concentrated under reduced pressure to obtain the title compound (380 mg) as a white amorphous substance.

MS (ESI+) 560 (M$^+$+1, 100%).

Reference Example 19 tert-Butyl {(3R)-1-[5-(2-chlorobenzyl)-1,3-dimethyl-7-(morpholin-4-ylcarbonyl)-2,4-dioxo-2,3,4,5-tetrahydro-1H-pyrrolo[3,2-d]pyrimidin-6-yl]piperidin-3-yl}carbamate

[Formula 111]

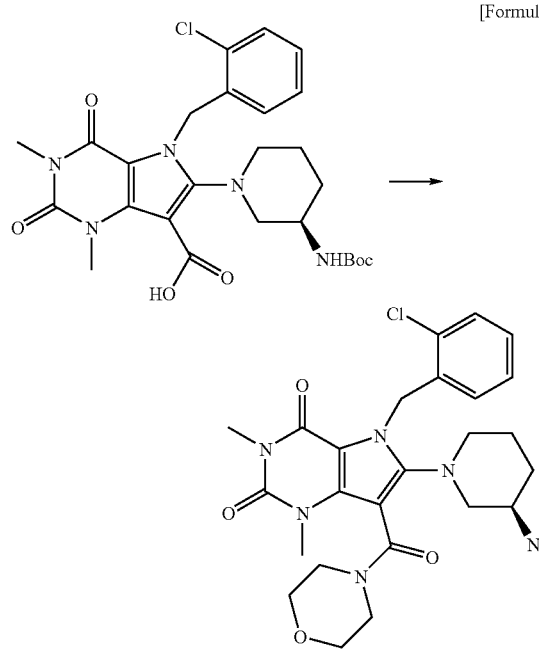

1-Hydroxybenzotriazole (117 mg), 1-(3-dimethylaminopropyl)-3-ethylcarbodiimide hydrochloride (147 mg), triethylamine (0.21 ml) and morpholine (63 μl) were added to a solution of 6-{(3R)-3-[(tertbutoxycarbonyl)amino]piperidin-1-yl}-5-(2-chlorobenzyl)-1,3-dimethyl-2,4-dioxo-2,3,4,5-tetrahydro-1H-pyrrolo[3,2-d]pyrimidine-7-carboxylic acid (140 mg) in N,N-dimethylformamide (3 ml), and the resulting mixture was stirred at 25° C. for 20 hours. A saturated aqueous ammonium chloride solution was added to the reaction solution, followed by extraction with ethyl acetate. The organic layer was washed with water and a saturated aqueous sodium chloride solution, dried over anhydrous sodium sulfate and then filtered and the filtrate was concentrated under reduced pressure. The resulting residue was purified by a preparative thin-layer chromatography (hexane/ethyl acetate=2/1) to obtain the title compound (106 mg) as a white solid.

MS (ESI+) 615 (M$^+$+1, 100%).

Reference Example 20

6-{(3R)-3-[(tert-Butoxycarbonyl)amino]piperidin-1-yl}-5-(2-chlorobenzyl)-1,3-dimethyl-2,4-dioxo-2,3,4,5-tetrahydro-1H-pyrrolo[3,2-d]pyrimidine-7-carboxylic acid

[Formula 112]

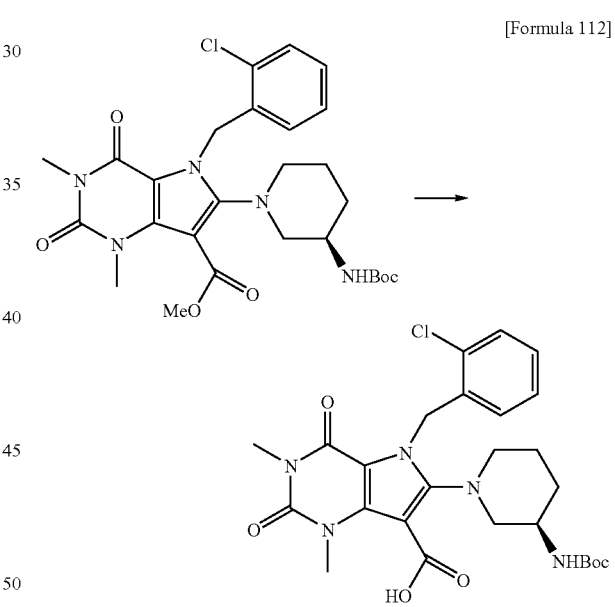

A 1M aqueous sodium hydroxide solution (10 ml) was added to a solution of methyl 6-{(3R)-3-[(tertbutoxycarbonyl)amino]piperidin-1-yl}-5-(2-chlorobenzyl)-1,3-dimethyl-2,4-dioxo-2,3,4,5-tetrahydro-1H-pyrrolo[3,2-d]pyrimidine-7-carboxylate (2.08 g) in 1,4-dioxane (10 ml), and the resulting mixture was stirred at 80° C. for 5 hours. After the reaction solution was cooled to 25° C., a saturated aqueous ammonium chloride solution was added thereto, followed by extraction with ethyl acetate. The organic layer was washed with a saturated aqueous sodium chloride solution, dried over anhydrous sodium sulfate and then filtered and the filtrate was concentrated under reduced pressure to obtain the title compound (1.95 g) as a light-yellow amorphous substance.

MS (ESI+) 546 (M$^+$+1, 100%).

145

Reference Example 21 tert-Butyl {(3R)-1-[5-(2-chloro-5-fluorobenzyl)-1,3-dimethyl-2,4-dioxo-2,3,4,5-tetrahydro-1H-pyrrolo[3,2-d]pyrimidin-6-yl]piperidin-3-yl}carbamate

[Formula 113]

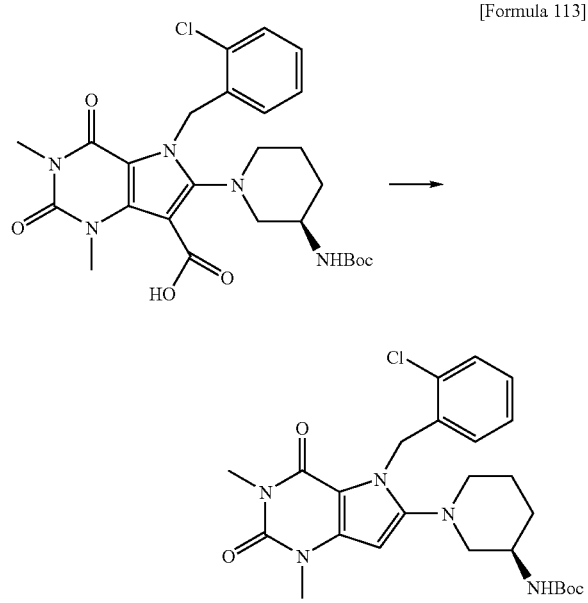

In acetonitrile (5 ml) was dissolved 6-{(3R)-3-[(tert-butoxycarbonyl)amino]piperidin-1-yl}-5-(2-chlorobenzyl)-1,3-dimethyl-2,4-dioxo-2,3,4,5-tetrahydro-1H-pyrrolo[3,2-d]pyrimidine-7-carboxylic acid (350 mg), and the solution was stirred at 80° C. for 1 hour. The reaction solution was cooled to 25° C. and concentrated under reduced pressure. The resulting residue was purified by a silica gel column chromatography (hexane/ethyl acetate=1/1) to obtain the title compound (270 mg) as a white amorphous substance.

MS (ESI+) 402 (M⁺+1, 100%).

Reference Example 22 tert-Butyl {(3R)-1-[7-chloro-5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate

[Formula 114]

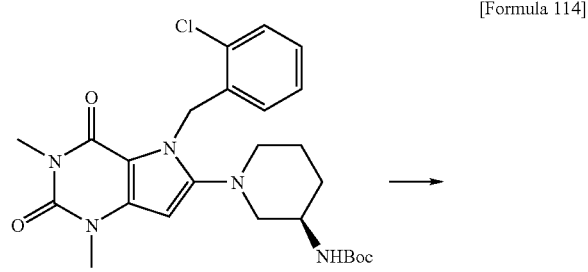

146

-continued

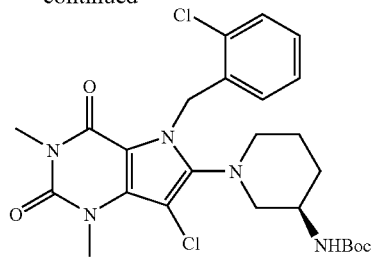

To a solution of tert-butyl {(3R)-1-[5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate (1.00 g) in N,N-dimethylformamide (20 ml) was added N-chlorosuccinimide (294 mg), and the resulting mixture was stirred overnight at room temperature. The reaction solution was adjusted to pH 2 with a 10% aqueous potassium hydrogensulfate solution and extracted with ethyl acetate (200 ml). The organic layer was washed with a 10% aqueous potassium hydrogensulfate solution and a saturated aqueous sodium chloride solution, dried over sodium sulfate and then filtered and the filtrate was concentrated under reduced pressure. The resulting residue was purified by a silica gel column chromatography (hexane/ethyl acetate=2/1) to obtain the title compound (917 mg).

$^{1}$H NMR (300 MHz, CDCl$_{3}$) δ 7.41-7.38 (m, 1H), 7.20-7.10 (m, 2H), 6.42 (d, J=6.6 Hz, 1H), 5.78-5.70 (m, 2H), 3.79 (s, 3H), 3.59-3.55 (m, 1H), 3.36 (s, 3H), 3.12-2.80 (m, 4H), 1.64-1.43 (m, 4H), 1.42 (s, 9H).

MS (ESI+) 536 (M⁺+1, 100%).

Reference Example 23 tert-Butyl {(3R)-1-[5-(2-chlorobenzyl)-7-[(dimethylamino)methyl]-1,3-dimethyl-2,4-dioxo-2,3,4,5-tetrahydro-1H-pyrrolo[3,2-d]pyrimidin-6-yl]piperidin-3-yl}carbamate

[Formula 115]

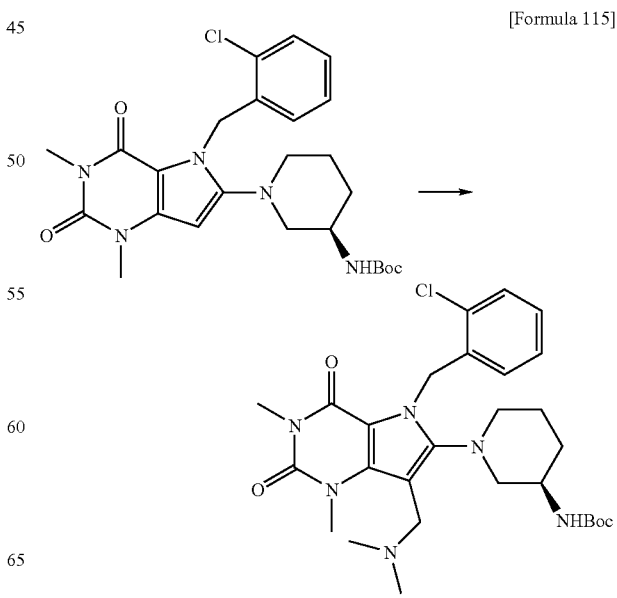

Paraformaldehyde (600 mg) and a 50% aqueous dimethylamine solution (1.80 g) were added to a solution of tert-butyl {(3R)-1-[5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate (1.00 g) in a mixture of ethanol (10 ml) and acetic acid (5 ml), and the resulting mixture was stirred with heating at 80° C. After the reaction solution was cooled to 25° C., toluene (30 ml) was added thereto and the resulting mixture was concentrated under reduced pressure. This procedure was repeated three times. The resulting residue was acidified with a 10% aqueous potassium hydrogensulfate solution and extracted twice with chloroform (100 ml). The organic layer was dried over sodium sulfate and filtered and the filtrate was concentrated under reduced pressure. The resulting residue was purified by a silica gel column chromatography (hexane/ethyl acetate=1/2) to obtain the title compound (913 mg).

$^1$H NMR (300 MHz, CDCl$_3$) δ 7.37 (d, J=7.3 Hz, 1H), 7.18-7.07 (m, 2H), 6.31 (d, J=7.5 Hz, 1H), 5.71-5.58 (m, 2H), 3.84 (s, 3H), 3.46-3.12 (m, 4H), 3.36 (s, 3H), 2.89-2.64 (m, 3H), 2.22 (s, 6H), 1.79-1.45 (m, 4H), 1.42 (s, 9H).

MS (ESI+) 559 (M$^+$+1, 43%).

Reference Example 24 tert-Butyl {(3R)-1-[5-(2-chlorobenzyl)-7-(methoxymethyl)-1,3-dimethyl-2,4-dioxo-2,3,4,5-tetrahydro-1H-pyrrolo[3,2-d]pyrimidin-6-yl]piperidin-3-yl}carbamate

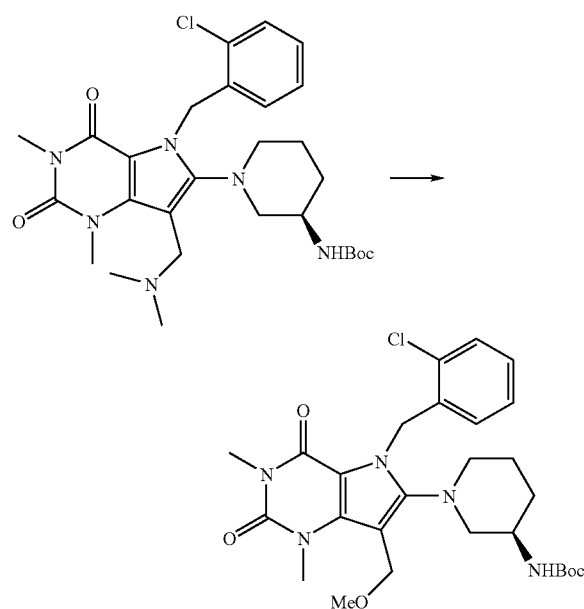

[Formulation 116]

Methyl iodide (25 μl) was added to a solution of tert-butyl {(3R)-1-[5-(2-chlorobenzyl)-7-[(dimethylamino)methyl]-1,3-dimethyl-2,4-dioxo-2,3,4,5-tetrahydro-1H-pyrrolo[3,2-d]pyrimidin-6-yl]piperidin-3-yl}carbamate (112 mg) in acetone (5 ml), and the resulting mixture was stirred overnight in a sealed tube at room temperature. The reaction solution was concentrated under reduced pressure, and to a solution of the resulting residue in methanol (2 ml) was added 28% methanol methoxide (2 ml), followed by stirring with heating at 60° C. for 4 hours. The methanol was distilled off under reduced pressure and the residue was adjusted to pH 2 with an aqueous potassium hydrogensulfate solution and extracted with ethyl acetate (100 ml). The organic layer was washed with a 10% aqueous potassium hydrogensulfate solution and a saturated aqueous sodium chloride solution, dried over sodium sulfate and then filtered and the filtrate was concentrated under reduced pressure. The resulting residue was purified by a thin-layer silica gel column chromatography (hexane/ethyl acetate=1/5) to obtain the title compound (26 mg).

$^1$H NMR (300 MHz, CDCl$_3$) δ 7.37 (d, J=7.7 Hz, 1H), 7.18-7.07 (m, 2H), 6.37 (d, J=7.0 Hz, 1H), 5.71-5.60 (m, 2H), 4.67-4.64 (m, 1H), 4.40 (s, 3H), 3.72 (s, 3H), 3.71-3.69 (m, 1H), 3.43 (s, 3H), 3.36 (s, 3H), 3.35-3.30 (m, 1H), 2.82-2.78 (m, 3H), 1.80-1.45 (m, 4H), 1.42 (s, 9H).

MS (ESI+) 546 (M$^+$+1, 36%).

Reference Example 25 tert-Butyl {(3R)-1-[7-bromo-5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate

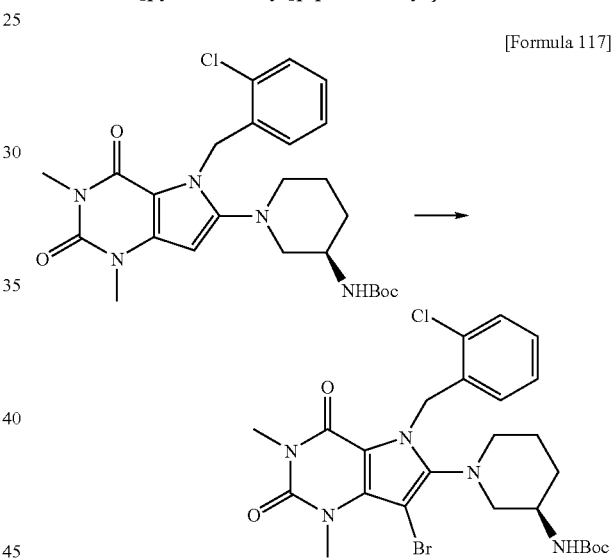

[Formula 117]

To a solution of tert-butyl {(3R)-1-[5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate (1.00 g) in N,N-dimethylformamide (20 ml) was added N-bromosuccinimide (392 mg), and the resulting mixture was stirred overnight at room temperature. The reaction solution was adjusted to pH 2 with a 10% aqueous potassium hydrogensulfate solution and extracted with ethyl acetate (200 ml). The organic layer was washed with a 10% aqueous potassium hydrogensulfate solution and a saturated aqueous sodium chloride solution, dried over sodium sulfate and then filtered and the filtrate was concentrated under reduced pressure. The resulting residue was purified by a silica gel column chromatography (hexane/ethyl acetate=2/1) to obtain the title compound (1.143 g).

$^1$H NMR (300 MHz, CDCl$_3$) δ 7.39 (d, J=7.3 Hz, 1H), 7.20-7.10 (m, 2H), 6.40 (d, J=7.1 Hz, 1H), 5.76 (s, 2H), 4.97-4.95 (m, 1H), 3.83 (s, 3H), 3.67-3.59 (m, 1H), 3.36 (s, 3H), 3.23-2.82 (m, 3H), 2.54-2.52 (m, 1H), 1.91-1.89 (m, 1H), 1.71-1.51 (m, 3H), 1.43 (sm, 9H).

MS (ESI+) 582 (M$^+$+1, 52%).

Reference Example 26 tert-Butyl {(3R)-1-[5-(2-chlorobenzyl)-7-fluoro-1,3-dimethyl-2,4-dioxo-2,3,4,5-tetrahydro-1H-pyrrolo[3,2-d]pyrimidin-6-yl]piperidin-3-yl}carbamate

[Formula 118]

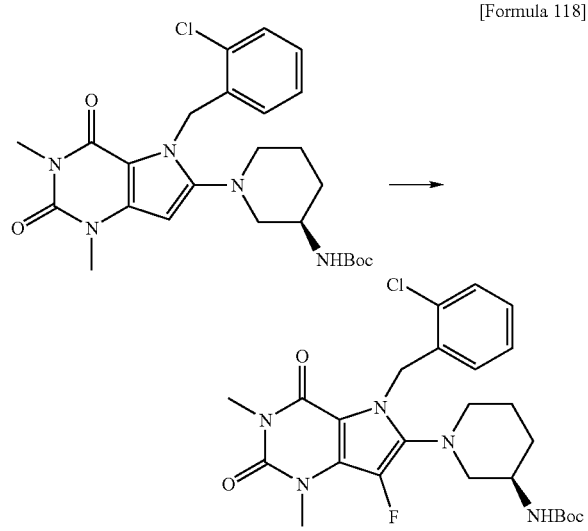

Xenon fluoride (56 mg) was added to a solution of tert-butyl {(3R)-1-[5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate (1.00 g) in acetonitrile (10 ml), and the resulting mixture was stirred overnight at room temperature. After a saturated aqueous sodium hydrogencarbonate solution was added to the reaction solution, the acetonitrile was distilled off under reduced pressure, and the residue was extracted twice with chloroform (50 ml). The organic layer was dried over sodium sulfate and filtered and the filtrate was concentrated under reduced pressure. The resulting residue was purified by a thin-layer silica gel column chromatography (hexane/ethyl acetate=1/1) to obtain the title compound (8 mg).

$^1$H NMR (300 MHz, CDCl$_3$) δ 7.41-7.37 (m, 1H), 7.20-7.11 (m, 2H), 6.46 (d, J=6.8 Hz, 1H), 5.69 (d, J=16.3 Hz, 1H), 5.59 (d, J=16.3 Hz, 1H), 4.73-4.69 (m, 1H), 3.76-3.74 (m, 1H), 3.61 (s, 3H), 3.36 (s, 3H), 3.29-3.25 (m, 1H), 2.78-2.76 (m, 3H), 1.69-1.45 (m, 4H), 1.42 (s, 9H).

MS (ESI+) 520 (M$^+$+1, 17%).

Reference Example 27 tert-Butyl {(3R)-1-[5-(2-chlorobenzyl)-1,3,7-trimethyl-2,4-dioxo-2,3,4,5-tetrahydro-1H-pyrrolo[3,2-d]pyrimidin-6-yl]piperidin-3-yl}carbamate

[Formula 119]

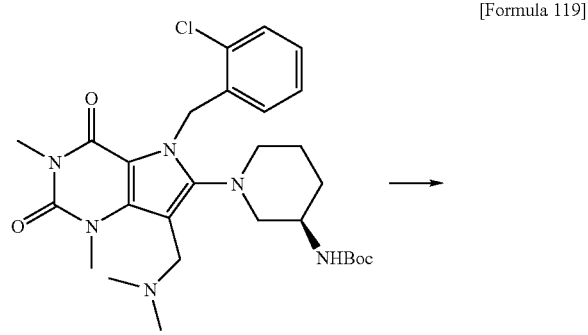

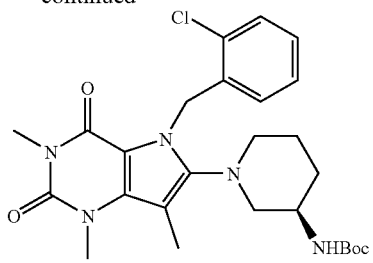

Methyl iodide (38 μl) was added to a solution of tert-butyl {(3R)-1-[5-(2-chlorobenzyl)-7-[(dimethylamino)methyl]-1,3-dimethyl-2,4-dioxo-2,3,4,5-tetrahydro-1H-pyrrolo[3,2-d]pyrimidin-6-yl]piperidin-3-yl}carbamate (168 mg) in acetone (4 ml), and the resulting mixture was stirred overnight in a sealed tube at room temperature. The reaction solution was concentrated under reduced pressure, and to a solution of the resulting residue in tetrahydrofuran (5 ml) was added a 1N aqueous sodium hydroxide solution (3 ml), followed by stirring with heating at 60° C. for 3 hours. The tetrahydrofuran was distilled off under reduced pressure and water was added to the residue, followed by two runs of extraction with chloroform (50 ml). The organic layer was dried over sodium sulfate and filtered and the filtrate was concentrated under reduced pressure. Then, a solution of the resulting residue in dichloromethane (6 ml) was added dropwise to an ice-cooled solution of triethylsilane (144 μl) and methanesulfonic acid (60 μl) in dichloromethane (10 ml), and the resulting mixture was stirred at 0° C. for 1 hour. A 10% aqueous potassium carbonate solution was added thereto, followed by two runs of extraction with chloroform (50 ml). The organic layer was dried over sodium sulfate and filtered and the filtrate was concentrated under reduced pressure. The resulting residue was purified by a silica gel column chromatography (hexane/ethyl acetate=1/1) to obtain the title compound (101 mg).

$^1$H NMR (300 MHz, CDCl$_3$) δ 7.37 (d, J=7.3 Hz, 1H), 7.17-7.07 (m, 2H), 6.35 (d, J=6.7 Hz, 1H), 5.70 (s, 1H), 4.93-4.91 (m, 1H), 4.93-4.91 (m, 1H), 3.75-3.73 (m, 1H), 3.70 (s, 3H), 3.36 (s, 3H), 3.31-3.29 (m, 1H), 2.90-2.63 (m, 3H), 2.33 (s, 3H), 1.92-1.90 (m, 1H), 1.63-1.46 (m, 3H), 1.42 (s, 9H).

MS (ESI+) 516 (M$^+$+1, 61%).

Reference Example 28 tert-Butyl {(3R)-1-[5-(2-chlorobenzyl)-7-formyl-1,3-dimethyl-2,4-dioxo-2,3,4,5-tetrahydro-1H-pyrrolo[3,2-d]pyrimidin-6-yl]piperidin-3-yl}carbamate

[Formula 120]

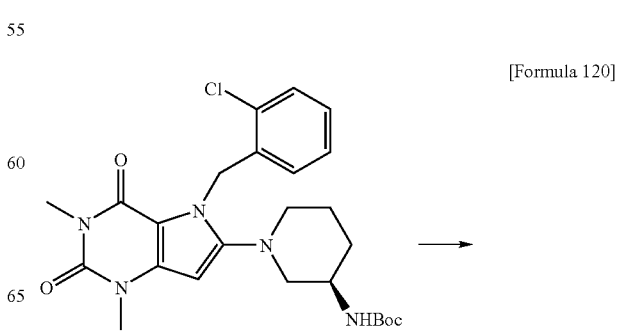

-continued

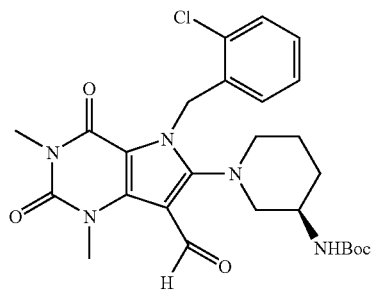

Phosphorus oxychloride (551 μl) was added to dimethylformamide (10 ml) at room temperature and stirred for 5 minutes. A solution of tert-butyl {(3R)-1-[5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate (502 mg) in N,N-dimethylformamide (1 ml) was added to the reaction solution, and the resulting mixture was stirred at room temperature for 3 hours. Water was added to the reaction solution, followed by extraction with ethyl acetate (100 ml). The organic layer was washed with a 10% aqueous potassium hydrogensulfate solution and a saturated aqueous sodium chloride solution, dried over sodium sulfate and then filtered and the filtrate was concentrated under reduced pressure. The resulting residue was purified by a silica gel column chromatography (hexane/ethyl acetate=1/1) to obtain the title compound (290 mg).

$^1$H NMR (300 MHz, CDCl$_3$) δ 10.10 (s, 1H), 7.43-7.40 (m, 1H), 7.23-7.12 (m, 2H), 6.46 (d, J=7.1 Hz, 1H), 5.80 (d, J=16.0 Hz, 1H), 5.59 (d, J=16.0 Hz, 1H), 4.61-4.59 (m, 1H), 3.84 (s, 3H), 3.66-3.64 (m, 1H), 3.38 (s, 3H), 3.37-3.31 (m, 1H), 2.90-2.85 (m, 3H), 1.88-1.85 (m, 1H), 1.59-1.55 (m, 3H), 1.42 (s, 9H).

MS (ESI+) 530 (M$^+$+1, 39%).

Reference Example 29 tert-Butyl {(3R)-1-[5-(2-chlorobenzyl)-7-(1-hydroxyethyl)-1,3-dimethyl-2,4-dioxo-2,3,4,5-tetrahydro-1H-pyrrolo[3,2-d]pyrimidin-6-yl]piperidin-3-yl}carbamate

[Formula 121]

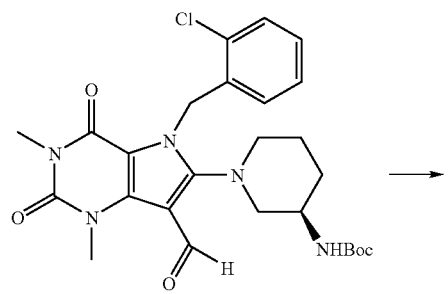

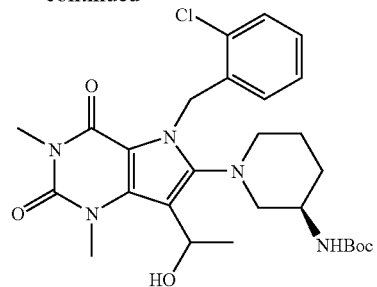

A solution of tert-butyl {(3R)-1-[5-(2-chlorobenzyl)-7-formyl-1,3-dimethyl-2,4-dioxo-2,3,4,5-tetrahydro-1H-pyrrolo[3,2-d]pyrimidin-6-yl]piperidin-3-yl}carbamate (132 mg) in tetrahydrofuran (4 ml) was cooled to 0° C., followed by adding thereto methylmagnesium bromide (417 μl), and the resulting mixture was stirred at 0° C. for 2 hours. A saturated aqueous ammonium chloride solution was added to the reaction solution, followed by two runs of extraction with chloroform (50 ml). The organic layer was dried over sodium sulfate and filtered and the filtrate was concentrated under reduced pressure to obtain a crude product of the title compound (167 mg).

MS (ESI+) 546 (M$^+$+1, 46%).

Reference Example 30 tert-Butyl {(3R)-1-[7-acetyl-5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate

[Formula 122]

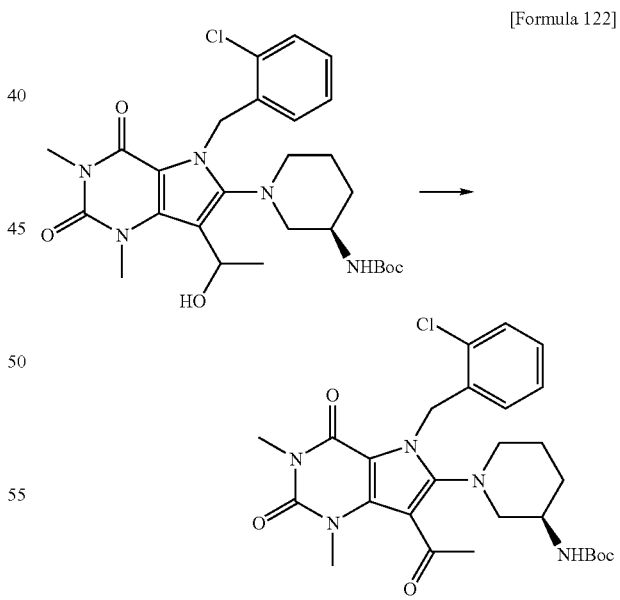

Manganese dioxide (0.66 g) was added to a solution of crude tert-butyl {(3R)-1-[5-(2-chlorobenzyl)-7-(1-hydroxyethyl)-1,3-dimethyl-2,4-dioxo-2,3,4,5-tetrahydro-1H-pyrrolo[3,2-d]pyrimidin-6-yl]piperidin-3-yl}carbamate (167 mg) in dichloromethane (5 ml), and the resulting mixture was stirred overnight at room temperature. Then, the reaction solution was heated to 45° C. and stirred for 3 hours. The reaction solution was filtered through Celite and the filtrate was concentrated under reduced pressure. The resulting residue was purified by a silica gel column chromatography (hexane/ethyl acetate=1/1) to obtain the title compound (33 mg).

MS (ESI+) 546 (M⁺+1, 46%). ¹H NMR (300 MHz, CDCl₃) δ 7.42-7.38 (m, 1H), 7.22-7.11 (m, 2H), 6.43-6.40 (m, 1H), 5.77-5.60 (m, 2H), 5.54-5.51 (m, 1H), 3.62-3.60 (m, 1H), 3.42 (s, 3H), 3.36 (s, 3H), 3.34-3.32 (m, 1H), 2.79-2.65 (m, 3H), 2.59 (s, 3H), 1.88-1.82 (m, 1H), 1.65-1.48 (m, 2H), 1.42 (s, 9H).

MS (ESI+) 544 (M⁺+1, 34%).

Reference Example 31 tert-Butyl {(3R)-1-[5-(2-chlorobenzyl)-7-(4-methoxyphenyl)-1,3-dimethyl-2,4-dioxo-2,3,4,5-tetrahydro-1H-pyrrolo[3,2-d]pyrimidin-6-yl]piperidin-3-yl}carbamate

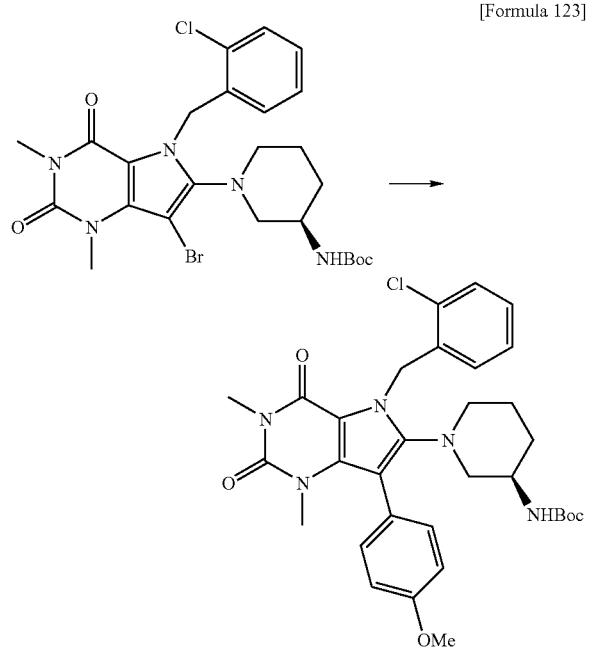

[Formula 123]

Bis(dibenzylideneacetone)palladium (18 mg), tri-tert-butylphosphonium tetrafluoroborate (22 mg), potassium phosphate (329 mg) and 4-methoxyphenylboronic acid (236 mg) were added to a solution of tert-butyl {(3R)-1-[7-bromo-5-(2-chlorobenzyl)-1,3-dimethyl-2,4-dioxo-2,3,4,5-tetrahydro-1H-pyrrolo[3,2-d]pyrimidin-6-yl]piperidin-3-yl}carbamate (90 mg) in dioxane (4 ml), and the resulting mixture was stirred with heating at 50° C. for 15 hours. The reaction solution was filtered through Celite and washed with tetrahydrofuran and the filtrate was concentrated under reduced pressure. A 10% aqueous potassium carbonate solution was added to the residue, followed by two runs of extraction with chloroform (50 ml). The organic layer was dried over sodium sulfate and filtered and the filtrate was concentrated under reduced pressure. The resulting residue was purified by a silica gel column chromatography (hexane/ethyl acetate=2/1) to obtain the title compound (10 mg).

¹H NMR (300 MHz, CDCl₃) δ 7.41-7.37 (m, 1H), 7.26-7.10 (m, 4H), 6.92 (d, J=8.8 Hz, 1H), 6.52-6.50 (m, 1H), 5.80 (d, J=16.7 Hz, 1H), 5.66 (d, J=16.7 Hz, 1H), 3.87 (s, 3H), 3.52-3.50 (m, 1H), 3.37 (s, 3H), 3.07 (s, 3H), 2.80-2.40 (m, 4H), 1.62-1.39 (m, 4H), 1.38 (s, 9H)

MS (ESI+) 608 (M⁺+1, 76%).

Reference Example 32 tert-Butyl {(3R)-1-[5-(2-chloro-5-fluorobenzyl)-7-cyano-3-(4-methoxybenzyl)-1-methyl-2,4-dioxo-2,3,4,5-tetrahydro-1H-pyrrolo[3,2-d]pyrimidin-6-yl]piperidin-3-yl}carbamate

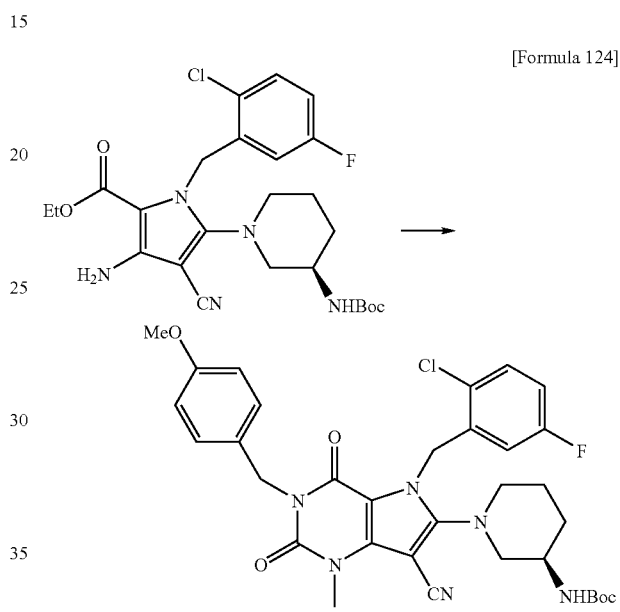

[Formula 124]

4-Methoxybenzyl isocyanate (0.5 ml) and potassium carbonate (486 mg) were added to a solution of ethyl 3-amino-5-{(3R)-3-[(tert-butoxycarbonyl)amino]piperidin-1-yl}-1-(2-chloro-5-fluorobenzyl)-4-cyano-1H-pyrrole-2-carboxylate (920 mg) in pyridine (1 ml), and the resulting mixture was stirred at 130° C. for 6 hours. 4-Methoxybenzyl isocyanate (2.0 ml) was added thereto, followed by stirring with heating for another 24 hours. The reaction solution was cooled to 25° C. and then concentrated under reduced pressure and water was added to the residue, followed by extraction with chloroform. The organic layer was washed with a saturated aqueous sodium chloride solution, dried over anhydrous sodium sulfate and then filtered and the filtrate was concentrated under reduced pressure. The residue was dissolved in N,N-dimethylformamide (15 ml), followed by adding thereto potassium carbonate (486 mg) and methyl iodide (0.33 ml), and the resulting mixture was stirred at 25° C. for 3 hours. A saturated aqueous ammonium chloride solution was added to the reaction solution, followed by extraction with chloroform. The organic layer was washed with water and a saturated aqueous sodium chloride solution, dried over anhydrous sodium sulfate and then filtered and the filtrate was concentrated under reduced pressure. The resulting residue was purified by a silica gel column chromatography (hexane/ethyl acetate) to obtain the title compound (750 mg) as a light-yellow amorphous substance.

MS (ESI+) 651 (M⁺+1, 100%).

Reference Example 33 tert-Butyl {(3R)-1-[7-(aminocarbonyl)-5-(2-chloro-5-fluorobenzyl)-3-(4-methoxybenzyl)-1-methyl-2,4-dioxo-2,3,4,5-tetrahydro-1H-pyrrolo[3,2-d]pyrimidin-6-yl]piperidin-3-yl}carbamate

[Formula 125]

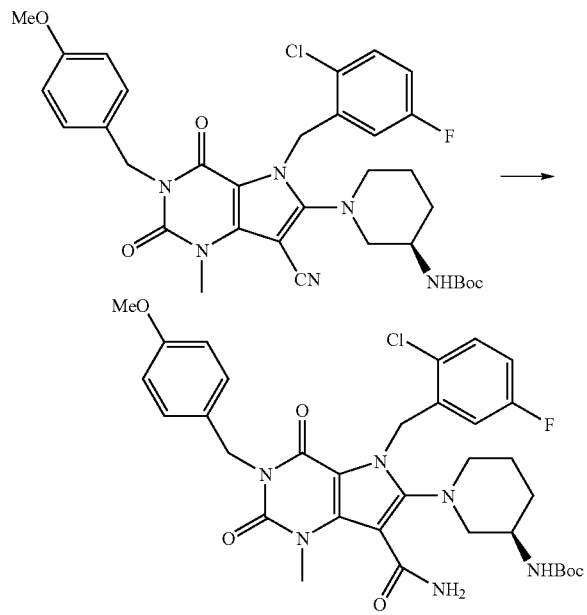

The title compound was synthesized from a corresponding compound by the same process as in Reference Example 15.
MS (ESI+) 669 (M⁺+1, 100%).

Reference Example 34

Methyl 6-{(3R)-3-[(tert-butoxycarbonyl)amino]piperidin-1-yl}-5-(2-chloro-5-fluorobenzyl)-3-(4-methoxybenzyl)-1-methyl-2,4-dioxo-2,3,4,5-tetrahydro-1H-pyrrolo[3,2-d]pyrimidine-7-carboxylate

[Formula 126]

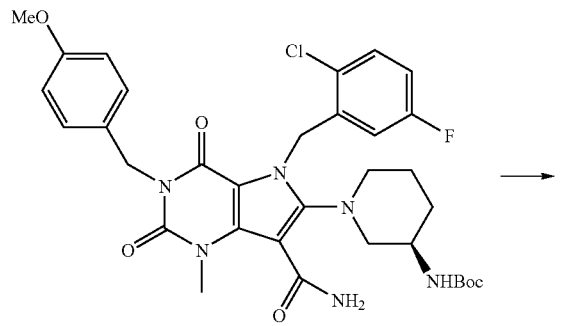

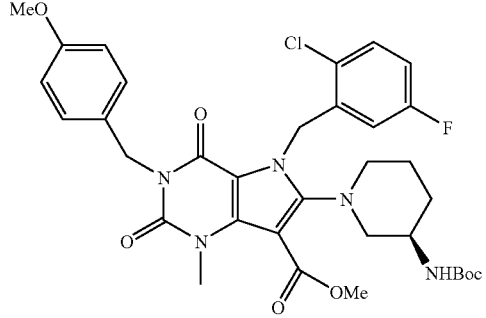

The title compound was synthesized from a corresponding compound by the same process as in Reference Examples 17 and 18.
MS (ESI+) 684 (M⁺+1, 100%).

Reference Example 35

Methyl 6-{(3R)-3-[(tert-butoxycarbonyl)amino]piperidin-1-yl}-5-(2-chloro-5-fluorobenzyl)-1-methyl-2,4-dioxo-2,3,4,5-tetrahydro-1H-pyrrolo[3,2-d]pyrimidine-7-carboxylate

[Formula 127]

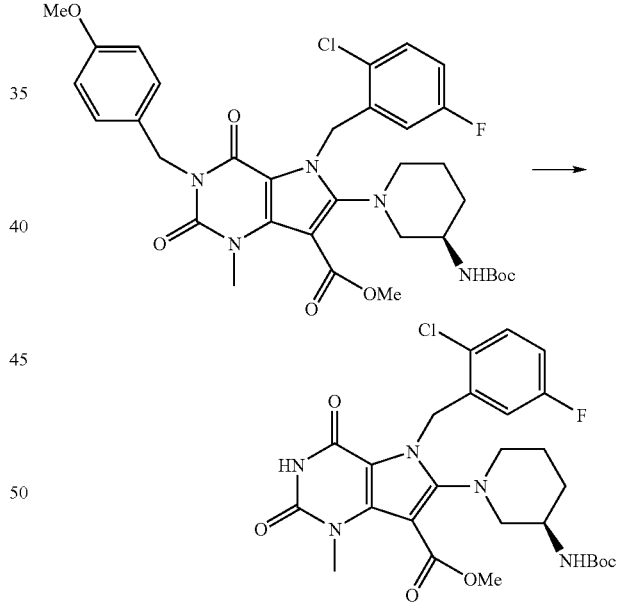

Under a nitrogen atmosphere, a solution of aluminum chloride (395 mg) in anisole (1.5 ml) was added to methyl 6-{(3R)-3-[(tert-butoxycarbonyl)amino]piperidin-1-yl}-5-(2-chloro-5-fluorobenzyl)-3-(4-methoxybenzyl)-1-methyl-2,4-dioxo-2,3,4,5-tetrahydro-1H-pyrrolo[3,2-d]pyrimidine-7-carboxylate (260 mg), and the resulting mixture was stirred at 65° C. for 4 hours. After the reaction solution was cooled to 25° C., 1N hydrochloric acid was added thereto and the aqueous layer was washed with ethyl acetate. The aqueous layer was neutralized with a 1N aqueous sodium hydroxide solution and extracted with chloroform. The organic layer was washed with a saturated aqueous sodium chloride solution, dried over anhydrous sodium sulfate and then filtered and the filtrate was concentrated under reduced pressure. To the resulting residue were added di-tert-butyl dicarbonate (415 mg), 1,4-dioxane (4 ml) and a saturated aqueous sodium hydrogencarbonate solution (4 ml) and the resulting mixture was stirred at 25° C. for 16 hours. Water was added to the reaction solution, followed by extraction with chloroform. The organic layer was washed with a saturated aqueous sodium chloride solution, dried over anhydrous sodium sulfate and then filtered and the filtrate was concentrated under reduced pressure. To the resulting residue was added diethyl ether/hexane and the resulting mixture was filtered and then washed with hexane to obtain the title compound (121 mg) as a light-yellow solid.

MS (ESI+) 564 (M$^+$+1, 100%).

Reference Example 36

Methyl 6-{(3R)-3-[(tert-butoxycarbonyl)amino]piperidin-1-yl}-5-(2-chloro-5-fluorobenzyl)-1-methyl-2,4-dioxo-3-(2-oxo-2-phenylethyl)-2,3,4,5-tetrahydro-1H-pyrrolo[3,2-d]pyrimidine-7-carboxylate

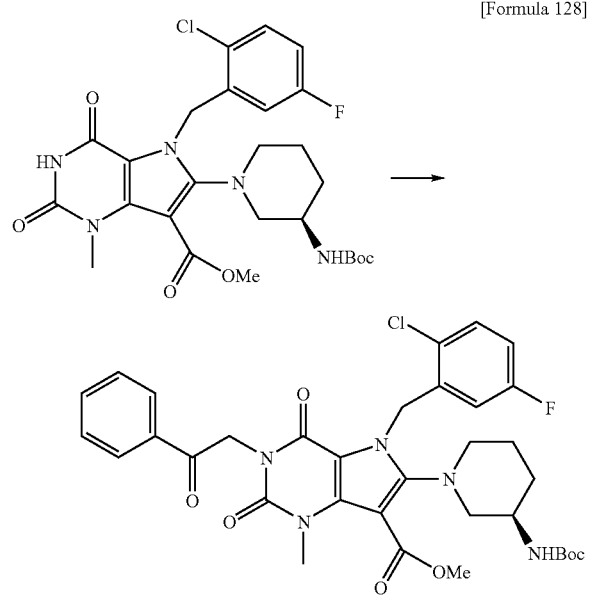

[Formula 128]

A solution of methyl 6-{(3R)-3-[(tertbutoxycarbonyl)amino]piperidin-1-yl}-5-(2-chloro-5-fluorobenzyl)-1-methyl-2,4-dioxo-2,3,4,5-tetrahydro-1H-pyrrolo[3,2-d]pyrimidine-7-carboxylate (50 mg), α-bromoacetophenone (27 mg) and potassium carbonate (25 mg) in N,N-dimethylformamide was stirred at 25° C. for 14 hours. Water was added to the reaction solution, followed by extraction with ethyl acetate. The organic layer was washed with water and a saturated aqueous sodium chloride solution, dried over anhydrous sodium sulfate and then filtered and the filtrate was concentrated under reduced pressure. The resulting residue was purified by a preparative thin-layer chromatography (hexane/ethyl acetate=2/1) to obtain the title compound (51 mg) as a white solid.

MS (ESI+) 682 (M$^+$+1, 100%).

Reference Example 37 tert-Butyl {(3R)-1-[5-(2-chloro-5-fluorobenzyl)-1-methyl-2,4-dioxo-3-(2-oxo-2-phenylethyl)-2,3,4,5-tetrahydro-1H-pyrrolo[3,2-d]pyrimidin-6-yl]piperidin-3-yl}carbamate

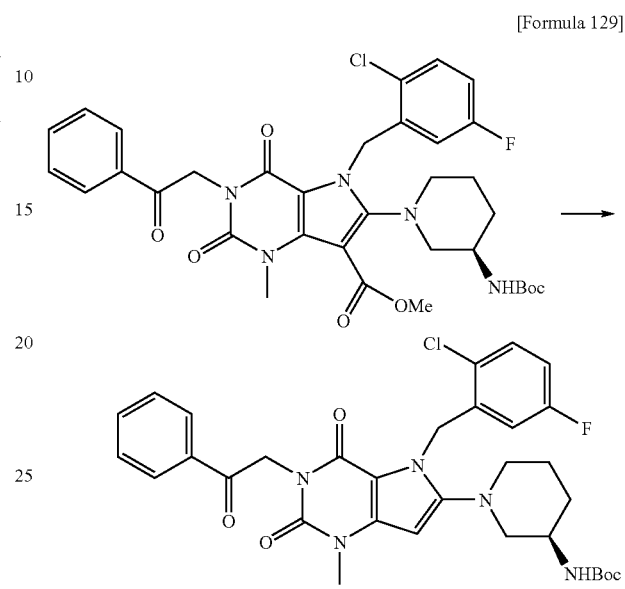

[Formula 129]

The title compound was synthesized from a corresponding compound by the same process as in Reference Examples 20 and 21.

MS (ESI+) 624 (M$^+$+1, 100%).

Reference Example 38 tert-Butyl {(3R)-1-[5-(2-chloro-5-fluorobenzyl)-7-cyano-3-methyl-4-oxo-2-thioxo-2,3,4,5-tetrahydro-1H-pyrrolo[3,2-d]pyrimidin-6-yl]piperidin-3-yl}carbamate

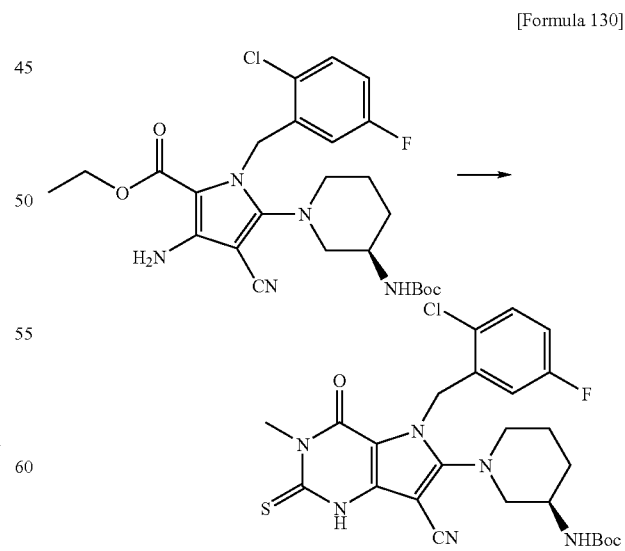

[Formula 130]

Methyl isothiocyanate (7.36 ml) and potassium carbonate (14.86 g) were added to a solution (200 ml) of ethyl 3-amino- 5-{(3R)-3-[(tert-butoxycarbonyl)amino]piperidin-1-yl}-1-(2-chloro-5-fluorobenzyl)-4-cyano-1H-pyrrole-2-carboxylate (27.96 g) in pyridine, and the resulting mixture was stirred with heating at 130° C. for 13 hours. After the reaction solution was cooled to 25° C., toluene (50 ml) was added thereto and the resulting mixture was concentrated under reduced pressure. This procedure was repeated three times. The resulting residue was adjusted to pH 2 with an aqueous potassium hydrogensulfate solution and the solid precipitated was collected by filtration and washed with water and then hexane. The solid thus obtained was dried at 45° C. under reduced pressure to obtain the title compound (28.56 g).

MS (ESI+) 547 (M$^+$+1, 86%).

Reference Example 39 tert-Butyl {(3R)-1-[5-(2-chloro-5-fluorobenzyl)-7-cyano-3-methyl-4-oxo-4,5-dihydro-3H-pyrrolo[3,2-d]pyrimidin-6-yl]piperidin-3-yl}carbamate

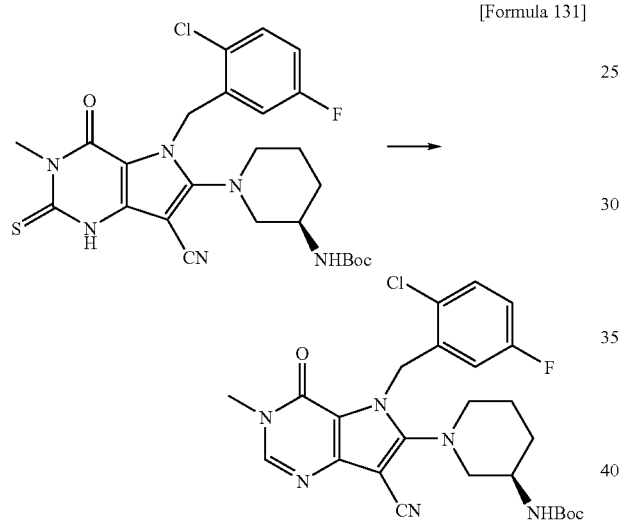

[Formula 131]

Sodium tungstate dihydrate (0.91 g) was added to a solution of tert-butyl {(3R)-1-[5-(2-chloro-5-fluorobenzyl)-7-cyano-3-methyl-4-oxo-2-thioxo-2,3,4,5-tetrahydro-1H-pyrrolo[3,2-d]pyrimidin-6-yl]piperidin-3-yl}carbamate (1.51 g) in a mixture of methanol (9 ml), acetic acid (3 ml) and water (1 ml), and a 30% aqueous hydrogen peroxide solution (0.29 ml) was added dropwise thereto at room temperature and stirred for 2 hours. After the reaction mixture was allowed to cool, the methanol was distilled off under reduced pressure and the residue was adjusted to pH 9 with an aqueous potassium carbonate solution. A 10% aqueous sodium hydrogensulfite solution was added thereto and stirred for 30 minutes, followed by extraction with ethyl acetate (200 mL). The organic layer was washed with a 10% aqueous potassium carbonate solution and a saturated aqueous sodium chloride solution, dried over sodium sulfate and then filtered and the filtrate was dried under reduced pressure to obtain the title compound (1.61 g).

$^1$H NMR (300 MHz, CDCl$_3$) δ 7.99 (s, 1H), 7.41-7.36 (m, 1H), 6.96-6.89 (m, 1H), 6.20 (d, J=7.5 Hz, 1H), 5.70 (d, J=16.7 Hz, 1H), 5.59 (d, J=16.7 Hz, 1H), 4.53-4.51 (m, 1H), 3.74-3.69 (m, 1H), 3.55 (s, 3H), 3.52-3.46 (m, 1H), 3.05-2.94 (m, 3H), 1.88-1.85 (m, 1H), 1.70-1.60 (m, 3H), 1.41 (s, 9H).

MS (ESI+) 515 (M$^+$+1, 66%).

Reference Example 40 tert-Butyl {(3R)-1-[7-(aminocarbonyl)-5-(2-chloro-5-fluorobenzyl)-3-methyl-4-oxo-4,5-dihydro-3H-pyrrolo[3,2-d]pyrimidin-6-yl]piperidin-3-yl}carbamate

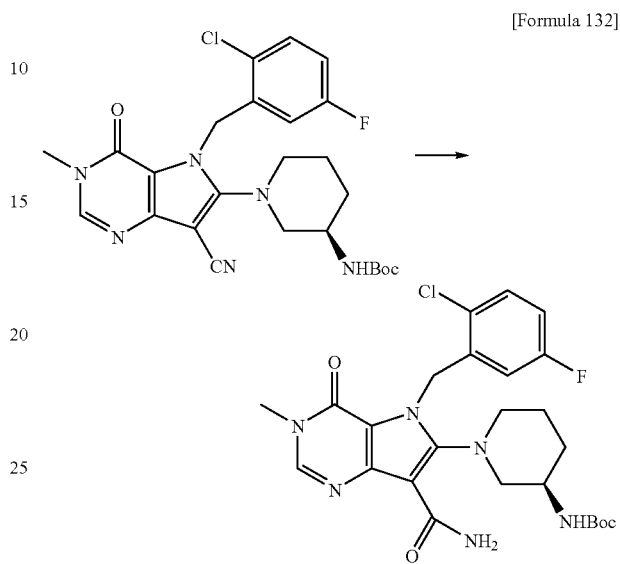

[Formula 132]

The title compound was synthesized from a corresponding compound by the same process as in Reference Example 15.

MS (ESI+) 533 (M$^+$+1, 73%).

Reference Example 41 tert-Butyl {(3R)-1-[5-(2-chloro-5-fluorobenzyl)-3-methyl-4-oxo-7-(1H-pyrrolo-1-ylcarbonyl)-4,5-dihydro-3H-pyrrolo[3,2-d]pyrimidin-6-yl]piperidin-3-yl}carbamate

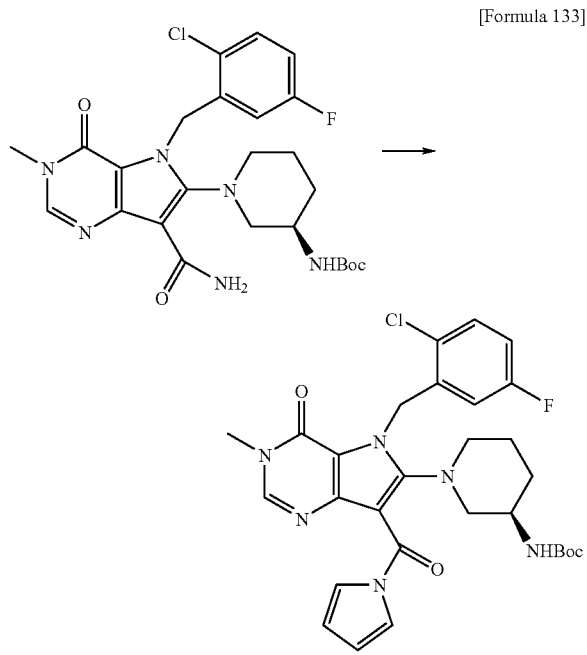

[Formula 133]

Reference Example 42

Methyl 6-{(3R)-3-[(tert-butoxycarbonyl)amino]piperidin-1-yl}-5-(2-chloro-5-fluorobenzyl)-3-methyl-4-oxo-4,5-dihydro-3H-pyrrolo[3,2-d]pyrimidine-7-carboxylate

[Formula 134]

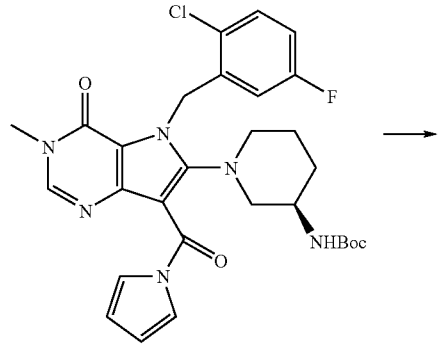

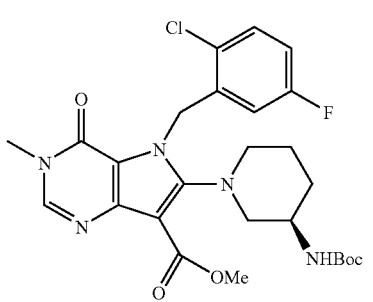

The title compound was synthesized from a corresponding compound by the same process as in Reference Example 18.
$^1$H NMR (300 MHz, CDCl$_3$) δ 8.04 (s, 1H), 7.40-7.35 (m, 1H), 6.93-6.86 (m, 1H), 6.03 (d, J=7.1 Hz, 1H), 5.85 (d, J=16.8 Hz, 1H), 5.74 (d, J=16.8 Hz, 1H), 4.68-4.66 (m, 1H), 3.98 (s, 3H), 3.68-3.66 (m, 1H), 3.56 (s, 3H), 3.33-3.31 (m, 1H), 2.97-2.93 (m, 3H), 1.83-1.81 (m, 1H), 1.65-1.56 (m, 3H), 1.41 (s, 9H). MS (ESI+) 548 (M$^+$+1, 41%).

Reference Example 43

6-{(3R)-3-[(tert-Butoxycarbonyl)amino]-piperidin-1-yl}-5-(2-chloro-5-fluorobenzyl)-3-methyl-4-oxo-4,5-dihydro-3H-pyrrolo[3,2-d]pyrimidine-7-carboxylic acid

[Formula 135]

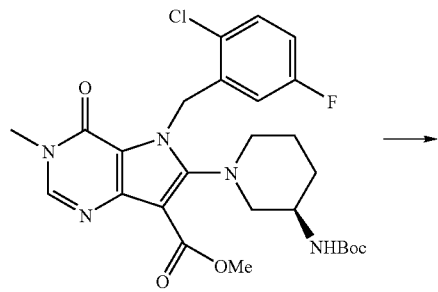

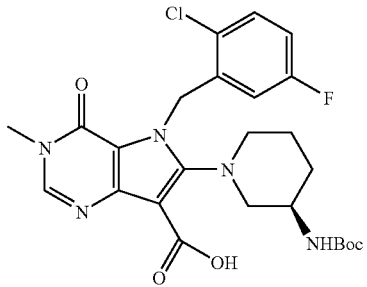

The title compound was synthesized from a corresponding compound by the same process as in Reference Example 20.
MS (ESI+) 534 (M$^+$+1, 6%).

Reference Example 44 tert-Butyl {(3R)-1-[5-(2-chloro-5-fluorobenzyl)-3-methyl-7-(morpholin-4-ylcarbonyl)-4-oxo-4,5-dihydro-3H-pyrrolo[3,2-d]pyrimidin-6-yl]piperidin-3-yl}carbamate

[Formula 136]

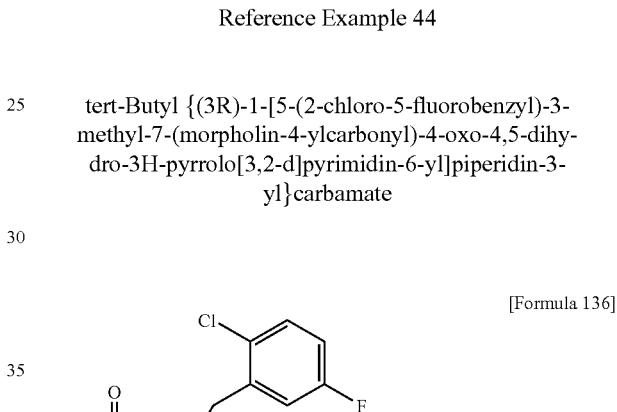

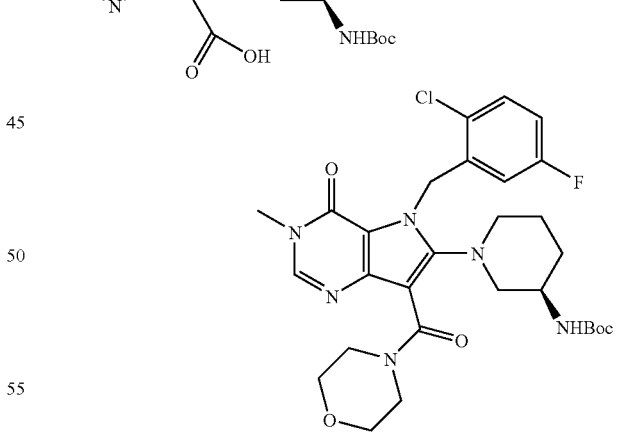

The title compound was synthesized from a corresponding compound by the same process as in Reference Example 19.
$^1$H NMR (300 MHz, CDCl$_3$) δ 7.89 (s, 1H), 7.39-7.34 (m, 1H), 6.92-6.87 (m, 1H), 6.21-6.19 (m, 1H), 5.74 (d, J=16.6 Hz, 1H), 5.59 (d, J=16.6 Hz, 1H), 4.60-4.58 (m, 1H), 3.92-3.71 (m, 7H), 3.57-3.51 (m, 2H), 3.54 (s, 3H), 3.30-3.28 (m, 1H), 2.87-2.76 (m, 3H), 1.78-1.57 (m, 4H), 1.41 (s, 9H). MS (ESI+) 603 (M$^+$+1, 19%).

Reference Example 45 tert-Butyl {(3R)-1-[5-(2-chloro-5-fluorobenzyl)-3-methyl-4-oxo-4,5-dihydro-3H-pyrrolo[3,2-d]pyrimidin-6-yl]piperidin-3-yl}carbamate

[Formula 137]

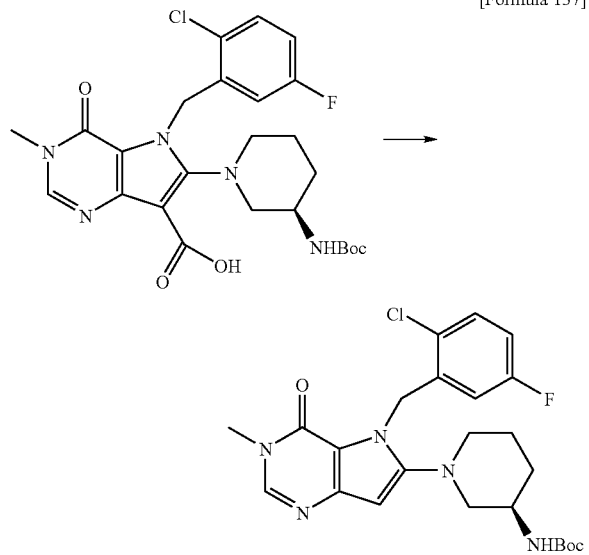

The title compound was synthesized from a corresponding compound by the same process as in Reference Example 21.

¹H NMR (300 MHz, CDCl₃) δ 7.88 (s, 1H), 7.37-7.32 (m, 1H), 6.90-6.83 (m, 1H), 6.09 (d, J=9.3 Hz, 1H), 6.06 (s, 1H), 5.73 (d, J=16.9 Hz, 1H), 5.62 (d, J=16.9 Hz, 1H), 4.69-4.65 (m, 1H), 3.80-3.78 (m, 1H), 3.54 (s, 3H), 3.13-3.08 (m, 1H), 2.77-2.74 (m, 3H), 1.72-1.60 (m, 4H), 1.42 (s, 9H). MS (ESI+) 490 (M⁺+1, 71%).

Reference Example 46 tert-Butyl {(3R)-1-[5-(2-chlorobenzyl)-7-hydroxy-1,3-dimethyl-2,4-dioxo-2,3,4,5-tetrahydro-1H-pyrrolo[3,2-d]pyrimidin-6-yl]piperidin-3-yl}carbamate

[Formula 138]

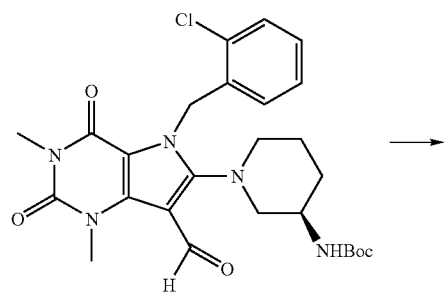

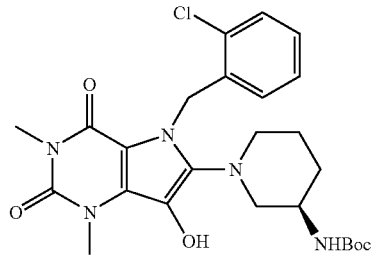

Methanesulfonic acid (21 μl) and a 30% aqueous hydrogen peroxide solution (54 μl) were added to a solution of tert-butyl {(3R)-1-[5-(2-chlorobenzyl)-7-formyl-1,3-dimethyl-2,4-dioxo-2,3,4,5-tetrahydro-1H-pyrrolo[3,2-d]pyrimidin-6-yl]piperidin-3-yl}carbamate (132 mg) in methanol (4 ml), and the resulting mixture was stirred at room temperature for 2 hours. A 10% aqueous sodium sulfite solution was added to the reaction solution, followed by extraction with ethyl acetate (50 ml). The organic layer was dried over sodium sulfate and filtered and the filtrate was concentrated under reduced pressure. The resulting residue was purified by a silica gel column chromatography (hexane/ethyl acetate=1/2) to obtain the title compound (54 mg).

¹H NMR (300 MHz, CDCl₃) δppm 7.35 (d, J=7.5 Hz, 1H), 7.17-7.07 (m, 2H), 6.37 (d, J=6.8 Hz, 1H), 5.86 (brs, 1H), 5.60-5.56 (m, 2H), 4.82 (brs, 1H), 3.71 (s, 3H), 3.65-3.63 (m, 1H), 3.37 (s, 3H), 3.35-3.33 (m, 1H), 2.84-2.70 (m, 3H), 1.95-1.93 (m, 1H), 1.62-1.41 (m, 3H), 1.41 (m, 9H). MS (ESI+) 518 (M⁺+1, 82%).

Reference Example 47 tert-Butyl {(3R)-1-[5-(2-chloro-5-fluorobenzyl)-2,7-dicyano-3-methyl-4-oxo-4,5-dihydro-3H-pyrrolo[3,2-d]pyrimidin-6-yl]piperidin-3-yl}carbamate

[Formula 139]

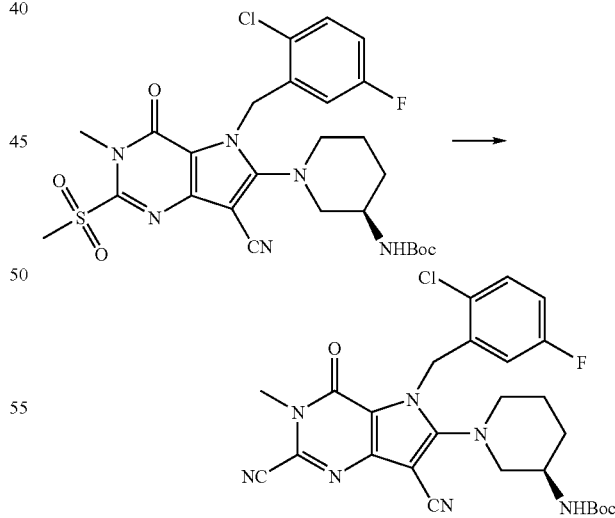

An aqueous solution (2 ml) of sodium cyanide (338 mg) was added to a solution of tert-butyl {(3R)-1-[5-(2-chloro-5-fluorobenzyl)-7-cyano-3-methyl-2-(methylsulfonyl)-4-oxo-4,5-dihydro-3H-pyrrolo[3,2-d]pyrimidin-6-yl]piperidin-3-yl}carbamate (890 mg) in tetrahydrofuran (10 ml), and the resulting mixture was stirred at room temperature for 3 hours. Water was added to the reaction solution, followed by extraction with ethyl acetate (200 ml). The organic layer was washed with a 10% aqueous potassium carbonate solution and a saturated aqueous sodium chloride solution, dried over sodium sulfate and then filtered and the filtrate was concentrated under reduced pressure. The resulting residue was purified by a silica gel column chromatography (hexane/ethyl acetate=2/1) to obtain the title compound (758 mg).

$^1$H NMR (300 MHz, CDCl$_3$) δ 7.42-7.37 (m, 1H), 6.99-6.91 (m, 1H), 6.19 (d, J=7.3 Hz, 1H), 5.68 (d, J=16.7 Hz, 1H), 5.57 (d, J=16.7 Hz, 1H), 4.52-4.49 (m, 1H), 3.78 (s, 3H), 3.72-3.70 (m, 1H), 3.55-3.50 (m, 1H), 3.10-3.06 (m, 2H), 3.00-2.93 (m, 1H), 1.91-1.89 (m, 1H), 1.74-1.58 (m, 3H), 1.41 (s, 9H).

MS (ESI+) 540 (M$^+$+1, 11%).

Reference Example 48 tert-Butyl {(3R)-1-[2-(aminocarbonyl)-5-(2-chloro-5-fluorobenzyl)-7-cyano-3-methyl-4-oxo-4,5-dihydro-3H-pyrrolo[3,2-d]pyrimidin-6-yl]piperidin-3-yl}carbamate

[Formula 140]

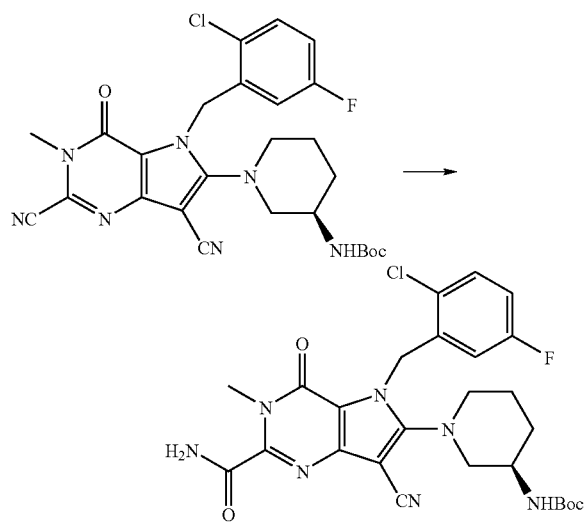

Potassium carbonate (42 mg) and then an aqueous hydrogen peroxide solution (a 30-35% aqueous solution, 170 μl) were added dropwise to a solution of tert-butyl {(3R)-1-[5-(2-chloro-5-fluorobenzyl)-2,7-dicyano-3-methyl-4-oxo-4,5-dihydro-3H-pyrrolo[3,2-d]pyrimidin-6-yl]piperidin-3-yl}carbamate (162 mg) in a mixture of dimethyl sulfoxide (10 ml) and water (2 ml), and the resulting mixture was stirred overnight at room temperature. A 10% aqueous sodium sulfite solution was added to the reaction solution, followed by extraction with ethyl acetate (200 ml). The organic layer was washed with a 10% aqueous potassium carbonate solution and a saturated aqueous sodium chloride solution, dried over sodium sulfate and then filtered and the filtrate was concentrated under reduced pressure. The resulting residue was purified by a silica gel column chromatography (hexane/ethyl acetate=1/1) to obtain the title compound (77 mg).

$^1$H NMR (300 MHz, CDCl$_3$) δ 7.62 (s, 1H), 7.42-7.37 (m, 1H), 6.97-6.91 (m, 1H), 6.21 (d, J=7.0 Hz, 1H), 5.84 (s, 1H), 5.71 (d, J=16.7 Hz, 1H), 5.60 (d, J=16.7 Hz, 1H), 4.58-4.55 (m, 1H), 3.87 (s, 3H), 3.75-3.73 (m, 1H), 3.54-3.49 (m, 1H), 3.05-2.95 (m, 3H), 1.87-1.85 (m, 1H), 1.70-1.66 (m, 3H), 1.42 (s, 9H)

MS (ESI+) 458 (M$^+$+1, 100%).

Reference Example 49 tert-Butyl {(3R)-1-[5-(2-chlorobenzyl)-7-methoxy-1,3-dimethyl-2,4-dioxo-2,3,4,5-tetrahydro-1H-pyrrolo[3,2-d]pyrimidin-6-yl]piperidin-3-yl}carbamate

[Formula 141]

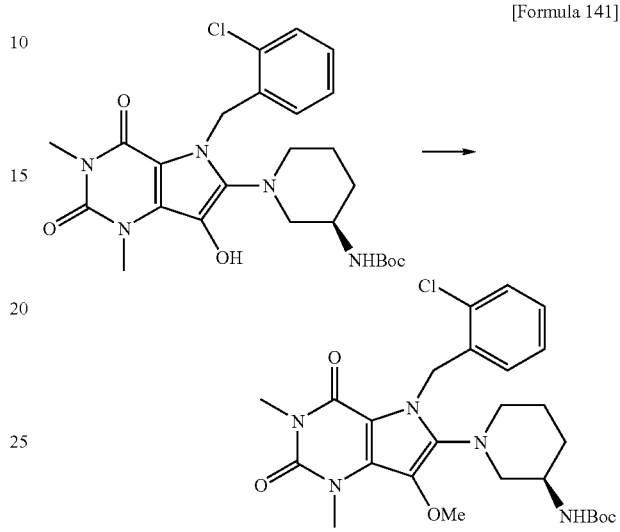

Potassium carbonate (41 mg) and methyl iodide (13 μl) were added to a solution of tert-butyl {(3R)-1-[5-(2-chlorobenzyl)-7-hydroxy-1,3-dimethyl-2,4-dioxo-2,3,4,5-tetrahydro-1H-pyrrolo[3,2-d]pyrimidin-6-yl]piperidin-3-yl}carbamate (50 mg) in N,N-dimethylformamide (2 ml), and the resulting mixture was stirred at room temperature for 5 hours. A 10% aqueous potassium hydrogensulfate solution was added to the reaction solution, followed by extraction with ethyl acetate (100 ml). The organic layer was washed with a 10% aqueous potassium hydrogensulfate solution and a saturated aqueous sodium chloride solution, dried over sodium sulfate and then filtered and the filtrate was concentrated under reduced pressure. The resulting residue was purified by a preparative thin-layer chromatography (hexane/ethyl acetate=1/1) to obtain the title compound (17 mg).

MS (ESI+) 532 (M$^+$+1, 69%).

Reference Example 50 tert-Butyl {(3R)-1-[5-(2-chloro-5-fluorobenzyl)-7-cyano-2,3-dimethyl-4-oxo-4,5-dihydro-3H-pyrrolo[3,2-d]pyrimidin-6-yl]piperidin-3-yl}carbamate

[Formula 142]

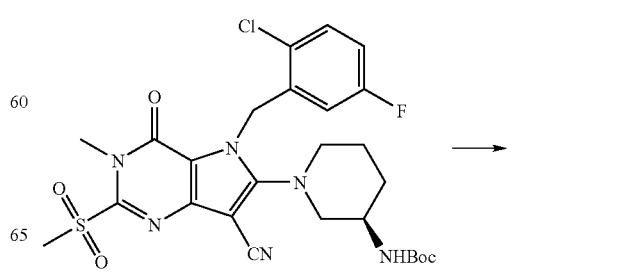

-continued

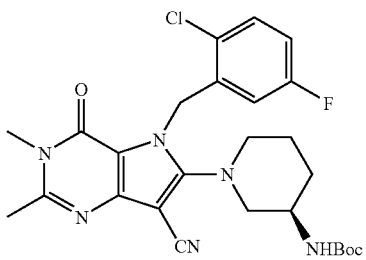

A solution of tert-butyl {(3R)-1-[5-(2-chloro-5-fluorobenzyl)-7-cyano-3-methyl-2-(methylsulfonyl)-4-oxo-4,5-dihydro-3H-pyrrolo[3,2-d]pyrimidin-6-yl]piperidin-3-yl}carbamate (890 mg) in tetrahydrofuran (2 ml) was cooled to 0° C. and a 3M methylmagnesium bromide/diethyl ether solution (333 μl) was added dropwise thereto. After 30 minutes, the reaction solution was warmed to room temperature and stirred for 1 hour. A saturated aqueous ammonium chloride solution was added to the reaction solution, followed by extraction with ethyl acetate (100 ml). The organic layer was washed with a saturated aqueous sodium chloride solution, dried over sodium sulfate and then filtered and the filtrate was concentrated under reduced pressure. The resulting residue was purified by a silica gel column chromatography (hexane/ethyl acetate=1/1) to obtain the title compound (64 mg).

$^1$H NMR (300 MHz, CDCl$_3$) δ 7.40-7.35 (m, 1H), 6.95-6.88 (m, 1H), 6.18 (d, J=6.9 Hz, 1H), 5.68 (d, J=16.8 Hz, 1H), 5.57 (d, J=16.8 Hz, 1H), 4.58-4.55 (m, 1H), 3.78-3.74 (m, 1H), 3.54 (s, 3H), 3.50-3.45 (m, 1H), 3.04-2.94 (m, 3H), 2.63 (s, 3H), 1.88-1.83 (m, 1H), 1.68-1.62 (m, 2H), 1.43-1.41 (m, 1H), 1.41 (s, 9H).

MS (ESI+) 529 (M$^+$+1, 100%).

In Vitro DPP-IV Inhibitory Effect Measurement Test

Human serum containing DPP-IV enzyme was diluted finally 9- to 20-fold with assay buffer and added to a microassay plate. Each of solutions of each test compound having various concentrations was added thereto, followed by adding thereto a substrate (Glycyl-L-Proline 4-Methyl-Coumaryl-7-Amide, Peptide Laboratories Co., Ltd.) to a final concentration of 10 to 100 μM, and the reaction was carried out at room temperature. Acetic acid was added thereto to a final concentration of 0.5% to terminate the reaction, and the intensity of fluorescence at an excitation wavelength of 360 nm and a measuring wavelength of 460 nm was measured by the use of a fluorescent plate reader. A compound concentration for 50% inhibition was calculated as an IC$_{50}$ value from enzyme inhibiting activity values obtained by adding each test compound to a plurality of concentrations.

TABLE 1

| Test Compound | Human DPP IV inhibiting activity IC$_{50}$ (nM) |
|---|---|
| Example 1 | 76 |
| Example 2 | 21 |
| Example 3 | 26 |
| Example 4 | 28 |
| Example 5 | 15 |
| Example 6 | 1.9 |
| Example 7 | 60 |
| Example 8 | 7.4 |
| Example 14 | 55 |
| Example 18 | 12 |

TABLE 1-continued

| Test Compound | Human DPP IV inhibiting activity IC$_{50}$ (nM) |
|---|---|
| Example 19 | 7.1 |
| Example 20 | 4.3 |
| Example 24 | 44 |
| Example 25 | 7.6 |
| Example 26 | 3.2 |
| Example 27 | 9.8 |
| Example 28 | 6.4 |
| Example 29 | 5.7 |
| Example 30 | 4.7 |
| Example 31 | 5.0 |
| Example 32 | 7.5 |
| Example 33 | 12.0 |
| Example 34 | 5.8 |
| Example 37 | 10 |
| Example 38 | 5.3 |
| Example 39 | 4.1 |
| Example 40 | 6.8 |
| Example 41 | 4.1 |
| Example 42 | 5.7 |
| Example 43 | 6.9 |
| Example 44 | 9.0 |
| Example 45 | 4.8 |
| Example 46 | 5.6 |
| Example 56 | 31 |
| Example 60 | 28 |
| Example 61 | 85 |
| Example 62 | 56 |
| Example 63 | 27 |
| Example 64 | 13 |
| Example 65 | 6.2 |
| Example 66 | 5.5 |
| Example 70 | 3800 |
| Example 72 | 1200 |

INDUSTRIAL APPLICABILITY

The present invention makes it possible to provide compounds that have DPP-IV inhibitory activity and possess improved safety, non-toxicity and the like.

The present inventive compounds are useful for the suppression of postprandial hyperglycemia in prediabetes, the treatment of non-insulin-dependent diabetes, the treatment of autoimmune diseases such as arthritis and articular rheumatism, the treatment of intestinal mucosa diseases, growth acceleration, the inhibition of transplantation rejection, the treatment of obesity, the treatment of eating disorder, the treatment of HIV infection, the suppression of cancer metastasis, the treatment of prostatomegaly, the treatment of periodontitis, and the treatment of osteoporosis.

The invention claimed is:

1. A compound represented by the formula:

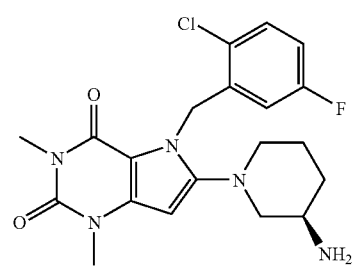

or a pharmaceutically acceptable salt thereof.

2. A compound according to claim 1, wherein the pharmaceutically acceptable sale is hydrochloride.

3. A method for treating diabetes comprising administering an effective amount of a compound, a prodrug thereof or a pharmaceutically acceptable salt of the compound or prodrug according to claim 1 to a patient who needs the treatment.

4. A method for treating diabetes comprising administering an effective amount of a compound, a prodrug thereof or a pharmaceutically acceptable salt of the compound or prodrug according to claim 2 to a patient who needs the treatment.

* * * * *